US009664681B2

(12) United States Patent
Imaizumi et al.

(10) Patent No.: US 9,664,681 B2
(45) Date of Patent: May 30, 2017

(54) LUNG CANCER EVALUATING APPARATUS, METHOD, SYSTEM, AND PROGRAM AND RECORDING MEDIUM THEREFOR

(75) Inventors: Akira Imaizumi, Kanagawa (JP); Nobukazu Ono, Kanagawa (JP); Ryosei Sakai, Kanagawa (JP); Toshihiko Ando, Kanagawa (JP); Naoyuki Okamoto, Kanagawa (JP); Fumio Imamura, Osaka (JP); Masahiko Higashiyama, Osaka (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/365,272

(22) Filed: Feb. 4, 2009

(65) Prior Publication Data

US 2010/0017144 A1 Jan. 21, 2010

Related U.S. Application Data

(63) Continuation of application No. PCT/JP2007/065179, filed on Aug. 2, 2007.

(30) Foreign Application Priority Data

Aug. 4, 2006 (JP) ................................ 2006-213919
Sep. 28, 2006 (JP) ................................ 2006-265973

(51) Int. Cl.
*G01N 33/48* (2006.01)
*G01N 33/50* (2006.01)
*G01N 33/574* (2006.01)
*G06F 19/22* (2011.01)
*G06F 19/24* (2011.01)
*G06F 19/16* (2011.01)
*G06F 19/18* (2011.01)

(52) U.S. Cl.
CPC ....... *G01N 33/57423* (2013.01); *G06F 19/22* (2013.01); *G06F 19/24* (2013.01); *G06F 19/16* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 6,059,724 A * | 5/2000 | Campell et al. | 600/300 |
| 6,631,330 B1 | 10/2003 | Poynard | |
| 6,964,850 B2 | 11/2005 | Bevilacqua et al. | |
| 8,244,476 B2 | 8/2012 | Zhang et al. | |
| 2004/0039553 A1 | 2/2004 | Poynard | |
| 2005/0283347 A1 | 12/2005 | Kimura et al. | |
| 2007/0281895 A1 | 12/2007 | Crockard et al. | |
| 2008/0147368 A1 | 6/2008 | Sugimoto et al. | |
| 2008/0154515 A1 | 6/2008 | Zhang et al. | |
| 2008/0305962 A1 | 12/2008 | Wirtz | |
| 2009/0253116 A1 | 10/2009 | Takahashi et al. | |
| 2010/0004871 A1 | 1/2010 | Goldknopf | |
| 2010/0009401 A1 | 1/2010 | Imaizumi et al. | |
| 2010/0009402 A1 | 1/2010 | Imaizumi et al. | |
| 2010/0017144 A1 | 1/2010 | Imaizumi et al. | |
| 2010/0017145 A1 | 1/2010 | Imaizumi et al. | |
| 2011/0035156 A1 | 2/2011 | Imaizumi et al. | |
| 2011/0091924 A1 | 4/2011 | Imaizumi et al. | |
| 2011/0138889 A1 | 6/2011 | Okamoto et al. | |
| 2011/0143444 A1 | 6/2011 | Muramatsu et al. | |
| 2011/0282585 A9 | 11/2011 | Zhang et al. | |

FOREIGN PATENT DOCUMENTS

| | | |
|---|---|---|
| CN | 1315998 A | 10/2001 |
| CN | 1367830 A | 9/2002 |
| CN | 1878876 A | 12/2006 |
| EP | 1 570 779 A1 | 9/2005 |
| EP | 1 862 797 A1 | 12/2007 |
| JP | 61-126472 A | 6/1986 |
| JP | 2005-508505 A | 3/2005 |
| JP | 5746811 B2 | 7/2015 |
| WO | WO 97/48982 A1 | 12/1997 |
| WO | WO 00/04149 A2 | 1/2000 |
| WO | WO 00/20587 A | 4/2000 |
| WO | WO 00/65472 A1 | 11/2000 |
| WO | WO 02/16949 A1 | 2/2002 |
| WO | WO 2004/052191 A1 | 6/2004 |
| WO | WO 2006/098182 A1 | 9/2006 |
| WO | WO 2006/129513 A1 | 12/2006 |
| WO | WO 2008/016111 A | 2/2008 |
| WO | WO 2008/036691 A2 | 3/2008 |
| WO | WO 2008/075662 A1 | 6/2008 |
| WO | WO 2008/075664 A1 | 6/2008 |
| WO | WO 2009/099005 A1 | 8/2009 |
| WO | WO 2009/110517 A1 | 9/2009 |
| WO | WO 2009/154296 A1 | 12/2009 |
| WO | WO 2009/154297 A1 | 12/2009 |

OTHER PUBLICATIONS

Noguchi et al. Abstract of "Network analysis of plasma and tissue amino acids and the generation of an amino index for potential diagnostic use." vol. 83 (supplement), pp. 513S-519S, Feb. 2006; abstract and bibliographic data only, two pages.*

Proenza et al. Breast and lung cancer are associated with a decrease in blood cell amino acid content. Journal of Nutritional Biochemistry. vol. 14, 2003, pp. 133-138.*

Kubota et al. Amino acid profiles correlate diagnostically with organ site in three kinds of malignant tumors. Cancer, 1992, vol. 69, pp. 2343-2348.*

Miyagi et al. Clinical Utility of AMINOINDEX Cancer Screening (AICS) for early detection of variaous cancers in comparison with detection using tumor markers. Physical Examination, vol. 29, 2014, pp. 585-591. Japanese document and English.*

Cascino et al., "Plasma Amino Acid Imbalance in Patients with Lung and Breast Cancer," Anticancer Research, 1995, 15:507-510.

(Continued)

*Primary Examiner* — Russell S Negin
(74) *Attorney, Agent, or Firm* — Foley & Lardner LLP

(57) ABSTRACT

According to the method of evaluating lung cancer, amino acid concentration data on the concentration value of amino acid in blood collected from a subject to be evaluated is measured, and a lung cancer state in the subject is evaluated based on the concentration value of at least one of Orn, Lys, ABA, Arg, Glu, His, Tau, Pro, Ala, Cit and Ile contained in the measured amino acid concentration data of the subject.

46 Claims, 120 Drawing Sheets

(56) References Cited

OTHER PUBLICATIONS

Cynober, Luc A., Ed., Metabolic and Therapeutic Aspects of Amino Acids in Clinical Nutrition, 2nd Ed., 2004, 339-355 and 689-704.
Evans et al., "Perturbations in Plasma Amino Acid Profiles in Small Cell Lung Cancer (SCLC) and their Response to Treatment," Proceedings of American Association Cancer Res. Ann. Meeting, Mar. 29, 1988, 29:18,69, one page.
Proenza et al., "Breast and lung cancer are associated with a decrease in blood cell amino acid content," Journal of Nutritional Biochemistry, 2003, 14:133-138.
Rodriguez et al., "Arginase I in myeloid suppressor cells is induced by COX-2 in lung carcinoma," J. Exp. Med., Sep. 26, 2005, 202(7):931-939.
Supplementary European Search Report mailed Aug. 26, 2009 in corresponding EP 07791853.0, 11 pages.
Lee et al., "Identification of optimal classification functions for biological sample and state discrimination from metabolic profiling data," Bioinformatics, 2004, 20(6):959-969.
Noguchi et al., "Network analysis of plasma and tissue amino acids and the generation of an amino index for potential diagnostic use," Am. J. Clin. Nutr., 2006, 83(Suppl):513S-519S.
Muscaritoli et al., "Plasma Amino Acid Profile in Cancer Patients: Moving Toward a New Set of Tumor Markers?", Nutritional Support in Cancer and Transplant Patients, 2001, 107-118.
Caballero et al., "Plasma amino acid concentrations in healthy elderly men and women," Am. J. Clin. Nutr., 1991, 53(5):1249-1252.
Vecer et al., "Tissue amino acids in patients with colorectal carcinoma," Vnitr. Lek., Apr. 1998, 44(4):192-194, Abstract.
Hirai, Yoshinori, "A Study of Amino Acid Metabolism in Patients with Gastric Cancer," Journal of Japan Surgical Society, Jul. 1, 1965, 66:983-1013, with English translation.
Kwon et al., "Plasma Free Amino Acids and Various Nutritional Indices Analyzed in Relation to Growth of Gastric Cancer," Japanese Journal of Surgical Metabolism and Nutrition, Apr. 1995, 29(2):129-134, with English translation.
Elling et al., "Therapy monitoring in endometrial carcinomas with and without progression by free serum amino acids," Zentralblatt fur Gynakologie, 1989, 111(18):1224-1230.
Elling et al., "Free amino acids in normal and ovarian cancer tissue in correlation to serum levels-tumour diagnostic possibilities," Zentralblatt fur Gynakologie, 1987, 109(16):1013-1022.
Miyake, Makoto, "Clinical Studies on the Metabolism of Plasma Amino Acids in Various Diseases," Journal of the Nagoya City University Medical Association, 1977, 28(2):308-351, with English translation.
Ando, Toshihiko, "Development of Health Check Method Based on Blood Amino Acid Concentration," Chemistry & Chemical Industry, Jan. 1, 2007, 60(1):40-41, with English translation.
Elling et al., "Freie Aminosauren im normalen und karzinomatosen Ovarialgewebe in Korrelation zum Seramspiegel-tumordiagnostische Moglichkeiten," Zent. Bl. Gynakol., 1987, 109:1013-1022, English abstract on first page.
Elling et al., "Therapiemonitoring bei Patientinnen mit Korpuskarzinom mit und ohne Progression durch freie Serumaminosaeuren," Zent. Bl. Gynakol., 1989, 111:1224-1230, English abstract on first page.
Fukasawa et al., "Serum free amino acid content in hamsters with cheek pouch carcinoma," Jpn. J. Oral Biol., Oct. 20, 1992, 34:555-559, with English translation, 7 pages.
Fukui et al., "A Study of the Metabolism of Branched Chain Amino Acids in Terminal Stage Liver Cancer," Journal of Clinical and Experimental Medicine (Rinsho to Kenkyu), Apr. 1989, 66(4):1183-1187, with English translation.
Hirayama et al., "Plasma Amino Acid Patterns in Hepatocellular Carcinoma," Biochemical Medicine and Metabolic Biology, 1987, 38(2):127-133.
Inoue et al., "Changes of Plasma Free Amino Acids in Hepatocellular Carcinoma: Clinical and Experimental Studies on Evaluation of Tyr/Phe Molar Ratio," J. Iwate Med. Assoc., Jun. 1988, 40(3):351-361, with English translation, 16 pages.
Iwagaki et al., "Observation on the Plasma Amino Acids of Patients with Colorectal Cancer," Japan Society of Coloproctology, 1991, 44(6):917-922, with English translation.
Kimura et al., "The Application of Amion Acid Informatics," Reports on the Research Committee of Essential Amino Acids, Japan, 2006, 177:28-31, with partial English translation.
Kwon et al., "Plasma Free Amino Acids and Biochemical Parameters for Nutrition Assessment in Gastric Cancer Patients," Journal of Surgery and Metabolism/Nutrition, Apr. 1995, 29(2):129-134, with English translation.
Lee et al., "Plasma Amino Acid Levels in Patients with Colorectal Cancers and Liver Cirrhosis with Hepatocellular Carcinoma," Hepato-Gastroenterology, Sep.-Oct. 2003, 50(53):1269-1273.
Murakami et al., "Changes of Amino Acids in Tumor-Bearing Rats with Total Parenternal Nutrition," JJPEN, Aug. 15, 1987, 9(4):615-621, with English translation, 12 pages.
Nefyodov et al., "Amino Acids and their Derivatives in Blood Plasma of Patients with Breast Cancer Treated with Ukrain. Part V," Drugs Exptl. Clin. Res., 1996, 22(3-4-5):155-157.
Okamoto et al., "Development of New Lung Cancer Screening Method by Plasma Free Amino Acid Profile," 65th Annual Meeting of the Japan Cancer Association, Aug. 28, 2006, 287:0-565, with English translation.
Okamoto et al., "Early Detection of Breast Cancer using Plasma Free Amino Acid Profiles," 66th Annual Meeting of the Japan Cancer Association, Aug. 25, 2007, 66:517, P-1210.
Okuyama et al., "Study on plasma amino acids pattern in liver diseases by using multivariate analysis," Journal of Liver, Gall-Bladder and Pancreas, 1987, 15(1):111-117, with partial English translation.
Rivera et al,. "Blood Amino Acid Compartmentation in Mice Bearing Lewis Lung Carcinoma," Cancer Research, Nov. 1, 1987, 47(21):5644-5646.
Shimazaki et al., "Free Amino Acids in Normal and Tumorous Tissues of Human Kidney, Bladder, and Prostate," GANN, Oct. 1974, 65(5):455-457.
Wilson et al., "Free Serum Amino Acids in Patients with Advanced Cervical Carcinoma," Gynecologic Oncology, 1976, 4(3):311-313.
Fortunato et al., "Multivariate Discriminant Function Based on Six Biochemical Markers in Blood Can Predict the Cirrhotic Evolution of Chronic Hepatitis," Clinical Chemistry, 2001, 47(9):1696-1700.
Shangyi et al., "Preliminary Observations on Free Amino Acid Values of Plasma of Patients with Ovarian Cancer and Uterine cervix cancer," Chinese Journal of Clinical Oncology, Dec. 31, 1994, 21:94, with English abstract.
Cascino et al., "Increased Plasma Free Tryptophan Levels in Human Cancer: A Tumor Related Effect?" Anticancer Research, 1991, 11:1313-1316.
Heber et al., "Metabolic Abnormalities in the Cancer Patient," Cancer, 1985, 55:225-229.
Lai et al., "Plasma free amino acid profile in cancer patients," Seminars in Cancer Biology, 2005, 15:267-276.
Landuyt et al., "Differential protein expression profile in gastrointestinal stromal tumors," Amino Acids, 2004 27:335-337.
Laviano et al., "Tumor-Induced Changes in Host Metabolism: A Possible Role for Free Tryptophan as a Marker of Neoplastic Disease," Developments in Tryptophan and Serotonin Metabolism, Allegri et al. Eds., 2003, 363-366.
Mellor et al., "IDO Expression by Dendritic Cells: Tolerance and Tryptophan Catabolism," Nature Reviews, Oct. 2004, 4:762-774.
Naini et al. "Preoperative and Postoperative Levels of Plasma Protein and Amino Acid in Esophageal and Lung Cancer Patients," Cancer, 1988, 62:355-360.
Norton et al., "Fasting Plasma Amino Acid Levels in Cancer Patients," Cancer, 1985, 56:1181-1186.
Rodriguez et al., "Arginase I in myeloid suppressor cells is induced by COX-2 in lung carcinoma," J. Exp. Med., Oct. 3, 2005, 202(7):931-939.

(56) References Cited

OTHER PUBLICATIONS

Vissers et al., "Plasma arginine concentrations are reduced in cancer patients: evidence for arginine deficiency?" Am. J. Clin. Nutr., 2005, 81:1142-1146.
Hirayama et al., "Quantitative Metabolome Profiling of Colon and Stomach Cancer Microenvironment by Capillary Electrophoresis Time-of-Flight Mass Spectrometry," Cancer Res., 2009, 69(11):4918-4925.
Leichtle et al., "Serum amino acid profiles and their alterations in colorectal cancer," Metabolomics, 2012, 8(4)1343-653.
Qiu et al., "Serum Metabolite Profiling of Human Colorectal Cancer Using GC-TOFMS and UPLC-QTOFMS," Journal of Proteome Research, 2009, 8(10):4844-4850.
Selamnia et al., "De novo synthesis of arginine and ornithine from citrulline in human colon carcinoma cells: metabolic fate of L-ornithine," Biochimica et Biophysica Acta, 1998, 1425(1):93-102.
Tan et al., "Metabonomics Identifies Serum Metabolite Markers of Colorectal Cancer," Journal of Proteome Research, 2013, 12(6):3000-3009.
Heintzelman et al., "Characterization of the Autofluorescence of Polymorphonuclear Leukocytes, Mononuclear Leukocytes and Cervical Epithelial Cancer Cells for Improved Spectroscopic Discrimination of Inflammation from Dysplasia," Photochemistry and Photobiology, 2000, 71(3):327-332.
Miyagi et al., "Plasma Free Amino Acid Profiling of Five Types of Cancer Patients and Its Application for Early Detection," PLoS One, Sep. 2011, 6:e24143, pp. 1-12.
Okamoto et al., "Alternative method for the diagnosis of early breast cancer using plasma free amino acid profiles," Breast, Mar. 2007, 16(sup.1):S22, Abstract P34.
Eagle, Harry M.D., "The Specific Amino Acid Requirements of a Human Carcinoma Cell (Strain HeLa) in Tissue Culture," The Journal of Experimental Medicine, 1955, 102(1):37-48.
Ito, lkuo, "Studies on Essential Amino Acids in Gynecological Field, Part 1. Fundamental Experiments and the Free Amino Acids Contents in the Normal Female Serum," Journal of the Nagoya City University Medical Association, 1961, 12(1):181-193, with English translation.
Ito, Ikuo, "Studies on Essential Amino Acids in Gynecological Field, Chapter 2. Vicissitudes of Serum-Containing Free Amino Acids in Gynecological Diseases and Operative Therapy," Journal of the Nagoya City University Medical Association, 1961, 12(1):193-224, with English translation.
Nakamura, Rokunosuke,"Aminoaciduria (III), Amino Acid in Urine of Patients with Cancer, Acatalasemia, and Anaemia Aplastica," Journal of Biochemistry, 1957, 29(2):77-80, with English translation.
Okano, Tadao M.D., "A Study of Protein and Amino Acid Metabolism in Patients with Carcinoma of the Uterus Cervix," Journal of Nihon University Medical Association, 1967, 26(2):163-178, with partial English translation.

* cited by examiner (BASIC PRINCIPLE OF THE INVENTION)

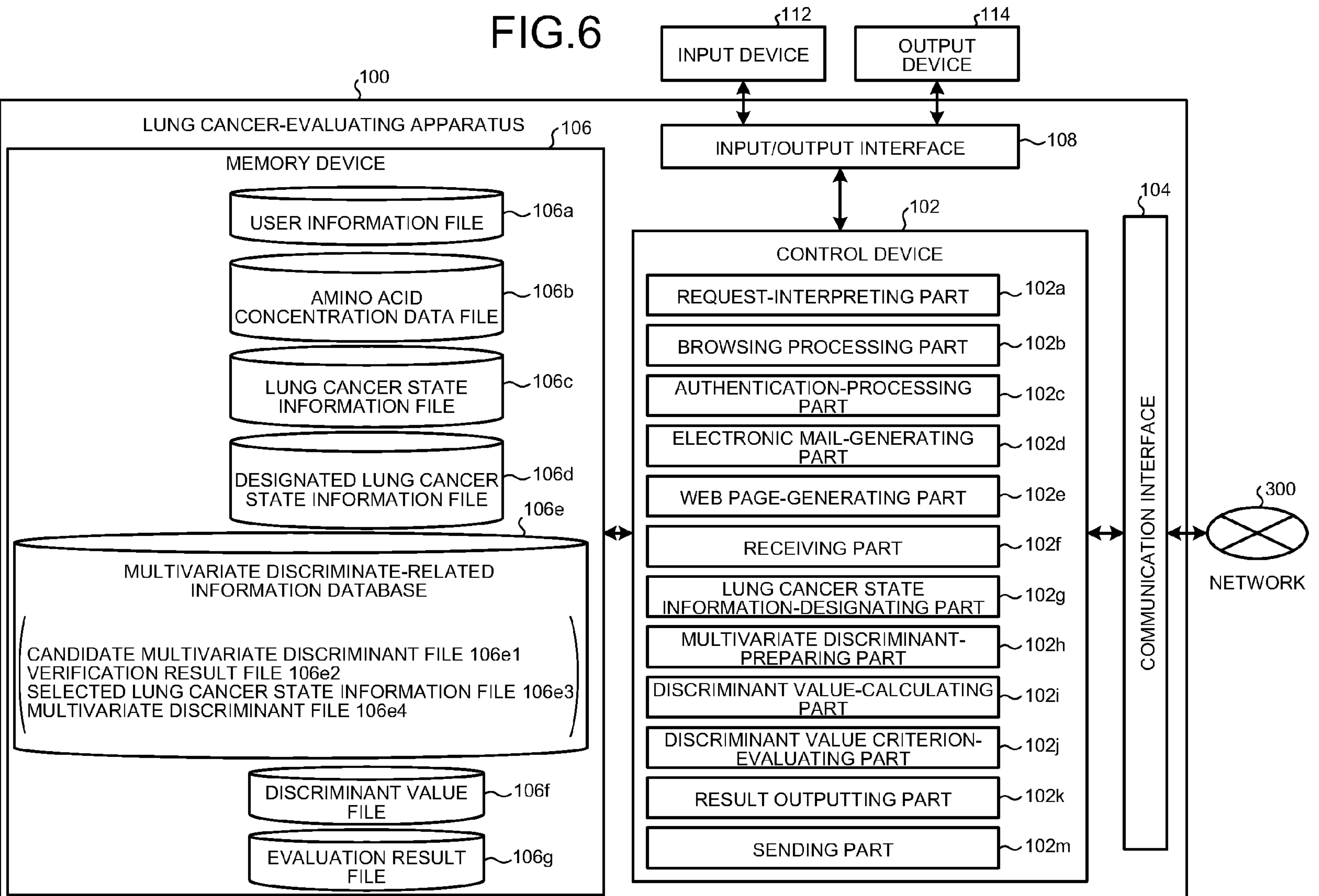

FIG.6
112
INPUT DEVICE
114
OUTPUT DEVICE
100
LUNG CANCER-EVALUATING APPARATUS
106
MEMORY DEVICE
USER INFORMATION FILE 106a
AMINO ACID CONCENTRATION DATA FILE 106b
LUNG CANCER STATE INFORMATION FILE 106c
DESIGNATED LUNG CANCER STATE INFORMATION FILE 106d
106e
MULTIVARIATE DISCRIMINATE-RELATED INFORMATION DATABASE
CANDIDATE MULTIVARIATE DISCRIMINANT FILE 106e1
VERIFICATION RESULT FILE 106e2
SELECTED LUNG CANCER STATE INFORMATION FILE 106e3
MULTIVARIATE DISCRIMINANT FILE 106e4
DISCRIMINANT VALUE FILE 106f
EVALUATION RESULT FILE 106g
INPUT/OUTPUT INTERFACE 108
102
CONTROL DEVICE
REQUEST-INTERPRETING PART 102a
BROWSING PROCESSING PART 102b
AUTHENTICATION-PROCESSING PART 102c
ELECTRONIC MAIL-GENERATING PART 102d
WEB PAGE-GENERATING PART 102e
RECEIVING PART 102f
LUNG CANCER STATE INFORMATION-DESIGNATING PART 102g
MULTIVARIATE DISCRIMINANT-PREPARING PART 102h
DISCRIMINANT VALUE-CALCULATING PART 102i
DISCRIMINANT VALUE CRITERION-EVALUATING PART 102j
RESULT OUTPUTTING PART 102k
SENDING PART 102m
104
COMMUNICATION INTERFACE
300
NETWORK

| USER ID | USER PASSWORD | NAME | ORGAN-IZATION ID | DEPART-MENT ID | DEPART-MENT NAME | E-MAIL ADDRESS | ··· |
|---|---|---|---|---|---|---|---|
| ⋮ | ⋮ | ⋮ | ⋮ | ⋮ | ⋮ | ⋮ | ⋮ |

| INDIVIDUAL (SAMPLE) NO. | AMINO ACID CONCENTRATION DATA | | | | | |
|---|---|---|---|---|---|---|
| | Gly | Leu | Val | Ile | Phe | ··· |
| U-1 | 9.5 | 11.2 | 2.7 | 8.5 | 4.9 | ··· |
| U-2 | 8.5 | 10.5 | 3.9 | 9.8 | 6.1 | ··· |
| ⋮ | ⋮ | ⋮ | ⋮ | ⋮ | ⋮ | ⋮ |

| INDIVIDUAL (SAMPLE) NO. | LUNG CANCER STATE INDEX DATA (T) | | | | AMINO ACID CONCENTRATION DATA | | | | | |
|---|---|---|---|---|---|---|---|---|---|---|
| | $T_1$ | $T_2$ | $T_3$ | … | Gly | Leu | Val | Ile | Phe | … |
| A-1 | 23.4 | 62.5 | 37.1 | … | 9.5 | 11.2 | 2.7 | 8.5 | 4.9 | … |
| A-2 | 27.5 | 66.1 | 39.5 | … | 8.5 | 10.5 | 3.9 | 9.8 | 6.1 | … |
| ⋮ | ⋮ | ⋮ | ⋮ | ⋮ | ⋮ | | | | | |

| INDIVIDUAL (SAMPLE) NO. | LUNG CANCER STATE INDEX DATA (T) | AMINO ACID CONCENTRATION DATA | | | |
|---|---|---|---|---|---|
| | $T_2$ | Gly | Leu | Phe | ⋯ |
| A-1 | 62.5 | 9.5 | 11.2 | 4.9 | ⋯ |
| A-2 | 66.1 | 8.5 | 10.5 | 6.1 | ⋯ |
| ⋮ | ⋮ | ⋮ | ⋮ | ⋮ | ⋮ |

| RANK | CANDIDATE MULTIVARIATE DISCRIMINANT |
|---|---|
| 1 | $F_1$ (Gly,Leu,Phe,...) |
| 2 | $F_2$ (Gly,Leu,Phe,...) |
| 3 | $F_3$ (Gly,Leu,Phe,...) |
| ⋮ | ⋮ |

| RANK | CANDIDATE MULTIVARIATE DISCRIMINANT | VERIFICATION RESULT |
|---|---|---|
| 1 | $F_k$ (Gly,Leu,Phe,…) | 1.22 |
| 2 | $F_m$ (Gly,Leu,Phe,…) | 2.28 |
| 3 | $F_l$ (Gly,Leu,Phe,…) | 2.95 |
| ⋮ | ⋮ | ⋮ |

| INDIVIDUAL (SAMPLE) NO. | LUNG CANCER STATE INDEX DATA (T) | AMINO ACID CONCENTRATION DATA | | |
|---|---|---|---|---|
| | $T_2$ | Leu | Phe | … |
| A-1 | 62.5 | 11.2 | 4.9 | … |
| A-2 | 66.1 | 10.5 | 6.1 | … |
| ⋮ | ⋮ | ⋮ | ⋮ | ⋮ |

| RANK | MULTIVARIATE DISCRIMINANT | THRESHOLD VALUE | VERIFICATIO N RESULT |
|---|---|---|---|
| 1 | $F_p$ (Phe,...) | 0.23 | 0.62 |
| 2 | $F_p$ (Gly,Leu,Phe) | -2.12 | 1.02 |
| 3 | $F_k$ (Gly,Leu,Phe,...) | 1.23 | 1.22 |
| ⋮ | ⋮ | ⋮ | ⋮ |

| INDIVIDUAL (SAMPLE) NO. | RANK | DISCRIMINANT VALUE |
|---|---|---|
| U-1 | 1 | 1.13 |
| ⋮ | ⋮ | ⋮ |

106g

| INDIVIDUAL (SAMPLE) NO. | AMINO ACID CONCENTRATION DATA | | | | DIS-CRIMINANT VALUE | EVAL-UATION RESULT |
|---|---|---|---|---|---|---|
| | Gly | Leu | Phe | ··· | | |
| U-1 | 9.5 | 11.2 | 4.9 | ··· | | |
| U-2 | 8.5 | 10.5 | 6.1 | ··· | | |
| ⋮ | ⋮ | ⋮ | ⋮ | ⋮ | ⋮ | ⋮ |

FIG.24

| SUBJECT TO BE DISCRIMINATED | LUNG CANCER GROUP<br>NON-LUNG CANCER GROUP | EARLY LUNG CANCER GROUP<br>NON-LUNG CANCER GROUP | ADENO-CARCINOMA GROUP<br>NON-LUNG CANCER GROUP |
|---|---|---|---|
| Tau | 0.83 | 0.79 | 0.81 |
| Thr | 0.68 | 0.62 | 0.67 |
| Ser | 0.68 | 0.68 | 0.65 |
| Asn | 0.72 | 0.70 | 0.73 |
| Glu | 0.67 | 0.64 | 0.66 |
| Gln | 0.63 | 0.57 | 0.60 |
| Pro | 0.66 | 0.67 | 0.64 |
| Gly | 0.68 | 0.71 | 0.66 |
| Ala | 0.59 | 0.60 | 0.61 |
| Cit | 0.70 | 0.69 | 0.70 |
| ABA | 0.72 | 0.77 | 0.78 |
| Val | 0.52 | 0.52 | 0.54 |
| Cys | 0.62 | 0.53 | 0.65 |
| Met | 0.59 | 0.54 | 0.58 |
| Ile | 0.56 | 0.51 | 0.54 |
| Leu | 0.56 | 0.51 | 0.57 |
| Tyr | 0.58 | 0.51 | 0.59 |
| Phe | 0.62 | 0.55 | 0.64 |
| His | 0.67 | 0.67 | 0.69 |
| Trp | 0.55 | 0.61 | 0.52 |
| Orn | 0.93 | 0.92 | 0.92 |
| Lys | 0.71 | 0.68 | 0.72 |
| Arg | 0.68 | 0.80 | 0.67 |

FIG.25

| ROC_AUC | INDEX |
|---|---|
| 0.973 | (Orn)/(Trp)+(Tau+ABA)/(Arg) |
| 0.973 | (Tau)/(Arg)+(Orn+ABA)/(Trp) |
| 0.972 | (Orn+ABA)/(Trp)+(Tau+Met)/(Arg) |
| 0.971 | (Orn)/(Trp)+(Tau)/(Arg) |
| 0.971 | (Orn+ABA)/(Trp)+(Tau+Cys)/(Arg) |
| 0.970 | (Orn)/(Trp)+(Tau+ABA+Met)/(Arg) |
| 0.970 | (Orn+Met)/(Trp)+(Tau+ABA)/(Arg) |
| 0.970 | (Orn)/(Trp)+(Tau+ABA+Cys)/(Arg) |
| 0.970 | (Orn+ABA)/(Trp)+(Tau+Tyr)/(Arg) |
| 0.969 | (Orn)/(Trp)+(Tau+Met)/(Arg) |
| 0.968 | (Orn+ABA)/(Trp)+(Tau+Asn)/(Arg) |
| 0.968 | (Orn+ABA)/(Trp)+(Tau+Cit)/(Arg) |
| 0.968 | (Orn+Cys)/(Trp)+(Tau+ABA)/(Arg) |
| 0.968 | (Orn+Tau)/(Trp)+(ABA+Tyr)/(Arg) |
| 0.967 | (Orn)/(Trp)+(Tau+Cys)/(Arg) |
| 0.966 | (Tau)/(Arg)+(Orn+Met)/(Trp) |
| 0.966 | (Orn)/(Trp)+(Tau+ABA+Cit)/(Arg) |
| 0.966 | (Orn+Met)/(Trp)+(Tau+Cys)/(Arg) |
| 0.965 | (Orn+ABA)/(Trp)+(Tau+Phe)/(Arg) |
| 0.965 | (Tau)/(Arg)+(Orn+ABA+Met)/(Trp) |
| 0.965 | (Orn)/(Trp)+(Tau+ABA+Asn)/(Arg) |
| 0.965 | (Orn+ABA)/(Trp)+(Tau+Age)/(Arg) |
| 0.965 | (Orn)/(Trp)+(Tau+Cys+Met)/(Arg) |
| 0.965 | (Orn)/(Trp)+(Tau+Asn)/(Arg) |
| 0.964 | (Orn+Cys)/(Trp)+(Tau+Tyr)/(Arg) |
| 0.964 | (Orn+Tau)/(Trp)+(Met+Tyr)/(Arg) |
| 0.964 | (Orn)/(Trp)+(ABA+Met)/(Arg) |
| 0.964 | (Orn+Tau)/(Trp)+(Cys+Tyr)/(Arg) |
| 0.964 | (Orn+ABA)/(Trp)+(Tau+Glu)/(Arg) |
| 0.963 | (Orn+Cys)/(Trp)+(Tau+Met)/(Arg) |
| 0.963 | (Orn)/(Trp)+(Tau+Cit)/(Arg) |
| 0.963 | (Orn+Met)/(Trp)+(Tau+Tyr)/(Arg) |
| 0.963 | (Orn)/(Trp)+(Tau+Tyr)/(Arg) |
| 0.963 | (Tyr)/(Arg)+(Orn+Tau)/(Trp) |
| 0.963 | (Orn+Tau)/(Trp)+(Asn+Tyr)/(Arg) |
| 0.962 | (Orn)/(Trp)+(ABA+Cys)/(Arg) |
| 0.962 | (Orn)/(Trp)+(Tau+Age+ABA)/(Arg) |
| 0.962 | (Orn)/(Trp)+(Tau+Age)/(Arg) |
| 0.962 | (Orn+Met)/(Trp)+(Tau+Asn)/(Arg) |
| 0.962 | (Orn)/(Trp)+(Tau+ABA+Tyr)/(Arg) |
| 0.962 | (Orn+Tau)/(Trp)+(Age+Tyr)/(Arg) |
| 0.962 | (Orn+Tyr)/(Trp)+(Tau+ABA)/(Arg) |
| 0.962 | (Orn+Tau)/(Trp)+(ABA+Met)/(Arg) |
| 0.962 | (Orn)/(Trp)+(Tau+Cit+Met)/(Arg) |
| 0.961 | (Orn+Tau)/(Trp)+(ABA+Asn)/(Arg) |
| 0.961 | (Orn+Tau)/(Trp)+(ABA+Cys)/(Arg) |
| 0.961 | (Orn+Met)/(Trp)+(Tau+Age)/(Arg) |
| 0.961 | (Orn+Tau)/(Trp)+(Thr+Tyr)/(Arg) |
| 0.961 | (Tau)/(Arg)+(Orn+Cys)/(Trp) |
| 0.961 | (Orn+Tau)/(Trp)+(ABA+Thr)/(Arg) |

FIG.26

| ROC_AUC | INDEX |
|---|---|
| 0.961 | (Orn+Tau)/(Trp)+(Thr+Met)/(Arg) |
| 0.961 | (Orn+ABA)/(Trp)+(Tau+His)/(Arg) |
| 0.961 | (Orn)/(Trp)+(ABA)/(Arg) |
| 0.961 | (Orn+Tau)/(Trp)+(ABA+Phe)/(Arg) |
| 0.961 | (Orn+ABA)/(Trp)+(Tau+Ile)/(Arg) |
| 0.961 | (Orn+Tau)/(Trp)+(Cit+Tyr)/(Arg) |
| 0.961 | (Orn)/(Trp)+(Tau+Asn+Met)/(Arg) |
| 0.961 | (Orn)/(Trp)+(Tau+ABA+Phe)/(Arg) |
| 0.961 | (Orn+Cys)/(Trp)+(Tau+Asn)/(Arg) |
| 0.961 | (Orn+ABA)/(Arg)+(Tau+Met)/(Trp) |
| 0.960 | (Orn)/(Trp)+(ABA+Cys+Met)/(Arg) |
| 0.960 | (Orn+Met)/(Trp)+(Tau+Cit)/(Arg) |
| 0.960 | (Orn)/(Trp)+(Tau+Asn+Cys)/(Arg) |
| 0.960 | (Thr)/(Arg)+(Orn+Tau)/(Trp) |
| 0.960 | (Tyr)/(Arg)+(Orn+Tau+ABA)/(Trp) |
| 0.960 | (Orn)/(Trp)+(Tau+Phe)/(Arg) |
| 0.960 | (Orn+Tau)/(Trp)+(ABA+His)/(Arg) |
| 0.960 | (Orn+Tau)/(Trp)+(Thr+Cys)/(Arg) |
| 0.960 | (Tyr)/(Arg)+(Orn+ABA)/(Trp) |
| 0.960 | (Orn+Tau)/(Trp)+(Age+ABA)/(Arg) |
| 0.960 | (Lys)/(Arg)+(Orn+Tau+ABA)/(Trp) |
| 0.960 | (Tau)/(Arg)+(Orn+ABA+Cys)/(Trp) |
| 0.959 | (Orn)/(Trp)+(Tau+Age+Met)/(Arg) |
| 0.959 | (Orn+Tau)/(Trp)+(Asn+Met)/(Arg) |
| 0.959 | (Orn+Tau)/(Trp)+(Phe+Tyr)/(Arg) |
| 0.959 | (Orn+ABA)/(Trp)+(Tau+Thr)/(Arg) |
| 0.959 | (Orn+Tau)/(Trp)+(ABA+Glu)/(Arg) |
| 0.959 | (Orn+Asn)/(Trp)+(Tau+ABA)/(Arg) |
| 0.959 | (Orn)/(Trp)+(ABA+Cit)/(Arg) |
| 0.959 | (Orn+Tyr)/(Trp)+(Tau+Cys)/(Arg) |
| 0.959 | (Orn)/(Arg)+(Tau)/(Trp) |
| 0.959 | (Orn+Cys)/(Trp)+(Tau+Age)/(Arg) |
| 0.959 | (Orn+Cys)/(Trp)+(Tau+Thr)/(Arg) |
| 0.959 | (Orn)/(Trp)+(Tau+Cit+Cys)/(Arg) |
| 0.959 | (Orn+Tyr)/(Trp)+(Tau+Met)/(Arg) |
| 0.959 | (Orn+ABA)/(Trp)+(Cys+Tyr)/(Arg) |
| 0.959 | (Orn+Tau)/(Trp)+(ABA+Lys)/(Arg) |
| 0.959 | (Tau)/(Trp)+(Orn+ABA)/(Arg) |
| 0.958 | (Orn+Cys)/(Trp)+(Tau+Glu)/(Arg) |
| 0.958 | (Tau)/(Trp)+(Orn+Met)/(Arg) |
| 0.958 | (Orn+Tau)/(Trp)+(Asn+Cys)/(Arg) |
| 0.958 | (Orn+Tau)/(Trp)+(Cys+Met)/(Arg) |
| 0.958 | (Orn+Met)/(Arg)+(Tau+ABA)/(Trp) |
| 0.958 | (Orn+Asn)/(Trp)+(Tau+Tyr)/(Arg) |
| 0.958 | (Orn+Tyr)/(Trp)+(Tau+Asn)/(Arg) |
| 0.958 | (Orn+Tau+ABA)/(Trp+Arg) |
| 0.958 | (Orn)/(Trp)+(Cys+Met)/(Arg) |
| 0.958 | (Orn+Cit)/(Trp)+(Tau+ABA)/(Arg) |
| 0.958 | (Orn+ABA)/(Trp)+(Met+Tyr)/(Arg) |
| 0.958 | (Orn+Met)/(Trp)+(Tau+Phe)/(Arg) |

FIG.28

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| 1.20 | 1.00 | 0.00 | 0.038 | 1.000 | 0.96 |
| 1.50 | 1.00 | 0.02 | 0.039 | 1.000 | 0.96 |
| 2.00 | 1.00 | 0.43 | 0.065 | 1.000 | 0.96 |
| 2.10 | 1.00 | 0.53 | 0.078 | 1.000 | 0.96 |
| 2.20 | 1.00 | 0.64 | 0.099 | 1.000 | 0.96 |
| 2.30 | 0.96 | 0.72 | 0.121 | 0.998 | 0.96 |
| 2.40 | 0.96 | 0.80 | 0.160 | 0.998 | 0.96 |
| 2.50 | 0.96 | 0.86 | 0.214 | 0.998 | 0.96 |
| 2.55 | 0.96 | 0.88 | 0.248 | 0.998 | 0.96 |
| 2.60 | 0.93 | 0.91 | 0.280 | 0.997 | 0.96 |
| 2.61 | 0.93 | 0.91 | 0.283 | 0.997 | 0.96 |
| 2.62 | 0.93 | 0.91 | 0.286 | 0.997 | 0.96 |
| 2.63 | 0.93 | 0.91 | 0.289 | 0.997 | 0.96 |
| 2.64 | 0.89 | 0.91 | 0.287 | 0.995 | 0.97 |
| 2.65 | 0.89 | 0.92 | 0.298 | 0.995 | 0.97 |
| 2.66 | 0.89 | 0.92 | 0.301 | 0.995 | 0.97 |
| 2.67 | 0.89 | 0.92 | 0.305 | 0.995 | 0.97 |
| 2.68 | 0.89 | 0.92 | 0.313 | 0.995 | 0.97 |
| 2.69 | 0.89 | 0.92 | 0.321 | 0.995 | 0.97 |
| 2.70 | 0.89 | 0.93 | 0.329 | 0.995 | 0.97 |
| 2.80 | 0.79 | 0.95 | 0.367 | 0.991 | 0.97 |
| 2.90 | 0.79 | 0.96 | 0.458 | 0.991 | 0.97 |
| 3.00 | 0.75 | 0.98 | 0.553 | 0.990 | 0.97 |
| 3.50 | 0.54 | 1.00 | 1.000 | 0.982 | 0.98 |

FIG.29

| ROC_AUC | INDEX |
|---|---|
| 0.981 | (Tau)/(Arg)+(Orn+ABA)/(Trp) |
| 0.981 | (Orn+ABA)/(Trp)+(Tau+Met)/(Arg) |
| 0.981 | (Orn)/(Trp)+(Tau+ABA)/(Arg) |
| 0.981 | (Orn+ABA)/(Trp)+(Tau+Asn)/(Arg) |
| 0.981 | (Orn+ABA)/(Trp)+(Tau+Cys)/(Arg) |
| 0.981 | (ABA)/(Trp)+(Orn+Tau)/(Leu+Arg) |
| 0.981 | (Orn)/(Trp)+(Tau+ABA)/(Ile+Arg) |
| 0.981 | (Orn)/(Trp)+(Tau+Tyr)/(Ile+Arg) |
| 0.980 | (Orn)/(Trp)+(Tau+ABA+Met)/(Arg) |
| 0.979 | (ABA)/(Trp)+(Orn+Tau)/(Ile+Arg) |
| 0.979 | (Orn+ABA)/(Trp)+(Tau+Cit)/(Arg) |
| 0.979 | (ABA)/(Trp)+(Orn+Cit)/(Ile+Arg) |
| 0.979 | (Orn)/(Trp)+(ABA+Met)/(Arg) |
| 0.979 | (Orn)/(Trp)+(Tau+ABA+Cys)/(Arg) |
| 0.979 | (Orn+Met)/(Trp)+(Tau+ABA)/(Arg) |
| 0.979 | (Orn+ABA)/(Trp)+(Tau+Tyr)/(Arg) |
| 0.978 | (Orn+Met)/(Arg)+(ABA+Cys)/(Trp) |
| 0.978 | (Orn+ABA)/(Trp)+(Cit+Tyr)/(Arg) |
| 0.978 | (Orn)/(Arg)+(ABA+Cys)/(Trp) |
| 0.978 | (Orn)/(Trp)+(Tau)/(Arg) |
| 0.978 | (Orn)/(Trp)+(Tau+ABA+Asn)/(Arg) |
| 0.978 | (Orn)/(Trp)+(Tau+Met)/(Ile+Arg) |
| 0.978 | (Orn)/(Trp)+(Tau+Tyr)/(Leu+Arg) |
| 0.978 | (Cys)/(Trp)+(Orn+ABA)/(Arg) |
| 0.978 | (Tyr)/(Arg)+(Orn+ABA)/(Trp) |
| 0.978 | (Orn+ABA)/(Trp)+(Met+Tyr)/(Arg) |
| 0.978 | (Orn+Cys)/(Trp)+(Tau+ABA)/(Arg) |
| 0.978 | (Orn)/(Trp)+(ABA+Cit+Met)/(Arg) |
| 0.977 | (Orn)/(Arg)+(ABA+Met)/(Trp) |
| 0.977 | (Orn)/(Trp)+(Tau+Met)/(Arg) |
| 0.977 | (Orn)/(Ile+Arg)+(ABA)/(Trp) |
| 0.977 | (Orn)/(Trp)+(Tau+ABA+Cit)/(Arg) |
| 0.977 | (Orn)/(Trp)+(Tau+Cys)/(Ile+Arg) |
| 0.977 | (Orn+ABA)/(Trp)+(Tau+Ser)/(Arg) |
| 0.977 | (Orn)/(Trp)+(ABA+Cit)/(Arg) |
| 0.977 | (Orn)/(Trp)+(Tau+Asn)/(Ile+Arg) |
| 0.977 | (Orn)/(Trp)+(ABA+Cys)/(Arg) |
| 0.977 | (Orn)/(Trp)+(ABA+Met+Cys)/(Arg) |
| 0.977 | (Orn)/(Trp)+(ABA+Asn)/(Arg) |
| 0.977 | (Orn+ABA)/(Trp)+(Asn+Tyr)/(Arg) |
| 0.977 | (Orn)/(Trp)+(ABA+Tyr)/(Ile+Arg) |
| 0.977 | (Orn+Tau)/(Trp)+(Ser+Tyr)/(Arg) |
| 0.977 | (Orn+ABA)/(Trp)+(Cys+Tyr)/(Arg) |
| 0.977 | (Orn+Cit)/(Arg)+(ABA+Cys)/(Trp) |
| 0.976 | (Orn+Tau)/(Arg)+(ABA+Cys)/(Trp) |
| 0.976 | (Orn)/(Trp)+(Tau+ABA)/(Leu+Arg) |
| 0.976 | (ABA)/(Trp)+(Orn+Met)/(Ile+Arg) |
| 0.976 | (Orn+Cys)/(Trp)+(Tau+Ser)/(Arg) |
| 0.976 | (Orn)/(Trp)+(Tau+Phe)/(Ile+Arg) |
| 0.976 | (Orn+Tau)/(Trp)+(ABA+Ser)/(Arg) |

FIG.30

| ROC_AUC | INDEX |
|---|---|
| 0.9760255 | (Orn+Asn)/(Arg)+(ABA+Cys)/(Trp) |
| 0.9759547 | (Orn)/(Trp)+(Tau+Asn)/(Arg) |
| 0.9759547 | (Orn+Tau+Cys)/(Leu+Trp+Arg) |
| 0.9759547 | (Orn)/(Trp)+(ABA+Cit+Cys)/(Arg) |
| 0.975884 | (Orn+ABA)/(Trp)+(Tau+Phe)/(Arg) |
| 0.9758133 | (ABA)/(Arg)+(Orn+Tau)/(Leu+Trp) |
| 0.9757426 | (Orn)/(Trp)+(Tau)/(Ile+Arg) |
| 0.9757426 | (Orn+ABA)/(Trp)+(Asn+Met)/(Arg) |
| 0.9756718 | (Orn)/(Trp)+(Tau+Glu)/(Leu+Arg) |
| 0.9756011 | (Orn+ABA)/(Trp)+(Asn+Cit)/(Arg) |
| 0.9754597 | (Orn)/(Trp)+(Tau+His)/(Leu+Arg) |
| 0.9753183 | (Orn)/(Trp)+(Tau+Cys)/(Arg) |
| 0.9752475 | (Orn)/(Trp)+(Tau+His)/(Ile+Arg) |
| 0.9752475 | (ABA)/(Trp)+(Orn+Cys)/(Ile+Arg) |
| 0.9751768 | (Orn)/(Trp)+(Tau+Lys)/(Ile+Arg) |
| 0.9751768 | (Orn+Met)/(Arg)+(ABA+Cit)/(Trp) |
| 0.9751061 | (Orn)/(Trp)+(Tau+Lys)/(Leu+Arg) |
| 0.9749646 | (Tau)/(Ile+Arg)+(Orn+ABA)/(Trp) |
| 0.9749646 | (Orn)/(Trp)+(ABA)/(Arg) |
| 0.9748939 | (Orn+ABA)/(Trp)+(Asn+Cys)/(Arg) |
| 0.9748232 | (Orn)/(Arg)+(ABA+Cit)/(Trp) |
| 0.9747525 | (Orn+ABA)/(Arg)+(Met+Cys)/(Trp) |
| 0.9747525 | (Orn+ABA)/(Trp)+(His+Met)/(Arg) |
| 0.9747525 | (Orn)/(Trp)+(Tau+Thr)/(Ile+Arg) |
| 0.9747525 | (Orn+Met)/(Trp)+(Tau+Asn)/(Arg) |
| 0.9746817 | (Orn+Met)/(Trp)+(Tau+Cys)/(Arg) |
| 0.9746817 | (Orn+ABA)/(Trp)+(Tau+Thr)/(Arg) |
| 0.9746817 | (Orn+Cys)/(Trp)+(Tau+Tyr)/(Arg) |
| 0.974611 | (Tau)/(Arg)+(Orn+ABA+Met)/(Trp) |
| 0.974611 | (Orn+Tau)/(Trp)+(ABA+Tyr)/(Arg) |
| 0.9745403 | (Orn+Tau)/(Arg)+(ABA+Asn)/(Trp) |
| 0.9744696 | (Orn+Tau)/(Trp)+(Ser+Cys)/(Arg) |
| 0.9744696 | (Orn+ABA)/(Trp)+(Cit+Met)/(Arg) |
| 0.9743989 | (Orn)/(Trp)+(Tau+Glu)/(Ile+Arg) |
| 0.9743282 | (Orn+Tau+ABA)/(Leu+Trp+Arg) |
| 0.9743282 | (His)/(Arg)+(Orn+ABA)/(Trp) |
| 0.9743282 | (Orn)/(Trp)+(Tau+Asn)/(Leu+Arg) |
| 0.9743282 | (Orn)/(Trp)+(ABA+Asn+Cit)/(Arg) |
| 0.9743282 | (Orn)/(Trp)+(ABA+Asn+Cys)/(Arg) |
| 0.9743282 | (Orn)/(Trp)+(Tau+Met+Cys)/(Arg) |
| 0.9742574 | (Tau)/(Arg)+(Orn+Met)/(Trp) |
| 0.9741867 | (Orn+ABA)/(Trp)+(Tau+His)/(Arg) |
| 0.974116 | (Orn)/(Trp)+(Tau+Ser)/(Ile+Arg) |
| 0.974116 | (Orn+Cit)/(Arg)+(ABA+Met)/(Trp) |
| 0.9740453 | (Cys)/(Leu)+(Orn+Tau)/(Trp+Arg) |
| 0.9739745 | (Orn)/(Trp)+(Tau+Cit)/(Ile+Arg) |
| 0.9739038 | (ABA)/(Leu)+(Orn+Tau)/(Trp+Arg) |
| 0.9738331 | (Orn)/(Trp)+(ABA+Tyr)/(Arg) |
| 0.9738331 | (Orn+Tau)/(Trp)+(Ser+Met)/(Arg) |
| 0.9738331 | (ABA)/(Arg)+(Orn+Cit)/(Leu+Trp) |

FIG.32

| ROC_AUC | INDEX |
|---|---|
| 0.969 | (Tau)/(Arg)+(Orn+ABA)/(Trp) |
| 0.968 | (Orn)/(Trp)+(Tau+ABA)/(Arg) |
| 0.968 | (Orn+ABA)/(Trp)+(Tau+Met)/(Arg) |
| 0.966 | (Orn+ABA)/(Trp)+(Tau+Cys)/(Arg) |
| 0.966 | (Orn)/(Trp)+(Tau)/(Arg) |
| 0.964 | (Orn+Met)/(Trp)+(Tau+ABA)/(Arg) |
| 0.964 | (Orn)/(Trp)+(Tau+ABA+Met)/(Arg) |
| 0.964 | (Orn+ABA)/(Trp)+(Tau+Tyr)/(Arg) |
| 0.964 | (Orn)/(Trp)+(Tau+ABA+Cys)/(Arg) |
| 0.963 | (Orn+Cys)/(Trp)+(Tau+ABA)/(Arg) |
| 0.963 | (Orn+Tau)/(Trp)+(ABA+Tyr)/(Arg) |
| 0.963 | (Orn+ABA)/(Trp)+(Tau+Cit)/(Arg) |
| 0.962 | (Orn+ABA)/(Trp)+(Tau+Asn)/(Arg) |
| 0.962 | (Orn)/(Trp)+(Tau+Met)/(Arg) |
| 0.961 | (Tau)/(Arg)+(Orn+ABA+Met)/(Trp) |
| 0.960 | (Orn)/(Trp)+(Tau+Cys)/(Arg) |
| 0.960 | (Tau)/(Arg)+(Orn+Met)/(Trp) |
| 0.959 | (Orn+Met)/(Trp)+(Tau+Cys)/(Arg) |
| 0.959 | (Orn)/(Trp)+(Tau+ABA+Cit)/(Arg) |
| 0.959 | (Orn+ABA)/(Trp)+(Tau+Phe)/(Arg) |
| 0.958 | (Orn+Tau)/(Trp)+(Cys+Tyr)/(Arg) |
| 0.958 | (Orn+Tau)/(Trp)+(Tyr+Met)/(Arg) |
| 0.958 | (Orn)/(Trp)+(Tau+ABA+Asn)/(Arg) |
| 0.958 | (Orn)/(Trp)+(Tau+Cys+Met)/(Arg) |
| 0.958 | (Orn+Cys)/(Trp)+(Tau+Tyr)/(Arg) |
| 0.957 | (Tyr)/(Arg)+(Orn+Tau)/(Trp) |
| 0.957 | (Orn)/(Trp)+(Tau+Asn)/(Arg) |
| 0.957 | (Orn+Cys)/(Trp)+(Tau+Met)/(Arg) |
| 0.957 | (Orn)/(Trp)+(ABA+Met)/(Arg) |
| 0.957 | (Orn+Tau)/(Trp)+(ABA+Cys)/(Arg) |
| 0.956 | (Orn+Tau)/(Trp)+(ABA+Met)/(Arg) |
| 0.956 | (Orn+Tyr)/(Trp)+(Tau+ABA)/(Arg) |
| 0.956 | (Orn)/(Trp)+(ABA+Cys)/(Arg) |
| 0.956 | (Orn)/(Trp)+(Tau+Cit)/(Arg) |
| 0.956 | (Orn+ABA)/(Trp)+(Tau+Glu)/(Arg) |
| 0.956 | (Orn+Tau)/(Trp)+(ABA+Asn)/(Arg) |
| 0.956 | (Orn+Tau)/(Trp)+(Asn+Tyr)/(Arg) |
| 0.956 | (Tau)/(Arg)+(Orn+ABA+Cys)/(Trp) |
| 0.956 | (Tau)/(Arg)+(Orn+Cys)/(Trp) |
| 0.955 | (Orn+Met)/(Trp)+(Tau+Tyr)/(Arg) |
| 0.955 | (Tyr)/(Arg)+(Orn+Tau+ABA)/(Trp) |
| 0.955 | (Orn)/(Trp)+(Tau+Tyr)/(Arg) |
| 0.955 | (Orn)/(Trp)+(ABA)/(Arg) |
| 0.955 | (Orn+Tau)/(Trp)+(ABA+Phe)/(Arg) |
| 0.954 | (Orn+Tau)/(Trp)+(Cit+Tyr)/(Arg) |
| 0.954 | (Orn+Met)/(Trp)+(Tau+Asn)/(Arg) |
| 0.954 | (Orn+Tau)/(Trp)+(ABA+Thr)/(Arg) |
| 0.954 | (Orn+Tau)/(Trp)+(Thr+Tyr)/(Arg) |
| 0.954 | (Orn+Tau)/(Trp)+(Thr+Met)/(Arg) |
| 0.954 | (Orn+ABA)/(Arg)+(Tau+Met)/(Trp) |

FIG.33

| ROC_AUC | INDEX |
|---|---|
| 0.954 | (Orn+Tau)/(Trp)+(ABA+His)/(Arg) |
| 0.954 | (Orn+Cys)/(Trp)+(Tau+Asn)/(Arg) |
| 0.954 | (Orn)/(Trp)+(Tau+Cit+Met)/(Arg) |
| 0.953 | (Orn)/(Trp)+(Tau+ABA+Tyr)/(Arg) |
| 0.953 | (Orn+Met)/(Trp)+(Tau+Cit)/(Arg) |
| 0.953 | (Orn+ABA)/(Trp)+(Tau+His)/(Arg) |
| 0.953 | (Tyr)/(Arg)+(Orn+ABA)/(Trp) |
| 0.953 | (Orn)/(Trp)+(ABA+Cys+Met)/(Arg) |
| 0.953 | (Orn+Tau)/(Trp)+(Asn+Met)/(Arg) |
| 0.953 | (Thr)/(Arg)+(Orn+Tau)/(Trp) |
| 0.953 | (Orn+Tyr)/(Trp)+(Tau+Cys)/(Arg) |
| 0.953 | (Orn+Tau)/(Trp)+(ABA+Cit)/(Arg) |
| 0.952 | (Orn+Tau)/(Trp)+(Thr+Cys)/(Arg) |
| 0.952 | (Orn)/(Trp)+(ABA+Cit)/(Arg) |
| 0.952 | (Orn+ABA)/(Trp)+(Tau+Ile)/(Arg) |
| 0.952 | (Orn+Tau)/(Trp)+(Cys+Met)/(Arg) |
| 0.952 | (Orn+Asn)/(Trp)+(Tau+ABA)/(Arg) |
| 0.952 | (Orn)/(Trp)+(Tau+Asn+Met)/(Arg) |
| 0.952 | (Orn)/(Trp)+(Tau+ABA+Phe)/(Arg) |
| 0.952 | (ABA)/(Arg)+(Orn+Tau)/(Trp) |
| 0.952 | (Lys)/(Arg)+(Orn+Tau+ABA)/(Trp) |
| 0.952 | (Orn+Tau)/(Trp)+(ABA+Glu)/(Arg) |
| 0.952 | (Orn+Tyr)/(Trp)+(Tau+Met)/(Arg) |
| 0.952 | (Orn+Tau)/(Trp)+(Phe+Tyr)/(Arg) |
| 0.952 | (Orn+Tau)/(Trp)+(Asn+Cys)/(Arg) |
| 0.952 | (Orn+ABA)/(Trp)+(Cys+Tyr)/(Arg) |
| 0.952 | (Tau)/(Arg)+(Orn+Tyr)/(Trp) |
| 0.952 | (Orn)/(Trp)+(Tau+Asn+Cys)/(Arg) |
| 0.951 | (Orn)/(Arg)+(Tau+ABA)/(Trp) |
| 0.951 | (Orn+Cit)/(Trp)+(Tau+ABA)/(Arg) |
| 0.951 | (Orn+Met)/(Arg)+(Tau+ABA)/(Trp) |
| 0.951 | (Orn)/(Trp)+(Tau+Phe)/(Arg) |
| 0.951 | (Orn+ABA)/(Trp)+(Cys+Met)/(Arg) |
| 0.951 | (Tau)/(Trp)+(Orn+ABA)/(Arg) |
| 0.951 | (Orn)/(Arg)+(Tau)/(Trp) |
| 0.951 | (His)/(Arg)+(Orn+Tau+ABA)/(Trp) |
| 0.951 | (Orn+ABA)/(Trp)+(Tau+Thr)/(Arg) |
| 0.951 | (Thr)/(Arg)+(Orn+Tau+ABA)/(Trp) |
| 0.950 | (Orn+Cys)/(Trp)+(Tau+Thr)/(Arg) |
| 0.950 | (Orn)/(Trp)+(Tau+Cit+Cys)/(Arg) |
| 0.950 | (Tau)/(Trp)+(Orn+Met)/(Arg) |
| 0.950 | (Orn+Tyr)/(Trp)+(Tau+Asn)/(Arg) |
| 0.950 | (Orn+Tau)/(Trp)+(ABA+Lys)/(Arg) |
| 0.950 | (Orn+Cys)/(Trp)+(Tau+Glu)/(Arg) |
| 0.950 | (Orn+ABA)/(Trp)+(Cit+Tyr)/(Arg) |
| 0.950 | (Orn+ABA)/(Trp)+(Cit+Cys)/(Arg) |
| 0.950 | (Orn+ABA)/(Trp)+(Tyr+Met)/(Arg) |
| 0.950 | (His)/(Arg)+(Orn+Tau)/(Trp) |
| 0.950 | (Orn+Cys)/(Trp)+(Tau+Cit)/(Arg) |
| 0.950 | (Orn)/(Trp)+(Cys+Met)/(Arg) |

FIG.35

| ROC_AUC | INDEX |
|---|---|
| 0.961 | (-17.6127±2.0812)+(0.13153±0.019117)*Orn+(0.073995±0.0154)*Tau |
| 0.958 | (-13.6975±2.4126)+(0.12905±0.019293)*Orn+(0.070901±0.015724)*Tau-(0.041143±0.01799)*Arg |
| 0.964 | (-18.8351±2.2844)+(0.12751±0.019006)*Orn+(0.069556±0.016161)*Tau+(0.073713±0.04438)*ABA |
| 0.965 | (-19.1273±2.4391)+(0.1305±0.019363)*Orn+(0.078808±0.016237)*Tau+(0.0089091±0.0057642)*Pro |
| 0.963 | (-15.1899±2.6605)+(0.12709±0.019378)*Orn+(0.076599±0.016868)*Tau-(0.044937±0.018054)*Arg+(0.011015±0.0057707)*Pro |
| 0.966 | (-19.0409±2.4363)+(0.13257±0.0195)*Orn+(0.074049±0.015235)*Tau+(0.0056674±0.004103)*Gly |
| 0.964 | (-15.6013±2.5316)+(0.13707±0.019766)*Orn+(0.077941±0.016137)*Tau-(0.01257±0.010409)*Lys |
| 0.964 | (-19.3997±2.6942)+(0.12701±0.019215)*Orn+(0.075408±0.015685)*Tau+(0.018541±0.015591)*Ser |
| 0.961 | (-14.9599±2.6114)+(0.12566±0.019187)*Orn+(0.067634±0.016222)*Tau+(0.064139±0.043861)*ABA-(0.039325±0.018181)*Arg |
| 0.960 | (-15.7971±2.9214)+(0.12353±0.019271)*Orn+(0.073101±0.015809)*Tau+(0.022539±0.015894)*Ser-(0.042521±0.017691)*Arg |
| 0.963 | (-18.7288±2.5191)+(0.13075±0.019297)*Orn+(0.074426±0.015652)*Tau+(0.0093069±0.010679)*Thr |
| 0.963 | (-15.9479±2.9333)+(0.13353±0.019244)*Orn+(0.074328±0.015433)*Tau-(0.030908±0.041787)*Phe |
| 0.964 | (-15.0002±2.7279)+(0.13023±0.019608)*Orn+(0.070755±0.015551)*Tau-(0.040288±0.01823)*Arg+(0.0048522±0.0039137)*Gly |
| 0.962 | (-17.4832±2.0989)+(0.13221±0.019171)*Orn+(0.076791±0.016962)*Tau-(0.0069088±0.016178)*Glu |
| 0.960 | (-17.1497±2.4363)+(0.13247±0.019345)*Orn+(0.07385±0.015452)*Tau-(0.01356±0.038749)*Cys |
| 0.961 | (-17.9968±2.3826)+(0.13001±0.019638)*Orn+(0.074336±0.015457)*Tau+(0.013482±0.038485)*Cit |
| 0.962 | (-16.8397±3.228)+(0.13232±0.019283)*Orn+(0.074338±0.015461)*Tau-(0.010315±0.033686)*His |
| 0.961 | (-17.9259±2.7632)+(0.13112±0.019279)*Orn+(0.073689±0.015521)*Tau+(0.0079465±0.045377)*Asn |
| 0.961 | (-17.2444±3.1284)+(0.13141±0.019045)*Orn+(0.074629±0.016004)*Tau-(0.00069341±0.0044596)*Gln |
| 0.960 | (-14.4001±2.5576)+(0.12543±0.019925)*Orn+(0.071309±0.015749)*Tau+(0.037776±0.039597)*Cit-(0.045593±0.018889)*Arg |
| 0.959 | (-14.6858±2.7314)+(0.12702±0.019506)*Orn+(0.070748±0.015866)*Tau-(0.040546±0.017706)*Arg+(0.0089577±0.0099154)*Thr |
| 0.959 | (-13.1518±2.5772)+(0.13232±0.020219)*Orn+(0.073117±0.016391)*Tau-(0.0057611±0.010873)*Lys-(0.037822±0.018794)*Arg |
| 0.958 | (-14.471±2.8949)+(0.12718±0.01969)*Orn+(0.069823±0.015983)*Tau+(0.023676±0.046215)*Asn-(0.042228±0.018084)*Arg |
| 0.958 | (-14.4222±3.2545)+(0.12908±0.019514)*Orn+(0.069287±0.016216)*Tau-(0.04251±0.018499)*Arg+(0.0016383±0.0048083)*Gln |
| 0.959 | (-13.8581±2.593)+(0.12842±0.019593)*Orn+(0.070808±0.015731)*Tau-(0.041805±0.018384)*Arg+(0.0069024±0.039633)*Cys |
| 0.968 | (-16.356±2.5551)+(0.13587±0.020021)*Orn+(0.074601±0.017058)*Tau+(0.093433±0.045238)*ABA-(0.018399±0.011042)*Lys |
| 0.958 | (-13.4887±2.8901)+(0.1296±0.019758)*Orn+(0.071052±0.015752)*Tau-(0.040418±0.018796)*Arg-(0.0054055±0.042187)*Phe |
| 0.958 | (-13.6801±2.419)+(0.12923±0.019345)*Orn+(0.071651±0.017174)*Tau-(0.0018631±0.01669)*Glu-(0.040904±0.018125)*Arg |
| 0.958 | (-13.6436±3.2858)+(0.12913±0.019578)*Orn+(0.07093±0.015769)*Tau-(0.00080073±0.033267)*His-(0.041093±0.018111)*Arg |
| 0.969 | (-20.7792±2.73)+(0.12771±0.019341)*Orn+(0.074451±0.017139)*Tau+(0.07892±0.042882)*ABA+(0.010127±0.0057413)*Pro |
| 0.971 | (-20.8436±2.7876)+(0.12774±0.019492)*Orn+(0.069418±0.015838)*Tau+(0.085894±0.046269)*ABA+(0.07213±0.0044777)*Gly |
| 0.967 | (-16.8068±2.9423)+(0.12519±0.019428)*Orn+(0.072873±0.017512)<br>*Tau+(0.067917±0.042091)*ABA-(0.04265±0.018102)*Arg+(0.011764±0.0057213)*Pro |
| 0.966 | (-16.4397±2.8741)+(0.13093±0.01919)*Orn+(0.069408±0.016184)*Tau+(0.086008±0.044671)*ABA-(0.049548±0.042138)*Phe |

FIG.36

| ROC_AUC | INDEX |
|---|---|
| 0.971 | (-20.5998±2.7675)+(0.1312±0.019702)*Orn+(0.079061±0.016048)*Tau+(0.005818±0.004178)*Gly+(0.0090977±0.0058439)*Pro |
| 0.965 | (-17.2047±3.1577)+(0.12197±0.019436)*Orn+(0.07798±0.016955)*Tau+(0.021983±0.016194)*Ser-(0.046323±0.017998)*Arg+(0.011053±0.0059581)*Pro |
| 0.968 | (-16.5353±2.9593)+(0.12791±0.019697)*Orn+(0.076625±0.016676)*Tau-(0.044254±0.018259)*Arg+(0.0050363±0.0039836)*Gly+(0.011286±0.0058663)*Pro |
| 0.968 | (-17.1112±2.865)+(0.13549±0.019924)*Orn+(0.082278±0.016807)*Tau-(0.012087±0.010455)*Lys+(0.0086842±0.0057738)*Pro |
| 0.966 | (-19.8922±2.6926)+(0.12425±0.019249)*Orn+(0.070856±0.016298)*Tau+(0.064999±0.0458)*ABA+(0.013063±0.016)*Ser |
| 0.968 | (-20.8573±3.0182)+(0.12637±0.019534)*Orn+(0.080118±0.016613)*Tau+(0.017932±0.015826)*Ser+(0.0088677±0.0059191)*Pro |
| 0.966 | (-17.2979±3.2064)+(0.12933±0.019214)*Orn+(0.070369±0.016263)*Tau+(0.079542±0.044887)*ABA-(0.022593±0.034741)*His |
| 0.970 | (-16.799±3.0527)+(0.12605±0.019511)*Orn+(0.067432±0.015944)*Tau+(0.075533±0.045772)*ABA-(0.03805±0.018515)*Arg+(0.0060873±0.0041641)*Gly |
| 0.963 | (-18.1788±2.5637)+(0.12879±0.019226)*Orn+(0.0693±0.016299)*Tau+(0.07633±0.044622)*ABA-(0.0205±0.038949)*Cys |
| 0.966 | (-19.4217±2.6062)+(0.12502±0.019665)*Orn+(0.069861±0.016177)*Tau+(0.076159±0.044911)*ABA+(0.019586±0.038958)*Cit |
| 0.967 | (-19.122±2.4496)+(0.13165±0.019347)*Orn+(0.08606±0.018738)*Tau-(0.015271±0.017122)*Glu+(0.010555±0.0059313)*Pro |
| 0.965 | (-18.1761±2.7303)+(0.1288±0.01921)*Orn+(0.070191±0.016168)*Tau-(0.02105±0.050016)*Asn+(0.080283±0.046616)*ABA |
| 0.965 | (-18.7033±2.3082)+(0.12797±0.019063)*Orn+(0.071935±0.017647)*Tau+(0.073848±0.044867)*ABA-(0.0060504±0.016321)*Glu |
| 0.965 | (-19.1971±2.5264)+(0.12719±0.019112)*Orn+(0.069879±0.016245)*Tau+(0.068226±0.046957)*ABA+(0.004059±0.011621)*Thr |
| 0.965 | (-18.3505±3.1483)+(0.12751±0.018881)*Orn+(0.070358±0.016718)*Tau+(0.074123±0.044408)*ABA-(0.00094656±0.004305)*Gln |
| 0.967 | (-17.3244±3.2375)+(0.13225±0.019411)*Orn+(0.078938±0.016195)*Tau+(0.0088197±0.0056598)*Pro-(0.032446±0.042597)*Phe |
| 0.966 | (-17.3837±3.1143)+(0.13259±0.020007)*Orn+(0.078748±0.01624)*Tau-(0.011703±0.010431)*Lys+(0.017149±0.015575)*Ser |
| 0.968 | (-20.2737±2.8411)+(0.13212±0.019729)*Orn+(0.074522±0.015413)*Tau+(0.0057323±0.0040133)*Gly+(0.0098368±0.010528)*Thr |
| 0.966 | (-15.2787±2.6851)+(0.12827±0.019419)*Orn+(0.082938±0.019624)*Tau-(0.012858±0.01769)*Glu-(0.044304±0.018122)*Arg+(0.012559±0.0060619)*Pro |
| 0.965 | (-16.7178±2.8105)+(0.13664±0.019908)*Orn+(0.078824±0.016415)*Tau-(0.013653±0.010191)*Lys+(0.010726±0.010171)*Thr |
| 0.966 | (-19.8965±2.7553)+(0.13033±0.019505)*Orn+(0.078867±0.01644)*Tau+(0.0070046±0.010609)*Thr+(0.0082991±0.0058389)*Pro |
| 0.964 | (-15.5538±2.7479)+(0.12452±0.019989)*Orn+(0.076537±0.01684)*Tau+(0.025197±0.041548)*Cit-(0.04743±0.018685)*Arg+(0.01028±0.0059338)*Pro |
| 0.967 | (-17.2636±3.2045)+(0.13615±0.020132)*Orn+(0.076307±0.015856)*Tau-(0.0088397±0.01135)*Lys+(0.0044116±0.0044641)*Gly |
| 0.968 | (-20.0211±2.8196)+(0.12941±0.019721)*Orn+(0.075049±0.015428)*Tau+(0.013153±0.01682)*Ser+(0.0044416±0.0043565)*Gly |
| 0.963 | (-15.7562±2.8975)+(0.12609±0.019504)*Orn+(0.075936±0.016927)*Tau-(0.044002±0.017955)*Arg+(0.0057511±0.010199)*Thr+(0.010295±0.0059039)*Pro |
| 0.962 | (-16.0836±3.1907)+(0.12524±0.019724)*Orn+(0.07528±0.017188)*Tau+(0.026062±0.047615)*Asn-(0.045933±0.018167)*Arg+(0.011138±0.0057943)*Pro |
| 0.962 | (-16.2868±3.6074)+(0.12748±0.0197)*Orn+(0.074379±0.017243)*Tau-(0.046809±0.018569)*Arg+(0.002331±0.0049581)*Gln+(0.011179±0.0057774)*Pro |
| 0.964 | (-18.5507±2.7363)+(0.13158±0.019561)*Orn+(0.078616±0.016307)*Tau+(0.0090756±0.0057618)*Pro-(0.017266±0.039682)*Cys |
| 0.967 | (-18.0537±3.4505)+(0.13147±0.019468)*Orn+(0.079379±0.016313)*Tau-(0.01465±0.034573)*His+(0.0091279±0.0057787)*Pro |
| 0.963 | (-14.8056±2.8728)+(0.12917±0.020337)*Orn+(0.077919±0.017374)*Tau-(0.0037268±0.011189)*Lys-(0.042673±0.01916)*Arg+(0.010815±0.0058072)*Pro |
| 0.965 | (-19.5515±3.1456)+(0.13015±0.019475)*Orn+(0.078479±0.016369)*Tau+(0.010111±0.046125)*Asn+(0.0089694±0.0057783)*Pro |
| 0.962 | (-16.2958±2.9406)+(0.12137±0.019354)*Orn+(0.069757±0.016215)*Tau+(0.05139±0.045691)*ABA+(0.017597±0.01648)*Ser-(0.040578±0.017885)*Arg |
| 0.964 | (-14.7625±3.4606)+(0.12774±0.019667)*Orn+(0.076927±0.016953)*Tau-(0.0065697±0.034661)*His-(0.044629±0.018105)*Arg+(0.011128±0.0057983)*Pro |

FIG.37

| ROC_AUC | INDEX |
|---|---|
| 0.965 | (-15.8465±2.7716)+(0.12113±0.019912)*Orn+(0.067758±0.016156)*Tau+(0.068869±0.044525)*ABA+(0.043298±0.039807)*Cit-(0.044309±0.019029)*Arg |
| 0.965 | (-18.9203±3.4977)+(0.13039±0.019364)*Orn+(0.079109±0.01668)*Tau-(0.00037233±0.0045486)*Gln+(0.0088908±0.0057722)*Pro |
| 0.965 | (-19.1708±2.6021)+(0.13027±0.019943)*Orn+(0.078834±0.016248)*Tau+(0.001955±0.040267)*Cit+(0.0088437±0.0059219)*Pro |
| 0.963 | (-15.2824±2.8399)+(0.12675±0.019679)*Orn+(0.076569±0.016867)*Tau-(0.045275±0.018401)*Arg+(0.010985±0.0057821)*Pro+(0.0038887±0.040997)*Cys |
| 0.963 | (-15.1173±3.1969)+(0.12725±0.019766)*Orn+(0.076629±0.016876)*Tau-(0.04469±0.019033)*Arg+(0.010994±0.0057898)*Pro-(0.0017521±0.043108)*Phe |
| 0.964 | (-14.2278±2.6677)+(0.13164±0.020231)*Orn+(0.071267±0.016952)*Tau+(0.076338±0.045515)*ABA-(0.010947±0.011416)*Lys-(0.032306±0.019165)*Arg |
| 0.964 | (-16.4952±2.8975)+(0.1367±0.019872)*Orn+(0.077858±0.016327)*Tau+(0.032258±0.047599)*Asn-(0.015155±0.010956)*Lys |
| 0.966 | (-18.3295±3.3042)+(0.13231±0.019357)*Orn+(0.075269±0.015872)*Tau-(0.0014±0.0045339)*Gln+(0.0058336±0.0041552)*Gly |
| 0.965 | (-17.8402±3.4136)+(0.12905±0.019402)*Orn+(0.075628±0.015674)*Tau+(0.018093±0.015597)*Ser-(0.028227±0.040585)*Phe |
| 0.966 | (-19.6251±3.1641)+(0.13199±0.019642)*Orn+(0.073682±0.01528)*Tau+(0.013578±0.045496)*Asn+(0.0057875±0.0041177)*Gly |
| 0.966 | (-18.2876±3.7307)+(0.13317±0.019587)*Orn+(0.07404±0.015253)*Tau+(0.0051833±0.0044871)*Gly-(0.011452±0.044165)*Phe |
| 0.966 | (-18.9399±2.482)+(0.13289±0.019552)*Orn+(0.075396±0.01676)*Tau-(0.0033251±0.016592)*Glu+(0.0055064±0.0041741)*Gly |
| 0.966 | (-19.1633±2.6281)+(0.13199±0.02004)*Orn+(0.074151±0.015271)*Tau+(0.005134±0.040282)*Cit+(0.0055749±0.0041664)*Gly |
| 0.966 | (-18.8394±3.6589)+(0.13277±0.019676)*Orn+(0.074115±0.015274)*Tau-(0.002482±0.03381)*His+(0.0056061±0.0041851)*Gly |
| 0.966 | (-18.9391±2.9211)+(0.13273±0.019664)*Orn+(0.074002±0.01526)*Tau+(0.0056089±0.0042095)*Gly-(0.0024921±0.039782)*Cys |
| 0.965 | (-18.3131±3.2959)+(0.12578±0.019052)*Orn+(0.077915±0.016654)*Tau+(0.021351±0.016511)*Ser-(0.0025356±0.0047169)*Gln |
| 0.962 | (-16.4577±3.0472)+(0.12033±0.019849)*Orn+(0.073316±0.015817)*Tau+(0.022178±0.015957)*Ser+(0.036086±0.039648)*Cit-(0.046544±0.018493)*Arg |
| 0.965 | (-19.2971±2.6995)+(0.12792±0.019292)*Orn+(0.078678±0.01728)*Tau+(0.018865±0.015507)*Ser-(0.0080722±0.016312)*Glu |
| 0.964 | (-19.7634±2.8402)+(0.12737±0.019356)*Orn+(0.075432±0.015812)*Tau+(0.015605±0.016849)*Ser+(0.0053288±0.011848)*Thr |
| 0.965 | (-18.3937±3.5349)+(0.12827±0.019402)*Orn+(0.075989±0.015778)*Tau+(0.019173±0.015614)*Ser-(0.014607±0.034391)*His |
| 0.965 | (-18.8989±2.937)+(0.12732±0.019133)*Orn+(0.076442±0.01585)*Tau-(0.020751±0.051176)*Asn+(0.021799±0.017484)*Ser |
| 0.963 | (-18.9015±2.9496)+(0.12793±0.019391)*Orn+(0.075337±0.015782)*Tau+(0.018867±0.015675)*Ser-(0.015422±0.03891)*Cys |
| 0.963 | (-16.1615±3.2205)+(0.13689±0.019778)*Orn+(0.078178±0.0162)*Tau-(0.014047±0.011543)*Lys+(0.010522±0.036506)*His |
| 0.964 | (-15.604±2.5288)+(0.13737±0.019818)*Orn+(0.079409±0.017418)*Tau-(0.012158±0.010556)*Lys-(0.00387±0.016458)*Glu |
| 0.963 | (-15.3521±2.7639)+(0.13764±0.019983)*Orn+(0.077722±0.016161)*Tau-(0.012306±0.010476)*Lys-(0.0086733±0.039693)*Cys |
| 0.964 | (-15.8701±2.8961)+(0.13612±0.020384)*Orn+(0.078013±0.016145)*Tau-(0.012293±0.01049)*Lys+(0.0078456±0.040296)*Cit |
| 0.964 | (-15.3849±2.9631)+(0.13711±0.019751)*Orn+(0.077683±0.016207)*Tau-(0.011681±0.012238)*Lys-(0.0066003±0.048003)*Phe |
| 0.965 | (-19.7052±2.9006)+(0.12579±0.019675)*Orn+(0.075644±0.015725)*Tau+(0.018345±0.015616)*Ser+(0.011449±0.038457)*Cit |
| 0.964 | (-15.7841±3.3439)+(0.1372±0.019869)*Orn+(0.077609±0.016576)*Tau-(0.012742±0.010608)*Lys+(0.00040086±0.0047627)*Gln |
| 0.976 | (-23.0408±3.2746)+(0.12771±0.019774)*Orn+(0.074847±0.016851)*Tau+(0.092652±0.045176)*ABA+(0.0077293±0.004663)*Gly+(0.010705±0.0058533)*Pro |
| 0.964 | (-17.0013±3.1608)+(0.13307±0.019467)*Orn+(0.074764±0.015679)*Tau+(0.010016±0.010477)*Thr-(0.033895±0.041023)*Phe |
| 0.963 | (-16.2247±3.0295)+(0.12551±0.01976)*Orn+(0.072596±0.015694)*Tau+(0.017963±0.017309)*Ser-(0.041373±0.017895)*Arg+(0.0030327±0.0042302)*Gly |
| 0.962 | (-14.2581±2.8785)+(0.12792±0.019665)*Orn+(0.067952±0.016183)*Tau+(0.070046±0.044999)*ABA-(0.035858±0.01911)*Arg-(0.022348±0.042853)*Phe |
| 0.961 | (-15.3519±2.7689)+(0.12464±0.019373)*Orn+(0.067701±0.016258)*Tau+(0.057252±0.046177)*ABA-(0.039204±0.017934)*Arg+(0.0050748±0.01071)*Thr |
| 0.966 | (-16.734±3.251)+(0.083±0.020)*Tau+(0.119±0.020)*Orn+(-0.048±0.018)*Arg+(0.023±0.016)*Ser+(-0.015±0.019)*Glu+(0.013±0.006)*Pro |

FIG.39

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| 0 | 1.00 | 0.04 | 0.042 | 1.000 | 0.08 |
| 0.0001 | 1.00 | 0.04 | 0.042 | 1.000 | 0.08 |
| 0.0005 | 1.00 | 0.25 | 0.053 | 1.000 | 0.28 |
| 0.001 | 1.00 | 0.41 | 0.067 | 1.000 | 0.44 |
| 0.0015 | 1.00 | 0.50 | 0.078 | 1.000 | 0.52 |
| 0.002 | 1.00 | 0.56 | 0.087 | 1.000 | 0.58 |
| 0.0025 | 1.00 | 0.60 | 0.096 | 1.000 | 0.62 |
| 0.003 | 1.00 | 0.64 | 0.105 | 1.000 | 0.65 |
| 0.004 | 0.97 | 0.69 | 0.116 | 0.998 | 0.70 |
| 0.005 | 0.97 | 0.73 | 0.131 | 0.998 | 0.74 |
| 0.006 | 0.97 | 0.76 | 0.146 | 0.998 | 0.77 |
| 0.007 | 0.97 | 0.77 | 0.153 | 0.998 | 0.78 |
| 0.008 | 0.93 | 0.79 | 0.156 | 0.996 | 0.79 |
| 0.009 | 0.93 | 0.80 | 0.167 | 0.996 | 0.81 |
| 0.01 | 0.93 | 0.81 | 0.172 | 0.997 | 0.81 |
| 0.015 | 0.93 | 0.85 | 0.207 | 0.997 | 0.85 |
| 0.0175 | 0.90 | 0.86 | 0.218 | 0.995 | 0.86 |
| 0.02 | 0.87 | 0.88 | 0.234 | 0.994 | 0.88 |
| 0.025 | 0.87 | 0.90 | 0.268 | 0.994 | 0.90 |
| 0.03 | 0.87 | 0.91 | 0.292 | 0.994 | 0.91 |
| 0.05 | 0.83 | 0.94 | 0.385 | 0.993 | 0.94 |
| 0.1 | 0.80 | 0.96 | 0.490 | 0.991 | 0.96 |
| 0.25 | 0.80 | 0.99 | 0.706 | 0.991 | 0.98 |
| 0.5 | 0.70 | 1.00 | 0.913 | 0.987 | 0.99 |
| 0.75 | 0.47 | 1.00 | 1.000 | 0.978 | 0.98 |
| 1 | 0.00 | 1.00 | 0.000 | 0.959 | 0.96 |

FIG.40

| ROC_AUC | INDEX |
|---|---|
| 0.981 | (-12.3674±2.3155)+(0.17822±0.032421)*Orn+(0.07798±0.019669)*Tau-(0.2007±0.050993)*Trp |
| 0.986 | (-14.0963±2.6163)+(0.1733±0.033832)*Orn+(0.075306±0.021579)<br>*Tau+(0.12381±0.059907)*ABA-(0.21832±0.056522)*Trp |
| 0.982 | (-7.6299±3.3655)+(0.1626±0.032984)*Orn-(0.042738±0.025222)*Arg+(0.073051±0.021122)<br>*Tau-(0.19326±0.053493)*Trp |
| 0.983 | (-14.9168±2.9571)+(0.18416±0.034858)*Orn+(0.080534±0.020482)<br>*Tau-(0.21625±0.055907)*Trp+(0.020844±0.012162)*Thr |
| 0.985 | (-15.6552±3.3927)+(0.17636±0.033669)*Orn+(0.082303±0.020288)<br>*Tau+(0.028438±0.018815)*Ser-(0.20204±0.052237)*Trp |
| 0.982 | (-14.2881±2.9237)+(0.18804±0.035972)*Orn+(0.076605±0.020572)<br>*Tau+(0.0064263±0.0047676)*Ala-(0.22578±0.058304)*Trp |
| 0.981 | (-15.4513±3.5356)+(0.17763±0.033046)*Orn+(0.076448±0.020367)<br>*Tau+(0.075827±0.059833)*Asn-(0.20626±0.052102)*Trp |
| 0.983 | (-13.4564±2.6236)+(0.17686±0.033324)*Orn+(0.079234±0.019732)<br>*Tau+(0.0076504±0.0066242)*Pro-(0.20023±0.05295)*Trp |
| 0.979 | (-15.0524±3.5684)+(0.17622±0.032797)*Orn+(0.077549±0.019722)<br>*Tau+(0.039621±0.036385)*His-(0.20941±0.052548)*Trp |
| 0.983 | (-9.4057±3.7324)+(0.18276±0.033662)*Orn+(0.08473±0.022201)<br>*Tau-(0.21418±0.054603)*Trp-(0.005443±0.0059074)*Gln |
| 0.981 | (-12.5474±2.3412)+(0.17993±0.033195)*Orn+(0.072859±0.020757)<br>*Tau+(0.013061±0.020993)*Glu-(0.20731±0.053814)*Trp |
| 0.987 | (-9.2481±3.6174)+(0.15827±0.034542)*Orn-(0.042684±0.026458)*Arg+(0.07169±0.022817)<br>*Tau+(0.11737±0.058576)*ABA-(0.21381±0.059724)*Trp |
| 0.981 | (-12.0335±2.65)+(0.18099±0.034478)*Orn+(0.073262±0.019958)<br>*Tau-(0.010801±0.042982)*Cit-(0.20444±0.053586)*Trp |
| 0.981 | (-12.6017±3.0076)+(0.17752±0.032807)*Orn+(0.077424±0.020158)<br>*Tau+(0.0017089±0.013794)*Lys-(0.20146±0.051377)*Trp |
| 0.981 | (-12.5299±2.68)+(0.17743±0.032965)*Orn+(0.078029±0.019616)<br>*Tau+(0.00059187±0.0048193)*Gly-(0.19891±0.052871)*Trp |
| 0.985 | (-11.0143±4.127)+(0.15673±0.033607)*Orn-(0.042867±0.024369)*Arg+(0.078425±0.021956)<br>*Tau+(0.0303±0.019294)*Ser-(0.19173±0.054898)*Trp |
| 0.983 | (-10.051±3.9048)+(0.16529±0.035234)*Orn-(0.038289±0.024088)*Arg+(0.075153±0.021656)<br>*Tau-(0.20788±0.057856)*Trp+(0.018924±0.012077)*Thr |
| 0.987 | (-15.6128±3.0645)+(0.17838±0.085694)*Orn+(0.077408±0.021928)<br>*Tau+(0.10328±0.062909)*ABA-(0.2278±0.059752)*Trp+(0.01535±0.013431)*Thr |
| 0.984 | (-8.6556±3.4628)+(0.15959±0.034177)*Orn-(0.047641±0.024763)*Arg+(0.075595±0.021739)<br>*Tau+(0.010864±0.0069235)*Pro-(0.19449±0.057652)*Trp |
| 0.987 | (-10.7516±3.8709)+(0.18013±0.036069)*Orn+(0.082664±0.024214)<br>*Tau+(0.13025±0.060012)*ABA-(0.23528±0.060719)*Trp-(0.0065087±0.0060427)*Gln |
| 0.987 | (-15.579±3.0786)+(0.18307±0.037255)*Orn+(0.07466±0.021956)<br>*Tau+(0.11886±0.062233)*ABA+(0.0050859±0.0046037)*Ala-(0.24022±0.063065)*Trp |
| 0.983 | (-9.6709±3.7258)+(0.17403±0.03746)*Orn-(0.043022±0.024223)*Arg+(0.070877±0.022161)<br>*Tau+(0.0078202±0.0049341)*Ala-(0.22443±0.062723)*Trp |
| 0.987 | (-16.136±3.4226)+(0.17164±0.034474)*Orn+(0.078844±0.021839)<br>*Tau+(0.10641±0.062563)*ABA+(0.020558±0.019972)*Ser-(0.21716±0.057159)*Trp |
| 0.987 | (-14.9681±2.8938)+(0.17384±0.034775)*Orn+(0.075003±0.021372)<br>*Tau+(0.11415±0.058555)*ABA+(0.0064069±0.0069288)*Pro-(0.21446±0.057992)*Trp |
| 0.982 | (-10.6746±4.2366)+(0.15889±0.03402)*Orn-(0.042712±0.024925)*Arg+(0.07138±0.021699)<br>*Tau+(0.07854±0.0602)*Asn-(0.19649±0.054049)*Trp |
| 0.984 | (-16.1352±3.6832)+(0.17216±0.034005)*Orn+(0.074648±0.021228)<br>*Tau+(0.12124±0.061856)*ABA+(0.032208±0.038088)*His-(0.22762±0.058868)*Trp |
| 0.987 | (-18.2939±4.037)+(0.1376±0.037969)*Orn+(0.082508±0.021387)<br>*Tau+(0.030965±0.018288)*Ser+(0.0076452±0.0049687)*Ala-(0.2324±0.061299)*Trp |
| 0.979 | (-10.5513±4.2377)+(0.15926±0.033796)*Orn-(0.043518±0.024676)*Arg+(0.071706±0.021246)<br>*Tau+(0.046607±0.038665)*His-(0.20382±0.055125)*Trp |
| 0.986 | (-15.5076±3.5698)+(0.17273±0.033847)*Orn+(0.07441±0.021587)<br>*Tau+(0.1119±0.064566)*ABA+(0.040746±0.066244)*Asn-(0.21948±0.056427)*Trp |
| 0.965 | (-3.223±2.7038)+(0.16473±0.030549)*Orn-(0.059032±0.022042)*Arg-(0.16923±0.045411)*Trp |
| 0.988 | (-12.1102±4.0768)+(0.18435±0.036607)*Orn+(0.095518±0.024558)<br>*Tau+(0.038651±0.021096)*Ser-(0.22523±0.058332)*Trp-(0.0088848±0.0062913)*Gln |
| 0.986 | (-11.793±4.0247)+(0.18856±0.036152)*Orn+(0.091638±0.025391)<br>*Tau+(0.12674±0.070098)*Asn-(0.24228±0.062003)*Trp-(0.010718±0.0067018)*Gln |
| 0.986 | (-14.2085±2.6401)+(0.17537±0.034731)*Orn+(0.071692±0.022678)<br>*Tau+(0.11929±0.05961)*ABA+(0.0094153±0.021744)*Glu-(0.22246±0.058615)*Trp |

FIG.41

| ROC_AUC | INDEX |
|---|---|
| 0.987 | (-14.7071±3.1073)+(0.16987±0.034618)*Orn+(0.075823±0.021538)*Tau+(0.12805±0.061461)*ABA+(0.0020761±0.0053151)*Gly-(0.21272±0.057759)*Trp |
| 0.986 | (-13.5534±3.1409)+(0.1749±0.034624)*Orn+(0.076524±0.022174)*Tau+(0.12687±0.06017)*ABA-(0.004372±0.014614)*Lys-(0.21617±0.057015)*Trp |
| 0.986 | (-13.9502±2.998)+(0.17459±0.036397)*Orn+(0.075492±0.021761)*Tau+(0.12303±0.060272)*ABA-(0.0044227±0.044918)*Cit-(0.21996±0.059134)*Trp |
| 0.980 | (-7.667±3.346)+(0.16444±0.034087)*Orn-(0.044697±0.024829)*Arg+(0.065617±0.022029)*Tau+(0.020238±0.022805)*Glu-(0.20482±0.058368)*Trp |
| 0.983 | (-4.9447±4.5036)+(0.16958±0.034768)*Orn-(0.041664±0.025094)*Arg+(0.08087±0.024115)*Tau-(0.21072±0.05902)*Trp-(0.0052856±0.0062353)*Gln |
| 0.986 | (-16.8948±3.7026)+(0.17636±0.035324)*Orn+(0.083594±0.020365)*Tau+(0.029201±0.019012)*Ser+(0.0084741±0.0071076)*Pro-(0.20501±0.055269)*Trp |
| 0.985 | (-12.[illegible]468±4.2516)+(0.18678±0.035555)*Orn+(0.08676±0.022964)*Tau-(0.22706±0.05876)*Trp+(0.019994±0.011881)*Thr-(0.0049739±0.0057385)*Gln |
| 0.985 | (-15.6906±3.1387)+(0.189±0.036802)*Orn+(0.078947±0.021037)*Tau+(0.0041897±0.0048172)*Ala-(0.22878±0.059879)*Trp+(0.017013±0.012863)*Thr |
| 0.985 | (-16.3685±3.5003)+(0.18134±0.035161)*Orn+(0.082036±0.020479)*Tau+(0.017821±0.020689)*Ser-(0.21246±0.055651)*Trp+(0.015965±0.014086)*Thr |
| 0.980 | (-11.539±2.2431)+(0.18023±0.032547)*Orn+(0.13346±0.04698)*ABA-(0.19214±0.045871)*Trp |
| 0.982 | (-8.179±3.6311)+(0.15908±0.033972)*Orn-(0.045267±0.026217)*Arg+(0.070419±0.021918)*Tau+(0.0061886±0.013618)*Lys-(0.195±0.053609)*Trp |
| 0.984 | (-17.3589±4.0836)+(0.18819±0.03691)*Orn+(0.076117±0.021061)*Tau+(0.075018±0.061658)*Asn+(0.006143±0.0047106)*Ala-(0.23127±0.059602)*Trp |
| 0.982 | (-7.858±3.5396)+(0.16116±0.033395)*Orn-(0.043076±0.025302)*Arg+(0.073023±0.021027)*Tau+(0.00096759±0.0043513)*Gly-(0.1902±0.054986)*Trp |
| 0.982 | (-7.7859±3.4426)+(0.15936±0.036031)*Orn-(0.044219±0.026219)*Arg+(0.072305±0.021219)*Tau+(0.010245±0.047279)*Cit-(0.18875±0.056922)*Trp |
| 0.984 | (-18.0909±4.3583)+(0.17331±0.03372)*Orn+(0.08176±0.020242)*Tau+(0.027793±0.019049)*Ser+(0.038765±0.038591)*His-(0.21126±0.054258)*Trp |
| 0.976 | (-5.773±3.0833)+(0.16187±0.032521)*Orn-(0.053972±0.022997)*Arg+(0.11401±0.048631)*ABA-(0.18016±0.048475)*Trp |
| 0.982 | (-11.7802±4.0886)+(0.18218±0.03423)*Orn+(0.088189±0.023028)*Tau+(0.059385±0.038219)*His-(0.23485±0.057989)*Trp-(0.0084843±0.0061506)*Gln |
| 0.983 | (-15.1934±3.0312)+(0.18286±0.035259)*Orn+(0.080432±0.020342)*Tau+(0.0043584±0.0074369)*Pro-(0.21404±0.056666)*Trp+(0.018204±0.013155)*Thr |
| 0.983 | (-16.0487±3.7445)+(0.1821±0.034879)*Orn+(0.079763±0.020393)*Tau+(0.021484±0.040988)*His-(0.21887±0.056231)*Trp+(0.018391±0.013062)*Thr |
| 0.983 | (-15.9025±3.6124)+(0.18262±0.034819)*Orn+(0.078969±0.020808)*Tau+(0.036406±0.071397)*Asn-(0.21574±0.05555)*Trp+(0.016974±0.014447)*Thr |
| 0.984 | (-14.5183±3.1853)+(0.18793±0.037129)*Orn+(0.080868±0.020855)*Tau-(0.013746±0.042217)*Cit-(0.22121±0.058603)*Trp+(0.021003±0.012155)*Thr |
| 0.984 | (-16.7861±3.7951)+(0.17567±0.033529)*Orn+(0.080242±0.020731)*Tau+(0.047115±0.065888)*Asn+(0.02224±0.020711)*Ser-(0.20541±0.052777)*Trp |
| 0.984 | (-16.4523±3.803)+(0.177±0.033977)*Orn+(0.077155±0.020307)*Tau+(0.07334±0.060457)*Asn+(0.0074433±0.0068654)*Pro-(0.20524±0.053939)*Trp |
| 0.983 | (-15.0297±3.5003)+(0.18392±0.035069)*Orn+(0.080274±0.020917)*Tau+(0.00078716±0.01296)*Lys-(0.21672±0.056485)*Trp+(0.02088±0.012209)*Thr |
| 0.983 | (-14.9612±3.1889)+(0.18388±0.035647)*Orn+(0.080522±0.02046)*Tau+(0.00017455±0.0046682)*Gly-(0.21558±0.058633)*Trp+(0.020811±0.012193)*Thr |
| 0.983 | (-14.9018±2.9812)+(0.18418±0.034879)*Orn+(0.080165±0.022699)*Tau+(0.0008473±0.022715)*Glu-(0.21656±0.056589)*Trp+(0.020671±0.013031)*Thr |
| 0.984 | (-15.3525±3.3959)+(0.18036±0.03511)*Orn+(0.083228±0.020767)*Tau+(0.033335±0.020496)*Ser-(0.0031013±0.0055258)*Gly-(0.21324±0.057358)*Trp |
| 0.981 | (-16.4359±3.9288)+(0.1861±0.036285)*Orn+(0.076445±0.02046)*Tau+(0.033339±0.037225)*His+(0.0058651±0.0048255)*Ala-(0.23071±0.058784)*Trp |
| 0.985 | (-15.6305±3.3827)+(0.17735±0.034175)*Orn+(0.078409±0.021809)*Tau+(0.027605±0.019064)*Ser+(0.0087772±0.020505)*Glu-(0.20656±0.054448)*Trp |
| 0.984 | (-11.4958±4.3869)+(0.19052±0.036429)*Orn+(0.082151±0.022797)*Tau+(0.0059893±0.0047777)*Ala-(0.23607±0.060785)*Trp-(0.0047032±0.0059822)*Gln |
| 0.985 | (-15.2789±3.5946)+(0.18001±0.03609)*Orn+(0.08227±0.020677)*Tau+(0.028722±0.018873)*Ser-(0.013536±0.044101)*Cit-(0.20694±0.055298)*Trp |
| 0.985 | (-16.1754±4.0154)+(0.17462±0.034016)*Orn+(0.081428±0.02058)*Tau+(0.028899±0.018923)*Ser+(0.0034748±0.013958)*Lys-(0.20365±0.052663)*Trp |
| 0.982 | (-15.8±3.7621)+(0.1753±0.03353)*Orn+(0.078569±0.019744)*Tau+(0.035544±0.03717)*His+(0.006942±0.0067179)*Pro-(0.20729±0.053941)*Trp |

FIG.42

| ROC_AUC | INDEX |
|---|---|
| 0.971 | (-8.9672±1.8215)+(0.182±0.0304)*Orn-(0.17894±0.042433)*Trp |
| 0.982 | (-14.4695±2.9769)+(0.18955±0.036595)*Orn+(0.072603±0.021352)*Tau+(0.011915±0.022187)*Glu+(0.0062098±0.0047464)*Ala-(0.23044±0.060267)*Trp |
| 0.983 | (-14.4518±2.9526)+(0.18419±0.036145)*Orn+(0.077161±0.020402)*Tau+(0.0041793±0.0079004)*Pro+(0.0049176±0.0055167)*Ala-(0.21713±0.059231)*Trp |
| 0.984 | (-10.5493±4.1165)+(0.18003±0.034272)*Orn+(0.08504±0.022005)*Tau+(0.0071114±0.0066053)*Pro-(0.21181±0.056096)*Trp-(0.0050711±0.0060026)*Gln |
| 0.983 | (-14.7557±3.3215)+(0.18642±0.03619)*Orn+(0.076878±0.020475)*Tau+(0.0014314±0.0046116)*Gly+(0.0066287±0.0048052)*Ala-(0.22223±0.059213)*Trp |
| 0.982 | (-16.212±3.9313)+(0.17669±0.033222)*Orn+(0.076159±0.020188)*Tau+(0.060163±0.069309)*Asn+(0.020853±0.044266)*His-(0.20948±0.052896)*Trp |
| 0.983 | (-15.0109±3.6519)+(0.18291±0.035683)*Orn+(0.077132±0.020973)*Tau+(0.079633±0.060385)*Asn-(0.019779±0.045291)*Cit-(0.21375±0.055616)*Trp |
| 0.983 | (-14.0155±3.2349)+(0.19024±0.037979)*Orn+(0.076863±0.020784)*Tau-(0.0081929±0.042881)*Cit+(0.0063845±0.0047763)*Ala-(0.22899±0.061118)*Trp |
| 0.982 | (-15.0453±3.6742)+(0.17941±0.033603)*Orn+(0.078442±0.021247)*Tau+(0.083426±0.062507)*Asn-(0.005236±0.014107)*Lys-(0.20459±0.052348)*Trp |
| 0.982 | (-15.335±3.5144)+(0.1784±0.033476)*Orn+(0.073179±0.021812)*Tau+(0.071073±0.060992)*Asn+(0.0077706±0.02109)*Glu-(0.20949±0.053878)*Trp |
| 0.982 | (-14.2798±3.4099)+(0.18807±0.036359)*Orn+(0.076622±0.02091)*Tau-(6.646e-005±0.013943)*Lys+(0.0064289±0.0047993)*Ala-(0.22575±0.058705)*Trp |
| 0.988 | (-10.7889±3.8847)+(0.16954±0.038689)*Orn-(0.043073±0.025601)*Arg+(0.070094±0.023106)*Tau+(0.11255±0.061933)*ABA+(0.0057823±0.0047941)*Ala-(0.24098±0.067879)*Trp |
| 0.987 | (-10.032±3.717)+(0.15805±0.035813)*Orn-(0.045644±0.025612)*Arg+(0.072645±0.022969)*Tau+(0.10125±0.057692)*ABA+(0.0088497±0.0071961)*Pro-(0.21092±0.062933)*Trp |
| 0.988 | (-11.4682±4.1631)+(0.15289±0.034712)*Orn-(0.043903±0.025674)*Arg+(0.076419±0.02327)*Tau+(0.10154±0.061191)*ABA+(0.023498±0.020059)*Ser-(0.21023±0.060598)*Trp |
| 0.969 | (-5.8473±3.0342)+(0.17405±0.033502)*Orn-(0.056224±0.021223)*Arg+(0.0084708±0.004327)*Ala-(0.20131±0.051924)*Trp |
| 0.982 | (-15.7181±3.8367)+(0.17627±0.033666)*Orn+(0.076733±0.020353)*Tau+(0.076272±0.05983)*Asn+(0.00090655±0.0049107)*Gly-(0.20364±0.053775)*Trp |
| 0.986 | (-13.8174±4.6235)+(0.1699±0.038706)*Orn-(0.04246±0.023323)*Arg+(0.07706±0.023126)*Tau+(0.032845±0.019018)*Ser+(0.0085582±0.0051778)*Ala-(0.22797±0.065891)*Trp |
| 0.987 | (-10.7095±3.9569)+(0.1611±0.03624)*Orn-(0.040538±0.025141)*Arg+(0.073625±0.023111)*Tau+(0.10219±0.060938)*ABA-(0.22444±0.063295)*Trp+(0.014361±0.012651)*Thr |
| 0.980 | (-14.7946±3.6132)+(0.1839±0.036011)*Orn+(0.078351±0.020416)*Tau-(0.027662±0.045638)*Cit+(0.047766±0.03857)*His-(0.2219±0.05784)*Trp |
| 0.988 | (-6.1009±4.6242)+(0.16876±0.037672)*Orn-(0.041699±0.026304)*Arg+(0.080566±0.02575)*Tau+(0.12379±0.058819)*ABA-(0.23575±0.065871)*Trp-(0.0066092±0.006446)*Gln |
| 0.983 | (-13.0158±2.8819)+(0.18082±0.035595)*Orn+(0.079464±0.020073)*Tau-(0.014816±0.04226)*Cit+(0.0078667±0.0066487)*Pro-(0.20567±0.055967)*Trp |
| 0.985 | (-11.5469±4.2745)+(0.15586±0.035136)*Orn-(0.044591±0.026021)*Arg+(0.069966±0.022461)*Tau+(0.11648±0.060703)*ABA+(0.040521±0.038733)*His-(0.22594±0.062438)*Trp |
| 0.982 | (-13.459±2.6207)+(0.17809±0.033927)*Orn+(0.076798±0.021342)*Tau+(0.007109±0.0070255)*Pro+(0.0063294±0.022634)*Glu-(0.20432±0.055684)*Trp |
| 0.983 | (-13.7783±3.0394)+(0.17534±0.033879)*Orn+(0.079407±0.019651)*Tau+(0.0010699±0.0048937)*Gly+(0.0077873±0.0066544)*Pro-(0.19677±0.05496)*Trp |
| 0.982 | (-13.73±3.3061)+(0.17621±0.033555)*Orn+(0.078599±0.020232)*Tau+(0.0019357±0.013967)*Lys+(0.0076783±0.0066394)*Pro-(0.20123±0.053466)*Trp |
| 0.982 | (-9.6537±3.7911)+(0.18359±0.034013)*Orn+(0.079639±0.023242)*Tau+(0.012789±0.021404)*Glu-(0.21955±0.056431)*Trp-(0.0052887±0.0058547)*Gln |
| 0.980 | (-14.914±3.5858)+(0.17708±0.033208)*Orn+(0.074475±0.02118)*Tau+(0.036131±0.03809)*His+(0.0077711±0.021759)*Glu-(0.21203±0.053911)*Trp |
| 0.980 | (-15.6984±4.0819)+(0.17359±0.033386)*Orn+(0.077897±0.019608)*Tau+(0.0017115±0.0050127)*Gly+(0.042367±0.037289)*His-(0.20505±0.053683)*Trp |
| 0.980 | (-14.7922±3.7343)+(0.17709±0.03311)*Orn+(0.078659±0.02043)*Tau-(0.0030835±0.013955)*Lys+(0.041936±0.037358)*His-(0.20815±0.052741)*Trp |
| 0.986 | (-12.1438±4.2984)+(0.15452±0.035039)*Orn-(0.046849±0.024314)*Arg+(0.08008±0.022374)*Tau+(0.030308±0.019503)*Ser+(0.011638±0.0074713)*Pro-(0.19443±0.059392)*Trp |
| 0.964 | (-4.4852±2.9129)+(0.16883±0.032072)*Orn-(0.059839±0.022433)*Arg+(0.037884±0.020884)*Glu-(0.18943±0.051408)*Trp |
| 0.983 | (-9.838±3.9461)+(0.18067±0.03376)*Orn+(0.083743±0.02243)*Tau+(0.0058397±0.014538)*Lys-(0.2185±0.055843)*Trp-(0.0060893±0.006085)*Gln |
| 0.983 | (-9.6294±3.9056)+(0.1814±0.034027)*Orn+(0.085063±0.022194)*Tau+(0.0011898±0.0049742)*Gly-(0.21112±0.055794)*Trp-(0.0056337±0.0059818)*Gln |
| 0.983 | (-9.3453±3.8557)+(0.1836±0.035283)*Orn+(0.0847±0.02225)*Tau-(0.0033718±0.041712)*Cit-(0.21513±0.055946)*Trp-(0.0053668±0.005997)*Gln |

FIG.44

| ROC_AUC | INDEX |
|---|---|
| 0.952 | (-16.7887±2.0923)+(0.12139±0.019351)*Orn+(0.069688±0.015615)*Tau |
| 0.958 | (-18.6752±2.3866)+(0.11473±0.019434)*Orn+(0.10891±0.049056)*ABA+(0.064043±0.016243)*Tau |
| 0.949 | (-13.543±2.5394)+(0.11835±0.019468)*Orn+(0.066757±0.01559)*Tau-(0.032525±0.018856)*Arg |
| 0.959 | (-18.1344±2.4559)+(0.12226±0.019622)*Orn+(0.07015±0.015456)*Tau+(0.0052906±0.0042083)*Gly |
| 0.956 | (-14.8669±2.5811)+(0.12734±0.020061)*Orn+(0.073502±0.016423)*Tau-(0.012274±0.01111)*Lys |
| 0.962 | (-16.1799±2.6551)+(0.12511±0.020758)*Orn+(0.12663±0.048555)*ABA+(0.069326±0.017168)*Tau-(0.019134±0.011559)*Lys |
| 0.956 | (-18.4657±2.8287)+(0.11816±0.019427)*Orn+(0.071579±0.01594)*Tau+(0.016453±0.016915)*Ser |
| 0.954 | (-18.2266±2.6528)+(0.12102±0.019503)*Orn+(0.069942±0.015901)*Tau+(0.01167±0.011866)*Thr |
| 0.953 | (-16.5943±2.1072)+(0.12339±0.019502)*Orn+(0.076358±0.018197)*Tau-(0.015043±0.018259)*Glu |
| 0.968 | (-20.6176±2.8993)+(0.11394±0.019685)*Orn+(0.12012±0.051037)*ABA+(0.065362±0.016099)*Tau+(0.0070186±0.0046881)*Gly |
| 0.953 | (-17.4037±2.4402)+(0.1189±0.019936)*Orn+(0.070099±0.015704)*Tau+(0.021835±0.041208)*Cit |
| 0.952 | (-17.7006±2.9272)+(0.1203±0.019556)*Orn+(0.022876±0.049348)*Asn+(0.068768±0.015815)*Tau |
| 0.953 | (-15.7984±3.3381)+(0.12091±0.019218)*Orn+(0.071216±0.016352)*Tau-(0.0018313±0.0049521)*Gln |
| 0.954 | (-16.009±3.0496)+(0.12236±0.019478)*Orn+(0.069875±0.015627)*Tau-(0.01444±0.042839)*Phe |
| 0.954 | (-17.1653±2.4207)+(0.12091±0.019413)*Orn+(0.070621±0.01599)*Tau+(0.0025628±0.0077905)*Pro |
| 0.953 | (-17.2044±2.5891)+(0.1208±0.019419)*Orn+(0.069824±0.015602)*Tau+(0.011427±0.04061)*Cys |
| 0.953 | (-16.647±3.3531)+(0.12156±0.019573)*Orn+(0.069756±0.015669)*Tau-(0.001903±0.035325)*His |
| 0.955 | (-15.8299±2.9695)+(0.11224±0.019502)*Orn+(0.094789±0.049768)*ABA+(0.062698±0.015948)*Tau-(0.025219±0.019154)*Arg |
| 0.959 | (-18.4191±2.3925)+(0.11565±0.01938)*Orn+(0.11352±0.050981)*ABA+(0.070615±0.018773)*Tau-(0.016475±0.018668)*Glu |
| 0.959 | (-17.1179±3.0221)+(0.1172±0.019566)*Orn+(0.11458±0.048803)*ABA+(0.064244±0.0162)*Tau-(0.03156±0.041509)*Phe |
| 0.959 | (-19.718±2.8235)+(0.1108±0.020025)*Orn+(0.11433±0.050091)*ABA+(0.064448±0.016329)*Tau+(0.032787±0.042023)*Cit |
| 0.959 | (-17.1828±3.4282)+(0.11411±0.019158)*Orn+(0.11238±0.049578)*ABA+(0.065822±0.016948)*Tau-(0.0028867±0.0049961)*Gln |
| 0.959 | (-17.5014±3.3495)+(0.11646±0.019707)*Orn+(0.11261±0.049058)*ABA+(0.06482±0.016406)*Tau-(0.01744±0.036238)*His |
| 0.959 | (-19.3459±2.8679)+(0.11336±0.01958)*Orn+(0.10311±0.050712)*ABA+(0.065082±0.016423)*Tau+(0.0078135±0.017577)*Ser |
| 0.959 | (-19.1688±2.7463)+(0.11489±0.019469)*Orn+(0.10801±0.048352)*ABA+(0.064969±0.016586)*Tau+(0.0031756±0.0080614)*Pro |
| 0.957 | (-18.1171±2.9424)+(0.11562±0.019615)*Orn+(0.11414±0.051393)*ABA-(0.017535±0.056016)*Asn+(0.064764±0.01637)*Tau |
| 0.958 | (-18.9827±2.7014)+(0.11479±0.019483)*Orn+(0.10427±0.052314)*ABA+(0.064143±0.016274)*Tau+(0.0033333±0.013334)*Thr |
| 0.958 | (-18.8202±2.832)+(0.11467±0.019437)*Orn+(0.10851±0.04925)*ABA+(0.064085±0.016244)*Tau+(0.0039215±0.040646)*Cys |
| 0.952 | (-15.5092±3.0983)+(0.11434±0.019427)*Orn+(0.069355±0.015755)*Tau+(0.020362±0.017062)*Ser-(0.034144±0.018348)*Arg |
| 0.957 | (-14.8421±2.8744)+(0.11955±0.019736)*Orn+(0.06704±0.015462)*Tau-(0.031609±0.019144)*Arg+(0.0047101±0.004072)*Gly |
| 0.949 | (-14.8241±2.9818)+(0.11659±0.019598)*Orn+(0.066574±0.015763)*Tau+(0.010769±0.011175)*Thr-(0.031453±0.018301)*Arg |
| 0.951 | (-14.2716±2.7077)+(0.11427±0.020198)*Orn+(0.067003±0.015675)*Tau+(0.03698±0.042118)*Cit-(0.035801±0.01951)*Arg |
| 0.952 | (-14.1659±2.6943)+(0.11721±0.019473)*Orn+(0.06877±0.016203)*Tau-(0.035377±0.018994)*Arg+(0.0059213±0.007498)*Pro |

FIG.45

| ROC_AUC | INDEX |
|---|---|
| 0.948 | (-14.7349±3.0924)+(0.11536±0.019966)*Orn+(0.036686±0.05022)*Asn+(0.064949±0.015921)*Tau-(0.03427±0.018874)*Arg |
| 0.951 | (-14.2231±2.7986)+(0.11625±0.019518)*Orn+(0.066215±0.015642)*Tau+(0.026499±0.04165)*Cys-(0.034696±0.019092)*Arg |
| 0.950 | (-13.0069±2.6731)+(0.12247±0.020806)*Orn+(0.069269±0.016478)*Tau-(0.0063933±0.011784)*Lys-(0.028514±0.01996)*Arg |
| 0.952 | (-13.5409±2.5739)+(0.11961±0.019589)*Orn+(0.071102±0.018131)*Tau-(0.010031±0.019193)*Glu-(0.030811±0.019236)*Arg |
| 0.948 | (-13.9153±3.4392)+(0.1177±0.019895)*Orn+(0.066505±0.015668)*Tau+(0.0056677±0.034821)*His-(0.032903±0.018997)*Arg |
| 0.949 | (-13.7578±3.024)+(0.11768±0.020126)*Orn+(0.066566±0.015671)*Tau-(0.033338±0.019883)*Arg+(0.0057948±0.043103)*Phe |
| 0.949 | (-13.5524±3.454)+(0.11835±0.019471)*Orn+(0.066738±0.016294)*Tau-(0.032542±0.019344)*Arg+(2.0948e-005±0.0052408)*Gln |
| 0.961 | (-19.6202±2.9579)+(0.12206±0.019783)*Orn+(0.070491±0.015659)*Tau+(0.011882±0.011832)*Thr+(0.005271±0.0041088)*Gly |
| 0.957 | (-16.2809±2.9693)+(0.12698±0.020037)*Orn+(0.073963±0.016677)*Tau-(0.012991±0.010731)*Lys+(0.012594±0.011371)*Thr |
| 0.957 | (-18.4811±2.7387)+(0.12423±0.019911)*Orn+(0.079361±0.019063)*Tau-(0.020273±0.018634)*Glu+(0.01518±0.012197)*Thr |
| 0.956 | (-16.2466±3.0311)+(0.12676±0.02011)*Orn+(0.049026±0.051507)*Asn+(0.073293±0.016774)*Tau-(0.016159±0.011605)*Lys |
| 0.959 | (-16.5128±3.2775)+(0.12377±0.02024)*Orn+(0.074863±0.016559)*Tau-(0.011374±0.011044)*Lys+(0.014966±0.016834)*Ser |
| 0.961 | (-16.4236±3.2942)+(0.12598±0.020315)*Orn+(0.072335±0.016104)*Tau-(0.008598±0.012086)*Lys+(0.0040509±0.004592)*Gly |
| 0.970 | (-17.9746±3.4104)+(0.12293±0.021458)*Orn+(0.13136±0.050156)*ABA+(0.068237±0.01676)*Tau-(0.015579±0.012564)*Lys+(0.0050083±0.0051757)*Gly |
| 0.960 | (-17.8545±2.4834)+(0.12379±0.019759)*Orn+(0.075531±0.018038)*Tau-(0.01212±0.01873)*Glu+(0.0047834±0.0042555)*Gly |
| 0.958 | (-18.4821±2.8653)+(0.12041±0.019563)*Orn+(0.079639±0.018783)*Tau+(0.018208±0.016815)*Ser-(0.01703±0.017964)*Glu |
| 0.967 | (-17.8009±3.4614)+(0.11197±0.019723)*Orn+(0.10673±0.051949)*ABA+(0.063724±0.015849)*Tau-(0.023359±0.019445)*Arg+(0.0062763±0.0044542)*Gly |
| 0.959 | (-19.3238±3.3296)+(0.12107±0.019814)*Orn+(0.027537±0.049277)*Asn+(0.069398±0.015554)*Tau+(0.0055237±0.0042349)*Gly |
| 0.961 | (-18.9448±2.9119)+(0.12014±0.019826)*Orn+(0.071331±0.015718)*Tau+(0.010419±0.018556)*Ser+(0.0042597±0.0045619)*Gly |
| 0.961 | (-19.1297±3.1121)+(0.12121±0.019625)*Orn+(0.07065±0.015452)*Tau+(0.02317±0.041629)*Cys+(0.005819±0.0043122)*Gly |
| 0.960 | (-16.7867±3.497)+(0.12152±0.01945)*Orn+(0.072276±0.016257)*Tau+(0.0055841±0.0042708)*Gly-(0.0026059±0.0050408)*Gln |
| 0.956 | (-14.9538±2.5757)+(0.12877±0.020339)*Orn+(0.078624±0.018631)*Tau-(0.010969±0.011256)*Lys-(0.012206±0.018488)*Glu |
| 0.961 | (-18.59±2.7758)+(0.12169±0.019697)*Orn+(0.071293±0.015872)*Tau+(0.0053641±0.0042256)*Gly+(0.0029691±0.0078285)*Pro |
| 0.960 | (-18.5036±2.6963)+(0.12051±0.020259)*Orn+(0.070338±0.015521)*Tau+(0.015226±0.042924)*Cit+(0.0050648±0.0042569)*Gly |
| 0.958 | (-18.6005±3.8161)+(0.12178±0.019887)*Orn+(0.069991±0.015462)*Tau+(0.0057445±0.03557)*His+(0.0054392±0.0043157)*Gly |
| 0.953 | (-15.9218±3.3316)+(0.12703±0.020123)*Orn+(0.073943±0.016566)*Tau-(0.015141±0.012263)*Lys+(0.019944±0.03812)*His |
| 0.959 | (-18.4829±3.8828)+(0.122±0.019797)*Orn+(0.070154±0.015452)*Tau+(0.0055158±0.0046361)*Gly+(0.0052467±0.044663)*Phe |
| 0.960 | (-15.1334±2.9706)+(0.12208±0.021243)*Orn+(0.11465±0.051562)*ABA+(0.0677±0.017055)*Tau-(0.015284±0.012643)*Lys-(0.014009±0.020652)*Arg |
| 0.965 | (-17.2453±3.138)+(0.12185±0.02141)*Orn+(0.13151±0.049512)*ABA+(0.069519±0.017241)*Tau-(0.018644±0.01157)*Lys+(0.029891±0.04359)*Cit |
| 0.958 | (-15.3924±2.9015)+(0.12644±0.020022)*Orn+(0.073906±0.016474)*Tau-(0.012851±0.011207)*Lys+(0.017526±0.041956)*Cys |
| 0.957 | (-15.443±2.9753)+(0.12523±0.020767)*Orn+(0.07357±0.016455)*Tau-(0.011744±0.011166)*Lys+(0.01738±0.043012)*Cit |
| 0.957 | (-16.9955±3.5368)+(0.11649±0.019269)*Orn+(0.07474±0.017043)*Tau+(0.019805±0.017832)*Ser-(0.0033327±0.0051152)*Gln |
| 0.965 | (-16.2057±2.6618)+(0.12553±0.02093)*Orn+(0.12836±0.049839)*ABA+(0.073217±0.019014)*Tau-(0.017854±0.011874)*Lys-(0.010834±0.018663)*Glu |

FIG.46

| ROC_AUC | INDEX |
|---|---|
| 0.957 | (-15.2516±2.8289)+(0.12671±0.020095)*Orn+(0.07453±0.016793)*Tau-(0.012361±0.01109)*Lys+(0.0027972±0.0077467)*Pro |
| 0.956 | (-15.3764±3.0419)+(0.12743±0.020153)*Orn+(0.074219±0.016706)*Tau-(0.014818±0.013521)*Lys+(0.016645±0.04953)*Phe |
| 0.955 | (-19.0594±3.0194)+(0.1189±0.019625)*Orn+(0.071213±0.016126)*Tau+(0.011877±0.018273)*Ser+(0.0085376±0.013192)*Thr |
| 0.956 | (-14.501±3.5216)+(0.12704±0.020118)*Orn+(0.074107±0.016988)*Tau-(0.011939±0.011339)*Lys-(0.00079051±0.0052272)*Gln |
| 0.962 | (-16.6521±2.8851)+(0.12505±0.020681)*Orn+(0.12073±0.05037)*ABA+(0.069569±0.017215)*Tau-(0.01946±0.011413)*Lys+(0.0054555±0.012325)*Thr |
| 0.957 | (-17.3504±2.4485)+(0.12296±0.019524)*Orn+(0.080456±0.019638)*Tau-(0.019457±0.019499)*Glu+(0.0054263±0.0077627)*Pro |
| 0.958 | (-18.9819±3.0497)+(0.11594±0.019974)*Orn+(0.071836±0.016003)*Tau+(0.019908±0.041155)*Cit+(0.01608±0.01695)*Ser |
| 0.962 | (-16.7007±2.9989)+(0.1248±0.02073)*Orn+(0.12326±0.049857)*ABA+(0.022533±0.057376)*Asn+(0.069069±0.017342)*Tau-(0.020995±0.012423)*Lys |
| 0.960 | (-16.9071±3.2803)+(0.12483±0.020748)*Orn+(0.12667±0.048956)*ABA+(0.069517±0.017248)*Tau-(0.021506±0.013008)*Lys+(0.014859±0.038227)*His |
| 0.955 | (-17.4241±2.516)+(0.1209±0.019968)*Orn+(0.077842±0.018576)*Tau+(0.028289±0.04244)*Cit-(0.016831±0.018547)*Glu |
| 0.964 | (-16.6244±2.9987)+(0.12481±0.020652)*Orn+(0.12633±0.048703)*ABA+(0.069673±0.017243)*Tau-(0.0197±0.011686)*Lys+(0.014328±0.042673)*Cys |
| 0.956 | (-18.7085±2.8824)+(0.11878±0.020086)*Orn+(0.070304±0.01598)*Tau+(0.018809±0.041018)*Cit+(0.011342±0.011992)*Thr |
| 0.963 | (-16.546±2.9496)+(0.12488±0.020709)*Orn+(0.12471±0.048381)*ABA+(0.069973±0.017441)*Tau-(0.018895±0.011533)*Lys+(0.0024414±0.0078642)*Pro |
| 0.954 | (-17.3193±3.3484)+(0.12225±0.01963)*Orn+(0.07015±0.015913)*Tau+(0.012026±0.011768)*Thr-(0.017673±0.041897)*Phe |
| 0.963 | (-16.6375±3.1396)+(0.1239±0.021114)*Orn+(0.12328±0.05014)*ABA+(0.069822±0.017209)*Tau-(0.018815±0.011633)*Lys+(0.0048877±0.017383)*Ser |
| 0.955 | (-17.1154±3.674)+(0.12022±0.019365)*Orn+(0.071544±0.016556)*Tau+(0.011845±0.011777)*Thr-(0.0020435±0.0048671)*Gln |
| 0.962 | (-16.5009±3.0088)+(0.12525±0.020791)*Orn+(0.12661±0.048689)*ABA+(0.069932±0.017499)*Tau-(0.021063±0.014257)*Lys+(0.011257±0.047991)*Phe |
| 0.962 | (-15.6894±3.5721)+(0.12471±0.020781)*Orn+(0.12699±0.048632)*ABA+(0.069928±0.017577)*Tau-(0.01858±0.011868)*Lys-(0.0010955±0.0054093)*Gln |
| 0.956 | (-17.7392±3.592)+(0.11906±0.019562)*Orn+(0.071741±0.015937)*Tau+(0.016295±0.016884)*Ser-(0.01316±0.04147)*Phe |
| 0.956 | (-17.4252±3.4674)+(0.12218±0.019758)*Orn+(0.070429±0.016017)*Tau-(0.013073±0.037605)*His+(0.013008±0.01241)*Thr |
| 0.954 | (-17.6372±2.9399)+(0.12222±0.019715)*Orn+(0.026277±0.049313)*Asn+(0.075639±0.018356)*Tau-(0.015731±0.018199)*Glu |
| 0.960 | (-16.8534±3.1962)+(0.10701±0.0203)*Orn+(0.10003±0.050678)*ABA+(0.06274±0.015966)*Tau+(0.044225±0.042611)*Cit-(0.02854±0.019622)*Arg |
| 0.957 | (-18.8051±3.1812)+(0.11775±0.019472)*Orn+(0.071679±0.015913)*Tau+(0.016257±0.01691)*Ser+(0.0097408±0.04054)*Cys |
| 0.956 | (-18.6869±3.0183)+(0.11787±0.019499)*Orn+(0.072154±0.016241)*Tau+(0.016043±0.017017)*Ser+(0.0018389±0.0082523)*Pro |
| 0.957 | (-18.0673±3.7164)+(0.11867±0.019642)*Orn+(0.07185±0.016046)*Tau-(0.0058519±0.035884)*His+(0.016733±0.016959)*Ser |
| 0.955 | (-18.4688±2.9789)+(0.12066±0.019572)*Orn+(0.070053±0.015882)*Tau+(0.011416±0.011947)*Thr+(0.0074344±0.04067)*Cys |
| 0.956 | (-18.5134±3.1246)+(0.11812±0.019464)*Orn+(0.0019794±0.054846)*Asn+(0.071462±0.016269)*Tau+(0.016149±0.018901)*Ser |
| 0.969 | (-18.7523±3.7276)+(0.113±0.019406)*Orn+(0.1251±0.051796)*ABA+(0.067678±0.016948)*Tau+(0.0074773±0.004798)*Gly-(0.0037986±0.0051193)*Gln |
| 0.954 | (-15.4009±3.3609)+(0.12309±0.019345)*Orn+(0.078499±0.019084)*Tau-(0.015775±0.018471)*Glu-(0.0022103±0.0050168)*Gln |
| 0.954 | (-18.3078±2.7875)+(0.12089±0.019546)*Orn+(0.070213±0.016175)*Tau+(0.01136±0.012289)*Thr+(0.00081458±0.0083387)*Pro |
| 0.954 | (-18.2094±3.014)+(0.12105±0.019674)*Orn-(0.0006951±0.057881)*Asn+(0.069972±0.016096)*Tau+(0.011754±0.013793)*Thr |
| 0.956 | (-17.1497±2.558)+(0.1225±0.019524)*Orn+(0.076857±0.018187)*Tau-(0.016223±0.018831)*Glu+(0.016467±0.041107)*Cys |
| 0.968 | (-20.2653±2.9258)+(0.11461±0.019626)*Orn+(0.012258±0.052273)*ABA+(0.070424±0.018584)*Tau-(0.012486±0.019107)*Glu+(0.006434±0.0047459)*Gly |
| 0.969 | (-21.4281±3.2379)+(0.11071±0.020303)*Orn+(0.12466±0.051865)*ABA+(0.065485±0.016138)*Tau+(0.027746±0.043453)*Cit+(0.0067213±0.0047096)*Gly |

FIG.48

| ROC_AUC | INDEX |
|---|---|
| 0.961 | (0.60856±0.087736)+(0.0046856±0.00096352)*Tau+(0.0056995±0.00080118)*Orn-(0.0019094±0.00066898)*Arg |
| 0.958 | (0.59106±0.09042)+(0.0047622±0.00096749)*Tau+(0.00555±0.0008226)*Orn-(0.0019886±0.00067586)*Arg+(0.00022657±0.00028749)*Pro |
| 0.964 | (0.58724±0.094181)+(0.0046304±0.00096728)*Tau+(0.0056025±0.00081601)*Orn+(0.0013516±0.0021761)*ABA-(0.0019022±0.00066887)*Arg |
| 0.965 | (0.59789±0.089622)+(0.0046587±0.00096443)*Tau+(0.005516±0.00086116)*Orn+(0.0011184±0.0019269)*Cit-(0.0020575±0.00071586)*Arg |
| 0.963 | (0.58333±0.10164)+(0.0046678±0.00096424)*Tau+(0.0056052±0.00082389)*Orn-(0.00194±0.00067191)*Arg+(0.0003358±0.00068304)*Ser |
| 0.966 | (0.58416±0.10177)+(0.0046442±0.00096756)*Tau+(0.0055926±0.00083249)*Orn-(0.0020008±0.00069634)*Arg+(0.00094878±0.0020047)*Asn |
| 0.964 | (0.59222±0.094595)+(0.0046434±0.00096794)*Tau+(0.0056806±0.00080233)*Orn-(0.0019185±0.00066935)*Arg+(9.1092e-005±0.00019707)*Gly |
| 0.964 | (0.57354±0.11869)+(0.0046822±0.00096372)*Tau+(0.00561±0.00082695)*Orn-(0.0019841±0.00069043)*Arg+(0.00058705±0.0013396)*His |
| 0.961 | (0.62598±0.096563)+(0.0047168±0.00096641)*Tau+(0.0057731±0.00081922)*Orn-(0.0018653±0.00067686)*Arg-(0.00074181±0.0017162)*Cys |
| 0.960 | (0.63217±0.11135)+(0.0047253±0.00097073)*Tau+(0.0057685±0.0008261)*Orn-(0.0018362±0.00070217)*Arg-(6.6132e-005±0.00019191)*Gln |
| 0.963 | (0.61665±0.096165)+(0.0046948±0.00096512)*Tau+(0.0057924±0.0009196)*Orn-(0.00010346±0.00050208)*Lys-(0.0018367±0.00075672)*Arg |
| 0.963 | (0.60506±0.092665)+(0.0046827±0.00096445)*Tau+(0.0056712±0.00083677)*Orn-(0.0019346±0.00070259)*Arg+(6.7733e-005±0.00057353)*Thr |
| 0.964 | (0.60483±0.093404)+(0.0046797±0.00096546)*Tau+(0.0056815±0.00081643)*Orn-(0.0019255±0.00068334)*Arg+(1.8558e-005±0.00015867)*Ala |
| 0.962 | (0.60922±0.088907)+(0.0046876±0.00096514)*Tau+(0.0057092±0.00082785)*Orn-(0.0019089±0.00066952)*Arg-(3.0077e-005±0.00064008)*Glu |
| 0.960 | (0.6124±0.097672)+(0.0048142±0.00097151)*Tau+(0.0056305±0.00083419)*Orn-(0.001939±0.00068117)*Arg+(0.00025552±0.00029178)*Pro-(0.0010038±0.0017398)*Cys |
| 0.961 | (0.57262±0.096142)+(0.0047079±0.00097213)*Tau+(0.0054698±0.00083469)*Orn+(0.0012296±0.0021806)*ABA-(0.0019777±0.00067603)*Arg+(0.00021433±0.00028827)*Pro |
| 0.962 | (0.58196±0.092007)+(0.0047343±0.00096884)*Tau+(0.0053872±0.00087726)*Orn+(0.0010301±0.0019289)*Cit-(0.0021217±0.00072033)*Arg+(0.00021723±0.000288)*Pro |
| 0.961 | (0.56385±0.10437)+(0.0047452±0.000968)*Tau+(0.0054461±0.0008463)*Orn-(0.0020231±0.00067905)*Arg+(0.0003565±0.00068282)*Ser+(0.00023221±0.00028768)*Pro |
| 0.961 | (0.57186±0.097679)+(0.0047183±0.00097115)*Tau+(0.005217±0.00082438)*Orn-(0.0020025±0.00067637)*Arg+(0.00023713±0.0002882)*Pro+(0.00010255±0.00019735)*Gly |
| 0.960 | (0.56981±0.10343)+(0.0047224±0.00097223)*Tau+(0.0054595±0.00085011)*Orn-(0.0020677±0.00070133)*Arg+(0.00084999±0.0020073)*Asn+(0.00021865±0.00028816)*Pro |
| 0.959 | (0.5751±0.09624)+(0.0045998±0.00096831)*Tau+(0.0054054±0.00087754)*Orn+(0.0014115±0.0021777)*ABA+(0.0011748±0.001928)*Cit-(0.0020574±0.00071556)*Arg |
| 0.959 | (0.61514±0.11331)+(0.0048031±0.00097477)*Tau+(0.0056199±0.0008464)*Orn-(0.001914±0.00070836)*Arg+(0.00022759±0.00028761)*Pro-(6.766e-005±0.00019174)*Gln |
| 0.958 | (0.56299±0.10306)+(0.0045678±0.00097312)*Tau+(0.0055625±0.00081877)*Orn+(0.0015734±0.0022091)*ABA-(0.0019125±0.00066897)*Arg+(0.00011579±0.00019998)*Gly |
| 0.958 | (0.5668±0.11896)+(0.0047547±0.0009682)*Tau+(0.0054949±0.00084145)*Orn-(0.0020375±0.00069387)*Arg+(0.000426±0.0013569)*His+(0.0002116±0.00029154)*Pro |
| 0.959 | (0.59335±0.090773)+(0.0047855±0.00097096)*Tau+(0.0055972±0.00083747)*Orn-(0.0019951±0.0006765)*Arg-(0.00020448±0.00067195)*Glu+(0.00025488±0.0003023)*Pro |
| 0.968 | (0.60646±0.1003)+(0.0046621±0.00096883)*Tau+(0.0056825±0.00082848)*Orn+(0.0015785±0.0022137)*ABA-(0.0018432±0.00067713)*Arg-(0.00097103±0.0017449)*Cys |
| 0.958 | (0.59943±0.098513)+(0.004772±0.00096913)*Tau+(0.0056462±0.00093716)*Orn-(0.00010773±0.00050162)*Lys-(0.0019131±0.00076215)*Arg+(0.00022723±0.00028767)*Pro |
| 0.958 | (0.59582±0.093986)+(0.0047795±0.0009725)*Tau+(0.0055669±0.00082806)*Orn-(0.0019685±0.00068476)*Arg+(0.00024791±0.00030952)*Pro-(3.1863e-005±0.00017056)*Ala |
| 0.958 | (0.59144±0.094218)+(0.0047627±0.00096904)*Tau+(0.005553±0.00084968)*Orn-(0.0019858±0.00070501)*Arg-(8.289e-006±0.00058127)*Thr+(0.00022727±0.00029183)*Pro |
| 0.969 | (0.57197±0.10343)+(0.0046402±0.00096516)*Tau+(0.0054169±0.00088353)*Orn+(0.0011355±0.0019272)*Cit-(0.002091±0.00071898)*Arg+(0.0003429±0.00068299)*Ser |
| 0.971 | (0.56813±0.10523)+(0.0046208±0.00096781)*Tau+(0.0055327±0.00083402)*Orn+(0.0012241±0.002199)*ABA-(0.0019285±0.00067214)*Arg+(0.00028116±0.00068997)*Ser |
| 0.967 | (0.61597±0.09797)+(0.0046909±0.00096713)*Tau+(0.0055878±0.00087547)*Orn+(0.0011555±0.0019288)*Cit-(0.0020157±0.00072177)*Arg-(0.00078508±0.0017173)*Cys |
| 0.966 | (0.56169±0.12035)+(0.0046548±0.00096462)*Tau+(0.0054209±0.00088676)*Orn+(0.001137±0.0019276)*Cit-(0.0021367±0.00073722)*Arg+(0.00060392±0.0013396)*His |

FIG.49

| ROC_AUC | INDEX |
|---|---|
| 0.971 | (0.57554±0.10294)+(0.0046212±0.00096833)*Tau+(0.0054239±0.00088621)*Orn+(0.001071±0.0019302)*Cit-(0.0021367±0.00073805)*Arg+(0.00088691±0.0020076)*Asn |
| 0.965 | (0.59911±0.099359)+(0.0046391±0.00096786)*Tau+(0.005762±0.00092009)*Orn+(0.0015658±0.0022502)*ABA-(0.0001949±0.0005187)*Lys-(0.001764±0.00076345)*Arg |
| 0.968 | (0.55843±0.12151)+(0.0046317±0.00096759)*Tau+(0.0055315±0.00083785)*Orn+(0.0012658±0.0021887)*ABA-(0.0019669±0.00069094)*Arg+(0.00050575±0.0013467)*His |
| 0.968 | (0.61361±0.11506)+(0.0046936±0.00097163)*Tau+(0.005663±0.00084222)*Orn-(0.0019163±0.00071308)*Arg+(0.0013667±0.0021443)*Asn-(0.00011259±0.00020522)*Gln |
| 0.966 | (0.02583±0.11177)+(0.0047049±0.00097094)*Tau+(0.0055842±0.0008700)*Orn+(0.0012173±0.0019417)*Cit-(0.001981±0.00073898)*Arg-(8.0882e-005±0.00019328)*Gln |
| 0.968 | (0.57184±0.10441)+(0.0046068±0.00097012)*Tau+(0.0055355±0.00083946)*Orn+(0.0011795±0.0022342)*ABA-(0.0019709±0.0006980)*Arg+(0.00070446±0.0020573)*Asn |
| 0.966 | (0.61041±0.11679)+(0.0046695±0.00097464)*Tau+(0.0056704±0.00084105)*Orn+(0.001341±0.0021772)*ABA-(0.0018309±0.00070201)*Arg-(6.4413e-005±0.00019187)*Gln |
| 0.970 | (0.58498±0.095597)+(0.0046253±0.00096852)*Tau+(0.0055164±0.0008614)*Orn+(0.0010185±0.0019444)*Cit-(0.002052±0.00071621)*Arg+(7.7346e-005±0.00019881)*Gly |
| 0.963 | (0.54702±0.1284)+(0.0046316±0.00096818)*Tau+(0.0055693±0.0008303)*Orn-(0.00201±0.00069204)*Arg+(0.00070684±0.0013576)*His+(0.00010806±0.00019974)*Gly |
| 0.966 | (0.54532±0.13084)-(0.0046636±0.0009644)*Tau+(0.0055067±0.00085117)*Orn-(0.00202±0.00069399)*Arg+(0.00035038±0.00068386)*Ser+(0.0006188±0.001341)*His |
| 0.967 | (0.61045±0.11749)+(0.0047185±0.00097061)*Tau+(0.0056802±0.00083993)*Orn-(0.0018462±0.00070225)*Arg+(0.00040457±0.00069928)*Ser-(9.04[illegible]e-005±0.00019641)*Gln |
| 0.965 | (0.60122±0.10788)+(0.0046751±0.0009698)*Tau+(0.0056644±0.00084602)*Orn-(0.0019603±0.00070156)*Arg+(0.0010361±0.0020132)*Asn-(0.00082242±0.0017233)*Cys |
| 0.965 | (0.58885±0.12285)+(0.0047177±0.00096647)*Tau+(0.0056819±0.00084025)*Orn-(0.0019435±0.00069555)*Arg+(0.00065902±0.0013479)*His-(0.00083504±0.0017268)*Cys |
| 0.965 | (0.60077±0.1095)+(0.0046989±0.00096716)*Tau+(0.0056788±0.00084176)*Orn-(0.0018961±0.00067983)*Arg+(0.00033351±0.0006832)*Ser-(0.00073526±0.0017163)*Cys |
| 0.965 | (0.57008±0.10681)+(0.0046067±0.00097157)*Tau+(0.0055806±0.0008331)*Orn-(0.0020044±0.00069652)*Arg+(0.00089718±0.0020086)*Asn+(8.5883e-005±0.00019745)*Gly |
| 0.967 | (0.62003±0.1136)+(0.0046874±0.0009732)*Tau+(0.0057673±0.00082604)*Orn-(0.0018244±0.00070246)*Arg-(8.6506e-005±0.00019559)*Gln+(0.00010827±0.0002009)*Gly |
| 0.966 | (0.58852±0.094642)+(0.0046348±0.00096834)*Tau+(0.0056295±0.00083698)*Orn+(0.0014025±0.002205)*ABA-(0.0019003±0.00066941)*Arg-(9.5006e-005±0.00064793)*Glu |
| 0.968 | (0.59719±0.13022)+(0.0047335±0.00097084)*Tau+(0.0056818±0.00084288)*Orn-(0.0019036±0.00071412)*Arg+(0.0007088±0.0013678)*His-(8.6581e-005±0.00019592)*Gln |
| 0.966 | (0.58671±0.09799)+(0.0046297±0.00096865)*Tau+(0.0055999±0.00082709)*Orn+(0.0013447±0.0022048)*ABA-(0.001905±0.00068396)*Arg+(3.2194e-006±0.00016061)*Ala |
| 0.965 | (0.58746±0.097033)+(0.0046305±0.00096797)*Tau+(0.0056045±0.00084366)*Orn+(0.0013559±0.0022249)*ABA-(0.0019001±0.00070467)*Arg-(5.5151e-006±0.00058583)*Thr |
| 0.966 | (0.59107±0.096142)+(0.0046475±0.00096668)*Tau+(0.0054769±0.00088428)*Orn+(0.00117±0.0019457)*Cit-(0.0020916±0.00073691)*Arg+(3.1516e-005±0.00016009)*Ala |
| 0.964 | (0.60913±0.1054)+(0.0046754±0.00097223)*Tau+(0.0057458±0.00082229)*Orn-(0.0018797±0.000678)*Arg+(7.9696e-005±0.00019961)*Gly-(0.00063302±0.0017381)*Cys |
| 0.967 | (0.57194±0.10776)+(0.0046424±0.00096794)*Tau+(0.0055513±0.00084134)*Orn-(0.0019985±0.00069663)*Arg+(0.00068527±0.0021452)*Asn+(0.0002529±0.00073094)*Ser |
| 0.968 | (0.59549±0.094135)+(0.0046569±0.00096532)*Tau+(0.0054974±0.00088972)*Orn+(0.0011088±0.0019315)*Cit-(0.0020742±0.00074336)*Arg+(4.8303e-005±0.00057443)*Thr |
| 0.963 | (0.60059±0.10056)+(0.0046622±0.00096688)*Tau+(0.0055486±0.0010224)*Orn+(0.0010881±0.001995)*Cit-(3.0727e-005±0.00051944)*Lys-(0.0020319±0.00083702)*Arg |
| 0.962 | (0.59749±0.09117)+(0.0046575±0.00096635)*Tau+(0.00551±0.00089645)*Orn+(0.0011242±0.0019429)*Cit-(0.0020585±0.0007[illegible]76)*Arg+(1.5776e-005±0.00064484)*Glu |
| 0.962 | (0.57849±0.10303)+(0.0046433±0.00096832)*Tau+(0.0056161±0.00082511)*Orn-(0.0019385±0.00067224)*Arg+(0.00025053±0.0007428)*Ser+(6.2761e-005±0.0002143)*Gly |
| 0.964 | (0.57912±0.11976)+(0.0046982±0.0009651)*Tau+(0.0057553±0.00092226)*Orn-(0.00018782±0.00052707)*Lys-(0.0018714±0.00075956)*Arg+(0.00073965±0.0014068)*His |
| 0.967 | (0.59315±0.10644)+(0.0046531±0.0009685)*Tau+(0.0057139±0.000932[illegible]2)*Orn-(0.00014762±0.00050934)*Lys-(0.0019066±0.00076877)*Arg+(0.001048±0.0020347)*Asn |
| 0.963 | (0.64987±0.1186)+(0.004757±0.00097366)*Tau+(0.005843±0.00084389)*Orn-(0.0017912±0.0007099)*Arg-(6.6674e-005±0.00019195)*Gln-(0.00074569±0.0017168)*Cys |
| 0.965 | (0.5652±0.12126)+(0.0046515±0.00096835)*Tau+(0.0055546±0.00084332)*Orn-(0.002032±0.00070506)*Arg+(0.00072759±0.0021478)*Asn+(0.00041316±0.001435)*His |
| 0.962 | (0.57632±0.10883)+(0.0046578±0.00096641)*Tau+(0.0055726±0.00084387)*Orn-(0.0019665±0.00068806)*Arg+(0.00035169±0.00068907)*Ser+(2.896e-005±0.00015958)*Ala |
| 0.964 | (0.59063±0.11058)+(0.0046759±0.00096602)*Tau+(0.0056837±0.00094752)*Orn-(8.4667e-005±0.00050366)*Lys-(0.0018797±0.00076214)*Arg+(0.00032678±0.00068557)*Ser |

FIG.50

| ROC_AUC | INDEX |
|---|---|
| 0.965 | (0.58406±0.10246)+(0.0046686±0.00096497)*Tau+(0.0056159±0.00084472)*Orn-(0.0019281±0.00070277)*Arg+(0.00035073±0.00073005)*Ser-(3.5671e-005±0.00061263)*Thr |
| 0.965 | (0.58347±0.10333)+(0.0046682±0.00096601)*Tau+(0.0056068±0.00085396)*Orn-(0.0019399±0.00067256)*Arg+(0.00033539±0.00068575)*Ser-(4.737e-006±0.00064221)*Glu |
| 0.965 | (0.62084±0.099442)+(0.0047092±0.00096759)*Tau+(0.005747±0.00082836)*Orn-(0.0018909±0.00068736)*Arg+(3.5498e-005±0.00016274)*Ala-(0.00082695±0.0017609)*Cys |
| 0.963 | (0.58494±0.10216)+(0.0046428±0.00096832)*Tau+(0.0056078±0.00084775)*Orn-(0.0019869±0.00071149)*Arg+(0.0010421±0.0022264)*Asn-(6.1523e-005±0.00063661)*Thr |
| 0.963 | (0.58771±0.10035)+(0.0046361±0.00097006)*Tau+(0.0056595±0.00081788)*Orn-(0.0019372±0.00068388)*Arg+(2.1515e-005±0.00015882)*Ala+(9.2158e-005±0.00019736)*Gly |
| 0.964 | (0.59779±0.10571)+(0.004651±0.00097068)*Tau+(0.005736±0.00092909)*Orn-(6.0592e-005±0.00051197)*Lys-(0.0018754±0.0007622)*Arg+(8.6459e-005±0.00020105)*Gly |
| 0.964 | (0.58329±0.10451)+(0.0046429±0.00096889)*Tau+(0.0055883±0.00084133)*Orn-(0.0020047±0.00070483)*Arg+(0.00093595±0.0020357)*Asn+(5.9678e-006±0.00016104)*Ala |
| 0.966 | (0.58467±0.10303)+(0.0046457±0.00096931)*Tau+(0.0055996±0.00085993)*Orn-(0.0020003±0.00069701)*Arg+(0.00094679±0.002007)*Asn-(2.0926e-005±0.00064044)*Glu |
| 0.965 | (0.58937±0.09881)+(0.0046413±0.00096881)*Tau+(0.0056566±0.00083749)*Orn-(0.0019399±0.00070278)*Arg+(5.7849e-005±0.00057402)*Thr+(9.0344e-005±0.00019734)*Gly |
| 0.966 | (0.59055±0.097558)+(0.0046386±0.00097099)*Tau+(0.0056648±0.00083345)*Orn-(0.0019196±0.00067)*Arg+(4.6791e-005±0.00066116)*Glu+(9.4697e-005±0.00020368)*Gly |
| 0.966 | (0.6305±0.10213)+(0.0047214±0.00096761)*Tau+(0.0058318±0.000925)*Orn-(6.9669e-005±0.00050914)*Lys-(0.0018187±0.00075823)*Arg-(0.00070263±0.001741)*Cys |
| 0.966 | (0.62216±0.10059)+(0.0047139±0.00096726)*Tau+(0.0057414±0.00085215)*Orn-(0.0018938±0.00070888)*Arg+(7.8325e-005±0.00057415)*Thr-(0.0007517±0.0017188)*Cys |
| 0.966 | (0.57397±0.11884)+(0.0046866±0.0009653)*Tau+(0.0056286±0.00084742)*Orn-(0.0019851±0.00069097)*Arg-(6.5485e-005±0.00064506)*Glu+(0.00060388±0.0013507)*His |
| 0.966 | (0.62577±0.096661)+(0.0047149±0.00096734)*Tau+(0.0057599±0.00083609)*Orn-(0.0018637±0.0006776)*Arg+(5.3724e-005±0.00066832)*Glu-(0.00078317±0.0017928)*Cys |
| 0.966 | (0.57337±0.11929)+(0.0046819±0.00096466)*Tau+(0.005607±0.00085067)*Orn-(0.0019868±0.00071352)*Arg+(0.0005821±0.0013794)*His+(8.9768e-006±0.00059031)*Thr |
| 0.965 | (0.57362±0.11914)+(0.0046827±0.00096569)*Tau+(0.0056109±0.00083355)*Orn-(0.0019832±0.00069705)*Arg+(0.00059063±0.0013991)*His-(1.4783e-006±0.00016565)*Ala |
| 0.962 | (0.63787±0.11616)+(0.0047312±0.00097192)*Tau+(0.0058438±0.00093339)*Orn-(8.7641e-005±0.00050462)*Lys-(0.0017781±0.00077803)*Arg-(6.2911e-005±0.00019292)*Gln |
| 0.965 | (0.62871±0.11346)+(0.0047236±0.00097139)*Tau+(0.0057335±0.00085456)*Orn-(0.0018667±0.0007275)*Arg+(9.3467e-005±0.00057813)*Thr-(6.9982e-005±0.0001935)*Gln |
| 0.964 | (0.63515±0.11462)+(0.0047325±0.00097355)*Tau+(0.0057959±0.00086265)*Orn-(0.0018307±0.0007044)*Arg-(7.2279e-005±0.00065102)*Glu-(7.0049e-005±0.00019525)*Gln |
| 0.965 | (0.62851±0.11627)+(0.0047195±0.00097279)*Tau+(0.005751±0.00084165)*Orn-(0.0018518±0.00071671)*Arg-(6.5731e-005±0.00019207)*Gln+(1.753e-005±0.00015876)*Ala |
| 0.965 | (0.61269±0.099247)+(0.004688±0.00096663)*Tau+(0.0057822±0.0009223)*Orn-(0.00012075±0.00051347)*Lys-(0.0018474±0.00076003)*Arg+(2.6445e-005±0.00016226)*Ala |
| 0.963 | (0.61305±0.099685)+(0.0046921±0.00096595)*Tau+(0.005765±0.00094116)*Orn-(0.00011014±0.00050471)*Lys-(0.0018617±0.00077841)*Arg+(7.9768e-005±0.0005765)*Thr |
| 0.963 | (0.61663±0.096343)+(0.0046947±0.00096636)*Tau+(0.0057921±0.00092566)*Orn-(0.00010384±0.00051788)*Lys-(0.0018365±0.00076118)*Arg+(2.0227e-006±0.00066016)*Glu |
| 0.964 | (0.60222±0.096857)+(0.0046779±0.00096625)*Tau+(0.0056589±0.00084612)*Orn-(0.0019456±0.00071133)*Arg+(5.9421e-005±0.00057976)*Thr+(1.6229e-005±0.0001604)*Ala |
| 0.963 | (0.60528±0.093624)+(0.0046822±0.00096659)*Tau+(0.0056955±0.00083457)*Orn-(0.0019278±0.00068439)*Arg-(5.4926e-005±0.00066638)*Glu+(2.2316e-005±0.0001652)*Ala |
| 0.964 | (0.60572±0.093497)+(0.004685±0.000966)*Tau+(0.0056818±0.00085864)*Orn-(0.0019349±0.00070308)*Arg-(3.5559e-005±0.00064208)*Glu+(6.997e-005±0.00057534)*Thr |
| 0.964 | (0.5944±0.1012)+(0.004759±0.00097444)*Tau+(0.0055497±0.0008423)*Orn+(0.0014944±0.0022133)*ABA-(0.0019155±0.00068171)*Arg+(0.00024665±0.00029193)*Pro-(0.0012117±0.001766)*Cys |
| 0.965 | (0.54573±0.10532)+(0.0046441±0.00097715)*Tau+(0.0054202±0.00083818)*Orn+(0.0014628±0.0022116)*ABA-(0.0019926±0.00067622)*Arg+(0.00022488±0.00028866)*Pro+(0.00012492±0.00020014)*Gly |
| 0.964 | (0.60363±0.09894)+(0.0047869±0.00097264)*Tau+(0.0054643±0.00088658)*Orn+(0.001067±0.0019294)*Cit-(0.0020754±0.00072436)*Arg+(0.00024674±0.00029218)*Pro-(0.0010348±0.0017405)*Cys |
| 0.976 | (0.56209±0.097929)+(0.0046757±0.00097366)*Tau+(0.0052939±0.0008911)*Orn+(0.001291±0.002183)*ABA+(0.0010871±0.0019308)*Cit-(0.0021177±0.00072019)*Arg+(0.00020387±0.00028882)*Pro |
| 0.964 | (0.5852±0.11073)+(0.0047973±0.00097202)*Tau+(0.0055266±0.0008576)*Orn-(0.0019735±0.00068436)*Arg+(0.00035595±0.00068269)*Ser+(0.00026111±0.00029197)*Pro-(0.0010026±0.0017398)*Cys |
| 0.963 | (0.55417±0.10587)+(0.0047167±0.00096935)*Tau+(0.0052791±0.00090054)*Orn+(0.0010458±0.001929)*Cit-(0.0021588±0.00072367)*Arg+(0.0003622±0.00068284)*Ser+(0.00022282±0.00028818)*Pro |
| 0.962 | (0.59006±0.10854)+(0.0047733±0.00097547)*Tau+(0.0055346±0.00085864)*Orn-(0.0020241±0.0007047)*Arg+(0.00095015±0.0020133)*Asn+(0.0002486±0.00029218)*Pro-(0.0010706±0.0017457)*Cys |
| 0.961 | (0.59356±0.10668)+(0.0047708±0.00097669)*Tau+(0.0055972±0.00083776)*Orn-(0.0019565±0.00068246)*Arg+(0.00026127±0.00029213)*Pro+(8.7692e-005±0.00019953)*Gly-(0.00089±0.0017593)*Cys |

FIG.52

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| -2.00 | 1.00 | 0.01 | 0.043 | 1.000 | 0.05 |
| -1.00 | 1.00 | 0.18 | 0.051 | 1.000 | 0.22 |
| 0.00 | 1.00 | 0.60 | 0.098 | 1.000 | 0.61 |
| 0.50 | 1.00 | 0.77 | 0.160 | 1.000 | 0.78 |
| 1.00 | 0.94 | 0.89 | 0.269 | 0.997 | 0.89 |
| 1.50 | 0.90 | 0.94 | 0.394 | 0.995 | 0.94 |
| 1.60 | 0.90 | 0.94 | 0.418 | 0.996 | 0.94 |
| 1.70 | 0.90 | 0.96 | 0.475 | 0.996 | 0.95 |
| 1.80 | 0.90 | 0.96 | 0.509 | 0.996 | 0.96 |
| 1.86 | 0.90 | 0.97 | 0.560 | 0.996 | 0.97 |
| 1.90 | 0.84 | 0.97 | 0.542 | 0.993 | 0.96 |
| 2.00 | 0.84 | 0.98 | 0.605 | 0.993 | 0.97 |
| 2.10 | 0.81 | 0.98 | 0.610 | 0.991 | 0.97 |
| 2.20 | 0.81 | 0.98 | 0.641 | 0.991 | 0.97 |
| 2.50 | 0.81 | 0.99 | 0.833 | 0.992 | 0.99 |
| 3.00 | 0.71 | 1.00 | 0.880 | 0.987 | 0.98 |
| 4.00 | 0.48 | 1.00 | 1.000 | 0.978 | 0.98 |
| 5.00 | 0.32 | 1.00 | 1.000 | 0.971 | 0.97 |
| 6.00 | 0.13 | 1.00 | 1.000 | 0.963 | 0.96 |

FIG.53

| ROC_AUC | INDEX |
|---|---|
| 0.981 | (0.63432±0.12305)+(0.0041163±0.00079982)*Orn-(0.0021169±0.00063151)*Arg+(0.0031553±0.00096546)*Tau+(0.0022322±0.0020167)*ABA+(0.00019583±0.00018346)*Gly+(0.00087628±0.001234)*His |
| 0.986 | (0.58868±0.1221)+(0.0044007±0.00081703)*Orn+(0.003365±0.00097173)*Tau+(0.0026173±0.0020373)*ABA+(0.00011198±0.00018529)*Gly+(0.00085162±0.0012629)*His-(0.0032518±0.0012038)*Trp |
| 0.982 | (0.52078±0.12171)+(0.0040694±0.00082282)*Orn+(0.0034456±0.00098938)*Tau+(0.0024308±0.0020741)*ABA+(0.00014901±0.00018822)*Gly-(0.0001433±0.0012305)*His |
| 0.983 | (0.65552±0.12326)+(0.00391±0.00085716)*Orn-(0.0024083±0.00067995)*Arg+(0.0032904±0.00095667)*Tau+(0.00039648±0.00062368)*Ser+(0.0019512±0.0017588)*Cit+(0.00085863±0.001216)*His |
| 0.985 | (0.65722±0.12489)+(0.0042457±0.00080195)*Orn-(0.0021547±0.00063631)*Arg+(0.0032815±0.00096133)*Tau+(0.00018495±0.00067687)*Ser+(0.00014177±0.00019675)*Gly+(0.00097319±0.0012345)*His |
| 0.982 | (0.51415±0.1225)+(0.0039973±0.00083633)*Orn+(0.0035019±0.00099629)*Tau+(0.0023794±0.002077)*ABA+(0.00015174±0.00018832)*Gly-(0.00024925±0.0012501)*His+(0.00013072±0.00027084)*Pro |
| 0.981 | (0.65515±0.12016)+(0.0039975±0.00083853)*Orn-(0.0023707±0.0006745)*Arg+(0.0032503±0.00095958)*Tau+(0.0017462±0.0017703)*Cit+(0.00014041±0.00018248)*Gly+(0.0009795±0.0012313)*His |
| 0.983 | (0.53226±0.12623)+(0.0041121±0.00083242)*Orn+(0.0034373±0.00099004)*Tau+(0.0026034±0.0021343)*ABA-(0.00024529±0.00071097)*Ser+(0.00017967±0.0002082)*Gly-(0.00013117±0.0012315)*His |
| 0.979 | (0.52957±0.12171)+(0.0042308±0.00083469)*Orn+(0.0034224±0.0009873)*Tau+(0.0028574±0.0021074)*ABA+(0.00017522±0.00018937)*Gly+(0.00026242±0.0012851)*His-(0.00057966±0.00054262)*Thr |
| 0.983 | (0.56938±0.12426)+(0.004652±0.000887)*Orn+(0.003443±0.00098259)*Tau+(0.0030729±0.0020946)*ABA+(0.00012445±0.0001875)*Gly-(0.00076693±0.00045407)*Lys+(0.00061819±0.0013026)*His |
| 0.981 | (0.65635±0.12015)+(0.0041469±0.00080023)*Orn-(0.0021994±0.00063545)*Arg+(0.0033758±0.00096423)*Tau+(0.0001705±0.00018137)*Gly+(0.00080768±0.0012458)*His+(0.00024363±0.00026461)*Pro |
| 0.987 | (0.66376±0.12285)+(0.0041498±0.00080992)*Orn-(0.0021037±0.00063671)*Arg+(0.0032663±0.00096107)*Tau+(0.0017367±0.0020183)*ABA+(0.00028945±0.00063165)*Ser+(0.00071013±0.001225)*His |
| 0.981 | (0.52609±0.12417)+(0.0041334±0.00087353)*Orn+(0.0034469±0.00098996)*Tau+(0.0024166±0.0020763)*ABA-(0.00037391±0.0017065)*Cit+(0.00015471±0.00019011)*Gly-(0.00011883±0.0012363)*His |
| 0.981 | (0.66681±0.1198)+(0.0042877±0.00078671)*Orn-(0.0021374±0.00063287)*Arg+(0.0032855±0.00096074)*Tau+(0.0001625±0.00018144)*Gly+(0.00097956±0.0012337)*His |
| 0.981 | (0.52185±0.12251)+(0.0040839±0.00084239)*Orn+(0.0034488±0.00099083)*Tau+(0.0024502±0.0020891)*ABA+(0.00014557±0.00019302)*Gly-(0.00013604±0.0012346)*His-(5.0744e-005±0.00062196)*Glu |
| 0.985 | (0.67628±0.12215)+(0.0042503±0.00080247)*Orn-(0.0021376±0.00063631)*Arg+(0.0033458±0.00095785)*Tau+(0.00037305±0.00062494)*Ser+(0.00082814±0.0012188)*His |
| 0.983 | (0.66655±0.12245)+(0.0041115±0.00081618)*Orn-(0.0021979±0.00063895)*Arg+(0.0034365±0.00096181)*Tau+(0.00039104±0.00062436)*Ser+(0.00065366±0.0012326)*His+(0.00023706±0.00026479)*Pro |
| 0.987 | (0.58994±0.12957)+(0.0042585±0.00082816)*Orn+(0.0035655±0.00098741)*Tau+(0.0024174±0.0020632)*ABA+(0.00021946±0.00019304)*Gly+(0.00044353±0.0012852)*His-(0.00027185±0.00018137)*Gln |
| 0.984 | (0.53292±0.12283)+(0.004139±0.0008281)*Orn+(0.0034711±0.00098938)*Tau+(0.0027743±0.0021284)*ABA-(0.0014413±0.0020295)*Asn+(0.0001733±0.00019118)*Gly+(0.00025354±0.0013507)*His |
| 0.987 | (0.52431±0.12207)+(0.0041044±0.0008277)*Orn+(0.003455±0.00098992)*Tau+(0.0025391±0.0020922)*ABA+(0.00015233±0.00018845)*Gly+(1.4084e-005±0.0012922)*His-(6.1999e-005±0.00015499)*Ala |
| 0.987 | (0.71795±0.12019)+(0.0045794±0.00078602)*Orn-(0.0019672±0.00062851)*Arg+(0.0032506±0.0009478)*Tau+(0.00012456±0.00017971)*Gly+(0.001752±0.0012611)*His-(0.0027688±0.0011859)*Trp |
| 0.983 | (0.73402±0.12296)+(0.0045825±0.00080404)*Orn-(0.0019523±0.00063253)*Arg+(0.0033053±0.00094486)*Tau+(0.0001794±0.00062187)*Ser+(0.0016343±0.0012503)*His-(0.0027974±0.0011929)*Trp |
| 0.987 | (0.69338±0.12558)+(0.004375±0.00079603)*Orn-(0.002021±0.00065391)*Arg+(0.0033585±0.00096577)*Tau+(0.00019321±0.00018654)*Gly+(0.0012015±0.0012729)*His-(0.00012871±0.00018357)*Gln |
| 0.987 | (0.66287±0.12099)+(0.0042568±0.00079764)*Orn-(0.0021682±0.00064609)*Arg+(0.0032661±0.00096467)*Tau+(0.00047137±0.0019673)*Asn+(0.00015699±0.00018299)*Gly+(0.00085977±0.0013317)*His |
| 0.982 | (0.66754±0.12168)+(0.0043016±0.00088078)*Orn-(0.0021269±0.00070042)*Arg+(0.0032878±0.00096362)*Tau+(0.00016149±0.00018382)*Gly-(1.7107e-005±0.00048487)*Lys+(0.0009921±0.0012847)*His |
| 0.984 | (0.69921±0.12761)+(0.004314±0.00080878)*Orn-(0.0020383±0.00065603)*Arg+(0.0034179±0.0009646)*Tau+(0.00046126±0.00064079)*Ser+(0.001001±0.00125)*His-(0.00011342±0.00018329)*Gln |
| 0.987 | (0.63789±0.12301)+(0.0045193±0.00082779)*Orn+(0.0034406±0.00096613)*Tau+(0.0025169±0.0020355)*ABA-(0.00020575±0.0006365)*Ser+(0.00076873±0.0012559)*His-(0.003355±0.001211)*Trp |
| 0.979 | (0.63723±0.12632)+(0.0046482±0.00082351)*Orn+(0.0035232±0.00096801)*Tau-(0.00021315±0.00068409)*Ser+(9.6914e-005±0.00019896)*Gly+(0.00097282±0.0012692)*His-(0.0032349±0.0012134)*Trp |
| 0.986 | (0.62438±0.11934)+(0.0045958±0.00080578)*Orn+(0.0035222±0.00096758)*Tau+(7.2985e-005±0.00018346)*Gly+(0.00094506±0.0012655)*His-(0.0031994±0.0012075)*Trp |
| 0.965 | (0.66591±0.12094)+(0.0042769±0.00080984)*Orn-(0.0021375±0.0006333)*Arg+(0.0032825±0.00096281)*Tau+(0.00016501±0.00018691)*Gly+(0.00097415±0.0012382)*His+(3.4057e-005±0.00060209)*Glu |
| 0.988 | (0.67286±0.12303)+(0.0042203±0.00081249)*Orn-(0.0021589±0.00064272)*Arg+(0.003332±0.00096007)*Tau+(0.00038947±0.00062896)*Ser+(0.00074361±0.0012688)*His+(3.6685e-005±0.000152)*Ala |
| 0.986 | (0.61453±0.11994)+(0.0044854±0.00081812)*Orn+(0.0036031±0.00097263)*Tau+(7.7548e-005±0.0001834)*Gly+(0.0007994±0.0012789)*His+(0.00020278±0.00026708)*Pro-(0.0032709±0.0012102)*Trp |
| 0.986 | (0.55737±0.12494)+(0.0042653±0.0008256)*Orn+(0.0035909±0.00098522)*Tau-(4.2041e-005±0.00069343)*Ser+(0.000117±0.00020242)*Gly-(3.82e-005±0.0012332)*His |

FIG.54

| ROC_AUC | INDEX |
|---|---|
| 0.987 | (0.66546±0.12016)+(0.0042705±0.0007941)*Orn-(0.0021503±0.0003381)*Arg+(0.0032773±0.00096263)*Tau+(0.00016214±0.00018157)*Gly+(0.00092083±0.001285)*His+(2.4848e-005±0.0001 5095)*Ala |
| 0.986 | (0.55499±0.11851)+(0.0042557±0.00080972)*Orn+(0.0035905±0.00098453)*Tau+(0.0001122±0.00018613)*Gly-(4.1517e-005±0.0012311)*His |
| 0.986 | (0.67447±0.12269)+(0.0042721±0.00081321)*Orn-(0.0021124±0.00065376)*Arg+(0.0033482±0.00095855)*Tau+(0.00041616±0.00067497)*Ser+(0.00088673±0.0012675)*His-(9.8267e-005±0.00057923)*Thr |
| 0.980 | (0.67860±0.12339)+(0.0043039±0.0008931)*Orn-(0.0020974±0.00070101)*Arg+(0.0033529±0.00096987)*Tau+(0.00036762±0.00062669)*Ser-(6.5841e-005±0.00048042)*Lys+(0.00088038±0.0012778)*His |
| 0.983 | (0.66683±0.12)+(0.0042883±0.00080705)*Orn-(0.0021368±0.00065398)*Arg+(0.0032856±0.00096174)*Tau+(0.00016256±0.00018214)*Gly+(0.00098071±0.0012741)*His-(1.9725e-006±0.00053779)*Thr |
| 0.986 | (0.6173±0.11973)+(0.0044825±0.00082246)*Orn+(0.0034815±0.00096892)*Tau+(0.00010186±0.00018823)*Gly+(0.00093705±0.0012649)*His+(0.00042393±0.00062473)*Glu-(0.0033921±0.0012399)*Trp |
| 0.985 | (0.56029±0.12213)-(0.0041442±0.00083267)*Orn+(0.0035378±0.00098445)*Tau+(0.0021489±0.002071)*ABA+(1.6517e-005±0.00064382)*Ser-(0.00027828±0.0012212)*His |
| 0.985 | (0.67728±0.12255)+(0.0042709±0.00082309)*Orn-(0.0021383±0.00065376)*Arg+(0.0033492±0.00095895)*Tau+(0.00036781±0.00062704)*Ser+(0.00084391±0.0012275)*His-(6.6856e-005±0.00058714)*Glu |
| 0.985 | (0.67595±0.12225)+(0.0042408±0.00080663)*Orn-(0.0021516±0.00064655)*Arg+(0.003336±0.00096172)*Tau+(0.00026454±0.0021272)*Asn+(0.00039962±0.0006807)*Ser+(0.00076131±0.0013327)*His |
| 0.980 | (0.65135±0.12294)+(0.0046539±0.00082338)*Orn+(0.0035649±0.00096414)*Tau-(8.4528e-005±0.00063104)*Ser+(0.00088613±0.0012566)*His-(0.0032573±0.0012125)*Trp |
| 0.982 | (0.55491±0.12197)+(0.0042619±0.0008385)*Orn+(0.0035186±0.00098246)*Tau+(0.0024155±0.0020822)*ABA+(0.0002889±0.00069362)*Ser+(0.00013851±0.0012826)*His-(0.00060604±0.00058201)*Thr |
| 0.984 | (0.54674±0.11948)+(0.0041704±0.00082488)*Orn+(0.0036502±0.00099061)*Tau+(0.00011613±0.00018626)*Gly-(0.00016278±0.0012513)*His+(0.00014663±0.00027124)*Pro |
| 0.982 | (0.54904±0.12588)+(0.0041796±0.00084062)*Orn+(0.0036505±0.00099131)*Tau-(4.045e-005±0.00069338)*Ser+(0.00012075±0.00020252)*Gly-(0.00015954±0.0012534)*His+(0.00014657±0.00027143)*Pro |
| 0.982 | (0.57377±0.1217)+(0.0042689±0.00082573)*Orn+(0.003642±0.00098745)*Tau+(0.0001149±0.00063819)*Ser-(0.00015146±0.0012177)*His |
| 0.984 | (0.64247±0.12343)+(0.0045464±0.00083532)*Orn+(0.0036463±0.00096957)*Tau-(7.9922e-005±0.00063057)*Ser+(0.00073941±0.001271)*His+(0.00019874±0.00026707)*Pro-(0.0033286±0.0012153)*Trp |
| 0.976 | (0.55592±0.12479)+(0.0043762±0.0008344)*Orn+(0.0035907±0.00098393)*Tau+(0.0002098±0.00075104)*Ser+(0.00010535±0.0002026)*Gly+(0.0003095±0.0012953)*His-(0.00050301±0.00058053)*Thr |
| 0.982 | (0.622±0.11957)+(0.0045674±0.00080992)*Orn+(0.0035057±0.000969)*Tau+(7.024e-005±0.00018368)*Gly+(0.00083022±0.0013057)*His+(5.5864e-005±0.00015547)*Ala-(0.0033001±0.0012401)*Trp |
| 0.983 | (0.66464±0.11491)+(0.0038714±0.00085096)*Orn-(0.0023369±0.00067363)*Arg+(0.0032247±0.000959)*Tau+(0.0019734±0.0019903)*ABA+(0.0019865±0.0017567)*Cit+(0.00069663±0.0012191)*His |
| 0.983 | (0.63838±0.1221)+(0.004757±0.00085894)*Orn+(0.0035217±0.00096749)*Tau-(0.00091471±0.001689)*Cit+(8.6586e-005±0.00018515)*Gly+(0.0010248±0.0012739)*His-(0.0032687±0.0012142)*Trp |
| 0.983 | (0.56357±0.12585)+(0.00417 7±0.00088565)*Orn+(0.0035401±0.00098533)*Tau+(0.002136±0.0020757)*ABA+(1.7981e-005±0.00064439)*Ser-(0.00018514±0.0016939)*Cit-(0.00026864±0.0012252)*His |
| 0.984 | (0.63458±0.12157)+(0.0046533±0.00081638)*Orn+(0.0035496±0.00096973)*Tau-(0.00086186±0.001949)*Asn+(8.4368e-005±0.00018529)*Gly+(0.0011916±0.0013831)*His-(0.0032016±0.0012078)*Trp |
| 0.984 | (0.55402±0.12291)-(0.0040749±0.00084635)*Orn+(0.0035926±0.0009918)*Tau+(0.0020913±0.0020751)*ABA+(2.4772e-005±0.00064416)*Ser-(0.00038099±0.0012417)*His+(0.00012446±0.00027129)*Pro |
| 0.984 | (0.64762±0.12289)+(0.0047524±0.00083117)*Orn+(0.0035609±0.00096309)*Tau+(0.0001373±0.00068577)*Ser+(0.0012082±0.001315)*His-(0.0032208±0.0012119)*Trp-(0.00046762±0.00056939)*Thr |
| 0.983 | (0.64568±0.12231)+(0.0048635±0.000875)*Orn+(0.0035444±0.0009671)*Tau+(6.0143e-005±0.00018402)*Gly-(0.00035865±0.00045923)*Lys+(0.0012334±0.0013171)*His-(0.0029389±0.0012517)*Trp |
| 0.983 | (0.63589±0.11996)+(0.004746±0.00082394)*Orn+(0.0035238±0.00096639)*Tau+(8.8152e-005±0.0001841)*Gly+(0.0012733±0.0013215)*His-(0.0032044±0.0012061)*Trp-(0.0004471±0.00052558)*Thr |
| 0.983 | (0.71605±0.12798)+(0.0048591±0.00081104)*Orn+(0.0036638±0.00096219)*Tau+(0.00015716±0.00018732)*Gly+(0.0017592±0.0013273)*His-(0.0034813±0.0012065)*Trp-(0.0003372±0.0001795)*Gln |
| 0.984 | (0.56389±0.12754)+(0.0043415±0.0008774)*Orn+(0.0035914±0.00093574)*Tau-(5.062e-005±0.00069459)*Ser-(0.00044183±0.0017138)*Cit+(0.00012496±0.00020487)*Gly-(9.3087e-006±0.0012389)*His |
| 0.981 | (0.55413±0.11973)+(0.0042454±0.00083353)*Orn+(0.0035878±0.00098666)*Tau+(0.00011459±0.00019178)*Gly-(4.6673e-005±0.0012359)*His+(3.2409e-005±0.00061975)*Glu |
| 0.985 | (0.56626±0.12256)+(0.0041867±0.00084075)*Orn+(0.0037009±0.00098795)*Tau+(0.00012127±0.00063829)*Ser-(0.0002717±0.0012395)*His+(0.00014102±0.00027134)*Pro |
| 0.984 | (0.55653±0.12601)-(0.004255±0.00084829)*Orn+(0.003588±0.00098735)*Tau-(4.2791e-005±0.00069405)*Ser+(0.00011953±0.00020801)*Gly-(4.3419e-005±0.0012379)*His+(3.3182e-005±0.0006203)*Glu |
| 0.985 | (0.56094±0.12086)+(0.004329±0.00085972)*Orn+(0.003591±0.00098505)*Tau-(0.00043585±0.0017107)*Cit+(0.00011908±0.00018818)*Gly-(1.3685e-005±0.0012366)*His |
| 0.985 | (0.67067±0.12158)-(0.0043839±0.00083429)*Orn+(0.0036365±0.00098001)*Tau+(0.00036052±0.00060287)*Ser+(0.00022181±0.0012843)*His-(0.00052304±0.00057927)*Thr |
| 0.982 | (0.64677±0.12362)+(0.0046189±0.00082913)*Orn+(0.0035457±0.00095589)*Tau-(6.8946e-005±0.00063267)*Ser+(0.00077038±0.0012959)*His+(5.7198e-005±0.00015574)*Ala-(0.0033554±0.0012419)*Trp |

FIG.55

| ROC_AUC | INDEX |
|---|---|
| 0.971 | (0.66693±0.12712)+(0.0048018±0.00087864)*Orn+(0.0035707±0.00096429)*Tau-(8.4831e-005±0.00063108)*Ser-(0.0008078±0.0016743)*Cit+(0.0009464±0.0012629)*His-(0.0033249±0.0012206)*Trp |
| 0.982 | (0.60673±0.12413)+(0.0047413±0.00089466)*Orn+(0.003521±0.00097726)*Tau+(0.0028768±0.0020977)*ABA-(2.3715e-005±0.0006395)*Ser-(0.00079092±0.00045353)*Lys+(0.00052756±0.0012973)*His |
| 0.983 | (0.70588±0.12347)+(0.0042807±0.00080885)*Orn-(0.0019899±0.00065451)*Arg+(0.0033402±0.00096898)*Tau+(0.001848±0.0019956)*ABA+(0.00078923±0.0012506)*His-(7.821e-005±0.00017865)*Gln |
| 0.984 | (0.56488±0.12082)+(0.0043116±0.00082058)*Orn+(0.0036173±0.00098678)*Tau-(0.00084025±0.001984)*Asn+(0.00012332±0.00018802)*Gly+(0.00019821±0.0013553)*His |
| 0.983 | (0.56165±0.12616)+(0.004297±0.00083557)*Orn+(0.003601±0.00098657)*Tau-(6.1162e-005±0.00069793)*Ser+(0.00012025±0.00020294)*Gly+(6.5511e-005±0.0013006)*His-(3.9133e-005±0.00015521)*Ala |
| 0.982 | (0.57868±0.12526)+(0.0043182±0.00087683)*Orn+(0.0036446±0.00098218)*Tau+(0.00011625±0.00063863)*Ser-(0.00028428±0.0016947)*Cit-(0.00013783±0.0012212)*His |
| 0.983 | (0.6037±0.12846)+(0.0047885±0.00089868)*Orn+(0.0036206±0.00098072)*Tau-(2.943e-006±0.00069064)*Ser+(8.3653e-005±0.00020278)*Gly-(0.00064596±0.00044945)*Lys+(0.00062273±0.0013106)*His |
| 0.983 | (0.55998±0.12246)+(0.0042887±0.00084507)*Orn+(0.0037154±0.00098604)*Tau+(0.00040307±0.00069519)*Ser+(0.00011102±0.0012935)*His+(0.00019046±0.00027516)*Pro-(0.00059534±0.00058827)*Thr |
| 0.982 | (0.56118±0.12528)+(0.0042985±0.0008293)*Orn+(0.0036197±0.00098764)*Tau-(0.00093479±0.0021548)*Asn+(8.4939e-005±0.0007528)*Ser+(0.00011487±0.00020252)*Gly+(0.00021848±0.001368)*His |
| 0.982 | (0.62419±0.1266)+(0.0044444±0.00081523)*Orn+(0.00371±0.00098258)*Tau+(0.00018309±0.00019109)*Gly+(0.00054673±0.0012859)*His-(0.00027277±0.00018191)*Gln |
| 0.982 | (0.61809±0.13062)+(0.0044179±0.00082738)*Orn+(0.0037115±0.0009832)*Tau+(0.00013399±0.00069951)*Ser+(0.0001693±0.0002043)*Gly+(0.00054887±0.0012868)*His-(0.00027867±0.0001846)*Gln |
| 0.988 | (0.56622±0.11917)+(0.0044031±0.00082843)*Orn+(0.0035922±0.00098344)*Tau+(0.00012719±0.00018682)*Gly+(0.00028019±0.0012904)*His-(0.00044025±0.00053503)*Thr |
| 0.987 | (0.55806±0.11924)+(0.004282±0.0008173)*Orn+(0.0036002±0.00098585)*Tau+(0.00011322±0.00018628)*Gly+(5.6824e-005±0.0012959)*His-(3.7655e-005±0.00015419)*Ala |
| 0.988 | (0.60354±0.12267)+(0.0047879±0.0008866)*Orn+(0.0036205±0.00098003)*Tau+(8.3314e-005±0.00018632)*Gly-(0.00064603±0.00044879)*Lys+(0.00062258±0.0013092)*His |
| 0.969 | (0.65026±0.12294)+(0.0045674±0.00083738)*Orn+(0.0035429±0.00096478)*Tau-(6.7196e-005±0.00063168)*Ser+(0.00085913±0.0012573)*His+(0.00034436±0.00060973)*Glu-(0.0034224±0.001247)*Trp |
| 0.982 | (0.56407±0.12225)+(0.0041802±0.00083445)*Orn+(0.0035681±0.00098537)*Tau+(0.0023464±0.0020951)*ABA-(0.0013376±0.0021745)*Asn+(0.00018507±0.00069952)*Ser+(8.0334e-005±0.0013529)*His |
| 0.986 | (0.61994±0.12995)+(0.0042895±0.0008369)*Orn+(0.0036716±0.00098601)*Tau+(0.0019189±0.0020706)*ABA+(0.0002376±0.00066332)*Ser+(0.0001941±0.0012692)*His-(0.00023833±0.0001825)*Gln |
| 0.987 | (0.56649±0.12336)+(0.0041842±0.00084019)*Orn+(0.0035494±0.00098531)*Tau+(0.0022549±0.0020921)*ABA-(9.7625e-006±0.00064808)*Ser-(0.00013869±0.0012806)*His-(5.675e-005±0.00015609)*Ala |
| 0.980 | (0.56199±0.12238)+(0.0041864±0.00084993)*Orn+(0.0035417±0.00098509)*Tau+(0.0022344±0.0020999)*ABA+(3.8069e-007±0.00064736)*Ser-(0.00024789±0.0012279)*His-(0.00015331±0.00061084)*Glu |
| 0.988 | (0.62033±0.11033)+(0.0044651±0.00081029)*Orn+(0.0034331±0.00096545)*Tau+(0.0024155±0.0020103)*ABA+(0.00076642±0.0012554)*His-(0.0033056±0.0012008)*Trp |
| 0.983 | (0.57138±0.12535)+(0.0043914±0.00087948)*Orn+(0.003637±0.00098084)*Tau+(0.00035957±0.00069424)*Ser-(4.6369e-005±0.0017135)*Cit+(0.00022226±0.0012853)*His-(0.00052056±0.0005869)*Thr |
| 0.985 | (0.73351±0.13084)+(0.0048558±0.00082553)*Orn+(0.0037201±0.00096121)*Tau+(0.00017675±0.00064413)*Ser+(0.0015656±0.001307)*His-(0.0035011±0.0012117)*Trp-(0.00031265±0.00017952)*Gln |
| 0.982 | (0.55356±0.12153)+(0.0042552±0.00086932)*Orn+(0.0036542±0.00099113)*Tau-(0.0005334±0.0017189)*Cit+(0.00012478±0.00018841)*Gly-(0.00013571±0.0012549)*His+(0.00015508±0.00027272)*Pro |
| 0.983 | (0.55721±0.11983)+(0.004314±0.0008382)*Orn+(0.0036686±0.00098926)*Tau+(0.00013424±0.000187)*Gly+(0.0001687±0.0013)*His+(0.00018722±0.00027437)*Pro-(0.00049956±0.00054176)*Thr |
| 0.982 | (0.6686±0.12465)+(0.0049205±0.00088594)*Orn+(0.0035802±0.00096331)*Tau-(7.0652e-005±0.0006306)*Ser-(0.00037067±0.00045767)*Lys+(0.0011949±0.0013119)*His-(0.0029778±0.0012594)*Trp |
| 0.982 | (0.65383±0.12318)+(0.004679±0.00082663)*Orn+(0.003588±0.00096661)*Tau-(0.00076038±0.0021174)*Asn+(1.7391e-005±0.00069212)*Ser+(0.0010916±0.0013811)*His-(0.0032415±0.0012137)*Trp |
| 0.980 | (0.5778±0.12321)+(0.004296±0.00083577)*Orn+(0.0036518±0.00098308)*Tau+(0.00010233±0.00064122)*Ser-(6.5875e-005±0.0012819)*His-(3.3304e-005±0.00015493)*Ala |
| 0.980 | (0.55684±0.12167)+(0.0042264±0.00083474)*Orn+(0.0036797±0.00099304)*Tau-(0.00087568±0.0019847)*Asn+(0.00012783±0.00018817)*Gly+(8.3865e-005±0.0013707)*His+(0.00015049±0.00027143)*Pro |
| 0.980 | (0.5481±0.12022)+(0.0041873±0.00084016)*Orn+(0.0036598±0.00099526)*Tau+(0.00011123±0.00019185)*Gly-(0.00015896±0.0012526)*His+(0.00015543±0.00028342)*Pro-(6.9762e-005±0.00064708)*Glu |
| 0.986 | (0.6168±0.12444)+(0.0048083±0.00089719)*Orn+(0.0036576±0.00097637)*Tau+(0.00010908±0.00063486)*Ser-(0.00066717±0.00044639)*Lys+(0.00056452±0.0013027)*His |
| 0.964 | (0.61599±0.12742)+(0.004357±0.00082979)*Orn+(0.0037723±0.00098866)*Tau+(0.0001875±0.00019122)*Gly+(0.000424±0.0013041)*His+(0.0001518±0.00026982)*Pro-(0.00027407±0.0001819)*Gln |
| 0.983 | (0.63549±0.12907)+(0.0044089±0.00082825)*Orn+(0.003772±0.0009816)*Tau+(0.0003817±0.00065543)*Ser+(0.00033504±0.0012621)*His-(0.00025272±0.00018213)*Gln |
| 0.983 | (0.55032±0.11975)+(0.0041963±0.00082689)*Orn+(0.0036888±0.00099423)*Tau+(0.00011945±0.00018642)*Gly-(2.715e-006±0.0012983)*His+(0.00019356±0.0002896)*Pro-(7.6151e-005±0.00016452)*Ala |
| 0.983 | (0.59529±0.12359)+(0.0047025±0.00090017)*Orn+(0.0036806±0.00098607)*Tau+(8.7245e-005±0.00018644)*Gly-(0.00064657±0.00044874)*Lys+(0.00050116±0.0013278)*His+(0.00014749±0.00026993)*Pro |

FIG.57

| ROC_AUC | INDEX |
|---|---|
| 0.952 | (0.53365±0.12393)+(0.0046395±0.00080435)*Orn+(0.0022151±0.0020733)*ABA+(0.0042757±0.00091165)*Tau+(0.00064643±0.0012683)*His-(0.0015868±0.00064805)*Arg+(0.00012299±0.00018845)*Gly |
| 0.958 | (0.45525±0.12154)+(0.0045722±0.00081606)*Orn+(0.0024195±0.002103)*ABA+(0.0043839±0.00092437)*Tau-(0.00013692±0.0012459)*His+(9.224e-005±0.00019088)*Gly |
| 0.949 | (0.4633±0.12163)+(0.0047185±0.00082919)*Orn+(0.0027994±0.0021374)*ABA+(0.0043685±0.00092295)*Tau+(0.00023227±0.0013034)*His-(0.00052907±0.00055858)*Thr+(0.00011638±0.00019225)*Gly |
| 0.959 | (0.49967±0.12416)+(0.0051256±0.00088568)*Orn+(0.0029932±0.0021231)*ABA+(0.0043968±0.00091912)*Tau-(0.00072007±0.00046198)*Lys+(0.00058784±0.0013231)*His+(6.8682e-005±0.00019038)*Gly |
| 0.956 | (0.47494±0.12744)+(0.00463±0.00082377)*Orn+(0.0026753±0.0021611)*ABA+(0.0043589±0.00092565)*Tau+(0.00010489±0.0013318)*His+(7.8278e-005±0.0001928)*Gly-(0.0007484±0.0014569)*Phe |
| 0.962 | (0.47024±0.12618)+(0.004631±0.00082692)*Orn+(0.0026429±0.0021629)*ABA+(0.0043691±0.00092513)*Tau-(0.00012195±0.0012465)*His-(0.00032017±0.00072263)*Ser+(0.00013277±0.00021169)*Gly |
| 0.956 | (0.47959±0.12671)+(0.0046636±0.00082679)*Orn+(0.0026351±0.002126)*ABA+(0.0044284±0.00092624)*Tau-(3.9677e-005±0.0012535)*His-(0.0011232±0.0016634)*Cys+(7.8379e-005±0.00019188)*Gly |
| 0.954 | (0.46578±0.12398)+(0.0046962±0.00086516)*Orn+(0.0023906±0.0021044)*ABA+(0.004391±0.0009247)*Tau-(0.00074981±0.0017343)*Cit-(8.6453e-005±0.0012516)*His+(0.00010379±0.00019277)*Gly |
| 0.953 | (0.45757±0.12235)+(0.0045958±0.00082789)*Orn+(0.0024388±0.0021072)*ABA+(0.0043656±0.00093097)*Tau-(9.5729e-005±0.0012691)*His+(9.1226e-005±0.00019108)*Gly-(4.8318e-005±0.00027896)*Pro |
| 0.968 | (0.45757±0.1222)+(0.0046069±0.00083608)*Orn+(0.002465±0.0021174)*ABA+(0.0043938±0.00092633)*Tau-(0.00011747±0.0012507)*His-(0.00012222±0.0006326)*Glu+(8.4101e-005±0.00019558)*Gly |
| 0.953 | (0.52905±0.13007)+(0.0047699±0.00082169)*Orn+(0.0024063±0.0020913)*ABA+(0.0044957±0.00092214)*Tau+(0.00046229±0.001299)*His+(0.00016555±0.00019573)*Gly-(0.00028347±0.00018465)*Gln |
| 0.952 | (0.4647±0.1227)+(0.004633±0.00082325)*Orn+(0.0026831±0.0021555)*ABA-(0.0011499±0.0020681)*Asn+(0.004408±0.00092526)*Tau+(0.00017932±0.0013694)*His+(0.00011158±0.00019399)*Gly |
| 0.953 | (0.56244±0.12655)+(0.0047859±0.00080437)*Orn+(0.0043838±0.0009091)*Tau+(0.00069368±0.0013392)*His-(0.0016275±0.00065669)*Arg+(9.5795e-005±0.00018999)*Gly+(0.00018656±0.0014163)*Phe |
| 0.954 | (0.49123±0.12171)+(0.0046475±0.00082679)*Orn+(0.0023141±0.0020992)*ABA+(0.0044347±0.00091954)*Tau-(0.00022818±0.0012354)*His-(0.00012431±0.00065191)*Ser |
| 0.954 | (0.56177±0.1235)+(0.004683±0.00081506)*Orn+(0.0019704±0.002074)*ABA+(0.00434±0.0009072)*Tau+(0.00053016±0.001258)*His+(6.1957e-005±0.00064722)*Ser-(0.0015661±0.00065202)*Arg |
| 0.953 | (0.56558±0.12572)+(0.0047954±0.00080819)*Orn+(0.0043819±0.000909)*Tau+(0.00074894±0.0012686)*His+(3.9454e-005±0.00069697)*Ser-(0.001618±0.00065207)*Arg+(8.6587e-005±0.000203)*Gly |
| 0.953 | (0.49097±0.11784)+(0.0047515±0.0008033)*Orn+(0.0045019±0.00092126)*Tau-(3.833e-005±0.0012464)*His+(5.6772e-005±0.0001889)*Gly |
| 0.955 | (0.56768±0.12005)+(0.0048046±0.00079122)*Orn+(0.0043817±0.00090836)*Tau+(0.0007503±0.0012675)*His-(0.0016147±0.00064904)*Arg+(9.1108e-005±0.0001865)*Gly |
| 0.959 | (0.57737±0.12261)+(0.004794±0.00080801)*Orn+(0.0044166±0.00090515)*Tau+(0.00066309±0.0012523)*His+(0.00015641±0.00064063)*Ser-(0.0016088±0.00065158)*Arg |
| 0.959 | (0.50737±0.12113)+(0.0047774±0.00082042)*Orn+(0.0045281±0.00091795)*Tau-(9.5733e-005±0.0012327)*His-(1.8849e-005±0.00064649)*Ser |
| 0.959 | (0.50141±0.12605)+(0.0047857±0.00081687)*Orn+(0.0044963±0.00092208)*Tau+(7.3853e-005±0.0013361)*His+(4.8895e-005±0.00019198)*Gly-(0.00033287±0.0014225)*Phe |
| 0.959 | (0.57559±0.12725)+(0.0047867±0.00082029)*Orn+(0.0044182±0.0009063)*Tau+(0.00063881±0.0013345)*His+(0.00015849±0.00064226)*Ser-(0.0016137±0.00065836)*Arg+(7.3789e-005±0.0013946)*Phe |
| 0.959 | (0.48719±0.12164)+(0.0047465±0.00083363)*Orn+(0.0025366±0.0021122)*ABA+(0.0044275±0.00091838)*Tau+(0.00012569±0.0012999)*His+(0.00010024±0.00070095)*Ser-(0.00051587±0.00059662)*Thr |
| 0.959 | (0.49751±0.1246)+(0.0047784±0.00082075)*Orn+(0.0045005±0.00092187)*Tau-(2.9734e-005±0.0012483)*His-(0.00011431±0.00070502)*Ser+(7.0073e-005±0.00020606)*Gly |
| 0.959 | (0.5678±0.1243)+(0.0046531±0.00086166)*Orn+(0.0043963±0.00090628)*Tau+(0.00085242±0.0018092)*Cit+(0.00067465±0.0012527)*His+(0.00016385±0.00064089)*Ser-(0.0017238±0.00069584)*Arg |
| 0.957 | (0.57496±0.1255)+(0.0048355±0.00080651)*Orn+(0.0043989±0.00091297)*Tau+(0.00077351±0.0012735)*His-(0.00032807±0.0016377)*Cys-(0.0015988±0.00065425)*Arg+(8.5798e-005±0.00018849)*Gly |
| 0.958 | (0.48101±0.10921)+(0.004617±0.00081072)*Orn+(0.0022554±0.0020752)*ABA+(0.0044322±0.0009189)*Tau-(0.00021984±0.0012339)*His |
| 0.958 | (0.53362±0.12383)+(0.0052139±0.00089464)*Orn+(0.002966±0.0021257)*ABA+(0.0044361±0.00091395)*Tau-(0.00073832±0.00046101)*Lys+(0.00053374±0.0013168)*His-(0.00016796±0.00064852)*Ser |
| 0.952 | (0.50201±0.12545)+(0.004752±0.00087757)*Orn+(0.0022711±0.0021034)*ABA+(0.0044453±0.00092035)*Tau-(0.00061289±0.0017193)*Cit-(0.00019504±0.0012393)*His-(0.00011869±0.00065233)*Ser |
| 0.957 | (0.51091±0.12458)+(0.0048293±0.00081868)*Orn+(0.0045418±0.00092484)*Tau+(3.8473e-005±0.0012562)*His-(0.00081364±0.0016501)*Cys+(4.4442e-005±0.00019056)*Gly |
| 0.949 | (0.5075±0.13206)+(0.0048109±0.00083331)*Orn+(0.0044951±0.00092269)*Tau+(8.01e-005±0.0013375)*His-(0.00010993±0.00070567)*Ser+(6.1828e-005±0.00020927)*Gly-(0.00032687±0.0014239)*Phe |
| 0.951 | (0.51217±0.12666)+(0.0047144±0.00083421)*Orn+(0.0026531±0.0021746)*ABA+(0.0043981±0.00092136)*Tau+(6.2496e-005±0.0013282)*His-(0.00015784±0.00065418)*Ser-(0.00086187±0.0014481)*Phe |
| 0.952 | (0.56229±0.12081)+(0.0046875±0.00084237)*Orn+(0.0043688±0.00090914)*Tau+(0.00074027±0.001823)*Cit+(0.00074883±0.0012678)*His-(0.0017113±0.00069143)*Arg+(8.1346e-005±0.00018809)*Gly |

FIG.58

| ROC_AUC | INDEX |
|---|---|
| 0.948 | (0.51816±0.12698)+(0.0048172±0.00083265)*Orn+(0.0045175±0.00091914)*Tau+(4.784e-005±0.0013324)*His-(2.7217e-005±0.00064746)*Ser-(0.00039907±0.0014021)*Phe |
| 0.951 | (0.56427±0.12138)+(0.0047777±0.00080358)*Orn+(0.00039673±0.0020323)*Asn+(0.0043671±0.00091197)*Tau+(0.00064979±0.0013688)*His-(0.0016399±0.0006621)*Arg+(8.6305e-005±0.00018823)*Gly |
| 0.950 | (0.5853±0.12626)+(0.0048323±0.00082121)*Orn+(0.0044361±0.00090857)*Tau+(0.00070121±0.0012611)*His+(0.00015533±0.00064097)*Ser-(0.0004304±0.0016221)*Cys-(0.0015897±0.00065591)*Arg |
| 0.952 | (0.51389±0.12555)+(0.0047403±0.00083603)*Orn+(0.0025756±0.0021283)*ABA+(0.0044748±0.00092053)*Tau-(0.00011135±0.001245)*His-(0.00013341±0.00065157)*Ser-(0.0012024±0.0016547)*Cys |
| 0.948 | (0.49386±0.12253)+(0.0046744±0.00083886)*Orn+(0.0023397±0.0021045)*ABA+(0.0044136±0.00092645)*Tau-(0.00018125±0.0012596)*His-(0.00012842±0.00065264)*Ser-(5.4176e-005±0.00027911)*Pro |
| 0.949 | (0.49369±0.12187)+(0.0046756±0.00082971)*Orn+(0.0024441±0.0021225)*ABA-(0.00092604±0.0022113)*Asn+(0.0044599±0.00092171)*Tau+(2.0242e-005±0.0013707)*His-(8.7296e-006±0.00070806)*Ser |
| 0.949 | (0.55645±0.13029)+(0.0047993±0.0008308)*Orn+(0.0020782±0.0020974)*ABA+(0.0045639±0.00092054)*Tau+(0.00026227±0.0012817)*His+(0.00010408±0.00067043)*Ser-(0.00025256±0.00018528)*Gln |
| 0.961 | (0.493±0.12189)+(0.0047014±0.00084492)*Orn+(0.0024193±0.0021268)*ABA+(0.004444±0.00092042)*Tau-(0.00018695±0.0012429)*His-(0.00014483±0.00065547)*Ser-(0.00019452±0.00062109)*Glu |
| 0.957 | (0.50531±0.12108)+(0.00487±0.00082985)*Orn+(0.0045296±0.00091731)*Tau+(0.00020884±0.0013022)*His+(0.00017614±0.00070029)*Ser-(0.00042859±0.00059404)*Thr |
| 0.957 | (0.49775±0.12021)+(0.0047923±0.00081602)*Orn-(0.00058367±0.0020243)*Asn+(0.0045206±0.00092398)*Tau+(0.00012764±0.0013735)*His+(6.4626e-005±0.00019094)*Gly |
| 0.956 | (0.56563±0.12065)+(0.0047789±0.00080419)*Orn+(0.0043987±0.00091375)*Tau+(0.00071343±0.0012844)*His-(0.0016287±0.00065403)*Arg+(9.2758e-005±0.00018684)*Gly+(5.036e-005±0.00277)*Pro |
| 0.959 | (0.60693±0.12669)+(0.0049247±0.00079978)*Orn+(0.0044645±0.00091093)*Tau+(0.0010531±0.0013044)*His-(0.0014532±0.00066961)*Arg+(0.00013453±0.00019165)*Gly-(0.00018071±0.00018914)*Gln |
| 0.961 | (0.49196±0.11892)+(0.0047641±0.00082751)*Orn+(0.0045059±0.000924)*Tau-(3.1308e-005±0.0012521)*His-(4.0291e-005±0.00063051)*Glu+(5.3869e-005±0.00019441)*Gly |
| 0.970 | (0.61316±0.12891)+(0.0048843±0.00081328)*Orn+(0.0045059±0.00090948)*Tau+(0.0009104±0.0012812)*His+(0.00028472±0.00065587)*Ser-(0.0014634±0.00067099)*Arg-(0.00016727±0.00018853)*Gln |
| 0.960 | (0.57555±0.12318)+(0.0047699±0.00082131)*Orn+(0.0044328±0.00091089)*Tau+(0.00062792±0.0012707)*His+(0.00016033±0.00064146)*Ser-(0.0016218±0.0006566)*Arg+(4.6211e-005±0.00027699)*Pro |
| 0.958 | (0.49266±0.11888)+(0.0047677±0.00081679)*Orn+(0.0044906±0.00092733)*Tau-(1.1174e-005±0.0012706)*His+(5.5933e-005±0.00018917)*Gly-(3.126e-005±0.00027937)*Pro |
| 0.967 | (0.52794±0.12714)+(0.0052494±0.00088578)*Orn+(0.0045438±0.00091913)*Tau-(0.0006418±0.0004846)*Lys+(0.00051905±0.0013726)*His+(3.5963e-005±0.00019147)*Gly+(0.00032474±0.0015013)*Phe |
| 0.959 | (0.57435±0.12212)+(0.0049268±0.00088884)*Orn+(0.0043972±0.00091023)*Tau-(0.00015136±0.0005008)*Lys+(0.00086185±0.0013207)*His-(0.0015211±0.00071938)*Arg+(8.2398e-005±0.0001888)*Gly |
| 0.961 | (0.56853±0.12108)+(0.0048156±0.00081503)*Orn+(0.0043851±0.00091107)*Tau+(0.00075638±0.0012729)*His-(3.5199e-005±0.00062081)*Glu-(0.0016146±0.00064949)*Arg+(8.8569e-005±0.00019193)*Gly |
| 0.961 | (0.5757±0.12306)+(0.0048166±0.00081865)*Orn+(0.0044188±0.0009058)*Tau+(0.00072548±0.0013026)*His+(0.00020151±0.00069065)*Ser-(0.00010551±0.00060154)*Thr-(0.0015822±0.0006695)*Arg |
| 0.960 | (0.50192±0.12015)+(0.0048836±0.00085163)*Orn+(0.0045081±0.00092146)*Tau-(0.00081233±0.0017382)*Cit+(1.5068e-005±0.0012518)*His+(6.9739e-005±0.00019095)*Gly |
| 0.956 | (0.49674±0.12453)+(0.0048686±0.00083025)*Orn+(0.0045054±0.00092133)*Tau+(0.00025881±0.0013136)*His+(8.7829e-005±0.00076121)*Ser-(0.00041777±0.00059543)*Thr+(6.1213e-005±0.00020631)*Gly |
| 0.961 | (0.52496±0.12562)+(0.0048546±0.00083333)*Orn+(0.0045645±0.00092048)*Tau-(1.0456e-006±0.0012456)*His-(1.6824e-005±0.00064647)*Ser-(0.00086389±0.0016361)*Cys |
| 0.960 | (0.50109±0.11861)+(0.0048807±0.00082306)*Orn+(0.0045042±0.00092067)*Tau+(0.00024651±0.0013084)*His-(0.00039177±0.00055078)*Thr+(7.052e-005±0.00018977)*Gly |
| 0.958 | (0.51967±0.12468)+(0.0048973±0.00086929)*Orn+(0.0045385±0.00091849)*Tau-(0.00071947±0.0017206)*Cit-(5.9719e-005±0.001236)*His-(1.4549e-005±0.00064671)*Ser |
| 0.953 | (0.51585±0.13026)+(0.0048497±0.00083396)*Orn+(0.0045399±0.00092554)*Tau+(4.4118e-005±0.0012577)*His-(9.2458e-005±0.00070652)*Ser-(0.00079979±0.0016545)*Cys+(5.5411e-005±0.00020829)*Gly |
| 0.959 | (0.5648±0.12666)+(0.0049488±0.00080912)*Orn+(0.0046134±0.00091904)*Tau+(0.00056218±0.0012998)*His+(0.0001305±0.0001939)*Gly-(0.00028434±0.00018517)*Gln |
| 0.960 | (0.53558±0.12208)+(0.005254±0.00088502)*Orn+(0.0045363±0.00091797)*Tau-(0.00060714±0.00045707)*Lys+(0.00059248±0.0013292)*His+(2.9817e-005±0.00018924)*Gly |
| 0.965 | (0.56262±0.12402)+(0.0048189±0.00082064)*Orn+(0.0021311±0.0020684)*ABA+(0.0045622±0.0009199)*Tau+(0.00024177±0.0012741)*His-(0.00024537±0.00017929)*Gln |
| 0.958 | (0.56645±0.11333)+(0.0046978±0.00079973)*Orn+(0.0020009±0.002048)*ABA+(0.0043417±0.00090642)*Tau+(0.00052244±0.0012545)*His-(0.0015586±0.00064689)*Arg |
| 0.957 | (0.58392±0.12402)+(0.0049379±0.0009028)*Orn+(0.0044308±0.00090634)*Tau-(0.0001775±0.00049621)*Lys+(0.0008039±0.0013131)*His+(0.00014121±0.00064226)*Ser-(0.0015±0.00071932)*Arg |
| 0.957 | (0.51504±0.12968)+(0.0048421±0.0008266)*Orn+(0.0045365±0.00092656)*Tau+(9.1135e-005±0.0013368)*His-(0.00076489±0.0017041)*Cys+(4.116e-005±0.00019278)*Gly-(0.00016991±0.0014683)*Phe |
| 0.965 | (0.49239±0.1137)+(0.0047242±0.00086366)*Orn+(0.0022145±0.002079)*ABA+(0.0044431±0.00091971)*Tau-(0.00062045±0.0017178)*Cit-(0.00018667±0.0012377)*His |

FIG.59

| ROC_AUC | INDEX |
|---|---|
| 0.957 | (0.57685±0.12273)+(0.0047795±0.00081274)*Orn+(0.00038424±0.002194)*Asn+(0.0044026±0.00090924)*Tau+(0.00056642±0.0013692)*His+(0.00010819±0.00069766)*Ser-(0.001629±0.00066205)*Arg |
| 0.956 | (0.55639±0.11507)+(0.0045466±0.00085405)*Orn+(0.0020411±0.0020496)*ABA+(0.0043187±0.00090758)*Tau+(0.00091098±0.0018056)*Cit+(0.00053152±0.0012547)*His-(0.00168±0.00069015)*Arg |
| 0.955 | (0.56844±0.12031)+(0.0048252±0.00081179)*Orn+(0.0043834±0.00090909)*Tau+(0.00078775±0.0013098)*His-(6.4159e-005±0.00056016)*Thr-(0.0015958±0.00066998)*Arg+(9.2959e-005±0.00018733)*Gly |
| 0.956 | (0.60676±0.12439)+(0.004809±0.00081152)*Orn+(0.0019504±0.0020471)*ABA+(0.0044258±0.00091192)*Tau+(0.00072779±0.0012805)*His-(0.0014221±0.00066942)*Arg-(0.00014371±0.00018363)*Gln |
| 0.962 | (0.57857±0.12295)+(0.0048222±0.00082976)*Orn+(0.004423±0.0009067)*Tau+(0.00068555±0.0012619)*His+(0.00014909±0.00064287)*Ser-(9.1425e-005±0.00060566)*Glu-(0.0016094±0.000652)*Arg |
| 0.957 | (0.50917±0.12207)+(0.0047956±0.00083391)*Orn+(0.0045153±0.00092432)*Tau-(6.4699e-005±0.0012585)*His-(2.0732e-005±0.00064708)*Ser-(3.4742e-005±0.00027929)*Pro |
| 0.958 | (0.54648±0.12404)+(0.0052798±0.0008974)*Orn+(0.0045512±0.00091429)*Tau-(0.00061515±0.0004545)*Lys+(0.00057016±0.0013225)*His-(3.0462e-005±0.00064386)*Ser |
| 0.962 | (0.51077±0.12667)+(0.0049117±0.00083565)*Orn+(0.004499±0.0009215)*Tau+(0.00034943±0.0013911)*His-(0.00038915±0.00055122)*Thr+(6.3068e-005±0.00019291)*Gly-(0.00031103±0.0014219)*Phe |
| 0.960 | (0.50229±0.12655)+(0.0047968±0.00082761)*Orn+(0.0044878±0.00092794)*Tau+(9.0234e-005±0.0013504)*His+(4.8572e-005±0.00019215)*Gly-(0.00031902±0.0014325)*Phe-(2.4228e-005±0.0002813)*Pro |
| 0.955 | (0.5052±0.12704)+(0.0048144±0.00082546)*Orn-(0.00051199±0.0020634)*Asn+(0.0045139±0.00092528)*Tau+(0.00019634±0.001425)*His+(5.7406e-005±0.00019512)*Gly-(0.00026432±0.0014498)*Phe |
| 0.964 | (0.50156±0.12635)+(0.0047893±0.00083544)*Orn+(0.0044977±0.00092522)*Tau+(7.4302e-005±0.0013372)*His-(1.3422e-005±0.00064197)*Glu+(4.806e-005±0.00019621)*Gly-(0.00032725±0.0014485)*Phe |
| 0.956 | (0.57476±0.12923)+(0.0049243±0.00082274)*Orn+(0.0046549±0.0009177)*Tau+(0.00010982±0.0012755)*His+(0.00021184±0.00066282)*Ser-(0.0002677±0.000185)*Gln |
| 0.963 | (0.50844±0.12146)+(0.0048029±0.0008425)*Orn+(0.0045339±0.00091954)*Tau-(7.5583e-005±0.0012425)*His-(2.555e-005±0.00064881)*Ser-(8.297e-005±0.00061498)*Glu |
| 0.954 | (0.50992±0.12751)+(0.0049059±0.00086031)*Orn+(0.0045033±0.00092236)*Tau-(0.0007795±0.001748)*Cit+(0.00010367±0.001338)*His+(6.2842e-005±0.00019454)*Gly-(0.00026929±0.0014298)*Phe |
| 0.963 | (0.56761±0.13274)+(0.0049582±0.00082037)*Orn+(0.0046111±0.00092021)*Tau+(0.00059327±0.0013722)*His+(0.00012774±0.00019788)*Gly-(0.00010116±0.001423)*Phe-(0.00028292±0.00018637)*Gln |
| 0.955 | (0.4984±0.12555)+(0.0047902±0.00084381)*Orn+(0.0045043±0.00092463)*Tau-(2.3097e-005±0.0012539)*His-(0.00011352±0.00070563)*Ser-(3.8422e-005±0.00063101)*Glu+(6.7213e-005±0.00021148)*Gly |
| 0.962 | (0.50938±0.12145)+(0.0047986±0.00082515)*Orn-(0.00055371±0.0021937)*Asn+(0.0045463±0.00092125)*Tau+(5.7254e-005±0.0013742)*His+(5.3805e-005±0.00070798)*Ser |
| 0.962 | (0.49925±0.12563)+(0.004795±0.00083424)*Orn+(0.0044891±0.00092795)*Tau-(2.1994e-006±0.0012726)*His-(0.00011497±0.00070551)*Ser+(6.9301e-005±0.0002063)*Gly-(3.1638e-005±0.00027955)*Pro |
| 0.956 | (0.50954±0.12716)+(0.0049165±0.00087078)*Orn+(0.0045066±0.00092205)*Tau-(0.00082713±0.0017411)*Cit+(2.5803e-005±0.0012539)*His-(0.00012981±0.00070584)*Ser+(8.508e-005±0.00020848)*Gly |
| 0.956 | (0.54027±0.12825)+(0.0052724±0.00089875)*Orn+(0.0045352±0.00091862)*Tau-(0.00060537±0.00045761)*Lys+(0.00059698±0.0013306)*His-(8.4378e-005±0.00070261)*Ser+(3.9714e-005±0.00020652)*Gly |
| 0.954 | (0.49856±0.11335)+(0.0046737±0.0008165)*Orn+(0.0025673±0.0021441)*ABA+(0.0043962±0.00092083)*Tau+(6.2853e-005±0.0013274)*His-(0.00083179±0.001442)*Phe |
| 0.960 | (0.56208±0.13092)+(0.0049367±0.000082279)*Orn+(0.0046151±0.00091989)*Tau+(0.000563±0.0013007)*His+(5.903e-005±0.00071028)*Ser+(0.00012428±0.00020797)*Gly-(0.00028683±0.0001877)*Gln |
| 0.957 | (0.51955±0.11122)+(0.0051689±0.0008772)*Orn+(0.0028823±0.0021)*ABA+(0.0044327±0.00091338)*Tau-(0.0007333±0.00046036)*Lys+(0.0005398±0.001316)*His |
| 0.956 | (0.49962±0.12497)+(0.004799±0.00082547)*Orn-(0.00053689±0.0021952)*Asn+(0.0045186±0.00092533)*Tau+(0.00011752±0.0013865)*His-(4.2284e-005±0.0007644)*Ser+(6.8917e-005±0.00020622)*Gly |
| 0.957 | (0.49311±0.11234)+(0.0046742±0.00082028)*Orn+(0.0024421±0.0021147)*ABA-(0.00093667±0.002035)*Asn+(0.00446±0.000921)*Tau+(2.3589e-005±0.0013426)*His |
| 0.955 | (0.5155±0.12695)+(0.0049068±0.00084148)*Orn+(0.0045195±0.00091853)*Tau+(0.00034163±0.0013935)*His+(0.00016659±0.00070154)*Ser-(0.00042496±0.00059449)*Thr-(0.00037627±0.0014015)*Phe |
| 0.956 | (0.5028±0.11322)+(0.0047071±0.00081969)*Orn+(0.0025111±0.0021037)*ABA+(0.0044719±0.00091989)*Tau-(0.00010304±0.0012436)*His-(0.0011959±0.0016534)*Cys |
| 0.969 | (0.54089±0.12761)+(0.0052773±0.00089803)*Orn+(0.0045598±0.00091598)*Tau-(0.0006464±0.00048402)*Lys+(0.00050313±0.0013702)*His-(2.5173e-005±0.00064485)*Ser+(0.00028037±0.0014863)*Phe |
| 0.954 | (0.48109±0.10926)+(0.0046625±0.00082586)*Orn+(0.0023441±0.0020982)*ABA+(0.0044405±0.00091976)*Tau-(0.00018025±0.0012419)*His-(0.00018081±0.00061763)*Glu |
| 0.954 | (0.48323±0.10991)+(0.0046421±0.00082213)*Orn+(0.0022782±0.00208)*ABA+(0.0044117±0.00092586)*Tau-(0.00017419±0.0012583)*His-(5.2398e-005±0.0002788)*Pro |
| 0.954 | (0.49455±0.11016)+(0.0047616±0.00082636)*Orn+(0.0025638±0.0021022)*ABA+(0.0044296±0.00091767)*Tau+(9.8206e-005±0.0012848)*His-(0.00048426±0.00055381)*Thr |
| 0.956 | (0.51579±0.12623)+(0.0048606±0.00082901)*Orn-(0.00049763±0.0020329)*Asn+(0.0045559±0.00092715)*Tau+(0.00017652±0.0013776)*His-(0.000777±0.0016577)*Cys+(5.1694e-005±0.00019295)*Gly |
| 0.968 | (0.54545±0.12712)+(0.005281±0.00089067)*Orn+(0.004558±0.00092166)*Tau-(0.00058577±0.00046361)*Lys+(0.00061437±0.0013321)*His-(0.00046716±0.001667)*Cys+(2.3687e-005±0.00019059)*Gly |
| 0.969 | (0.51466±0.12485)+(0.0049535±0.00087298)*Orn+(0.0045373±0.00091805)*Tau-(0.00053854±0.0017412)*Cit+(0.0002151±0.0013029)*His+(0.0001661±0.00070135)*Ser-(0.00039946±0.00060172)*Thr |

FIG.61

| ROC_AUC | 0.7 | | 0.75 | | 0.8 | | 0.85 | |
|---|---|---|---|---|---|---|---|---|
| RANK | AMINO ACID | FREQUENCY | AMINO ACID | FREQUENCY | AMINO ACID | FREQUENCY | AMINO ACID | FREQUENCY |
| 1 | Lys | 9083 | Lys | 6842 | Orn | 3965 | Arg | 524 |
| 2 | ABA | 8733 | Orn | 6714 | Lys | 3018 | Lys | 466 |
| 3 | Orn | 8619 | ABA | 6379 | ABA | 2861 | Orn | 359 |
| 4 | His | 8485 | His | 5847 | Arg | 2518 | ABA | 290 |
| 5 | Glu | 7109 | Glu | 5021 | His | 2506 | His | 238 |
| 6 | Arg | 6675 | Arg | 4934 | Glu | 1669 | Gly | 212 |
| 7 | Gly | 6493 | Tau | 4289 | Gly | 1484 | Glu | 144 |
| 8 | Ser | 6490 | Gly | 3936 | Tau | 1412 | Tau | 132 |
| 9 | Tau | 6477 | Ser | 3809 | Ser | 1149 | Ser | 124 |
| 10 | Leu | 6264 | Leu | 3396 | Ile | 1135 | Cit | 98 |
| 11 | Thr | 5933 | Thr | 3301 | Thr | 1031 | Thr | 85 |
| 12 | Val | 5914 | Ile | 3217 | Leu | 1000 | Trp | 85 |
| 13 | Met | 5700 | Val | 3066 | Tyr | 963 | Tyr | 69 |
| 14 | Ile | 5666 | Met | 2977 | Met | 930 | Ile | 65 |
| 15 | Cit | 5463 | Cit | 2894 | Trp | 918 | Ala | 58 |
| 16 | Asn | 5444 | Pro | 2809 | Val | 894 | (Cys)2 | 56 |
| 17 | Pro | 5348 | Tyr | 2769 | Pro | 889 | Phe | 54 |
| 18 | Ala | 5250 | Asn | 2744 | Cit | 855 | Leu | 49 |
| 19 | Tyr | 5239 | Trp | 2656 | (Cys)2 | 849 | Met | 44 |
| 20 | Phe | 5194 | Ala | 2597 | Phe | 842 | Asn | 43 |
| 21 | (Cys)2 | 5117 | Phe | 2519 | Asn | 838 | Gln | 42 |
| 22 | Trp | 5077 | (Cys)2 | 2508 | Ala | 793 | Pro | 42 |
| 23 | Gln | 5072 | Gln | 2368 | Gln | 765 | Val | 39 |

| | HEALTHY | LUNG CANCER | OTHER CANCER |
|---|---|---|---|
| MEAN | -0.17 | 3.96 | 1.36 |
| AVERAGE DERIVATION | 0.96 | 1.69 | 1.04 |

FIG.65

| SUBJECT TO BE DISC-RIMINATED | LUNG CANCER | EARLY LUNG CANCER | ADENO-CARCINOMA |
|---|---|---|---|
| Tau | 0.539 | 0.592 | 0.479 |
| Thr | 0.532 | 0.568 | 0.558 |
| Ser | 0.517 | 0.562 | 0.504 |
| Asn | 0.478 | 0.587 | 0.482 |
| Glu | 0.702 | 0.696 | 0.655 |
| Gln | 0.599 | 0.740 | 0.557 |
| Pro | 0.633 | 0.600 | 0.621 |
| Gly | 0.550 | 0.496 | 0.542 |
| Ala | 0.618 | 0.678 | 0.607 |
| Cit | 0.652 | 0.549 | 0.685 |
| ABA | 0.531 | 0.574 | 0.558 |
| Val | 0.572 | 0.534 | 0.600 |
| Cys2 | 0.534 | 0.613 | 0.514 |
| Met | 0.618 | 0.516 | 0.642 |
| Ile | 0.627 | 0.527 | 0.678 |
| Leu | 0.486 | 0.545 | 0.573 |
| Tyr | 0.601 | 0.579 | 0.652 |
| Phe | 0.495 | 0.482 | 0.539 |
| His | 0.721 | 0.660 | 0.723 |
| Trp | 0.513 | 0.626 | 0.514 |
| Orn | 0.570 | 0.623 | 0.508 |
| Lys | 0.589 | 0.631 | 0.534 |
| Arg | 0.550 | 0.513 | 0.574 |

FIG.66

| NO. | FORMULA | ROC_AUC |
|---|---|---|
| 1 | (Glu)/(Tyr)+(Pro+Lys)/(Ile+His) | 0.88994 |
| 2 | (Glu+Pro)/(His)+(Lys+ABA)/(Ile) | 0.886642 |
| 3 | (Lys)/(Ile)+(Glu+Pro+Trp)/(His) | 0.88624 |
| 4 | (Glu)/(Ile)+(Pro+Lys)/(Tyr+His) | 0.886109 |
| 5 | (Glu+Lys)/(Ile)+(Pro+Trp)/(His) | 0.885163 |
| 6 | (Lys)/(Ile)+(Glu+Pro+Cys2)/(His) | 0.882412 |
| 7 | (Lys)/(Ile)+(Glu+Pro+Tau)/(His) | 0.881824 |
| 8 | (Glu+Lys)/(Ile)+(Pro+ABA)/(His) | 0.881754 |
| 9 | (Glu+Pro)/(His)+(Lys+Cys2)/(Ile) | 0.881556 |
| 10 | (Lys)/(Ile)+(Glu+Pro)/(His) | 0.880861 |
| 11 | (Lys)/(Ile)+(Glu+Pro+ABA)/(His) | 0.880654 |
| 12 | (Glu+Pro+Lys)/(Met+Ile+His) | 0.880497 |
| 13 | (Lys)/(Tyr+Ile)+(Glu+Trp)/(His) | 0.880369 |
| 14 | (Glu+Pro+Lys+Trp)/(Ile+His) | 0.879636 |
| 15 | (Glu+Lys)/(Ile)+(Pro+Cys2)/(His) | 0.879601 |
| 16 | (Glu+Pro)/(His)+(Lys+Trp)/(Ile) | 0.878823 |
| 17 | (Lys)/(Tyr)+(Glu+Pro+Ser)/(His) | 0.878427 |
| 18 | (Pro)/(His)+(Glu+Lys)/(Met+Ile) | 0.878406 |
| 19 | (Lys)/(His)+(Glu+Pro+ABA)/(Ile) | 0.877861 |
| 20 | (Lys)/(Met+Ile)+(Glu+Pro)/(His) | 0.877737 |
| 21 | (Glu+Pro+Lys)/(Ile+Cit+His) | 0.87752 |
| 22 | (Lys)/(Ile)+(Glu+Pro)/(Cit+His) | 0.877513 |
| 23 | (Glu+Pro+Lys)/(Tyr+Ile+His) | 0.877052 |
| 24 | (Pro)/(His)+(Glu+Lys+ABA)/(Ile) | 0.87691 |
| 25 | (Lys)/(Ile+Cit)+(Glu+Pro)/(His) | 0.876898 |
| 26 | (Pro)/(His)+(Glu+Lys)/(Ile+Cit) | 0.876824 |
| 27 | (Lys)/(Ile)+(Glu+Pro+Orn)/(His) | 0.876424 |
| 28 | (Glu+Lys)/(Ile)+(Pro+Tau)/(His) | 0.875779 |
| 29 | (Lys)/(His)+(Glu+Pro)/(Ile+Cit) | 0.875603 |
| 30 | (Lys)/(His)+(Glu+Pro+Cys2)/(Ile) | 0.875386 |
| 31 | (Lys)/(Ile)+(Glu+Pro+Asn)/(His) | 0.875109 |
| 32 | (Glu+Pro)/(Ile)+(Lys+ABA)/(His) | 0.874885 |
| 33 | (Pro)/(His)+(Glu+Lys)/(Ile) | 0.87456 |
| 34 | (Lys)/(Ile)+(Pro+Gln)/(Cit+His) | 0.874557 |
| 35 | (Glu+Pro)/(His)+(Lys+Asn)/(Ile) | 0.874551 |
| 36 | (Glu+Pro+Lys+ABA)/(Ile+His) | 0.874534 |
| 37 | (Glu)/(Arg)+(Pro+Lys)/(Ile+His) | 0.874525 |
| 38 | (Glu+Pro+Lys+Cys2)/(Ile+His) | 0.874386 |
| 39 | (Glu+Lys)/(Ile)+(Pro+Orn)/(His) | 0.874099 |
| 40 | (Glu)/(Cit)+(Lys+Gln)/(Ile+His) | 0.873873 |
| 41 | (Glu+Lys)/(His)+(Pro+ABA)/(Ile) | 0.873873 |
| 42 | (Glu+Pro)/(Ile)+(Lys+Trp)/(His) | 0.873829 |
| 43 | (Lys)/(His)+(Glu+Pro)/(Met+Ile) | 0.87375 |
| 44 | (Glu+Lys)/(Ile)+(Pro+Asn)/(His) | 0.873686 |
| 45 | (Pro)/(Ile)+(Glu+Lys+ABA)/(His) | 0.873346 |
| 46 | (Glu+Pro)/(Ile)+(Lys+Cys2)/(His) | 0.873266 |
| 47 | (Glu+Lys)/(His)+(Pro+Trp)/(Ile) | 0.873125 |
| 48 | (Glu+Pro)/(Ile)+(Lys+Tau)/(His) | 0.872911 |
| 49 | (Glu)/(Thr)+(Pro+Lys)/(Ile+His) | 0.872818 |
| 50 | (Lys)/(Ile)+(Glu+Pro+Ser)/(His) | 0.872653 |

FIG.67

| NO. | FORMULA | ROC_AUC |
|---|---|---|
| 51 | (Lys)/(Tyr)+(Glu+Pro+Asn)/(His) | 0.872352 |
| 52 | (Glu+ABA)/(Cit)+(Lys+Gln)/(His) | 0.872049 |
| 53 | (Glu+Pro)/(His)+(Lys+Orn)/(Ile) | 0.871909 |
| 54 | (Glu+Pro)/(Ile)+(Lys+Asn)/(His) | 0.871727 |
| 55 | (Lys)/(His)+(Glu+Pro)/(Ile) | 0.871611 |
| 56 | (Lys)/(His)+(Glu+Pro+Trp)/(Ile) | 0.871516 |
| 57 | (Pro)/(Val)+(Glu+Lys)/(Ile+His) | 0.871293 |
| 58 | (Glu+Lys)/(His)+(Pro+Cys2)/(Ile) | 0.871262 |
| 59 | (Glu+Lys)/(His)+(Pro+ABA)/(Tyr) | 0.871132 |
| 60 | (Pro)/(His)+(Glu+Lys+Cys2)/(Ile) | 0.87111 |
| 61 | (Lys)/(Tyr)+(Glu+Pro+Trp)/(His) | 0.8711 |
| 62 | (Gln)/(Tyr+Ile)+(Pro+Lys)/(His) | 0.871079 |
| 63 | (Pro)/(His)+(Glu+Lys+Trp)/(Ile) | 0.870672 |
| 64 | (Lys)/(Tyr)+(Glu+Pro+ABA)/(His) | 0.870633 |
| 65 | (Lys)/(Ile)+(Glu+Pro)/(Met+His) | 0.870562 |
| 66 | (Glu)/(Ile)+(Pro+Lys)/(Met+His) | 0.870447 |
| 67 | (Lys)/(Tyr+Cit)+(Glu+Pro)/(His) | 0.870347 |
| 68 | (Pro)/(Ile+Cit)+(Glu+Lys)/(His) | 0.870292 |
| 69 | (Lys)/(Tyr)+(Glu+Pro+Tau)/(His) | 0.870258 |
| 70 | (Lys)/(Met+His)+(Glu+Asn)/(Ile) | 0.870216 |
| 71 | (Glu+Lys)/(Ile)+(Pro+Ser)/(His) | 0.870183 |
| 72 | (Glu+ABA)/(Cit)+(Pro+Gln)/(His) | 0.870091 |
| 73 | (Glu+Lys)/(His)+(Pro+Asn)/(Ile) | 0.869914 |
| 74 | (Lys)/(Ile)+(Pro+Cys2+Trp)/(His) | 0.869908 |
| 75 | (Lys)/(Met+His)+(Glu+ABA)/(Ile) | 0.869815 |
| 76 | (Lys)/(Tyr+Ile)+(Glu+Pro)/(His) | 0.869733 |
| 77 | (Pro)/(Val)+(Glu+Lys)/(Met+His) | 0.869548 |
| 78 | (Pro)/(Cit+His)+(Glu+Lys)/(Ile) | 0.869335 |
| 79 | (Glu+Pro+Lys)/(Ile+His) | 0.869216 |
| 80 | (Glu+Pro)/(Ile)+(Lys+Orn)/(His) | 0.869212 |
| 81 | (Pro)/(Tyr)+(Glu+Lys+ABA)/(His) | 0.869104 |
| 82 | (Glu+ABA)/(Met)+(Pro+Lys)/(His) | 0.869091 |
| 83 | (Lys)/(Tyr+Ile)+(Glu+Asn)/(His) | 0.869054 |
| 84 | (Lys)/(His)+(Glu+Pro)/(Tyr+Ile) | 0.869049 |
| 85 | (Pro+Trp)/(His)+(Lys+ABA)/(Ile) | 0.869016 |
| 86 | (Pro)/(Ile)+(Glu+Lys+Asn)/(His) | 0.868857 |
| 87 | (Lys)/(His)+(Glu+Pro+Asn)/(Ile) | 0.868852 |
| 88 | (Lys)/(Met)+(Glu+Pro+Gln)/(His) | 0.868829 |
| 89 | (Pro)/(Ile)+(Glu+Lys)/(His) | 0.868749 |
| 90 | (Glu+Lys)/(Met)+(Pro+Gln)/(His) | 0.868726 |
| 91 | (Pro+Trp)/(His)+(Lys+Cys2)/(Ile) | 0.868601 |
| 92 | (Pro)/(His)+(Glu+Lys+Orn)/(Ile) | 0.868553 |
| 93 | (Glu+Lys)/(Tyr)+(Pro+Ser)/(His) | 0.868544 |
| 94 | (Glu+Pro)/(His)+(Lys+ABA)/(Tyr) | 0.868538 |
| 95 | (Glu)/(Cit)+(Pro+Lys+Gln)/(His) | 0.868526 |
| 96 | (Glu+Pro+Lys+Asn)/(Ile+His) | 0.868404 |
| 97 | (Pro)/(Tyr+Ile)+(Lys)/(Met+His) | 0.86834 |
| 98 | (Pro)/(Ile)+(Glu+Lys)/(Met+His) | 0.868285 |
| 99 | (Pro)/(Met+Ile)+(Glu+Lys)/(His) | 0.86824 |
| 100 | (Gln)/(Cit+His)+(Glu+Lys)/(Ile) | 0.868188 |

FIG.69

| NO. | FORMULA | ROC_AUC |
|---|---|---|
| 1 | 'His/Lys-0.24246*Glu/Ile+0.079067*Tyr/Asn-0.87142*Leu/Val' | 0.8903 |
| 2 | 'Glu/His+0.85767*Ser/Val+0.11151*Ala/Tyr-2.4652*Ile/Leu' | 0.8702 |
| 3 | 'Glu/His-0.88743*Met/Asn+3.4729*Leu/Val-1.4015*Ile/Pro' | 0.8538 |
| 4 | 'Gln/His+5.1137*Glu/Ile+20.9767*Leu/Val+0.025667*Ser' | 0.8814 |
| 5 | 'Glu/His+1.1017*Phe/Ile+0.0011828*Gln+0.11628*Ser/Met' | 0.8503 |
| 6 | 'Gln/His+5.997*Glu/Ile+0.10899*Asn-27.9786*Cit/Lys' | 0.8615 |
| 7 | 'Glu/His+0.5207*Asn/Ile+0.096396*Ala/Tyr+0.0037988*Ser' | 0.867 |
| 8 | 'Gln/His-0.35329*Val/Glu+2.1923*Leu/Tyr+1.0837*Pro/Ile' | 0.8633 |
| 9 | 'Glu/His+0.48995*Asn/Met+0.10987*Ala/Tyr+1.1441*Lys/Val' | 0.8595 |
| 10 | 'Gln/His+1.4459*Glu/Cit-17.4736*Ile/Leu+0.03699*Arg' | 0.8811 |
| 11 | 'His/Lys-0.27291*Glu/Ile-0.2237*Asn/Tyr-0.76094*Leu/Val' | 0.8756 |
| 12 | 'His/Lys-0.074282*Pro/Tyr+0.59258*Ile/Leu-0.054836*Tau/Cit' | 0.8914 |
| 13 | 'His/Lys-0.69444*Glu/Val-0.075099*Ser/Tyr-0.053102*Pro/Ile' | 0.8839 |
| 14 | 'Glu/His-6.1173*Ile/Gln+0.0030636*Pro+0.29079*Leu/Tyr' | 0.8831 |
| 15 | 'His/Lys-0.31321*Pro/Val-0.11647*Leu/Tyr-0.076482*Ser/Ile' | 0.8871 |
| 16 | 'His/Lys+0.60302*Ile/Leu-0.10695*Gln/Val+0.11777*Cit/Glu' | 0.8779 |
| 17 | 'His/Lys+0.047851*Tyr/Glu+0.24028*Val/Leu-0.042295*Pro/Ile' | 0.8837 |
| 18 | 'Glu/His+0.43244*Gln/Val-5.2502*Cit/Lys+0.0094933*Asn' | 0.8842 |
| 19 | 'His/Lys-0.22341*Glu/Ile-0.27161*Asn/Tyr+0.19739*Val/Leu' | 0.892 |
| 20 | 'Glu/His-0.30484*Val/Ser-2.7257*Tyr/Ala-2.307*Ile/Leu' | 0.873 |
| 21 | 'His/Lys-0.0057323*Gln/Cit-0.64019*Glu/Val+0.6448*Ile/Leu' | 0.8782 |
| 22 | 'Glu/His+0.10995*Ala/Tyr+1.2275*Lys/Val-0.15533*Cit/a-ABA' | 0.8673 |
| 23 | 'His/Lys+0.055686*Ile/Glu+0.41591*Tyr/Pro+0.047399*Cit/a-ABA' | 0.8673 |
| 24 | 'Glu/His+0.26594*Pro/Ile-0.85882*Val/Leu-0.76507*Tyr/Ser' | 0.8641 |
| 25 | 'His/Lys-0.74635*Glu/Val-0.065618*Pro/Tyr-0.00034742*Gly' | 0.8612 |
| 26 | 'His/Lys+0.065803*Ile/Glu-0.28468*Asn/Tyr-0.0057014*Ala/Cys2' | 0.8503 |
| 27 | 'Glu/His+1.1867*Asn/Tyr+0.10817*Ala/Ile+0.0011893*Gln' | 0.8785 |
| 28 | 'Glu/His+0.40481*Pro/Ile-0.87999*Val/Leu+0.18242*Tau/Cit' | 0.8495 |
| 29 | 'His/Lys-0.19967*Glu/Ile-0.015651*Gln/Tyr-0.72183*Leu/Val' | 0.8857 |
| 30 | 'Glu/His+1.2353*Asn/Ile-1.0964*Tyr/Leu-1.3019*Met/Arg' | 0.8684 |
| 31 | 'Glu/His-0.86857*Val/Lys+0.12551*Ala/Tyr+0.8164*Leu/Ile' | 0.8696 |
| 32 | 'Glu/His+1.0238*Asn/Tyr+0.1762*Pro/Ile-0.71813*Val/Leu' | 0.8483 |
| 33 | 'Glu/His+0.72349*Asn/Tyr+0.65519*Leu/Ile+0.0010041*Gln' | 0.8641 |
| 34 | 'Glu/His+1.1719*Asn/Ile+2.8601*Leu/Val+0.00092944*Gln' | 0.8589 |
| 35 | 'His/Lys+0.92371*Ile/Ala-0.10893*Leu/Tyr-0.71843*Glu/Val' | 0.896 |
| 36 | 'His/Lys-0.097716*Gln/Val-0.040263*Glu/Cit-0.19786*Leu/Ile' | 0.8839 |
| 37 | 'His/Lys-0.76352*Glu/Val-0.081807*Pro/Tyr-0.11099*a-ABA/Cit' | 0.8762 |
| 38 | 'Glu/His+0.97308*Ser/Val-1.9788*Tyr/Ala-2.1853*Ile/Leu' | 0.869 |
| 39 | 'Gln/His+1.2908*Glu/Cit-4.6259*Val/Lys+0.057501*Asn' | 0.8722 |
| 40 | 'His/Lys-0.18697*Glu/Ile-0.075582*Gln/Val-0.067702*Leu/Tyr' | 0.8799 |
| 41 | 'Glu/His+0.071876*Ser/Cit+0.0013508*Gln+1.0368*Lys/Val' | 0.877 |
| 42 | 'His/Lys-0.20278*Glu/Ile-0.066835*Pro/Tyr-0.017679*Ser/Cit' | 0.8897 |
| 43 | 'His/Lys+0.9536*Tyr/Ala-0.19946*Glu/Ile-0.19215*Ser/Val' | 0.8704 |
| 44 | 'His/Lys-0.23428*Glu/Ile-0.22622*Trp/Tyr+0.61216*Cit/Arg' | 0.8509 |
| 45 | 'His/Lys-0.24465*Leu/Ile-0.070206*Pro/Tyr+0.013544*Val/Glu' | 0.8946 |
| 46 | 'His/Lys-0.74028*Glu/Val-0.10488*Ser/Tyr-0.0068881*Ala/Cys2' | 0.8814 |
| 47 | 'His/Lys+0.014271*Val/Glu-0.018901*Gln/Tyr-0.002237*Asn' | 0.85 |
| 48 | 'Glu/His+0.93018*Ser/Val+0.27631*Pro/Tyr-2.5621*Ile/Leu' | 0.8569 |
| 49 | 'His/Lys+0.013608*Val/Glu-0.068217*Pro/Tyr-0.055008*Ser/Ile' | 0.8871 |
| 50 | 'Glu/His+0.14916*Ala/Tyr+1.5651*Ser/Val+0.0065382*Leu' | 0.8661 |

FIG.70

| NO. | FORMULA | ROC_AUC |
|---|---|---|
| 51 | 'His/Lys+0.80772*Ile/Leu+0.59517*Val/Gln-0.049093*Glu/Cit' | 0.8782 |
| 52 | 'His/Lys-0.25803*Glu/Ile+4.5207*Cit/Gln-0.88621*Leu/Val' | 0.8911 |
| 53 | 'His/Lys-0.084481*Pro/Tyr+0.77535*Ile/Leu-0.9798*Trp/Val' | 0.8756 |
| 54 | 'Gln/His+5.8036*Glu/Ile+0.11385*Asn+1.169*Tau/Cit' | 0.8667 |
| 55 | 'His/Lys-0.0054444*Gln/Cit+0.21881*Val/Leu+0.35766*Ile/Pro' | 0.927 |
| 56 | 'Glu/His+0.90512*Asn/Ile+0.37655*Leu/Tyr+0.1111*Arg/Met' | 0.8477 |
| 57 | 'His/Lys+1.0619*Ile/Ala-0.15278*Leu/Tyr-0.28721*Ser/Val' | 0.8819 |
| 58 | 'His/Lys+0.64429*Ile/Leu-0.065301*Pro/Tyr-0.036586*Glu/Cit' | 0.9023 |
| 59 | 'His/Lys+0.077781*Ile/Glu-0.33554*Asn/Tyr-0.0054726*Ala/Cys2' | 0.8865 |
| 60 | 'Gln/His-20.1548*Ile/Leu+19.4284*Glu/Val+0.034413*Ser' | 0.8949 |
| 61 | 'Glu/His+0.28221*Ser/Tyr+0.0011355*Gln-2.1943*Ile/Leu' | 0.844 |
| 62 | 'Glu/His-2.1667*Ile/Leu-0.81132*Tyr/Arg-7.5573*Cit/Ala' | 0.8877 |
| 63 | 'Gln/His+1.2096*Glu/Cit-16.7287*Ile/Leu+0.064676*Asn' | 0.8814 |
| 64 | 'His/Lys-0.89546*Glu/Val+0.19532*Tyr/Ser-0.00031951*Gln' | 0.8745 |
| 65 | 'His/Lys+0.046832*Ile/Glu-0.0056681*Gln/Cit+0.20726*Val/Leu' | 0.8926 |
| 66 | 'Glu/His+0.29407*Pro/Ile-0.68237*Tyr/Ser-0.658*Val/Leu' | 0.871 |
| 67 | 'Glu/His+0.11673*Gln/Ile+0.10028*Arg/Cit+0.0064308*Leu' | 0.89 |
| 68 | 'His/Lys-0.052651*Ala/Tyr-0.47903*Ser/Val-0.0036144*Glu' | 0.875 |
| 69 | 'His/Lys+1.1308*Ile/Ala-0.13134*Leu/Tyr-0.3306*Ser/Val' | 0.8851 |
| 70 | 'Glu/His-2.5385*Ile/Leu+0.10103*Ala/Tyr+0.0045092*Ser' | 0.8753 |
| 71 | 'Glu/His-2.644*Ile/Leu+0.10072*Ala/Tyr+0.0011864*Gln' | 0.8842 |
| 72 | 'His/Lys+0.015112*Val/Glu-0.31863*Asn/Tyr-0.0050622*Ala/Cys2' | 0.8704 |
| 73 | 'His/Lys-0.23526*Glu/Ile-0.032918*Ala/Tyr-0.19791*Ser/Val' | 0.873 |
| 74 | 'His/Lys+0.041375*Ile/Glu+0.17182*Val/Leu-0.062275*Pro/Tyr' | 0.8974 |
| 75 | 'His/Lys-0.22862*Glu/Ile-0.24945*Asn/Tyr-0.00031075*Gln' | 0.8725 |
| 76 | 'Glu/His-0.29931*Tyr/Asn-0.86477*Val/Lys-5.923*Met/Ala' | 0.8624 |
| 77 | 'His/Lys-0.20334*Glu/Ile+0.91424*Tyr/Gln-0.088683*Ala/Val' | 0.9035 |
| 78 | 'Glu/His+0.791*Asn/Tyr+0.2705*Pro/Ile+3.5257*Leu/Val' | 0.848 |
| 79 | 'Glu/His+0.96014*Ser/Val+0.090242*Ala/Tyr-2.2075*Ile/Leu' | 0.875 |
| 80 | 'His/Lys+0.61403*Tyr/Ala+0.60877*Ile/Leu-0.078009*Gln/Val' | 0.8874 |
| 81 | 'His/Lys-0.25304*Glu/Ile+0.40972*Tyr/Leu+0.27696*Val/Ala' | 0.8871 |
| 82 | 'His/Lys-0.28878*Glu/Ile+0.058566*Tyr/Asn+0.20021*Val/Leu' | 0.8857 |
| 83 | 'His/Lys+0.018885*Val/Glu-0.12592*Ser/Tyr+1.9269*Cit/Ala' | 0.8733 |
| 84 | 'His/Lys-0.97842*Glu/Val+0.20891*Tyr/Ser-0.0048082*Gln/Cit' | 0.8946 |
| 85 | 'His/Lys-0.028319*Ala/Tyr-0.23235*Glu/Ile+0.21077*Val/Leu' | 0.8837 |
| 86 | 'His/Lys+0.61668*Ile/Leu+0.49514*Val/Gln+0.13072*Cit/Glu' | 0.9052 |
| 87 | 'His/Lys-0.044122*Glu/Cit+0.4538*Val/Gln-0.085449*Leu/Tyr' | 0.8814 |
| 88 | 'Glu/His+0.8971*Asn/Tyr+0.21041*Pro/Ile+2.5633*Leu/Val' | 0.8768 |
| 89 | 'Glu/His+0.94843*Asn/Tyr-1.9239*Cit/Arg-1.3602*Cys2/Pro' | 0.8483 |
| 90 | 'His/Lys+0.73643*Ile/Leu-0.041579*Ala/Tyr-0.28721*Ser/Val' | 0.8681 |
| 91 | 'Gln/His+6.9225*Glu/Ile+2.5195*Leu/Tyr+0.10615*Asn' | 0.8716 |
| 92 | 'His/Lys-0.2423*Glu/Ile-0.031221*Ala/Tyr+0.22052*Val/Leu' | 0.8785 |
| 93 | 'His/Lys+0.80212*Tyr/Ala+0.62429*Ile/Leu-0.71238*Glu/Val' | 0.8923 |
| 94 | 'His/Lys+0.1357*Cit/Glu-0.090318*Gln/Val-0.028695*Ala/Tyr' | 0.8905 |
| 95 | 'Glu/His+0.098878*Ala/Ile+0.0015386*Gln-2.3088*Cit/Arg' | 0.846 |
| 96 | 'His/Lys-0.33948*Glu/Ile-0.34468*Asn/Tyr+0.62941*Cit/Arg' | 0.8903 |
| 97 | 'His/Lys+0.64215*Val/Gln-0.047936*Glu/Cit-0.0038321*Asn' | 0.8667 |
| 98 | 'Ala/His+4.9146*Leu/Ile+2.6786*Gln/Val-26.0977*Cit/Lys' | 0.8647 |
| 99 | 'His/Lys-0.22205*Glu/Ile+0.38171*Tyr/Pro+0.16513*Val/Leu' | 0.9063 |
| 100 | 'His/Lys+0.85327*Ile/Leu-0.29217*Pro/Val+0.13194*Tyr/Arg' | 0.8589 |

FIG.72

| NO. | FORMULA | ROC_AUC |
|---|---|---|
| 1 | '-0.92648-0.12889*His+0.070292*Glu+0.017996*Pro-0.091969*Ile+0.0090209*Gln+0.030838*Lys' | 0.9081 |
| 2 | '0.59009-0.12243*His+0.074145*Glu-0.070026*Cit-0.06683*Ile+0.010159*Gln+0.029971*Lys' | 0.8966 |
| 3 | '0.9211-0.11752*His+0.073336*Glu+0.019995*Pro-0.081607*Ile+0.028901*Lys+0.094868*a-ABA' | 0.8972 |
| 4 | '2.1184-0.10496*His+0.067701*Glu+0.023298*Pro-0.06711*Ile-0.043455*Tyr+0.03679*Lys' | 0.9015 |
| 5 | '-1.2723-0.12866*His+0.070929*Glu-0.081956*Ile+0.0063294*Ala+0.0092811*Gln+0.029859*Lys' | 0.8995 |
| 6 | '0.32279-0.12951*His+0.077508*Glu-0.072748*Ile+0.0094177*Gln+0.029868*Lys' | 0.8943 |
| 7 | '0.79902-0.12678*His+0.085203*Glu+0.020068*Pro-0.06496*Ile+0.0084199*Gln+0.11846*a-ABA' | 0.896 |
| 8 | '0.17656-0.13795*His+0.082264*Glu-0.068163*Ile+0.0085229*Gln+0.027541*Lys+0.068034*a-ABA' | 0.8934 |
| 9 | '1.7596-0.12821*His+0.072277*Glu-0.077864*Ile+0.0097509*Gln+0.030565*Lys-0.0051889*Gly' | 0.8954 |
| 10 | '0.50578-0.12583*His+0.073458*Glu-0.066866*Ile-0.042491*Met+0.0094481*Gln+0.032181*Lys' | 0.8949 |
| 11 | '0.038103-0.13256*His+0.076458*Glu-0.073268*Ile+0.009235*Gln+0.029238*Lys+0.01578*Tau' | 0.8957 |
| 12 | '0.67836-0.12847*His+0.077322*Glu-0.062209*Ile-0.020884*Tyr+0.0092621*Gln+0.032391*Lys' | 0.8957 |
| 13 | '0.49478-0.12919*His+0.078855*Glu-0.072641*Ile+0.0094036*Gln+0.02966*Lys-0.0077788*Cys2' | 0.896 |
| 14 | '-0.56108-0.10409*His+0.023688*Pro-0.067392*Ile-0.14524*Met+0.0083946*Gln+0.041924*Lys' | 0.8874 |
| 15 | '0.38759-0.13041*His+0.078934*Glu-0.071759*Ile+0.0096233*Gln+0.029996*Lys-0.0047717*Orn' | 0.8951 |
| 16 | '0.30832-0.12982*His+0.077634*Glu-0.072692*Ile+0.0094059*Gln+0.029767*Lys+0.00051348*Thr' | 0.8943 |
| 17 | '0.33129-0.12944*His+0.077375*Glu-0.0727*Ile+0.0094211*Gln+0.029922*Lys-0.00024351*Arg' | 0.8946 |
| 18 | '1.8298-0.096481*His+0.064303*Glu-0.056829*Cit+0.020593*Pro-0.079237*Ile+0.031831*Lys' | 0.894 |
| 19 | '0.57902-0.12667*His+0.082187*Glu-0.057429*Ile+0.0099733*Gln+0.031874*Lys-0.0097721*Val' | 0.896 |
| 20 | '1.8216-0.097901*His+0.059786*Glu+0.020693*Pro-0.075077*Ile-0.070001*Met+0.035438*Lys' | 0.8934 |
| 21 | '1.5968-0.10311*His+0.06638*Glu+0.019431*Pro-0.084697*Ile+0.031679*Lys' | 0.8871 |
| 22 | '-1.1252-0.12731*His+0.062134*Glu+0.017145*Pro-0.057893*Tyr+0.007018*Gln+0.027957*Lys' | 0.8854 |
| 23 | '1.424-0.10692*His+0.065857*Glu+0.018807*Pro-0.0842*Ile+0.030675*Lys+0.014343*Tau' | 0.886 |
| 24 | '1.9384-0.10784*His+0.068714*Glu-0.058465*Ile+0.0077425*Ala-0.036003*Tyr+0.036005*Lys' | 0.8934 |
| 25 | '0.80674-0.1036*His+0.064644*Glu+0.016072*Pro-0.0884*Ile+0.0040128*Ala+0.032082*Lys' | 0.8931 |
| 26 | '0.79643-0.12828*His+0.072823*Glu+0.0202*Pro-0.06692*Tyr+0.027876*Lys+0.11178*a-ABA' | 0.8903 |
| 27 | '2.6867-0.10051*His+0.062712*Glu+0.019634*Pro-0.088287*Ile+0.032008*Lys-0.0038962*Gly' | 0.8894 |
| 28 | '1.6152-0.10273*His+0.066165*Glu+0.019483*Pro-0.084748*Ile+0.031808*Lys-0.00062846*Thr' | 0.8868 |
| 29 | '0.40891-0.11041*His+0.078256*Glu-0.095671*Cit+0.010841*Gln+0.033215*Lys-0.024661*Val' | 0.89 |
| 30 | '1.6145-0.10292*His+0.06611*Glu+0.019444*Pro-0.084578*Ile+0.03179*Lys-0.00051849*Arg' | 0.8877 |
| 31 | '1.5524-0.10288*His+0.065765*Glu+0.019363*Pro-0.085373*Ile+0.031612*Lys+0.0022007*Orn' | 0.886 |
| 32 | '-2.5542-0.1126*His+0.054811*Glu-0.11061*Cit+0.013186*Pro+0.0090072*Gln+0.018248*Lys' | 0.8802 |
| 33 | '1.8087-0.10099*His+0.067398*Glu+0.019449*Pro-0.074798*Ile+0.032702*Lys-0.005268*Val' | 0.8857 |

FIG.73

| NO. | FORMULA | ROC_AUC |
|---|---|---|
| 34 | '1.5483-0.10322*His+0.06602*Glu+0.019453*Pro-0.084749*Ile+0.031731*Lys+0.0023055*Cys2' | 0.8871 |
| 35 | '-0.95777-0.10527*His-0.08365*Cit+0.022969*Pro-0.077191*Ile+0.0089037*Gln+0.03525*Lys' | 0.8862 |
| 36 | '-1.1091-0.11597*His+0.072252*Glu+0.014615*Pro+0.0094661*Gln+0.030751*Lys-0.028747*Val' | 0.8883 |
| 37 | '1.2322-0.098718*His+0.073565*Glu-0.071041*Cit+0.018536*Pro-0.052876*Ile+0.010269*Gln' | 0.8805 |
| 38 | '-1.3317-0.12729*His+0.071082*Glu-0.096723*Cit+0.008731*Gln+0.017052*Lys+0.081503*a-ABA' | 0.8845 |
| 39 | '-0.13509-0.11355*His+0.024917*Pro-0.070597*Ile-0.037285*Tyr+0.0075894*Gln+0.039347*Lys' | 0.8822 |
| 40 | '0.74836-0.1242*His+0.072976*Glu+0.0068789*Ala-0.057616*Tyr+0.026994*Lys+0.10026*a-ABA' | 0.8874 |
| 41 | '-1.318-0.1263*His+0.064723*Glu+0.0065583*Ala-0.052383*Tyr+0.0074819*Gln+0.025708*Lys' | 0.8868 |
| 42 | '1.1314-0.10523*His+0.074871*Glu+0.017776*Pro-0.057823*Ile+0.0092821*Gln' | 0.8785 |
| 43 | '1.7974-0.10403*His+0.066147*Glu+0.019915*Pro-0.047625*Tyr+0.037861*Lys-0.015675*Val' | 0.8883 |
| 44 | '0.96855-0.11555*His+0.073219*Glu-0.072338*Ile+0.0062298*Ala+0.02952*Lys+0.081753*a-ABA' | 0.8877 |
| 45 | '0.65992-0.11227*His+0.060314*Glu+0.014967*Pro+0.0042443*Ala-0.063718*Tyr+0.029932*Lys' | 0.8834 |
| 46 | '0.38179-0.10437*His+0.071148*Glu+0.013549*Pro-0.06222*Ile+0.0044205*Ala+0.0093909*Gln' | 0.8842 |
| 47 | '1.8726-0.12588*His+0.077433*Glu-0.063247*Ile+0.027449*Lys+0.02973*Tau+0.1018*a-ABA' | 0.8837 |
| 48 | '1.793-0.08774*His+0.062525*Glu-0.086251*Cit+0.017788*Pro+0.035355*Lys-0.023623*Val' | 0.8828 |
| 49 | '1.5895-0.10808*His+0.021321*Pro-0.096658*Ile+0.0086152*Gln+0.034831*Lys-0.0089131*Gly' | 0.8831 |
| 50 | '2.3711-0.10341*His+0.071163*Glu+0.018065*Pro-0.063138*Ile+0.0096428*Gln-0.004357*Gly' | 0.8791 |
| 51 | '1.6934-0.091475*His+0.024302*Pro-0.059035*Ile-0.1387*Met+0.039725*Lys+0.070974*a-ABA' | 0.8753 |
| 52 | '-1.521-0.11886*His+0.071995*Glu-0.088352*Cit+0.015024*Pro+0.0092528*Gln+0.097156*a-ABA' | 0.8805 |
| 53 | '-0.34578-0.13737*His+0.079016*Glu-0.044528*Tyr+0.0072225*Gln+0.02419*Lys+0.093723*a-ABA' | 0.8814 |
| 54 | '1.3831-0.10348*His+0.075178*Glu+0.019044*Pro-0.052433*Ile-0.012031*Tyr+0.0092228*Gln' | 0.8793 |
| 55 | '-0.059186-0.11873*His+0.067265*Glu-0.074659*Cit-0.034534*Tyr+0.0087166*Gln+0.026704*Lys' | 0.8848 |
| 56 | '-1.6314-0.096498*His-0.086625*Cit+0.020875*Pro-0.1716*Met+0.0087437*Gln+0.034513*Lys' | 0.8793 |
| 57 | '0.42618-0.12164*His+0.081729*Glu-0.054419*Ile+0.0066882*Ala+0.0090178*Gln+0.09554*a-ABA' | 0.8828 |
| 58 | '-1.6061-0.10944*His+0.068688*Glu-0.13465*Cit+0.013806*Pro+0.0099359*Gln+0.020231*Arg' | 0.8782 |
| 59 | '-0.4292-0.10473*His+0.022637*Pro-0.089127*Ile+0.0081898*Gln+0.036838*Lys-0.01257*Thr' | 0.8831 |
| 60 | '-1.2415-0.11724*His+0.075609*Glu+0.0059619*Ala+0.010264*Gln+0.029485*Lys-0.029011*Val' | 0.8839 |
| 61 | '1.0996-0.10615*His+0.074072*Glu+0.017733*Pro-0.061772*Ile+0.009158*Gln+0.0019346*Val' | 0.8779 |
| 62 | '0.92615-0.1093*His+0.076325*Glu+0.017058*Pro-0.057593*Ile+0.0090384*Gln+0.0061564*Thr' | 0.8759 |
| 63 | '0.092124-0.13121*His+0.091524*Glu+0.0090439*Gln+0.027199*Lys-0.025492*Val+0.094713*a-ABA' | 0.8883 |
| 64 | '-0.36541-0.10867*His+0.02182*Pro-0.084217*Ile+0.0082669*Gln+0.037409*Lys-0.014664*Arg' | 0.8808 |
| 65 | '0.61534-0.10906*His+0.078749*Glu+0.017428*Pro-0.060984*Ile+0.0091171*Gln+0.0097177*Arg' | 0.8759 |
| 66 | '1.206-0.11199*His+0.076844*Glu+0.017364*Pro+0.028852*Lys-0.026496*Val+0.11301*a-ABA' | 0.8874 |
| 67 | '0.93149-0.10884*His+0.076972*Glu+0.017274*Pro-0.062507*Ile+0.027947*Met+0.00926*Gln' | 0.8756 |

FIG.74

| NO. | FORMULA | ROC_AUC |
|---|---|---|
| 68 | '1.2087-0.10537*His+0.075603*Glu+0.017748*Pro-0.057774*Ile+0.0092861*Gln-0.0036276*Cys2' | 0.8768 |
| 69 | '1.2129-0.10693*His+0.077434*Glu+0.018079*Pro-0.056548*Ile+0.0096648*Gln-0.0073345*Orn' | 0.8776 |
| 70 | '1.3425-0.10439*His+0.060308*Glu-0.054032*Cit+0.019318*Pro-0.055461*Tyr+0.031195*Lys' | 0.8845 |
| 71 | '1.4651-0.10344*His+0.066585*Glu-0.075938*Ile+0.006461*Ala+0.032009*Lys' | 0.8788 |
| 72 | '1.888-0.10422*His+0.068763*Glu+0.0071457*Ala-0.042658*Tyr+0.036338*Lys-0.014962*Val' | 0.8814 |
| 73 | '1.7355-0.099961*His+0.061768*Glu-0.068068*Ile+0.0067351*Ala-0.059072*Met+0.035311*Lys' | 0.8808 |
| 74 | '1.1113-0.1193*His+0.065197*Glu+0.018293*Pro-0.065629*Tyr+0.02875*Lys+0.012837*Thr' | 0.8802 |
| 75 | '2.5334-0.11504*His+0.077599*Glu-0.062748*Ile+0.029472*Lys+0.082638*a-ABA' | 0.8773 |
| 76 | '1.2727-0.11097*His+0.060948*Glu+0.018772*Pro-0.06092*Tyr+0.030425*Lys' | 0.8762 |
| 77 | '0.85837-0.10824*His+0.07456*Glu+0.017017*Pro-0.057069*Ile+0.0090204*Gln+0.013742*Tau' | 0.8733 |
| 78 | '-0.73922-0.11552*His+0.021931*Pro-0.084523*Ile+0.0071961*Gln+0.032848*Lys+0.049355*a-ABA' | 0.8822 |
| 79 | '-0.84146-0.12864*His+0.088071*Glu-0.13143*Cit+0.0096236*Gln+0.024678*Arg+0.097863*a-ABA' | 0.8793 |
| 80 | '-0.58131-0.11085*His+0.021337*Pro-0.085859*Ile+0.0077054*Gln+0.034206*Lys' | 0.8745 |
| 81 | '2.1851-0.10427*His+0.025996*Pro-0.06127*Ile-0.041332*Tyr+0.037937*Lys+0.066367*a-ABA' | 0.8753 |
| 82 | '1.2153-0.10836*His+0.065272*Glu-0.075646*Ile+0.0062834*Ala+0.030787*Lys+0.01831*Tau' | 0.8805 |
| 83 | '-1.6853-0.11*His+0.044706*Glu+0.014863*Pro-0.15143*Met+0.007807*Gln+0.026648*Lys' | 0.8819 |
| 84 | '2.8533-0.11021*His+0.075378*Glu-0.043274*Cit-0.058959*Ile+0.030075*Lys+0.080779*a-ABA' | 0.8793 |
| 85 | '-1.5012-0.11431*His+0.021389*Pro-0.087251*Ile+0.0080584*Gln+0.034683*Lys+0.037501*Cys2' | 0.8796 |
| 86 | '0.37614-0.12071*His+0.08039*Glu-0.025242*Tyr+0.0093297*Gln+0.033844*Lys-0.019535*Val' | 0.8805 |
| 87 | '0.39163-0.11355*His+0.075109*Glu-0.077342*Met+0.0099039*Gln+0.03528*Lys-0.022261*Val' | 0.8793 |
| 88 | '2.7257-0.11154*His+0.073608*Glu-0.057045*Ile-0.042899*Met+0.031948*Lys+0.08337*a-ABA' | 0.8819 |
| 89 | '2.9616-0.11574*His+0.078107*Glu-0.049114*Ile-0.026604*Tyr+0.03243*Lys+0.086012*a-ABA' | 0.8811 |
| 90 | '2.4775-0.08925*His+0.026642*Pro-0.053664*Ile-0.099293*Met-0.029793*Tyr+0.043403*Lys' | 0.8762 |
| 91 | '2.5741-0.10082*His+0.062693*Glu-0.079483*Ile+0.0065443*Ala+0.03245*Lys-0.0040617*Gly' | 0.8822 |
| 92 | '4.2752-0.079181*His+0.02428*Pro-0.069576*Ile-0.14055*Met+0.042103*Lys-0.0073699*Gly' | 0.8782 |
| 93 | '1.7354-0.08872*His+0.056096*Glu+0.018531*Pro-0.10752*Met+0.038283*Lys-0.020127*Val' | 0.8811 |
| 94 | '-1.0488-0.10901*His+0.064964*Glu-0.10281*Cit+0.013192*Pro+0.0093189*Gln+0.013151*Thr' | 0.8704 |
| 95 | '1.7301-0.088792*His+0.023536*Pro-0.060262*Ile-0.13915*Met+0.040676*Lys+0.02019*Tau' | 0.873 |
| 96 | '2.1661-0.084346*His+0.024132*Pro-0.061578*Ile-0.1322*Met+0.041222*Lys' | 0.8676 |
| 97 | '-1.0548-0.11359*His+0.06145*Glu-0.099182*Cit+0.0090598*Gln+0.019206*Lys' | 0.871 |
| 98 | '1.6936-0.10047*His+0.065286*Glu-0.02501*Cit-0.072164*Ile+0.0061529*Ala+0.032007*Lys' | 0.8799 |
| 99 | '-1.2764-0.095754*His-0.11385*Cit+0.022546*Pro+0.0093018*Gln+0.038992*Lys-0.02486*Val' | 0.875 |
| 100 | '-0.71646-0.095335*His+0.022312*Pro-0.16641*Met+0.0082227*Gln+0.043583*Lys-0.019056*Val' | 0.875 |

FIG.76

| NO. | FORMULA | ROC_AUC |
|---|---|---|
| 1 | 'His-0.56613*Glu-0.25337*Pro+0.62838*Ile+0.43723*Tyr-0.36752*Lys' | 0.9012 |
| 2 | 'His-0.54769*Glu+0.63358*Ile-0.060059*Ala-0.07535*Gln-0.23912*Lys' | 0.8986 |
| 3 | 'His-0.56051*Glu-0.20285*Pro+0.73503*Ile-0.2696*Lys-0.72407*a-ABA' | 0.8995 |
| 4 | 'His-0.58387*Glu+0.77005*Cit-0.24308*Pro+0.80043*Ile-0.35491*Lys' | 0.8937 |
| 5 | 'His-0.56772*Glu-0.21812*Pro+0.79519*Ile-0.31459*Lys' | 0.888 |
| 6 | 'His-0.54825*Glu-0.17838*Pro+0.80372*Ile-0.039771*Ala-0.29992*Lys' | 0.8934 |
| 7 | 'His-0.52508*Glu-0.24338*Pro+0.74202*Ile+0.82155*Met-0.38885*Lys' | 0.8934 |
| 8 | 'His-0.54601*Glu-0.22382*Pro+0.86584*Ile-0.33086*Lys+0.046599*Gly' | 0.8885 |
| 9 | 'His-0.58848*Glu+0.55567*Ile-0.076831*Ala+0.37315*Tyr-0.35581*Lys' | 0.8923 |
| 10 | 'His-0.5122*Glu-0.18599*Pro+0.52242*Tyr-0.23011*Lys-0.74007*a-ABA' | 0.8871 |
| 11 | 'His-0.54967*Glu-0.21185*Pro+0.78201*Ile-0.30832*Lys-0.066613*Tau' | 0.888 |
| 12 | 'His-0.55611*Glu-0.22222*Pro+0.79941*Ile-0.3296*Lys+0.040928*Arg' | 0.8868 |
| 13 | 'His-0.58837*Glu-0.063568*Ala-0.082567*Gln-0.27119*Lys+0.2309*Val' | 0.8811 |
| 14 | 'His-0.56661*Glu-0.22655*Pro+0.82136*Ile-0.33217*Lys+0.038004*Thr' | 0.8854 |
| 15 | 'His-0.57436*Glu-0.21692*Pro+0.79368*Ile-0.31526*Lys+0.057083*Cys2' | 0.8883 |
| 16 | 'His-0.57307*Glu-0.21861*Pro+0.78954*Ile-0.31541*Lys+0.021128*Orn' | 0.888 |
| 17 | 'His-0.51487*Glu-0.19742*Pro+0.54339*Tyr-0.26846*Lys' | 0.8745 |
| 18 | 'His-0.49518*Glu-0.15918*Pro-0.040008*Ala+0.56527*Tyr-0.25631*Lys' | 0.8854 |
| 19 | 'His-0.5805*Glu+0.65736*Ile-0.061389*Ala-0.26986*Lys-0.68136*a-ABA' | 0.8883 |
| 20 | 'His-0.58724*Glu+0.70973*Ile-0.067415*Ala-0.31117*Lys' | 0.8791 |
| 21 | 'His-0.52629*Glu+0.59302*Cit-0.21341*Pro+0.52064*Tyr-0.29433*Lys' | 0.8828 |
| 22 | 'His-0.64549*Glu-0.16965*Pro+0.55548*Ile-0.050628*Ala-0.095288*Gln' | 0.8776 |
| 23 | 'His-0.50668*Glu-0.057243*Ala+0.4055*Tyr-0.058944*Gln-0.20642*Lys' | 0.8868 |
| 24 | 'His-0.22369*Pro+0.62809*Ile-0.051467*Ala+0.44388*Tyr-0.38339*Lys' | 0.8745 |
| 25 | 'His-0.47914*Glu-0.2182*Pro+0.73507*Met+0.48595*Tyr-0.33283*Lys' | 0.8799 |
| 26 | 'His-0.52401*Glu-0.18374*Pro+0.55142*Tyr-0.23681*Lys-0.10021*Thr' | 0.8791 |
| 27 | 'His-0.48361*Glu-0.18802*Pro+0.53914*Tyr-0.26071*Lys-0.1226*Tau' | 0.8785 |
| 28 | 'His-0.27376*Pro+0.62773*Ile+0.41479*Tyr-0.40044*Lys' | 0.8693 |
| 29 | 'His-0.56398*Glu+0.78388*Ile-0.06981*Ala-0.32835*Lys+0.050206*Gly' | 0.8822 |
| 30 | 'His-0.60332*Glu+0.45962*Cit+0.70167*Ile-0.065925*Ala-0.33811*Lys' | 0.8782 |
| 31 | 'His-0.29788*Pro+0.58884*Ile+1.0442*Met+0.34192*Tyr-0.4826*Lys' | 0.8773 |
| 32 | 'His-0.62068*Glu+0.57638*Ile-0.073347*Ala-0.35517*Lys+0.099221*Val' | 0.8756 |
| 33 | 'His-0.26902*Pro+0.61942*Ile+1.5861*Met-0.43913*Lys-0.78672*a-ABA' | 0.8768 |
| 34 | 'His-0.59871*Glu-0.16356*Pro-0.045469*Ala-0.33653*Lys+0.27401*Val' | 0.8776 |

FIG.77

| NO. | FORMULA | ROC_AUC |
|---|---|---|
| 35 | 'His-0.55752*Glu+0.66123*Ile-0.072362*Ala+0.62084*Met-0.36747*Lys' | 0.8819 |
| 36 | 'His-0.53284*Glu-0.19518*Pro+0.54741*Tyr-0.27176*Lys+0.15062*Cys2' | 0.8716 |
| 37 | 'His-0.54525*Glu+0.68867*Ile-0.065546*Ala-0.29671*Lys-0.14336*Tau' | 0.8811 |
| 38 | 'His-0.16753*Pro+0.71813*Ile-0.042445*Ala-0.063616*Gln-0.27161*Lys' | 0.8788 |
| 39 | 'His+0.67795*Cit-0.29395*Pro+0.64325*Ile+0.38559*Tyr-0.43331*Lys' | 0.8719 |
| 40 | 'His-0.28017*Pro+0.73672*Ile+0.40512*Tyr-0.42138*Lys+0.069101*Gly' | 0.8727 |
| 41 | 'His-0.26034*Pro+0.58204*Ile+0.40598*Tyr-0.36225*Lys-0.59158*a-ABA' | 0.8742 |
| 42 | 'His-0.28389*Pro+0.68917*Ile+1.5153*Met-0.48234*Lys' | 0.8684 |
| 43 | 'His-0.65642*Glu+0.43348*Ile-0.067683*Ala-0.088542*Gln-0.80019*a-ABA' | 0.8788 |
| 44 | 'His-0.52419*Glu-0.19844*Pro+0.53686*Tyr-0.27029*Lys+0.03446*Orn' | 0.8768 |
| 45 | 'His-0.2932*Pro+0.81887*Ile+1.529*Met-0.51095*Lys+0.085689*Gly' | 0.8796 |
| 46 | 'His-0.51967*Glu-0.19767*Pro+0.54252*Tyr-0.2678*Lys-0.0080916*Gly' | 0.8765 |
| 47 | 'His-0.23257*Pro+0.70173*Ile-0.049736*Ala+1.492*Met-0.46044*Lys' | 0.8727 |
| 48 | 'His-0.52063*Glu-0.19609*Pro+0.54662*Tyr-0.26236*Lys-0.019363*Arg' | 0.8759 |
| 49 | 'His-0.60743*Glu-0.076693*Ala+0.38853*Tyr-0.36189*Lys+0.16054*Val' | 0.8802 |
| 50 | 'His-0.62775*Glu-0.064649*Ala-0.30273*Lys+0.24433*Val-0.8903*a-ABA' | 0.8742 |
| 51 | 'His-0.53298*Glu-0.058978*Ala+0.467*Tyr-0.23181*Lys-0.69622*a-ABA' | 0.8874 |
| 52 | 'His+0.75792*Cit-0.30466*Pro+0.70391*Ile+1.3613*Met-0.5096*Lys' | 0.8719 |
| 53 | 'His-0.57559*Glu+0.72234*Ile-0.067791*Ala-0.30914*Lys-0.043403*Orn' | 0.8788 |
| 54 | 'His-0.5868*Glu+0.72474*Ile-0.06935*Ala-0.32233*Lys+0.024593*Thr' | 0.8793 |
| 55 | 'His-0.58067*Glu+0.7112*Ile-0.068079*Ala-0.32004*Lys+0.024173*Arg' | 0.8776 |
| 56 | 'His-0.59538*Glu+0.70833*Ile-0.066831*Ala-0.31208*Lys+0.070308*Cys2' | 0.8776 |
| 57 | 'His-0.2539*Pro+0.5901*Ile+0.41659*Tyr-0.37942*Lys-0.19103*Tau' | 0.8756 |
| 58 | 'His-0.27031*Pro+0.6633*Ile+0.44278*Tyr-0.39449*Lys-0.17035*Orn' | 0.8727 |
| 59 | 'His-0.6374*Glu+0.4729*Ile+0.28637*Tyr-0.33345*Lys-0.76923*a-ABA' | 0.8773 |
| 60 | 'His+1.3601*Cit-0.27415*Pro+0.88753*Ile-0.4046*Lys-0.34183*Orn' | 0.8719 |
| 61 | 'His-0.28111*Pro+0.64544*Ile+0.39637*Tyr-0.43278*Lys+0.099095*Arg' | 0.8707 |
| 62 | 'His-0.53509*Glu-0.064217*Ala+0.48567*Tyr-0.26706*Lys' | 0.8699 |
| 63 | 'His-0.63108*Glu+0.60022*Ile-0.2981*Lys-0.72934*a-ABA' | 0.8765 |
| 64 | 'His+0.91422*Cit-0.27077*Pro+0.79187*Ile-0.3994*Lys' | 0.8653 |
| 65 | 'His-0.42184*Glu-0.18123*Pro+1.6114*Met-0.28765*Lys-0.88633*a-ABA' | 0.8805 |
| 66 | 'His-0.68395*Glu+0.45685*Ile-0.076946*Ala-0.10037*Gln' | 0.8638 |
| 67 | 'His-0.26415*Pro+0.66018*Ile+1.4516*Met-0.45778*Lys-0.17099*Tau' | 0.8742 |

FIG.78

| NO. | FORMULA | ROC_AUC |
|---|---|---|
| 68 | 'His-0.43227*Glu-0.053577*Ala+1.2299*Met-0.074899*Gln-0.24311*Lys' | 0.8733 |
| 69 | 'His-0.65075*Glu+0.52534*Ile+0.28801*Tyr-0.38377*Lys' | 0.867 |
| 70 | 'His-0.27629*Pro+0.63476*Ile+0.40966*Tyr-0.39642*Lys-0.17861*Cys2' | 0.8736 |
| 71 | 'His-0.60662*Glu-0.20814*Pro-0.35437*Lys+0.27089*Val+0.023091*Gly' | 0.8725 |
| 72 | 'His-0.28361*Pro+0.66486*Ile+0.4047*Tyr-0.42147*Lys+0.048292*Thr' | 0.8716 |
| 73 | 'His-0.6437*Glu+0.65062*Ile-0.3456*Lys' | 0.865 |
| 74 | 'His-0.27944*Pro+0.72606*Ile+1.5201*Met-0.47525*Lys-0.13702*Orn' | 0.8716 |
| 75 | 'His+0.83904*Cit-0.27614*Pro+0.90675*Ile-0.41959*Lys+0.07571*Gly' | 0.8647 |
| 76 | 'His-0.62931*Glu-0.070442*Ala-0.34293*Lys+0.24427*Val' | 0.8564 |
| 77 | 'His-0.2868*Pro+0.69653*Ile+1.4946*Met-0.47648*Lys-0.21277*Cys2' | 0.869 |
| 78 | 'His-0.28708*Pro+0.70503*Ile+1.3936*Met-0.49792*Lys+0.075043*Arg' | 0.8727 |
| 79 | 'His-0.22032*Pro+0.88987*Ile-0.35121*Lys+0.10584*Gly-0.29664*Tau' | 0.8727 |
| 80 | 'His+0.98476*Cit-0.24776*Pro+0.74551*Ile-0.37627*Lys-0.24209*Tau' | 0.8745 |
| 81 | 'His-0.24908*Pro+0.91343*Ile-0.37709*Lys+0.083653*Gly' | 0.8601 |
| 82 | 'His-0.20082*Pro+0.92206*Ile-0.047259*Ala-0.35781*Lys+0.082418*Gly' | 0.8667 |
| 83 | 'His+0.75216*Ile-0.071166*Ala-0.078676*Gln-0.29866*Lys+0.092824*Gly' | 0.8762 |
| 84 | 'His-0.48365*Glu-0.062678*Ala+0.4871*Tyr-0.2541*Lys-0.18571*Tau' | 0.8753 |
| 85 | 'His-0.56718*Glu+0.56662*Ile-0.27057*Lys-0.20559*Tau-0.81267*a-ABA' | 0.8828 |
| 86 | 'His+0.52301*Ile-0.076546*Ala+1.2206*Met-0.075845*Gln-0.37943*Lys' | 0.8765 |
| 87 | 'His-0.27746*Pro+0.64985*Ile+1.6406*Met-0.47232*Lys-0.045452*Thr' | 0.8687 |
| 88 | 'His-0.66531*Glu+0.66963*Cit+0.64078*Ile-0.38375*Lys' | 0.8621 |
| 89 | 'His-0.64894*Glu+0.54785*Cit+0.59289*Ile-0.32998*Lys-0.71904*a-ABA' | 0.8788 |
| 90 | 'His-0.59185*Glu-0.14999*Pro-0.0477*Ala+0.33941*Tyr-0.077903*Gln' | 0.8676 |
| 91 | 'His-0.58005*Glu-0.078292*Ala+0.97515*Met-0.43083*Lys+0.22208*Val' | 0.8681 |
| 92 | 'His+0.7724*Cit-0.22792*Pro+0.79928*Ile-0.03745*Ala-0.37682*Lys' | 0.8667 |
| 93 | 'His-0.65837*Glu+0.69813*Cit-0.069252*Ala-0.3913*Lys+0.25126*Val' | 0.8647 |
| 94 | 'His-0.50899*Glu+0.82811*Cit-0.038216*Ala-0.080873*Gln-0.15925*Lys' | 0.8722 |
| 95 | 'His-0.19473*Pro+0.79593*Ile-0.044822*Ala-0.33242*Lys' | 0.8601 |
| 96 | 'His-0.24037*Pro+0.78596*Ile-0.35033*Lys' | 0.8567 |
| 97 | 'His+0.81985*Cit-0.25661*Pro+0.7487*Ile-0.36212*Lys-0.5132*a-ABA' | 0.871 |
| 98 | 'His-0.67291*Glu-0.066987*Ala-0.090761*Gln+0.13147*Val-0.90314*a-ABA' | 0.8679 |
| 99 | 'His-0.54354*Glu-0.058782*Ala+0.49592*Tyr-0.23708*Lys-0.096774*Thr' | 0.8742 |
| 100 | 'His-0.66304*Glu+0.52076*Ile-0.079803*Ala-0.10777*Gln+0.053727*Gly' | 0.8719 |

FIG.80

| NO. | FORMULA | ROC_AUC |
|---|---|---|
| 1 | (Gln)/(Cit+His)+(Glu+ABA)/(Cys2) | 0.881313 |
| 2 | (Glu)/(Cys2)+(Ala+Gln)/(Tyr+His) | 0.879724 |
| 3 | (ABA)/(Tyr)+(Glu+Trp)/(Cys2+His) | 0.876185 |
| 4 | (Glu)/(Cys2)+(Ala+Gln)/(Ile+His) | 0.873212 |
| 5 | (ABA)/(Tyr)+(Glu+Asn)/(Cys2+His) | 0.872504 |
| 6 | (Glu)/(Cys2)+(Ala+Lys)/(Tyr+His) | 0.871547 |
| 7 | (Ala)/(Cys2+Tyr)+(Glu+Lys)/(His) | 0.871407 |
| 8 | (Lys)/(Tyr)+(Ala+Orn)/(Cys2+His) | 0.86932 |
| 9 | (Gln)/(Met+His)+(Glu+ABA)/(Cys2) | 0.869298 |
| 10 | (Lys)/(Tyr)+(Ala+Glu)/(Cys2+His) | 0.869097 |
| 11 | (Ala+Lys)/(His)+(Glu+ABA)/(Cys2) | 0.868521 |
| 12 | (Ala)/(Cys2+Tyr)+(Lys+Tau)/(His) | 0.868411 |
| 13 | (Ala+Thr)/(His)+(Glu+ABA)/(Cys2) | 0.867777 |
| 14 | (Glu+Trp+ABA+Asn)/(Tyr+His) | 0.867593 |
| 15 | (Ala+Asn)/(His)+(Glu+ABA)/(Cys2) | 0.866291 |
| 16 | (Ala)/(Tyr)+(Glu+Lys+Tau)/(His) | 0.866174 |
| 17 | (Ala)/(His)+(Glu+ABA)/(Cys2) | 0.865967 |
| 18 | (Ala)/(Cys2+Tyr)+(Lys+Orn)/(His) | 0.865827 |
| 19 | (Ala)/(Cys2+His)+(Glu+Lys)/(Tyr) | 0.865633 |
| 20 | (Ala+Arg)/(His)+(Glu+ABA)/(Cys2) | 0.865603 |
| 21 | (Glu)/(Cys2)+(Ala+Thr)/(Tyr+His) | 0.865172 |
| 22 | (Lys)/(Tyr)+(Ala+Tau)/(Cys2+His) | 0.865017 |
| 23 | (Lys)/(Ile+Tyr)+(Glu+Trp)/(His) | 0.864677 |
| 24 | (Ala+Ser)/(His)+(Glu+ABA)/(Cys2) | 0.864547 |
| 25 | (ABA)/(Ile)+(Glu+Trp)/(Cys2+His) | 0.864254 |
| 26 | (Gln)/(Cys2+His)+(Glu+ABA)/(Cit) | 0.864216 |
| 27 | (ABA)/(Tyr)+(Glu+Trp)/(Ile+His) | 0.863786 |
| 28 | (Glu+Trp)/(His)+(ABA+Asn)/(Tyr) | 0.863716 |
| 29 | (Glu+Asn)/(His)+(Trp+ABA)/(Tyr) | 0.863709 |
| 30 | (Ala+Trp)/(His)+(Glu+ABA)/(Cys2) | 0.863143 |
| 31 | (Ala+Tau)/(His)+(Glu+ABA)/(Cys2) | 0.862915 |
| 32 | (ABA)/(Tyr)+(Glu+Leu)/(Ile+His) | 0.862761 |
| 33 | (Glu+ABA)/(Cys2)+(Lys+Asn)/(His) | 0.862684 |
| 34 | (Ala)/(Met+His)+(Glu+ABA)/(Cys2) | 0.862621 |
| 35 | (Ala+Glu)/(His)+(Lys+Leu)/(Tyr) | 0.862597 |
| 36 | (Glu)/(Cys2)+(Gln+Lys)/(Ile+His) | 0.862441 |
| 37 | (ABA)/(Cys2)+(Glu+Trp+Orn)/(His) | 0.862274 |
| 38 | (Ala+Phe)/(His)+(Glu+ABA)/(Cys2) | 0.861592 |
| 39 | (Glu)/(Cys2)+(Gln+ABA)/(Cit+His) | 0.861501 |
| 40 | (Ala)/(His)+(Glu+Lys+ABA)/(Tyr) | 0.86146 |
| 41 | (Lys)/(Tyr)+(Ala+Leu)/(Cys2+His) | 0.860816 |
| 42 | (Glu+ABA+Asn)/(Cys2+Tyr+His) | 0.860446 |
| 43 | (ABA)/(Cys2)+(Glu+Lys)/(Met+His) | 0.86042 |
| 44 | (Ala+Orn)/(His)+(Glu+ABA)/(Cys2) | 0.860284 |
| 45 | (Glu+ABA)/(Cys2)+(Gln+Trp)/(His) | 0.860272 |
| 46 | (Glu)/(Cys2)+(Gln+Lys)/(Cit+His) | 0.86024 |
| 47 | (Ala+Glu)/(Tyr)+(Lys+Tau)/(His) | 0.86011 |
| 48 | (Glu+ABA)/(Cys2)+(Lys+Trp)/(His) | 0.860075 |
| 49 | (Ala+Glu)/(His)+(Lys+Thr)/(Tyr) | 0.860038 |
| 50 | (Glu)/(Cys2)+(Gln+Thr)/(Cit+His) | 0.859906 |

FIG.81

| NO. | FORMULA | ROC_AUC |
|---|---|---|
| 51 | (Ala)/(Tyr+His)+(Glu+ABA)/(Cys2) | 0.859882 |
| 52 | (Glu)/(Cys2)+(Gln+Arg)/(Cit+His) | 0.859762 |
| 53 | (Gln)/(His)+(Glu+ABA)/(Cys2) | 0.859701 |
| 54 | (Ala)/(His)+(Glu+Lys+Trp)/(Tyr) | 0.859611 |
| 55 | (Glu+Trp+ABA)/(Cys2+Tyr+His) | 0.859562 |
| 56 | (Ala+Leu)/(His)+(Glu+ABA)/(Cys2) | 0.859552 |
| 57 | (Glu)/(Cys2)+(Gln+Leu)/(Ile+His) | 0.85949 |
| 58 | (Glu+Asn)/(Tyr)+(Trp+ABA)/(His) | 0.859438 |
| 59 | (Ala)/(Cys2+Tyr)+(Lys+Trp)/(His) | 0.859433 |
| 60 | (Glu)/(Cys2)+(Gln+Lys)/(Tyr+His) | 0.859395 |
| 61 | (Glu)/(Cys2)+(Gln+Leu)/(Cit+His) | 0.85937 |
| 62 | (Ala)/(Ile+Tyr)+(Glu+Leu)/(His) | 0.859134 |
| 63 | (Ala+Tau)/(His)+(Glu+Lys)/(Tyr) | 0.85911 |
| 64 | (ABA)/(Cys2)+(Glu+Trp+Asn)/(His) | 0.859037 |
| 65 | (Ala)/(Cys2+Tyr)+(Lys+Leu)/(His) | 0.859022 |
| 66 | (Ala+Orn)/(His)+(Lys+Leu)/(Tyr) | 0.858956 |
| 67 | (Glu+ABA)/(Cys2)+(Lys+Orn)/(His) | 0.858944 |
| 68 | (Ala)/(Met+Tyr)+(Lys+Tau)/(His) | 0.858824 |
| 69 | (Glu)/(Cys2)+(Ala+Ser)/(Tyr+His) | 0.858822 |
| 70 | (Glu)/(Cys2)+(Ala+Arg)/(Tyr+His) | 0.858743 |
| 71 | (Lys)/(Cys2+Tyr)+(Glu+Trp)/(His) | 0.858679 |
| 72 | (Ala+Tau)/(His)+(Lys+Leu)/(Tyr) | 0.858656 |
| 73 | (ABA)/(Cys2)+(Ala+Lys)/(Met+His) | 0.858637 |
| 74 | (Ala+Glu)/(His)+(Lys+Trp)/(Tyr) | 0.858575 |
| 75 | (Asn)/(His)+(Glu+ABA)/(Cys2+Tyr) | 0.858511 |
| 76 | (Ala+Glu)/(His)+(Lys+Arg)/(Tyr) | 0.858488 |
| 77 | (Trp)/(His)+(Glu+ABA+Asn)/(Tyr) | 0.858477 |
| 78 | (Lys)/(His)+(Ala+Glu)/(Cys2+Tyr) | 0.858313 |
| 79 | (ABA)/(Ile)+(Glu+Trp)/(Tyr+His) | 0.85829 |
| 80 | (Ala)/(Tyr)+(Glu+Lys+Leu)/(His) | 0.858249 |
| 81 | (Ala+ABA)/(His)+(Glu+Lys)/(Tyr) | 0.858216 |
| 82 | (Ala+Glu)/(His)+(Lys+ABA)/(Tyr) | 0.858092 |
| 83 | (Trp)/(Tyr)+(Glu+ABA)/(Cys2+His) | 0.858084 |
| 84 | (Ala)/(Tyr)+(Glu+Lys+Trp)/(His) | 0.858005 |
| 85 | (Ala+Glu)/(His)+(Lys+Ser)/(Tyr) | 0.85795 |
| 86 | (Glu+ABA)/(Cys2)+(Lys+Leu)/(His) | 0.857931 |
| 87 | (Ala)/(Cys2+His)+(Lys+Orn)/(Tyr) | 0.857742 |
| 88 | (Glu)/(Cys2)+(Ala+Leu)/(Tyr+His) | 0.857678 |
| 89 | (Ala)/(Tyr)+(Lys+Tau+Leu)/(His) | 0.857585 |
| 90 | (Glu+ABA)/(Cys2)+(Gln+Lys)/(His) | 0.857466 |
| 91 | (Ala)/(Met+Tyr)+(Glu+Lys)/(His) | 0.857425 |
| 92 | (Glu+ABA)/(Cys2)+(Gln+Orn)/(His) | 0.857371 |
| 93 | (Ala+Glu)/(His)+(Lys+Tau)/(Tyr) | 0.857359 |
| 94 | (Lys)/(Tyr)+(Ala+Phe)/(Cys2+His) | 0.857318 |
| 95 | (Lys)/(His)+(Ala+Tau)/(Cys2+Tyr) | 0.85727 |
| 96 | (Lys)/(Cit+Tyr)+(Glu+Trp)/(His) | 0.857159 |
| 97 | (Ala)/(Tyr)+(Lys+Orn+Tau)/(His) | 0.857147 |
| 98 | (Glu)/(Cys2)+(Ala+Gln)/(Met+His) | 0.857064 |
| 99 | (Ala)/(His)+(Glu+Lys+Leu)/(Tyr) | 0.856936 |
| 100 | (Ala)/(Tyr)+(Glu+Lys+Orn)/(His) | 0.856867 |

FIG.83

| NO. | FORMULA | ROC_AUC |
|---|---|---|
| 1 | 'Ala/His+0.0124*Gln+5.7935*Glu/Ile-0.13181*Val/a-ABA' | 0.9074 |
| 2 | 'Ala/His+0.0149*Gln-13.0563*Ile/Leu+21.9094*Glu/Val' | 0.8843 |
| 3 | 'Ala/His+0.0080088*Gln-12.0182*Ile/Leu-1.3769*Cys2/Glu' | 0.908 |
| 4 | 'Ala/His+0.009412*Gln-10.7844*Ile/Leu+3.3199*Glu/Tyr' | 0.89 |
| 5 | 'Ala/His+0.0056092*Gln-16.2378*Ile/Leu+0.98426*Orn/Cys2' | 0.8953 |
| 6 | 'Ala/His+0.016668*Gln+5.5626*Leu/Ile+24.4135*Glu/Val' | 0.9028 |
| 7 | 'Ala/His+0.011907*Gln+6.9349*Glu/Ile+3.2686*a-ABA/Cys2' | 0.9132 |
| 8 | 'Ala/His-24.3126*Tyr/Gln-10.4952*Ile/Leu+0.015892*Lys' | 0.8993 |
| 9 | 'Ala/His+0.010309*Gln+4.3854*Leu/Ile+1.595*Glu/Cys2' | 0.9219 |
| 10 | 'Ala/His+0.012421*Gln+10.2469*a-ABA/Tyr-0.18554*Val/Glu' | 0.8987 |
| 11 | 'Ala/His+0.012472*Gln-0.28967*Val/Glu-4.1332*Tyr/Ser' | 0.8738 |
| 12 | 'Ala/Tyr+1.027*Gln/His+0.11951*Glu-1.5385*Cys2/a-ABA' | 0.919 |
| 13 | 'Ala/His+0.012114*Gln+6.5377*Glu/Tyr+5.3785*Ser/Val' | 0.897 |
| 14 | 'Ala/His+3.2239*Glu/Cys2-11.9488*Tyr/Lys-1.9752*Val/Ser' | 0.8935 |
| 15 | 'Ala/His+0.011863*Gln+7.5839*Glu/Tyr+3.5847*a-ABA/Cys2' | 0.8935 |
| 16 | 'Ala/His-79.209*Cys2/Gln+2.2892*Leu/Tyr+7.6808*Lys/Val' | 0.8733 |
| 17 | 'Ala/His+0.014397*Gln+4.6368*Leu/Ile+19.4504*Glu/Val' | 0.9034 |
| 18 | 'Ala/His+0.013578*Gln+7.6956*Glu/Ile+2.9217*a-ABA/Cys2' | 0.9201 |
| 19 | 'Ala/His+0.010833*Gln-0.88628*Ile/Glu-1.2766*Cys2/a-ABA' | 0.886 |
| 20 | 'His/Lys-0.00060101*Gln-0.034805*Ala/Ile-1.1974*Leu/Val' | 0.9057 |
| 21 | 'Ala/His+0.0097358*Gln+12.4387*a-ABA/Tyr+19.8295*Glu/Val' | 0.9149 |
| 22 | 'Ala/His+0.0077544*Gln+0.7672*Tau/Cys2+1.4714*Lys/Tyr' | 0.8796 |
| 23 | 'Ala/His+0.017413*Gln+7.609*Glu/Ile-5.1012*Val/Leu' | 0.8993 |
| 24 | 'Ala/His+0.0104*Gln-9.1887*Tyr/Lys+4.2059*Glu/Ile' | 0.8976 |
| 25 | 'Ala/His+0.1733*Gln/Cys2+24.7747*Glu/Val+0.18785*a-ABA' | 0.9138 |
| 26 | 'Ala/His-8.2825*Tyr/Lys+0.0086645*Gln-9.5405*Ile/Leu' | 0.8825 |
| 27 | 'Ala/His+0.012488*Gln+6.4318*Glu/Tyr+4.7359*Ser/Val' | 0.8848 |
| 28 | 'Ala/His+0.012464*Gln-0.39802*Tyr/a-ABA+1.8104*Glu/Cys2' | 0.9086 |
| 29 | 'Ala/His+0.98055*Gln/Ile+0.051313*Leu-0.2073*Val/Glu' | 0.8889 |
| 30 | 'His/Lys+2.3441*Cys2/Ala-0.35564*Glu/Tyr-0.28713*Ser/Val' | 0.8924 |
| 31 | 'Ala/His+0.12079*Gln/Cys2-1.0636*Tyr/Glu+0.044938*Ser' | 0.8924 |
| 32 | 'Ala/His+0.0097435*Gln+24.1442*Glu/Val+0.44997*Ser/Cys2' | 0.8964 |
| 33 | 'Ala/His+0.0082676*Gln-1.4454*Tyr/Tau+2.4456*a-ABA/Cys2' | 0.8993 |
| 34 | 'Ala/His+0.058274*Gln/Cys2+1.255*Leu/Tyr-3.6776*Val/Lys' | 0.8756 |
| 35 | 'Ala/His+0.01068*Gln-0.47033*Tyr/a-ABA+2.1814*Glu/Cys2' | 0.9051 |
| 36 | 'Ala/His-13.6359*Ile/Leu+0.0098391*Gln-0.70463*Tyr/Glu' | 0.8976 |
| 37 | 'Ala/His+0.0078243*Gln+0.88784*Tau/Cys2-0.10811*Val/a-ABA' | 0.8825 |
| 38 | 'Ala/His+0.015312*Gln-0.47068*Tyr/a-ABA+23.6985*Glu/Val' | 0.8814 |
| 39 | 'Ala/His-89.703*Cys2/Gln+6.0707*Glu/Tyr+0.13656*a-ABA' | 0.8981 |
| 40 | 'Ala/His+0.0091844*Gln-0.367*Tyr/a-ABA+1.5975*Glu/Cys2' | 0.9196 |
| 41 | 'Ala/His+0.01256*Gln+30.4378*Glu/Val+0.4428*Ser/Cys2' | 0.9022 |
| 42 | 'Ala/His+0.013162*Gln+2.0465*Glu/Cys2+5.717*Ser/Val' | 0.9132 |
| 43 | 'Ala/His+0.010909*Gln-0.3894*Tyr/a-ABA+17.217*Glu/Val' | 0.9306 |
| 44 | 'Ala/His-3.3634*Cys2/Glu+11.8322*a-ABA/Tyr+0.032335*Asn' | 0.8958 |
| 45 | 'Ala/His+0.010595*Gln-12.2902*Ile/Leu+4.0323*Glu/Tyr' | 0.8958 |
| 46 | 'Ala/His-13.8485*Tyr/Lys-2.218*Cys2/Glu+0.043054*Asn' | 0.8819 |
| 47 | 'Ala/His+0.014679*Gln+5.6326*Glu/Ile+7.254*Met/Tyr' | 0.8999 |
| 48 | 'Ala/His+0.0092903*Gln+5.9048*Glu/Ile+10.6516*a-ABA/Tyr' | 0.9265 |
| 49 | 'Ala/His+0.012287*Gln+27.7794*Glu/Val+3.576*a-ABA/Cys2' | 0.9039 |
| 50 | 'Ala/His+0.011321*Gln-1.0023*Tyr/Glu+3.731*Ser/Val' | 0.8802 |

FIG.84

| NO. | FORMULA | ROC_AUC |
| --- | --- | --- |
| 51 | 'Ala/His+0.012136*Gln-4.5934*Val/Leu-3.8185*Ile/Ser' | 0.8877 |
| 52 | 'Ala/His+0.010817*Gln-1.2024*Ile/Glu-12.7338*Cys2/Thr' | 0.9016 |
| 53 | 'Ala/His+0.010949*Gln+6.2048*Glu/Ile-1.2723*Cys2/a-ABA' | 0.9045 |
| 54 | 'Ala/His+0.013061*Gln+6.727*Glu/Tyr+4.6763*Ser/Val' | 0.8628 |
| 55 | 'Ala/His+0.013515*Gln+28.0578*Glu/Val+3.4075*a-ABA/Cys2' | 0.923 |
| 56 | 'Ala/His+0.0080399*Gln-1.0696*Ile/Glu+3.3515*a-ABA/Cys2' | 0.9045 |
| 57 | 'Ala/His+0.010084*Gln-6.1302*Val/Lys+1.2718*Leu/Tyr' | 0.864 |
| 58 | 'Ala/His+0.013525*Gln+8.4897*Glu/Tyr+5.946*Ser/Val' | 0.897 |
| 59 | 'Ala/His+0.011771*Gln+6.3252*Glu/Tyr-1.1685*Val/Ser' | 0.8825 |
| 60 | 'Ala/His-24.8403*Cys2/Lys+1.7188*Leu/Tyr-1.516*Ile/Tau' | 0.8727 |
| 61 | 'Ala/His+0.01009*Gln-0.90522*Tyr/Glu+2.7566*a-ABA/Cys2' | 0.9074 |
| 62 | 'Ala/His+0.012114*Gln+6.0149*Glu/Tyr+3.7551*Ser/Val' | 0.8762 |
| 63 | 'Ala/His+0.010711*Gln+7.1225*Glu/Tyr-1.5426*Cys2/a-ABA' | 0.8791 |
| 64 | 'Ala/His+0.011137*Gln+7.0075*Glu/Ile+3.1213*a-ABA/Cys2' | 0.9317 |
| 65 | 'Ala/His+0.010091*Gln-13.019*Ile/Leu+4.4635*Glu/Tyr' | 0.89 |
| 66 | 'Ala/His-9.9088*Tyr/Lys+0.010775*Gln+20.375*Glu/Val' | 0.8889 |
| 67 | 'Ala/His-35.4929*Cys2/Lys-0.32703*Val/Glu+0.07278*Asn' | 0.8524 |
| 68 | 'Ala/His-95.0598*Cys2/Gln+5.7824*Glu/Tyr-12.7589*Ile/Leu' | 0.8819 |
| 69 | 'Ala/His+0.011034*Gln-0.94111*Ile/Glu+8.6936*a-ABA/Tyr' | 0.8993 |
| 70 | 'Ala/His+0.10893*Gln/Cys2+0.11042*Glu+15.4846*a-ABA/Tyr' | 0.9172 |
| 71 | 'Ala/His+2.3759*Lys/Tyr-2.8414*Cys2/Glu+0.048412*Asn' | 0.8999 |
| 72 | 'Ala/His+0.012637*Gln-2.8507*Cys2/Glu+5.4883*Ser/Val' | 0.8565 |
| 73 | 'Ala/His+0.011284*Gln+2.8486*Leu/Tyr+6.0658*Glu/Ile' | 0.9039 |
| 74 | 'Ala/His+0.015394*Gln+6.1775*Glu/Ile+4.8101*Ser/Val' | 0.8773 |
| 75 | 'Ala/His+2.398*Glu/Cys2+0.35819*Gln/Tyr+37.3528*a-ABA/Val' | 0.9225 |
| 76 | 'Ala/His+0.011085*Gln-1.1099*Ile/Glu+0.41758*Ser/Cys2' | 0.8738 |
| 77 | 'Ala/His+0.012105*Gln+6.4653*Glu/Ile+0.46284*Ser/Cys2' | 0.8831 |
| 78 | 'Ala/His+1.0197*Tau/Cys2+12.3042*a-ABA/Tyr+0.058757*Glu' | 0.9144 |
| 79 | 'Ala/His+0.00878*Gln+12.9711*a-ABA/Tyr-2.6336*Cys2/Glu' | 0.9074 |
| 80 | 'Ala/His+0.012701*Gln+5.9025*Leu/Ile-0.25517*Val/Glu' | 0.8947 |
| 81 | 'Ala/His+0.011652*Gln-13.1226*Ile/Leu+3.5137*Glu/Tyr' | 0.9126 |
| 82 | 'Ala/His+0.01502*Gln-15.8502*Ile/Leu+20.5877*Glu/Val' | 0.9034 |
| 83 | 'Ala/His+0.01258*Gln-4.1725*Val/Leu+0.58857*Ser/Met' | 0.8802 |
| 84 | 'Ala/His+0.0091884*Gln+7.0518*Glu/Tyr+2.7755*a-ABA/Cys2' | 0.9068 |
| 85 | 'Ala/His+0.013034*Gln+7.0836*Ser/Val+6.5233*Glu/Tyr' | 0.8802 |
| 86 | 'Ala/His+0.0074536*Gln-0.3403*Tyr/a-ABA-2.3956*Cys2/Glu' | 0.8953 |
| 87 | 'Ala/His+0.01131*Gln+3.4956*Tau/Tyr+14.8929*Glu/Val' | 0.8808 |
| 88 | 'Ala/His+0.0099218*Gln-11.9163*Ile/Leu-0.48703*Tyr/Glu' | 0.8981 |
| 89 | 'Ala/His+0.017042*Gln+6.23*Glu/Ile+18.0903*Leu/Val' | 0.8981 |
| 90 | 'Ala/His+0.010843*Gln+24.6381*Glu/Val+2.7538*a-ABA/Cys2' | 0.9005 |
| 91 | 'Ala/His+0.1019*Gln/Cys2-0.91621*Tyr/Glu+0.11295*a-ABA' | 0.8773 |
| 92 | 'Ala/His+0.012205*Gln+5.9706*Glu/Tyr+6.0882*Ser/Val' | 0.8924 |
| 93 | 'Ala/His+0.79537*Gln/Ile+0.053179*Leu+16.7622*Glu/Val' | 0.9034 |
| 94 | 'Ala/His+0.015438*Gln-4.5525*Val/Lys-0.63889*Tyr/Glu' | 0.8767 |
| 95 | 'Ala/His+0.012092*Gln-13.7425*Ile/Leu+2.1319*Glu/Cys2' | 0.8993 |
| 96 | 'Gln/His+0.091931*Glu+3.9043*a-ABA/Cys2+4.3541*Lys/Val' | 0.9358 |
| 97 | 'Ala/His+0.13798*Gln/Cys2+8.7964*Glu/Tyr+0.11711*Asn' | 0.8623 |
| 98 | 'Ala/His+0.0095331*Gln+2.5217*Glu/Cys2+10.4376*a-ABA/Tyr' | 0.8987 |
| 99 | 'Ala/His+0.0083653*Gln-10.8564*Ile/Leu-3.4838*Cys2/Tau' | 0.8883 |
| 100 | 'Ala/His+0.013061*Gln+27.5834*Glu/Val+0.50763*Ser/Cys2' | 0.8964 |

FIG.86

| NO. | FORMULA | ROC_AUC |
|---|---|---|
| 1 | '-6.1249+0.011601*Gln+0.10168*Glu-0.14098*His+0.025112*Lys-0.1688*Cys2+0.17346*a-ABA' | 0.9126 |
| 2 | '-7.094+0.012285*Gln+0.07573*Glu+0.0075267*Ala-0.11043*His+0.022325*Lys-0.16654*Cys2' | 0.8953 |
| 3 | '-9.9887+0.014245*Gln+0.087536*Glu+0.010218*Ala-0.10529*His-0.14752*Cys2+0.035315*Ser' | 0.9016 |
| 4 | '-5.0429+0.011356*Gln+0.089146*Glu-0.11718*His+0.039295*Lys-0.14701*Cys2-0.031815*Tyr' | 0.8958 |
| 5 | '-0.18715+0.10517*Glu-0.12532*His+0.037947*Lys-0.16995*Cys2-0.036246*Tyr+0.16324*a-ABA' | 0.8929 |
| 6 | '-1.6392+0.086967*Glu+0.0053216*Ala-0.11903*His+0.02499*Lys-0.19047*Cys2+0.156*a-ABA' | 0.8854 |
| 7 | '-6.202+0.01407*Gln+0.091659*Glu-0.11463*His+0.036451*Lys-0.1579*Cys2-0.1072*Cit' | 0.8976 |
| 8 | '-1.2833+0.08582*Glu+0.0072939*Ala-0.094615*His+0.03926*Lys-0.17372*Cys2-0.04335*Tyr' | 0.8831 |
| 9 | '-6.8919+0.01352*Gln+0.095948*Glu-0.13835*His+0.078873*Trp-0.1783*Cys2+0.19289*a-ABA' | 0.9207 |
| 10 | '-5.8086+0.012606*Gln+0.09008*Glu+0.0077529*Ala-0.11265*His-0.17338*Cys2+0.16799*a-ABA' | 0.9207 |
| 11 | '-1.6883+0.092233*Glu-0.12632*His+0.026788*Lys-0.18152*Cys2+0.032182*Tau+0.1699*a-ABA' | 0.8791 |
| 12 | '-7.8991+0.012471*Gln+0.093123*Glu-0.1194*His+0.023534*Lys-0.13869*Cys2+0.024521*Ser' | 0.8918 |
| 13 | '-6.2135+0.011633*Gln+0.081416*Glu-0.11475*His+0.027943*Lys-0.14713*Cys2+0.019987*Tau' | 0.886 |
| 14 | '-6.9635+0.012252*Gln+0.090489*Glu-0.11855*His+0.02328*Lys-0.14529*Cys2+0.052788*Asn' | 0.8924 |
| 15 | '-0.80155+0.084595*Glu-0.10135*His+0.045011*Lys-0.1553*Cys2+0.037959*Tau-0.051777*Tyr' | 0.8785 |
| 16 | '-7.0559+0.01305*Gln+0.079446*Glu+0.0096825*Ala-0.095735*His-0.16025*Cys2+0.01888*Thr' | 0.8843 |
| 17 | '-7.472+0.013529*Gln+0.081144*Glu+0.0087152*Ala-0.099826*His-0.15178*Cys2+0.061221*Asn' | 0.8883 |
| 18 | '-5.6594+0.011905*Gln+0.083576*Glu-0.11407*His+0.028715*Lys-0.1442*Cys2' | 0.8802 |
| 19 | '-2.2787+0.066828*Glu+0.0066613*Ala-0.091359*His+0.025655*Lys-0.17938*Cys2+0.025574*Tau' | 0.8663 |
| 20 | '-0.56888+0.095951*Glu-0.12506*His+0.028447*Lys-0.17823*Cys2+0.1675*a-ABA' | 0.8791 |
| 21 | '-6.1797+0.01284*Gln+0.091107*Glu-0.11824*His+0.032456*Lys-0.014244*Orn-0.14406*Cys2' | 0.8883 |
| 22 | '-6.8338+0.012438*Gln+0.080564*Glu-0.12053*His+0.023699*Lys+0.042475*Trp-0.15207*Cys2' | 0.8953 |
| 23 | '-6.8993+0.013524*Gln+0.1048*Glu-0.12294*His-0.13957*Cys2+0.17367*a-ABA+0.025282*Ser' | 0.9207 |
| 24 | '-1.0922+0.090475*Glu-0.12827*His+0.024174*Lys+0.034336*Trp-0.18663*Cys2+0.16323*a-ABA' | 0.8831 |
| 25 | '-0.46922+0.097538*Glu-0.12288*His+0.030494*Lys-0.17967*Cys2+0.16412*a-ABA-0.029505*Cit' | 0.8773 |
| 26 | '-1.3811+0.070228*Glu+0.006771*Ala-0.091728*His+0.027053*Lys-0.17736*Cys2' | 0.86 |
| 27 | '-5.7377+0.011905*Gln+0.08329*Glu-0.11375*His+0.028377*Lys-0.14331*Cys2+0.00070523*Pro' | 0.8791 |
| 28 | '-1.3528+0.098771*Glu-0.12618*His+0.026828*Lys-0.17334*Cys2+0.15998*a-ABA+0.0094704*Ser' | 0.8791 |
| 29 | '-5.846+0.013311*Gln+0.072553*Glu+0.0096362*Ala-0.086931*His-0.14132*Cys2' | 0.8808 |
| 30 | '-0.69985+0.095449*Glu-0.12445*His+0.027818*Lys-0.17794*Cys2+0.001432*Pro+0.16729*a-ABA' | 0.8791 |
| 31 | '-6.8385+0.013436*Gln+0.071773*Glu+0.0078725*Ala-0.096051*His+0.038295*Trp-0.146*Cys2' | 0.8883 |
| 32 | '-6.2021+0.011822*Gln+0.086247*Glu-0.1132*His+0.025405*Lys-0.14254*Cys2+0.009556*Thr' | 0.8831 |
| 33 | '-3.4447+0.076613*Glu+0.0073369*Ala-0.095296*His+0.022902*Lys-0.16908*Cys2+0.021415*Ser' | 0.8756 |

FIG.87

| NO. | FORMULA | ROC_AUC |
|---|---|---|
| 34 | '-0.89816+0.097846*Glu-0.12501*His+0.02712*Lys-0.17774*Cys2+0.015201*Asn+0.15966*a-ABA' | 0.8796 |
| 35 | '-6.2212+0.012922*Gln+0.069222*Glu+0.0092493*Ala-0.08746*His-0.13922*Cys2+0.016166*Tau' | 0.8791 |
| 36 | '-1.0078+0.098976*Glu-0.12779*His+0.024419*Lys-0.17722*Cys2+0.17019*a-ABA+0.011419*Thr' | 0.8837 |
| 37 | '-0.44876+0.090044*Glu-0.12463*His+0.025046*Lys+0.01423*Orn-0.18632*Cys2+0.17593*a-ABA' | 0.8825 |
| 38 | '-12.231+0.01453*Gln+0.072423*Glu+0.0076123*Ala-0.10201*His+0.03468*Ser' | 0.8779 |
| 39 | '-4.6559+0.011947*Gln+0.093929*Glu-0.11985*His-0.14435*Cys2+0.029933*Tau+0.19613*a-ABA' | 0.9149 |
| 40 | '-13.1039+0.014696*Gln+0.071513*Glu+0.0062977*Ala-0.11028*His+0.031373*Trp+0.03439*Ser' | 0.8843 |
| 41 | '-2.2202+0.075873*Glu+0.0064194*Ala-0.094657*His+0.024371*Lys-0.17766*Cys2+0.035362*Asn' | 0.8657 |
| 42 | '-0.64271+0.077718*Glu-0.092331*His+0.033429*Lys-0.17116*Cys2+0.034911*Tau-0.069578*Cit' | 0.8605 |
| 43 | '-3.888+0.012483*Gln+0.096753*Glu-0.11376*His-0.14274*Cys2+0.19442*a-ABA' | 0.9172 |
| 44 | '-1.1605+0.0725*Glu+0.0064035*Ala-0.091612*His+0.028497*Lys-0.17885*Cys2-0.019566*Cit' | 0.8605 |
| 45 | '-1.302+0.070583*Glu+0.006881*Ala-0.092056*His+0.02759*Lys-0.17836*Cys2-0.0012472*Pro' | 0.8588 |
| 46 | '-0.67926+0.086541*Glu-0.11228*His+0.040128*Lys+0.069599*Trp-0.1617*Cys2-0.058323*Tyr' | 0.8831 |
| 47 | '-5.7945+0.013113*Gln+0.071425*Glu+0.0095693*Ala-0.086857*His+0.0026461*Orn-0.14263*Cys2' | 0.8814 |
| 48 | '-1.5414+0.068978*Glu+0.0061842*Ala-0.093503*His+0.025523*Lys+0.014882*Trp-0.17846*Cys2' | 0.8617 |
| 49 | '-5.0996+0.012222*Gln+0.10265*Glu-0.12399*His-0.15275*Cys2+0.19037*a-ABA+0.018982*Thr' | 0.9277 |
| 50 | '-5.9235+0.013272*Gln+0.072349*Glu+0.0095029*Ala-0.086933*His-0.14035*Cys2+0.00083252*Pro' | 0.8819 |
| 51 | '-12.7546+0.014233*Gln+0.082383*Glu+0.0066444*Ala-0.12316*His+0.12994*a-ABA+0.033107*Ser' | 0.9068 |
| 52 | '-12.664+0.014144*Gln+0.070702*Glu+0.0066563*Ala-0.11126*His+0.0099104*Lys+0.031752*Ser' | 0.8837 |
| 53 | '-12.4441+0.014569*Gln+0.073283*Glu+0.0072094*Ala-0.10508*His+0.022774*Asn+0.030759*Ser' | 0.8819 |
| 54 | '-1.3414+0.067058*Glu+0.0068092*Ala-0.090364*His+0.025552*Lys+0.0054147*Orn-0.17865*Cys2' | 0.8628 |
| 55 | '-1.867+0.07235*Glu+0.0068277*Ala-0.091292*His+0.023363*Lys-0.17746*Cys2+0.010108*Thr' | 0.8669 |
| 56 | '-5.8639+0.011255*Gln+0.0081144*Ala-0.10877*His+0.019771*Lys-0.12818*Cys2+0.028044*Tau' | 0.8744 |
| 57 | '-12.2393+0.014295*Gln+0.068689*Glu+0.0075157*Ala-0.10177*His+0.0094331*Tau+0.033089*Ser' | 0.8785 |
| 58 | '-5.3605+0.012689*Gln+0.10422*Glu-0.11974*His-0.1476*Cys2+0.047095*Asn+0.16688*a-ABA' | 0.9144 |
| 59 | '-12.3226+0.01449*Gln+0.072067*Glu+0.0074372*Ala-0.1018*His+0.0014434*Pro+0.034209*Ser' | 0.8767 |
| 60 | '-2.1237+0.10157*Glu-0.10293*His+0.042502*Lys-0.14146*Cys2-0.050018*Tyr+0.024765*Ser' | 0.8831 |
| 61 | '-1.3075+0.10191*Glu-0.10173*His+0.039888*Lys-0.15007*Cys2+0.058455*Asn-0.047326*Tyr' | 0.8819 |
| 62 | '-5.4753+0.013174*Gln+0.07413*Glu+0.0099104*Ala-0.084362*His-0.13879*Cys2-0.0088106*Tyr' | 0.8837 |
| 63 | '-12.2282+0.014473*Gln+0.072378*Glu+0.0075613*Ala-0.10207*His+0.0010819*Thr+0.034116*Ser' | 0.8767 |
| 64 | '-5.7521+0.013709*Gln+0.073792*Glu+0.0094455*Ala-0.085317*His-0.14055*Cys2-0.01922*Cit' | 0.8866 |
| 65 | '-9.7558+0.014064*Gln+0.09355*Glu-0.11705*His+0.070982*Trp-0.12813*Cys2+0.03352*Ser' | 0.8941 |
| 66 | '-4.4821+0.012216*Gln+0.095993*Glu-0.11288*His-0.14109*Cys2+0.0043634*Pro+0.19101*a-ABA' | 0.9178 |
| 67 | '-3.7971+0.013276*Gln+0.098825*Glu-0.10911*His-0.14047*Cys2+0.19261*a-ABA-0.044287*Cit' | 0.9201 |

FIG.88

| NO. | FORMULA | ROC_AUC |
|---|---|---|
| 68 | '-2.1628+0.092074*Glu+0.0077244*Ala-0.10163*His-0.17168*Cys2+0.15851*a-ABA+0.025093*Ser' | 0.8767 |
| 69 | '-12.3475+0.015831*Gln+0.076578*Glu+0.0070729*Ala-0.097921*His+0.038412*Ser-0.060157*Cit' | 0.89 |
| 70 | '-1.1594+0.07606*Glu-0.095001*His+0.030041*Lys-0.1617*Cys2+0.03003*Tau' | 0.8519 |
| 71 | '-11.9534+0.014287*Gln+0.081965*Glu+0.0088697*Ala-0.093439*His-0.032613*Tyr+0.042342*Ser' | 0.8958 |
| 72 | '0.18092+0.08944*Glu-0.096605*His+0.043317*Lys-0.15097*Cys2-0.040959*Tyr' | 0.8646 |
| 73 | '-12.7269+0.015684*Gln+0.082799*Glu+0.0080832*Ala-0.10703*His-0.016137*Orn+0.039638*Ser' | 0.8825 |
| 74 | '-10.107+0.01419*Gln+0.066569*Glu+0.0060794*Ala-0.095765*His+0.058476*Asn' | 0.8738 |
| 75 | '-10.4714+0.013977*Gln+0.063309*Glu+0.0059714*Ala-0.096812*His+0.016096*Tau+0.055513*Asn' | 0.8646 |
| 76 | '-3.6762+0.012379*Gln+0.097546*Glu-0.11259*His-0.14082*Cys2-0.0042282*Tyr+0.19566*a-ABA' | 0.9167 |
| 77 | '-3.742+0.011728*Gln+0.093408*Glu-0.11448*His+0.0097794*Orn-0.14844*Cys2+0.19595*a-ABA' | 0.9144 |
| 78 | '-10.9255+0.01447*Gln+0.06578*Glu+0.0049728*Ala-0.1033*His+0.028073*Trp+0.056034*Asn' | 0.875 |
| 79 | '-7.8437+0.013848*Gln+0.088774*Glu-0.11244*His+0.059096*Trp-0.13488*Cys2+0.066546*Asn' | 0.8895 |
| 80 | '-10.8937+0.013858*Gln+0.065465*Glu+0.005073*Ala-0.10883*His+0.012837*Lys+0.049546*Asn' | 0.8727 |
| 81 | '-2.0536+0.082885*Glu-0.098531*His+0.027031*Lys-0.16435*Cys2+0.027486*Tau+0.038977*Asn' | 0.86 |
| 82 | '-1.4933+0.07337*Glu-0.097927*His+0.026482*Lys+0.028955*Trp-0.16821*Cys2+0.025377*Tau' | 0.8536 |
| 83 | '-10.2461+0.014144*Gln+0.066149*Glu+0.0058077*Ala-0.095922*His+0.0022746*Pro+0.056834*Asn' | 0.875 |
| 84 | '-0.43543+0.088717*Glu-0.09424*His+0.041709*Lys-0.14486*Cys2+0.0069088*Pro-0.047007*Tyr' | 0.8698 |
| 85 | '-0.50542+0.078039*Glu+0.006531*Ala-0.095602*His-0.17641*Cys2+0.032499*Tau+0.17561*a-ABA' | 0.8634 |
| 86 | '-12.122+0.016596*Gln+0.084601*Glu-0.1177*His+0.024227*Lys+0.036685*Ser-0.13246*Cit' | 0.8981 |
| 87 | '-1.1868+0.075996*Glu-0.094859*His+0.0299*Lys-0.16142*Cys2+0.00030015*Pro+0.029913*Tau' | 0.853 |
| 88 | '-10.2323+0.013936*Gln+0.06659*Glu+0.0059657*Ala-0.096288*His+0.05038*Asn+0.0062848*Thr' | 0.8779 |
| 89 | '-9.601+0.013536*Gln+0.058346*Glu+0.0055158*Ala-0.10007*His+0.015395*Lys' | 0.864 |
| 90 | '0.22908+0.089799*Glu-0.096009*His+0.043337*Lys-0.15181*Cys2-0.039275*Tyr-0.0098064*Cit' | 0.8628 |
| 91 | '-8.8169+0.013597*Gln+0.054654*Glu+0.0067331*Ala-0.084612*His+0.019349*Tau' | 0.86 |
| 92 | '-10.0007+0.013295*Gln+0.055204*Glu+0.0054224*Ala-0.10077*His+0.014691*Lys+0.016956*Tau' | 0.8617 |
| 93 | '-7.1356+0.012972*Gln+0.084379*Glu-0.10511*His+0.062821*Trp-0.13113*Cys2+0.018268*Thr' | 0.8848 |
| 94 | '-0.68136+0.073969*Glu-0.099128*His+0.026731*Lys+0.037534*Trp-0.16704*Cys2' | 0.8536 |
| 95 | '-2.2527+0.081315*Glu-0.097364*His+0.028137*Lys-0.1565*Cys2+0.026092*Tau+0.013223*Ser' | 0.8623 |
| 96 | '-9.39+0.013727*Gln+0.072944*Glu+0.0066758*Ala-0.088514*His+0.069753*Asn-0.024847*Tyr' | 0.8791 |
| 97 | '-1.1595+0.074946*Glu-0.094485*His+0.029461*Lys+0.0026125*Orn-0.16182*Cys2+0.029633*Tau' | 0.8524 |
| 98 | '-9.6026+0.013393*Gln+0.058676*Glu+0.0062329*Ala-0.090813*His+0.018117*Tau+0.012912*Thr' | 0.8652 |
| 99 | '-10.1787+0.013866*Gln+0.061596*Glu+0.0051903*Ala-0.097085*His+0.030998*Trp+0.013435*Thr' | 0.8733 |
| 100 | '0.30375+0.082692*Glu-0.094455*His+0.041559*Lys+0.012924*Orn-0.15358*Cys2-0.045513*Tyr' | 0.8709 |

FIG.90

| NO. | FORMULA | ROC_AUC |
|---|---|---|
| 1 | 'Gln+7.2511*Glu+0.49528*Ala-9.0735*His-11.0994*Cys2+12.6323*a-ABA' | 0.9225 |
| 2 | 'Gln+6.9563*Glu+0.65304*Ala-8.1245*His-8.9897*Cys2+2.4113*Ser' | 0.901 |
| 3 | 'Gln+5.8466*Glu+0.47601*Ala-8.4835*His+8.0962*a-ABA+1.7907*Ser' | 0.9028 |
| 4 | 'Gln+5.2917*Glu+0.40627*Ala-8.0718*His+9.79*a-ABA' | 0.9005 |
| 5 | 'Gln+6.132*Glu+0.58292*Ala-7.2925*His-9.4844*Cys2' | 0.8796 |
| 6 | 'Gln+6.896*Glu+0.54153*Ala-7.9623*His-9.6879*Cys2+4.1196*Asn' | 0.8866 |
| 7 | 'Gln+6.7433*Glu+0.55799*Ala-9.0917*His+1.2919*Lys-11.7211*Cys2' | 0.8872 |
| 8 | 'Gln+5.0086*Glu+0.42258*Ala-8.5647*His+1.8794*Tau+10.5241*a-ABA' | 0.8987 |
| 9 | 'Gln+5.4984*Glu+0.55967*Ala-7.5946*His+2.3365*Ser' | 0.875 |
| 10 | 'Gln+6.8413*Glu+0.57987*Ala-8.1745*His-10.3568*Cys2+1.2893*Thr' | 0.8877 |
| 11 | 'Gln+5.7985*Glu+0.47249*Ala-7.9503*His-1.5019*Tyr+10.4241*a-ABA' | 0.9016 |
| 12 | 'Gln+6.244*Glu+0.6648*Ala-7.4555*His-1.9689*Tyr+2.705*Ser' | 0.8918 |
| 13 | 'Gln+5.587*Glu+0.40097*Ala-8.4989*His+9.6654*a-ABA+0.68668*Thr' | 0.8981 |
| 14 | 'Gln+5.5666*Glu+0.39342*Ala-8.2589*His+1.8678*Asn+8.9575*a-ABA' | 0.8987 |
| 15 | 'Gln+5.864*Glu+0.60103*Ala-7.6116*His-9.4908*Cys2+1.5175*Tau' | 0.8802 |
| 16 | 'Gln+5.366*Glu+0.39197*Ala-8.591*His+0.41138*Lys+9.6864*a-ABA' | 0.8987 |
| 17 | 'Gln+6.1504*Glu+0.51473*Ala-7.9493*His+2.0816*Trp-10.1323*Cys2' | 0.8848 |
| 18 | 'Gln+5.2562*Glu+0.37321*Ala-8.3478*His+0.91476*Trp+9.8152*a-ABA' | 0.9016 |
| 19 | 'Gln+5.3167*Glu+0.3952*Ala-8.1371*His+0.10288*Pro+9.7993*a-ABA' | 0.8993 |
| 20 | 'Gln+5.3121*Glu+0.40328*Ala-7.9697*His-0.17791*Orn+9.6306*a-ABA' | 0.8993 |
| 21 | 'Gln+5.3005*Glu+0.4109*Ala-8.1126*His+9.8206*a-ABA+0.20045*Cit' | 0.8999 |
| 22 | 'Gln+6.4104*Glu+0.62695*Ala-7.1587*His-9.4065*Cys2-0.94226*Tyr' | 0.8837 |
| 23 | 'Gln+5.6882*Glu+0.53674*Ala-7.1551*His-0.99847*Orn+2.3748*Ser' | 0.8837 |
| 24 | 'Gln+5.2561*Glu+0.57397*Ala-7.8539*His+1.2933*Tau+2.302*Ser' | 0.8773 |
| 25 | 'Gln+6.1383*Glu+0.59076*Ala-7.4032*His+0.21041*Orn-9.7565*Cys2' | 0.8779 |
| 26 | 'Gln+6.1758*Glu+0.60093*Ala-7.4252*His-9.6142*Cys2+0.68518*Cit' | 0.8773 |
| 27 | 'Gln+6.1409*Glu+0.57779*Ala-7.3208*His-9.4708*Cys2+0.046694*Pro' | 0.8796 |
| 28 | 'Gln+5.4608*Glu+0.51685*Ala-7.9698*His+1.2201*Trp+2.3686*Ser' | 0.8814 |
| 29 | 'Gln+5.5553*Glu+0.54355*Ala-8.0822*His+0.39131*Lys+2.282*Ser' | 0.8791 |
| 30 | 'Gln+5.6337*Glu+0.53962*Ala-7.7119*His+1.2362*Asn+2.1115*Ser' | 0.8819 |
| 31 | 'Gln+5.4494*Glu+0.51822*Ala-7.2864*His+2.3625*Ser-1.7346*Cit' | 0.8837 |
| 32 | 'Gln+5.5884*Glu+0.55443*Ala-7.7425*His+0.2765*Thr+2.2503*Ser' | 0.8808 |
| 33 | 'Gln+5.5111*Glu+0.55307*Ala-7.6307*His+0.060414*Pro+2.3322*Ser' | 0.875 |

FIG.91

| NO. | FORMULA | ROC_AUC |
|---|---|---|
| 34 | 'Gln+4.6234*Glu+0.48686*Ala-6.7616*His' | 0.8594 |
| 35 | 'Glu+0.067474*Ala-1.174*His+0.20699*Lys-1.9798*Cys2+1.5893*a-ABA' | 0.8814 |
| 36 | 'Gln+5.2773*Glu+0.44803*Ala-7.35*His+3.682*Asn' | 0.8709 |
| 37 | 'Glu-0.97923*His+0.28417*Lys-1.6144*Cys2-0.34435*Tyr+1.4598*a-ABA' | 0.8831 |
| 38 | 'Glu+0.085416*Ala-1.1634*His+0.32517*Orn-2.1889*Cys2+2.0563*a-ABA' | 0.8767 |
| 39 | 'Gln+4.3159*Glu+0.50749*Ala-7.1259*His+1.7347*Tau' | 0.8576 |
| 40 | 'Gln+5.0852*Glu+0.47725*Ala-7.436*His+1.0436*Thr' | 0.8692 |
| 41 | 'Gln+6.0533*Glu+0.52957*Ala-7.2443*His+4.6856*Asn-1.9369*Tyr' | 0.8721 |
| 42 | 'Gln+4.7796*Glu+0.45779*Ala-7.7846*His+0.7895*Lys' | 0.8634 |
| 43 | 'Glu-1.0791*His+0.23473*Lys-1.7967*Cys2+1.5473*a-ABA' | 0.8779 |
| 44 | 'Glu+0.079863*Ala-0.97947*His-1.7989*Cys2+1.7234*a-ABA' | 0.8559 |
| 45 | 'Glu+0.087308*Ala-1.1276*His-1.9119*Cys2+0.36557*Tau+1.9601*a-ABA' | 0.8669 |
| 46 | 'Gln+5.0102*Glu+0.54648*Ala-6.5894*His-1.2532*Tyr' | 0.864 |
| 47 | 'Glu+0.071196*Ala-1.0066*His-1.7402*Cys2+1.5441*a-ABA+0.18768*Thr' | 0.8767 |
| 48 | 'Glu+0.083364*Ala-0.96961*His-1.6291*Cys2+1.4079*a-ABA+0.21554*Ser' | 0.8727 |
| 49 | 'Gln+5.6937*Glu+0.55811*Ala-8.2118*His+1.3923*Lys-2.5759*Tyr' | 0.8796 |
| 50 | 'Gln+4.98*Glu+0.46765*Ala-7.6158*His+1.4431*Tau+3.4488*Asn' | 0.8657 |
| 51 | 'Gln+4.5698*Glu+0.43953*Ala-7.1546*His+1.3182*Trp' | 0.864 |
| 52 | 'Glu-1.1867*His+0.23598*Lys-1.8688*Cys2+0.2891*Tau+1.7316*a-ABA' | 0.8814 |
| 53 | 'Gln+5.3324*Glu+0.43091*Ala-8.0166*His+0.55196*Lys+3.3775*Asn' | 0.8744 |
| 54 | 'Gln+4.6726*Glu+0.46468*Ala-6.8908*His+0.20754*Pro' | 0.8605 |
| 55 | 'Gln+5.8083*Glu+0.5629*Ala-7.3951*His-1.8653*Tyr+1.3768*Thr' | 0.8762 |
| 56 | 'Glu-1.1916*His+0.19572*Lys+0.40672*Trp-1.9188*Cys2+1.609*a-ABA' | 0.8773 |
| 57 | 'Gln+4.6749*Glu+0.47979*Ala-6.6287*His-0.29289*Orn' | 0.8588 |
| 58 | 'Gln+5.4579*Glu+0.44796*Ala-7.6673*His+3.1434*Asn+0.62421*Thr' | 0.8744 |
| 59 | 'Gln+4.7763*Glu+0.59417*Ala-6.9735*His+2.1356*Tau-1.7221*Tyr' | 0.8617 |
| 60 | 'Gln+4.6261*Glu+0.48877*Ala-6.7759*His+0.078084*Cit' | 0.86 |
| 61 | 'Glu+0.065482*Ala-1.108*His+0.41066*Trp-1.9187*Cys2+1.7558*a-ABA' | 0.8617 |
| 62 | 'Glu+0.083995*Ala-0.88192*His-1.6492*Cys2-0.23855*Tyr+1.6858*a-ABA' | 0.8727 |
| 63 | 'Gln+4.7688*Glu+0.49756*Ala-7.7585*His+1.6733*Tau+0.99897*Thr' | 0.8628 |
| 64 | 'Gln+5.3622*Glu+0.43611*Ala-7.1199*His-0.50083*Orn+3.6644*Asn' | 0.8727 |
| 65 | 'Gln+4.4684*Glu+0.47952*Ala-8.0977*His+0.75323*Lys+1.7147*Tau' | 0.8605 |
| 66 | 'Gln+5.2281*Glu+0.42399*Ala-7.5411*His+0.7034*Trp+3.5658*Asn' | 0.8721 |
| 67 | 'Glu-1.1581*His+0.20723*Lys+0.20192*Orn-1.9988*Cys2+1.77*a-ABA' | 0.875 |

FIG.92

| NO. | FORMULA | ROC_AUC |
|---|---|---|
| 68 | 'Gln+5.2948*Glu+0.43733*Ala-7.4084*His+0.10409*Pro+3.6417*Asn' | 0.8704 |
| 69 | 'Gln+5.2575*Glu+0.43127*Ala-7.2284*His+3.6999*Asn-0.68005*Cit' | 0.875 |
| 70 | 'Glu+0.091394*Ala-1.0693*His-1.8417*Cys2+1.765*a-ABA+0.63149*Cit' | 0.8628 |
| 71 | 'Glu+0.090242*Ala-1.0236*His+0.36164*Lys-1.852*Cys2-0.50283*Tyr' | 0.8785 |
| 72 | 'Glu-1.0645*His+0.19331*Lys-1.7316*Cys2+1.455*a-ABA+0.12599*Thr' | 0.8802 |
| 73 | 'Glu-1.2198*His+0.60004*Trp+0.30088*Orn-2.1333*Cys2+2.0553*a-ABA' | 0.8721 |
| 74 | 'Glu-1.0635*His+0.61208*Trp-1.7934*Cys2+1.7503*a-ABA' | 0.8594 |
| 75 | 'Gln+5.3381*Glu+0.4529*Ala-7.144*His-0.93074*Orn+1.2454*Thr' | 0.8762 |
| 76 | 'Gln+5.1111*Glu+0.4575*Ala-8.0651*His+0.58719*Lys+0.83972*Thr' | 0.8681 |
| 77 | 'Gln+5.1265*Glu+0.48669*Ala-7.2716*His+2.6211*Trp-1.9753*Tyr' | 0.8744 |
| 78 | 'Glu+0.074529*Ala-0.96703*His-1.7214*Cys2+0.28703*Asn+1.5228*a-ABA' | 0.8634 |
| 79 | 'Glu-1.0719*His+0.52269*Trp-1.7269*Cys2+1.5703*a-ABA+0.18308*Thr' | 0.8738 |
| 80 | 'Gln+0.71981*Ala-8.966*His-6.9444*Cys2+3.5164*Tau+10.171*a-ABA' | 0.8802 |
| 81 | 'Gln+4.4008*Glu+0.49559*Ala-6.9019*His-0.502*Orn+1.7531*Tau' | 0.8588 |
| 82 | 'Gln+4.9363*Glu+0.43524*Ala-7.5682*His+0.89377*Lys-0.77445*Orn' | 0.8686 |
| 83 | 'Glu-1.0538*His+0.21743*Lys-1.6992*Cys2+1.4196*a-ABA+0.094263*Ser' | 0.8773 |
| 84 | 'Gln+5.0259*Glu+0.43789*Ala-7.7441*His+1.1043*Trp+1.011*Thr' | 0.8721 |
| 85 | 'Gln+4.2975*Glu+0.47555*Ala-7.3622*His+0.8586*Trp+1.6412*Tau' | 0.8617 |
| 86 | 'Gln+4.3553*Glu+0.49166*Ala-7.21*His+0.1449*Pro+1.7057*Tau' | 0.8576 |
| 87 | 'Glu-1.0107*His+0.33322*Orn-1.929*Cys2+2.0333*a-ABA' | 0.8634 |
| 88 | 'Gln+5.0744*Glu+0.4363*Ala-7.2008*His+1.1448*Thr-1.6425*Cit' | 0.8727 |
| 89 | 'Gln+4.2759*Glu+0.4853*Ala-6.9648*His+1.7816*Tau-0.93394*Cit' | 0.8571 |
| 90 | 'Gln+5.2713*Glu+0.52063*Ala-6.8088*His+0.46097*Pro-1.7456*Tyr' | 0.8669 |
| 91 | 'Glu-1.0607*His+0.21884*Lys-1.7412*Cys2+0.18254*Asn+1.4309*a-ABA' | 0.8796 |
| 92 | 'Gln+5.089*Glu+0.47151*Ala-7.4569*His+0.055536*Pro+1.0225*Thr' | 0.8681 |
| 93 | 'Gln+4.7397*Glu+0.4358*Ala-7.9053*His+0.72704*Lys+0.67643*Trp' | 0.8634 |
| 94 | 'Gln+4.7484*Glu+0.42738*Ala-7.6264*His+0.83418*Lys-1.1808*Cit' | 0.8681 |
| 95 | 'Gln+4.794*Glu+0.45008*Ala-7.8052*His+0.76706*Lys+0.079846*Pro' | 0.8611 |
| 96 | 'Glu-1.0842*His+0.22767*Lys-1.7845*Cys2+0.019278*Pro+1.5466*a-ABA' | 0.8814 |
| 97 | 'Glu+0.077356*Ala-0.98789*His-1.7862*Cys2+0.020018*Pro+1.7171*a-ABA' | 0.8576 |
| 98 | 'Glu-1.0721*His+0.23956*Lys-1.8007*Cys2+1.5378*a-ABA-0.11077*Cit' | 0.8785 |
| 99 | 'Gln+0.61693*Ala-8.4126*His+3.2984*Tau+8.8597*a-ABA' | 0.8559 |
| 100 | 'Glu+0.090448*Ala-1.1008*His+0.22229*Lys-1.8161*Cys2+0.28009*Ser' | 0.8686 |

FIG.94

| NO. | FORMULA | ROC_AUC |
|---|---|---|
| 1 | (Glu+Pro)/(His)+(ABA+Lys)/(Ile) | 0.871793 |
| 2 | (ABA)/(Met)+(Pro+Lys)/(Ile+His) | 0.870612 |
| 3 | (Glu+Lys)/(Ile)+(Pro+ABA)/(His) | 0.869377 |
| 4 | (Pro)/(His)+(Glu+ABA+Lys)/(Ile) | 0.865594 |
| 5 | (Glu+Pro)/(His)+(Lys+Cys2)/(Ile) | 0.865442 |
| 6 | (Lys)/(Ile)+(Glu+Pro+ABA)/(His) | 0.864819 |
| 7 | (Lys)/(Ile)+(Glu+Pro)/(Cit+His) | 0.864797 |
| 8 | (Lys)/(Ile)+(Glu+Pro+Cys2)/(His) | 0.864274 |
| 9 | (Glu+Lys)/(Ile)+(Pro+Cys2)/(His) | 0.864109 |
| 10 | (Glu)/(Cit)+(Gln+Lys)/(Ile+His) | 0.862981 |
| 11 | (Lys)/(Ile)+(Glu+Pro)/(His) | 0.862295 |
| 12 | (Pro+Ala)/(His)+(Gln+Lys)/(Ile) | 0.861854 |
| 13 | (Lys)/(Ile)+(Pro+Gln)/(Cit+His) | 0.861577 |
| 14 | (Glu+Pro+Lys)/(Met+Ile+His) | 0.861365 |
| 15 | (Glu)/(Tyr)+(Pro+Lys)/(Ile+His) | 0.860307 |
| 16 | (Lys)/(Ile)+(Pro+Ala)/(Tyr+His) | 0.860055 |
| 17 | (Glu+Pro+Lys)/(Ile+Cit+His) | 0.859456 |
| 18 | (Glu+Pro)/(His)+(Lys+Asn)/(Ile) | 0.859434 |
| 19 | (Pro+Ala+Gln+Lys)/(Ile+His) | 0.859407 |
| 20 | (Pro)/(His)+(Glu+Lys)/(Met+Ile) | 0.859031 |
| 21 | (Pro)/(His)+(Glu+Lys)/(Ile) | 0.859013 |
| 22 | (Pro+Gln)/(His)+(Ala+Lys)/(Ile) | 0.858953 |
| 23 | (Pro)/(His)+(Glu+Lys)/(Ile+Cit) | 0.858675 |
| 24 | (ABA)/(Cit)+(Pro+Lys)/(Ile+His) | 0.858213 |
| 25 | (Pro+Gln)/(Ile)+(Ala+Lys)/(His) | 0.858171 |
| 26 | (ABA)/(Tyr)+(Pro+Lys)/(Ile+His) | 0.858155 |
| 27 | (Pro+ABA+Lys)/(Met+Ile+His) | 0.857973 |
| 28 | (Lys)/(Ile)+(Glu+Pro)/(Met+His) | 0.857757 |
| 29 | (Glu+Lys)/(Ile)+(Pro+Asn)/(His) | 0.857551 |
| 30 | (Gln)/(His)+(Pro+Ala+Lys)/(Ile) | 0.857332 |
| 31 | (Pro)/(Cit+His)+(Glu+Lys)/(Ile) | 0.857264 |
| 32 | (Pro+ABA+Lys)/(Ile+Cit+His) | 0.857079 |
| 33 | (Pro)/(His)+(Glu+Lys+Cys2)/(Ile) | 0.857039 |
| 34 | (Lys)/(Ile)+(Pro+Orn)/(Met+Cit) | 0.856888 |
| 35 | (Glu)/(Ile)+(Pro+Lys)/(Tyr+His) | 0.856793 |
| 36 | (Pro+Cys2)/(His)+(ABA+Lys)/(Ile) | 0.856538 |
| 37 | (Lys)/(Ile)+(Glu+Pro+Asn)/(His) | 0.856443 |
| 38 | (Pro)/(Met+His)+(Lys)/(Ile+Cit) | 0.856364 |
| 39 | (Gln)/(Cit+His)+(Glu+Lys)/(Ile) | 0.856281 |
| 40 | (Glu+Lys)/(Ile)+(Pro+Orn)/(His) | 0.856059 |
| 41 | (Lys)/(Ile)+(Pro+Gln)/(Met+His) | 0.85599 |
| 42 | (Lys)/(His)+(Glu+Pro+ABA)/(Ile) | 0.855984 |
| 43 | (Gln)/(Cit+His)+(Pro+Lys)/(Ile) | 0.855892 |
| 44 | (Lys)/(Ile+Cit)+(Glu+Pro)/(His) | 0.855869 |
| 45 | (Lys)/(Arg)+(Ala+Gln)/(Ile+His) | 0.85578 |
| 46 | (Lys)/(Ile)+(Pro+ABA+Cys2)/(His) | 0.855728 |
| 47 | (Lys)/(Ile)+(Glu+Pro+Orn)/(His) | 0.855577 |
| 48 | (Lys)/(Ile)+(Pro+Orn)/(Cit+His) | 0.855451 |
| 49 | (Glu+Pro+ABA+Lys)/(Ile+His) | 0.855355 |
| 50 | (Ala)/(His)+(Gln+Lys)/(Met+Ile) | 0.855183 |

FIG.95

| NO. | FORMULA | ROC_AUC |
|---|---|---|
| 51 | (Glu+Pro+Lys)/(Tyr+Ile+His) | 0.855172 |
| 52 | (Lys)/(Ile)+(Ala+Gln)/(Met+His) | 0.855115 |
| 53 | (Gln)/(Ile)+(Pro+Ala+Lys)/(His) | 0.854965 |
| 54 | (Glu)/(Cit)+(Pro+Gln)/(Ile+His) | 0.85485 |
| 55 | (Glu+Pro)/(His)+(Lys+Orn)/(Ile) | 0.854839 |
| 56 | (Lys)/(His)+(Pro+Ala)/(Tyr+Ile) | 0.854839 |
| 57 | (Ala)/(His)+(Gln+Lys)/(Ile+Cit) | 0.854825 |
| 58 | (Pro)/(His)+(ABA+Lys)/(Ile+Cit) | 0.854655 |
| 59 | (Lys)/(Ile)+(Pro+Ala)/(Met+His) | 0.854593 |
| 60 | (Pro+ABA)/(His)+(Lys+Cys2)/(Ile) | 0.854553 |
| 61 | (Pro)/(His)+(ABA+Lys)/(Met+Ile) | 0.854293 |
| 62 | (Lys)/(Ile+Cit)+(Pro+ABA)/(His) | 0.854162 |
| 63 | (Pro)/(Cit+His)+(Lys)/(Met+Ile) | 0.85412 |
| 64 | (Lys)/(Met+Ile)+(Glu+Pro)/(His) | 0.854109 |
| 65 | (Pro+Asn)/(His)+(ABA+Lys)/(Ile) | 0.853958 |
| 66 | (Glu+Gln)/(Ile)+(Pro+Ala)/(His) | 0.853734 |
| 67 | (Gln)/(His)+(Glu+Pro+Lys)/(Ile) | 0.853606 |
| 68 | (Lys)/(Ile)+(Pro+ABA)/(Cit+His) | 0.853543 |
| 69 | (Glu+Pro+Lys+Cys2)/(Ile+His) | 0.853469 |
| 70 | (Pro)/(His)+(Glu+Lys+Orn)/(Ile) | 0.853468 |
| 71 | (Lys)/(Ile)+(Pro+ABA+Asn)/(His) | 0.853237 |
| 72 | (Glu)/(Cit)+(Ala+Gln)/(Ile+His) | 0.853154 |
| 73 | (Lys)/(Met+Ile)+(Pro+ABA)/(His) | 0.853096 |
| 74 | (Pro)/(His)+(Glu+Lys+Asn)/(Ile) | 0.853067 |
| 75 | (Pro)/(His)+(Lys+Asn)/(Ile+Cit) | 0.852934 |
| 76 | (Glu+Gln)/(Ile)+(Ala+Lys)/(His) | 0.852535 |
| 77 | (Lys)/(Ile)+(Pro+ABA)/(His) | 0.852455 |
| 78 | (Lys)/(Ile)+(Pro+Orn)/(Met+His) | 0.851837 |
| 79 | (Pro)/(Met+His)+(Glu+Lys)/(Ile) | 0.851833 |
| 80 | (Pro)/(His)+(ABA+Lys)/(Ile) | 0.851783 |
| 81 | (Pro)/(His)+(Lys+Cys2)/(Ile+Cit) | 0.851737 |
| 82 | (ABA)/(Arg)+(Pro+Lys)/(Ile+His) | 0.851707 |
| 83 | (Gln)/(His)+(Glu+Pro+Ala)/(Ile) | 0.851641 |
| 84 | (Gln)/(Ile)+(Glu+Pro+Ala)/(His) | 0.851527 |
| 85 | (Gln)/(Ile)+(Glu+Ala+Lys)/(His) | 0.851447 |
| 86 | (Lys)/(His)+(Glu+Pro+Cys2)/(Ile) | 0.85144 |
| 87 | (Lys)/(Ile)+(Pro+Asn+Cys2)/(His) | 0.851431 |
| 88 | (Gln)/(Ile)+(Ala+ABA+Lys)/(His) | 0.851346 |
| 89 | (Ala)/(His)+(Glu+Pro+Lys)/(Ile) | 0.851207 |
| 90 | (Glu+Ala)/(His)+(Pro+Lys)/(Ile) | 0.85112 |
| 91 | (Lys)/(Ile)+(Pro+Asn)/(Cit+His) | 0.851051 |
| 92 | (Lys)/(Ile+Cit)+(Pro+Asn)/(His) | 0.851002 |
| 93 | (Pro)/(Ile)+(Glu+Lys)/(Met+His) | 0.850989 |
| 94 | (Pro+Orn)/(His)+(ABA+Lys)/(Ile) | 0.850966 |
| 95 | (Lys)/(Ile)+(Ala+Gln)/(Cit+His) | 0.850749 |
| 96 | (Pro)/(Tyr+His)+(Lys)/(Ile+Cit) | 0.850429 |
| 97 | (Gln)/(Ile+Cit)+(Pro+Lys)/(His) | 0.850316 |
| 98 | (Pro)/(His)+(Lys+Asn)/(Met+Ile) | 0.850281 |
| 99 | (Pro)/(His)+(ABA+Lys+Cys2)/(Ile) | 0.85028 |
| 100 | (Lys)/(Ile)+(Pro+Cys2)/(His) | 0.850067 |

FIG.97

| NO. | FORMULA | ROC_AUC |
|---|---|---|
| 1 | 'Glu/His+0.32216*Ser/Tyr+0.093159*Ala/Ile+0.00093751*Gln' | 0.8258 |
| 2 | 'Ala/Ile-14.9203*His/Leu+2.6836*Gln/Val-0.45217*Tyr/Glu' | 0.8734 |
| 3 | 'Glu/His+0.98594*Asn/Tyr-4.9161*Cit/Lys-1.2777*Met/Arg' | 0.8652 |
| 4 | 'Ala/Ile+4.8981*Leu/His+3.344*Gln/Val+1.5091*Glu/Cit' | 0.8649 |
| 5 | 'Cit/Lys-0.029014*Pro/Ile-0.071534*Arg/His-0.047789*Leu/Tyr' | 0.8488 |
| 6 | 'Glu/His-0.93864*Ile/Ser+0.09289*Ala/Tyr-0.58647*Val/Leu' | 0.8586 |
| 7 | 'His/Lys-0.035828*Ala/Tyr-0.34434*Leu/Ile+0.11797*Val/Pro' | 0.8725 |
| 8 | 'His/Lys-0.048269*Ala/Ile+0.28207*Val/Leu-0.0094335*Gln/Met' | 0.8682 |
| 9 | 'His/Lys-0.04746*Ala/Tyr+0.9705*Ile/Leu+0.065817*Val/Ser' | 0.8738 |
| 10 | 'Glu/His+0.96274*Asn/Ile-0.87503*Tyr/Leu+0.071876*Pro/Orn' | 0.8399 |
| 11 | 'Ala/Ile+4.8376*Leu/His+2.7309*Gln/Val-1.9286*Cit/Glu' | 0.8544 |
| 12 | 'His/Lys+0.95292*Ile/Leu-0.027724*Ala/Tyr+0.01015*Val/Glu' | 0.8679 |
| 13 | 'Ala/His-19.8159*Ile/Leu-0.037894*Tyr-11.4892*Cit/Arg' | 0.8642 |
| 14 | 'Glu/Cit-20.9272*His/Gln+2.8224*Asn/Ile-2.2183*Tyr/Leu' | 0.8655 |
| 15 | 'His/Lys-0.049149*Ala/Ile+0.31581*Val/Leu+0.036087*Tyr/Glu' | 0.8629 |
| 16 | 'Ala/Ile+2.8609*Leu/Tyr+0.84917*Gln/His+3.4298*Glu/Orn' | 0.8547 |
| 17 | 'Glu/His+0.75554*Leu/Ile+0.11641*Arg/Cit+0.048214*Gln/Tyr' | 0.883 |
| 18 | 'Glu/His-2.2953*Tyr/Ala+0.47171*Ser/Val+0.71962*Leu/Ile' | 0.8554 |
| 19 | 'Ala/Ile+0.9447*Gln/His+26.9194*Leu/Val+0.060079*Glu' | 0.881 |
| 20 | 'Glu/His+0.30661*Ser/Tyr-2.4986*Ile/Ala-0.54718*Val/Leu' | 0.8669 |
| 21 | 'Glu/His+1.0125*Asn/Tyr-2.3736*Cit/Arg-1.7775*Ile/Leu' | 0.8715 |
| 22 | 'His/Lys+0.97647*Tyr/Ala+1.0627*Ile/Leu+0.10814*Val/Pro' | 0.8682 |
| 23 | 'Glu/His-0.31619*Ile/Asn-0.94448*Tyr/Leu-2.1543*Cit/Arg' | 0.8672 |
| 24 | 'His/Lys+0.54951*Ile/Pro+0.31045*Val/Leu-0.061988*Glu/Cit' | 0.8807 |
| 25 | 'Ala/His-18.4374*Ile/Leu+6.3315*Asn/Tyr-1.3019*Cit/Glu' | 0.8856 |
| 26 | 'Ala/Ile-15.7844*His/Leu+3.4547*Gln/Val+1.3604*Glu/Cit' | 0.8679 |
| 27 | 'His/Lys-0.085169*Pro/Ile+0.32222*Val/Leu-0.0087659*Gln/Cit' | 0.8649 |
| 28 | 'His/Lys-0.059635*Ala/Ile-0.16984*Leu/Tyr-0.022592*Ser/Cit' | 0.8586 |
| 29 | 'Ala/Tyr-27.4946*Ile/Leu+1.0562*Gln/His-2.4751*Cit/Glu' | 0.8738 |
| 30 | 'Glu/His+0.89735*Ser/Val+0.36451*Leu/Tyr+0.083187*Ala/Ile' | 0.8432 |
| 31 | 'Glu/His-0.62243*Tyr/Ser-1.0174*Ile/Pro+2.0609*Leu/Val' | 0.8734 |
| 32 | 'Glu/His-0.87023*Ile/Ser+0.36472*Leu/Tyr+0.085054*Arg/Cit' | 0.8734 |
| 33 | 'Glu/His+0.90938*Asn/Tyr+0.095821*Ala/Ile+2.4275*Leu/Val' | 0.8386 |
| 34 | 'Ala/His+5.866*Leu/Ile+3.2314*Asn/Tyr+15.4884*Phe/Val' | 0.8918 |
| 35 | 'Glu/Cit-31.7927*His/Gln-11.3577*Ile/Leu-9.975*Tyr/Ala' | 0.8951 |
| 36 | 'Cit/Lys-0.023702*Gln/His-0.18725*Glu/Ile-0.021566*Ala/Tyr' | 0.858 |
| 37 | 'Glu/His+0.65443*Leu/Ile-1.3186*Cit/Ser-0.43109*Tyr/Arg' | 0.854 |
| 38 | 'Glu/His-0.27069*Val/Ser+0.10166*Ala/Tyr+0.70754*Leu/Ile' | 0.8649 |
| 39 | 'Glu/His+0.25079*Pro/Ile-0.7649*Val/Leu-0.70126*Tyr/Ser' | 0.8554 |
| 40 | 'Ala/Ile+2.0512*Lys/His+3.3948*Leu/Tyr+5.3223*Ser/Val' | 0.8636 |
| 41 | 'His/Lys-0.31331*Leu/Ile+0.0030003*Tyr-0.046649*Arg/Cit' | 0.8642 |
| 42 | 'Glu/Cit+0.45106*Gln/His+3.679*Ser/Val-8.3559*Ile/Leu' | 0.8849 |
| 43 | 'His/Lys+1.0659*Ile/Leu-0.03729*Ala/Tyr+0.41135*Val/Gln' | 0.8876 |
| 44 | 'His/Lys-0.04799*Ala/Ile-0.14211*Leu/Tyr+0.073112*Val/Ser' | 0.8573 |
| 45 | 'Glu/His+0.81148*Asn/Tyr+0.18568*Pro/Ile+0.096315*Arg/Cit' | 0.831 |
| 46 | 'His/Lys+1.1677*Ile/Leu+0.76378*Tyr/Ala-0.33315*Pro/Val' | 0.8734 |
| 47 | 'Ala/His+5.0828*Leu/Ile+1.9862*Ser/Tyr-0.48401*Orn/Glu' | 0.8889 |
| 48 | 'Pro/Ile+3.3434*Glu/His+0.93643*Ser/Tyr+9.186*Leu/Val' | 0.836 |
| 49 | 'Ala/His-17.3714*Ile/Leu+2.0789*Ser/Tyr-0.7243*Orn/Glu' | 0.86 |
| 50 | 'Glu/His+0.30516*Ser/Tyr+0.014692*Ala/Cit-0.99823*Ile/Pro' | 0.8176 |

FIG.98

| NO. | FORMULA | ROC_AUC |
|---|---|---|
| 51 | 'Ala/Ile+0.90058*Gln/His+1.3453*Glu/Cit+2.4454*Leu/Tyr' | 0.8632 |
| 52 | 'Glu/His+0.82736*Asn/Tyr-2.3851*Cit/Arg-1.9144*Ile/Leu' | 0.8554 |
| 53 | 'Glu/His-2.4839*Ile/Leu-0.82401*Tyr/Ser+0.088517*Pro/Orn' | 0.8547 |
| 54 | 'Ala/Ile-16.6029*His/Leu+3.1013*Gln/Val+1.1091*Glu/Cit' | 0.8728 |
| 55 | 'Ala/Ile-13.9945*His/Leu-2.0552*Tyr/Asn+19.306*Glu/Val' | 0.8817 |
| 56 | 'His/Lys-0.06459*Pro/Ile+0.1736*Cit/Glu+0.59244*Val/Gln' | 0.8662 |
| 57 | 'Glu/His+0.053783*Ala/Ile+0.75745*Asn/Tyr-1.7679*Cit/Arg' | 0.8705 |
| 58 | 'Glu/His+0.32904*Ser/Ile+0.38053*Leu/Tyr-0.6259*Val/Ala' | 0.8383 |
| 59 | 'Glu/His-2.7041*Ile/Leu-2.8614*Cit/Arg+0.24504*Pro/Tyr' | 0.8912 |
| 60 | 'His/Lys-0.3023*Leu/Ile-0.039164*Ala/Tyr+0.49489*Cit/Ser' | 0.8672 |
| 61 | 'Glu/Cit+0.72036*Gln/His-16.8243*Ile/Leu+0.69715*Ala/Tyr' | 0.9037 |
| 62 | 'His/Lys-0.047198*Ala/Tyr+0.95952*Ile/Leu+0.010068*Val/Glu' | 0.8968 |
| 63 | 'Glu/His+0.86287*Asn/Tyr+0.093158*Arg/Cit-1.6689*Ile/Leu' | 0.8807 |
| 64 | 'His/Lys+0.92838*Tyr/Ala+0.87087*Ile/Leu-0.077257*Gln/Val' | 0.8629 |
| 65 | 'His/Lys-0.046157*Ala/Tyr+1.0378*Ile/Leu-0.29134*Pro/Val' | 0.8905 |
| 66 | 'Glu/His+0.68495*Asn/Tyr+0.1558*Pro/Ile+2.2755*Leu/Val' | 0.8136 |
| 67 | 'Glu/His+0.35233*Ser/Ile+0.32193*Leu/Tyr-5.0428*Cit/Ala' | 0.8494 |
| 68 | 'Ala/Ile+4.1296*Leu/His+3.0347*Ser/Tyr+3.7824*Glu/Orn' | 0.8524 |
| 69 | 'Ala/Ile-62.4012*His/Gln+2.8396*Leu/Tyr+1.7498*Glu/Cit' | 0.859 |
| 70 | 'His/Lys+1.0992*Ile/Leu-0.039523*Ala/Tyr-0.31475*Pro/Val' | 0.881 |
| 71 | 'His/Lys-0.054746*Ala/Tyr-0.32081*Leu/Ile+0.85083*Cit/Arg' | 0.8912 |
| 72 | 'His/Lys-0.010431*Gln/Cit-0.064331*Arg/Met+0.81849*Ile/Leu' | 0.8905 |
| 73 | 'Glu/His+1.1447*Ser/Val+0.1178*Ala/Tyr-2.126*Ile/Leu' | 0.8695 |
| 74 | 'Glu/His+0.20717*Ser/Ile+0.31498*Leu/Tyr-2.3881*Cit/Arg' | 0.8379 |
| 75 | 'Glu/His+0.66111*Asn/Tyr+0.094968*Ala/Ile-0.54925*Val/Leu' | 0.8517 |
| 76 | 'Glu/His+0.83091*Asn/Tyr+0.61514*Leu/Ile-2.0082*Cit/Arg' | 0.8488 |
| 77 | 'Glu/His-2.6732*Ile/Leu+0.096737*Ala/Tyr+0.7188*Ser/Val' | 0.8616 |
| 78 | 'Glu/His+0.96761*Asn/Ile+0.39173*Leu/Tyr+0.096552*Arg/Cit' | 0.8524 |
| 79 | 'Ala/His+4.7872*Leu/Ile+1.5939*Ser/Tyr+1.9166*Glu/Orn' | 0.8761 |
| 80 | 'Gln/His-21.1603*Ile/Leu+0.70546*Ala/Tyr-0.94695*Orn/Glu' | 0.8682 |
| 81 | 'Glu/His-0.24908*Tyr/Asn+0.10136*Arg/Cit+0.16593*Pro/Ile' | 0.8353 |
| 82 | 'His/Lys-0.039842*Ala/Tyr+0.96205*Ile/Leu+0.010337*Val/Glu' | 0.8794 |
| 83 | 'His/Lys+1.0836*Ile/Leu-0.042911*Ala/Tyr-0.98196*Glu/Val' | 0.8941 |
| 84 | 'His/Lys-1.355*Glu/Val+4.7602*Cit/Gln+0.86452*Ile/Leu' | 0.8774 |
| 85 | 'Glu/His+0.022475*Gln/Cit+0.85028*Asn/Ile+0.26287*Leu/Tyr' | 0.8649 |
| 86 | 'Glu/His-0.24193*Tyr/Asn+0.10385*Pro/Ile+0.090827*Arg/Cit' | 0.8176 |
| 87 | 'Pro/Ile+0.40612*Gln/His+0.62331*Glu/Cit+1.3066*Leu/Tyr' | 0.8501 |
| 88 | 'Gln/His-22.931*Ile/Leu-1.7763*Cit/Glu+0.77383*Ala/Tyr' | 0.8899 |
| 89 | 'Glu/His+0.11688*Ala/Ile+0.46893*Leu/Tyr-0.25966*Val/Ser' | 0.8662 |
| 90 | 'Glu/His+1.0268*Asn/Tyr+0.096647*Ala/Ile-0.62975*Val/Leu' | 0.8419 |
| 91 | 'Glu/His+0.2581*Pro/Ile-0.91621*Tyr/Ser-0.91294*Cit/Trp' | 0.8445 |
| 92 | 'His/Lys-0.29783*Leu/Ile-0.041073*Ala/Tyr+0.075801*Val/Ser' | 0.8859 |
| 93 | 'Glu/His-2.792*Tyr/Ala-2.5348*Ile/Leu+0.20565*Gln/Val' | 0.8685 |
| 94 | 'His/Lys+0.9773*Ile/Leu-0.034279*Ala/Tyr+0.48846*Cit/Ser' | 0.8787 |
| 95 | 'Glu/Cit+0.4577*Gln/His+3.5684*Asn/Tyr-7.3651*Ile/Leu' | 0.8948 |
| 96 | 'Glu/His-0.35624*Ile/Asn+0.085327*Ala/Tyr-0.48148*Val/Leu' | 0.8527 |
| 97 | 'Ala/His-17.7452*Ile/Leu+0.37328*Gln/Tyr+0.77713*Glu/Cit' | 0.9011 |
| 98 | 'His/Lys-0.049111*Ala/Ile-0.15114*Leu/Tyr-0.20425*Ser/Val' | 0.836 |
| 99 | 'His/Lys+1.3957*Ile/Ala-0.17789*Leu/Tyr+0.76261*Met/Ser' | 0.878 |
| 100 | 'His/Lys+1.1474*Ile/Leu+0.77207*Tyr/Ala+0.10082*Val/Pro' | 0.8826 |

FIG.100

| NO. | FORMULA | ROC_AUC |
|---|---|---|
| 1 | '3.5765-0.14992*His-0.20956*Ile+0.054489*Glu+0.025371*Pro+0.091665*Leu+0.00838*Gln' | 0.9226 |
| 2 | '3.3649-0.12322*His-0.20577*Ile-0.086659*Met+0.029161*Pro+0.10717*Leu+0.0080334*Gln' | 0.9092 |
| 3 | '1.658-0.13317*His-0.2246*Ile+0.023249*Pro+0.0069302*Ala+0.10307*Leu+0.0079393*Gln' | 0.9083 |
| 4 | '2.7156-0.12008*His-0.075263*Cit-0.2063*Ile+0.029203*Pro+0.10377*Leu+0.0079885*Gln' | 0.91 |
| 5 | '1.4753-0.13169*His-0.20722*Ile+0.027361*Pro+0.093994*Leu+0.0072149*Gln+0.011902*Lys' | 0.9109 |
| 6 | '3.4176-0.12801*His-0.21912*Ile-0.038827*Tyr+0.033004*Pro+0.11877*Leu+0.0074614*Gln' | 0.914 |
| 7 | '2.8279-0.13753*His-0.21458*Ile+0.026961*Pro+0.096296*Leu+0.0069482*Gln+0.033631*Trp' | 0.9083 |
| 8 | '5.5126-0.12804*His-0.22242*Ile+0.029581*Pro+0.10036*Leu+0.0082056*Gln-0.0097454*Gly' | 0.9109 |
| 9 | '2.9239-0.12983*His-0.21141*Ile+0.027982*Pro+0.10303*Leu+0.0071951*Gln' | 0.9053 |
| 10 | '3.3029-0.1317*His-0.20252*Ile+0.030606*Pro-0.021699*Val+0.12995*Leu+0.0085025*Gln' | 0.9057 |
| 11 | '5.614-0.11861*His-0.21159*Ile-0.040705*Tyr+0.028202*Pro+0.0066416*Ala+0.11225*Leu' | 0.9057 |
| 12 | '6.9197-0.1311*His-0.20048*Ile+0.053238*Glu-0.044329*Tyr+0.031244*Pro+0.10715*Leu' | 0.9083 |
| 13 | '2.2883-0.13559*His-0.20705*Ile+0.030556*Pro+0.096432*Leu+0.062976*a-ABA+0.0071565*Gln' | 0.9079 |
| 14 | '4.3795-0.11549*His-0.19125*Ile-0.046998*Tyr+0.032191*Pro+0.099574*Leu+0.017283*Lys' | 0.9061 |
| 15 | '4.743-0.12938*His-0.18686*Ile+0.048059*Glu+0.024659*Pro+0.07962*Leu+0.011116*Lys' | 0.9079 |
| 16 | '4.1706-0.1167*His-0.17038*Ile+0.028608*Pro-0.023818*Val+0.11038*Leu+0.018793*Lys' | 0.9048 |
| 17 | '4.3206-0.10492*His-0.17952*Ile-0.099262*Met+0.027728*Pro+0.087988*Leu+0.01652*Lys' | 0.9 |
| 18 | '3.2207-0.12909*His-0.21162*Ile+0.028242*Pro-0.0048367*Arg+0.10356*Leu+0.0073185*Gln' | 0.9035 |
| 19 | '2.893-0.13028*His-0.21142*Ile+0.027911*Pro+0.10309*Leu+0.00086779*Thr+0.007146*Gln' | 0.9061 |
| 20 | '2.9738-0.12981*His-0.21129*Ile+0.028083*Pro+0.10359*Leu+0.0072215*Gln-0.0023571*Phe' | 0.9053 |
| 21 | '6.1755-0.12862*His-0.19247*Ile+0.049025*Glu+0.025635*Pro+0.088174*Leu' | 0.904 |
| 22 | '6.1293-0.14121*His-0.19608*Ile+0.050652*Glu+0.024395*Pro+0.078162*Leu+0.043482*Trp' | 0.9096 |
| 23 | '6.0838-0.12778*His-0.20868*Ile-0.045853*Tyr+0.031972*Pro+0.10581*Leu+0.05288*Trp' | 0.9048 |
| 24 | '5.5069-0.11812*His-0.19486*Ile+0.024677*Pro+0.0062819*Ala-0.016304*Val+0.11634*Leu' | 0.9044 |
| 25 | '6.4399-0.12247*His-0.054957*Cit-0.19024*Ile+0.049195*Glu+0.02695*Pro+0.089081*Leu' | 0.9044 |
| 26 | '2.7478-0.14383*His-0.18166*Ile+0.051022*Glu+0.0088265*Ala+0.082858*Leu+0.0085828*Gln' | 0.9044 |
| 27 | '6.6743-0.12838*His-0.17991*Ile+0.051945*Glu+0.026549*Pro-0.017429*Val+0.10954*Leu' | 0.9061 |
| 28 | '3.3258-0.11906*His-0.20153*Ile+0.022884*Pro+0.0060515*Ala+0.088129*Leu+0.011979*Lys' | 0.8992 |
| 29 | '4.8447-0.11778*His-0.20546*Ile+0.023314*Pro+0.0061624*Ala+0.096873*Leu' | 0.8944 |
| 30 | '5.5102-0.13858*His-0.18517*Ile+0.056657*Glu+0.028244*Pro+0.077599*Leu+0.081901*a-ABA' | 0.9057 |
| 31 | '4.0261-0.11509*His-0.19216*Ile+0.026917*Pro+0.088535*Leu+0.012299*Lys' | 0.8966 |
| 32 | '5.4122-0.12925*His-0.20159*Ile+0.043799*Glu+0.021969*Pro+0.0053518*Ala+0.088983*Leu' | 0.9057 |
| 33 | '5.3335-0.11315*His-0.20063*Ile-0.0511*Met+0.024046*Pro+0.005979*Ala+0.099029*Leu' | 0.8983 |

FIG.101

| NO. | FORMULA | ROC_AUC |
|---|---|---|
| 34 | '6.2223-0.11384*His-0.20385*Ile-0.03801*Tyr+0.032836*Pro+0.11366*Leu' | 0.8953 |
| 35 | '4.9965-0.15699*His-0.16114*Ile+0.06208*Glu+0.068189*Leu+0.0073492*Gln+0.048731*Trp' | 0.9126 |
| 36 | '7.1604-0.11431*His-0.21226*Ile+0.024378*Pro+0.0062511*Ala+0.093888*Leu-0.0076863*Gly' | 0.8974 |
| 37 | '6.4237-0.12545*His-0.19058*Ile+0.046982*Glu-0.028692*Met+0.026256*Pro+0.089714*Leu' | 0.9044 |
| 38 | '6.0836-0.12761*His-0.18979*Ile+0.028412*Pro-0.019595*Val+0.111*Leu+0.051597*Trp' | 0.9044 |
| 39 | '5.5394-0.11382*His-0.19777*Ile+0.027837*Pro+0.098432*Leu' | 0.8857 |
| 40 | '5.7475-0.1342*His-0.19433*Ile+0.050435*Glu+0.025002*Pro+0.08891*Leu+0.0082994*Thr' | 0.9061 |
| 41 | '6.0875-0.10846*His-0.19371*Ile-0.059811*Met+0.028734*Pro+0.10139*Leu' | 0.8883 |
| 42 | '5.9352-0.12923*His-0.19283*Ile+0.049291*Glu+0.025141*Pro+0.085474*Leu+0.01056*Phe' | 0.904 |
| 43 | '4.413-0.11824*His-0.20688*Ile+0.022417*Pro+0.0063441*Ala+0.093144*Leu+0.016294*Phe' | 0.8987 |
| 44 | '3.6821-0.14626*His-0.14923*Ile+0.060899*Glu+0.069031*Leu+0.0074402*Gln+0.011768*Lys' | 0.9044 |
| 45 | '3.9984-0.12506*His-0.19617*Ile+0.025822*Pro+0.079851*Leu+0.011619*Lys+0.040458*Trp' | 0.8992 |
| 46 | '5.7904-0.11509*His-0.20343*Ile-0.040626*Tyr+0.03201*Pro+0.10924*Leu+0.020101*Phe' | 0.8961 |
| 47 | '7.7968-0.12634*His-0.19603*Ile+0.044333*Glu+0.026334*Pro+0.086273*Leu-0.004973*Gly' | 0.9027 |
| 48 | '5.4662-0.11907*His-0.19931*Ile-0.041941*Tyr+0.036249*Pro+0.10696*Leu+0.075622*a-ABA' | 0.9048 |
| 49 | '5.4098-0.12446*His-0.20058*Ile+0.026554*Pro+0.088884*Leu+0.041485*Trp' | 0.8922 |
| 50 | '6.0607-0.11365*His-0.18928*Ile+0.029455*Pro-0.014293*Val+0.11581*Leu' | 0.8918 |
| 51 | '5.723-0.10788*His-0.19317*Ile-0.07374*Met+0.027987*Pro+0.097245*Leu+0.019329*Phe' | 0.89 |
| 52 | '5.9525-0.12941*His-0.19229*Ile+0.049908*Glu+0.02535*Pro+0.0029789*Arg+0.087881*Leu' | 0.9022 |
| 53 | '4.002-0.10564*His-0.063505*Cit-0.18489*Ile+0.027858*Pro+0.087201*Leu+0.013236*Lys' | 0.9009 |
| 54 | '5.9689-0.11902*His-0.19535*Ile-0.06283*Met+0.027297*Pro+0.092*Leu+0.04126*Trp' | 0.8948 |
| 55 | '3.701-0.11589*His-0.19332*Ile+0.02644*Pro+0.086149*Leu+0.011473*Phe+0.012575*Lys' | 0.8953 |
| 56 | '6.2625-0.10564*His-0.061405*Cit-0.18761*Ile+0.030847*Pro-0.015183*Val+0.11917*Leu' | 0.8922 |
| 57 | '5.6576-0.10559*His-0.056696*Cit-0.1942*Ile+0.028852*Pro+0.099132*Leu' | 0.8905 |
| 58 | '5.3771-0.1385*His-0.07432*Cit-0.14752*Ile+0.062347*Glu+0.076664*Leu+0.0086893*Gln' | 0.9113 |
| 59 | '5.768-0.11603*His-0.20318*Ile-0.042652*Tyr+0.032771*Pro+0.0080854*Arg+0.11428*Leu' | 0.8957 |
| 60 | '6.2425-0.1074*His-0.042004*Cit-0.20224*Ile-0.034955*Tyr+0.033261*Pro+0.11366*Leu' | 0.897 |
| 61 | '4.7677-0.12371*His-0.20539*Ile+0.02292*Pro+0.0053894*Ala+0.090191*Leu+0.028261*Trp' | 0.894 |
| 62 | '6.4031-0.11454*His-0.19983*Ile-0.034059*Tyr+0.033107*Pro-0.0072296*Val+0.12197*Leu' | 0.8935 |
| 63 | '8.0493-0.11186*His-0.20773*Ile-0.034638*Tyr+0.032996*Pro+0.11011*Leu-0.0061943*Gly' | 0.8974 |
| 64 | '7.9905-0.1113*His-0.20331*Ile+0.028582*Pro+0.095194*Leu-0.0078534*Gly' | 0.8914 |
| 65 | '6.4044-0.11275*His-0.19646*Ile+0.027552*Pro+0.08519*Leu-0.0075619*Gly+0.012098*Lys' | 0.8966 |
| 66 | '4.9104-0.11399*His-0.020533*Cit-0.20264*Ile+0.024007*Pro+0.0056497*Ala+0.096791*Leu' | 0.8966 |
| 67 | '8.6252-0.10521*His-0.19965*Ile-0.063868*Met+0.029723*Pro+0.098071*Leu-0.0079264*Gly' | 0.8944 |

FIG.102

| NO. | FORMULA | ROC_AUC |
|---|---|---|
| 68 | '4.3003-0.12064*His-0.19876*Ile+0.024768*Pro+0.0058914*Ala+0.090907*Leu+0.048563*a-ABA' | 0.894 |
| 69 | '4.9663-0.11716*His-0.20535*Ile+0.023449*Pro+0.0061457*Ala-0.0019248*Arg+0.096984*Leu' | 0.8948 |
| 70 | '6.0892-0.10217*His-0.050983*Cit-0.19269*Ile-0.048199*Met+0.02961*Pro+0.10211*Leu' | 0.8948 |
| 71 | '4.5142-0.12213*His-0.20739*Ile+0.022961*Pro+0.0062522*Ala+0.097854*Leu+0.0060949*Thr' | 0.8987 |
| 72 | '6.3517-0.10975*His-0.18805*Ile-0.042182*Met+0.029786*Pro-0.012331*Val+0.116*Leu' | 0.8935 |
| 73 | '8.3331-0.11223*His-0.19535*Ile+0.029724*Pro-0.012669*Val+0.1114*Leu-0.0074244*Gly' | 0.8979 |
| 74 | '4.9097-0.14426*His-0.15165*Ile+0.062789*Glu+0.076835*Leu+0.0078417*Gln' | 0.8996 |
| 75 | '5.3278-0.11411*His-0.19808*Ile+0.027425*Pro+0.096574*Leu+0.0080842*Phe' | 0.8887 |
| 76 | '5.2513-0.10533*His-0.062229*Cit-0.19352*Ile+0.027954*Pro+0.0948*Leu+0.016717*Phe' | 0.8918 |
| 77 | '3.6569-0.11742*His-0.1876*Ile+0.028444*Pro+0.084016*Leu+0.045328*a-ABA+0.010869*Lys' | 0.8957 |
| 78 | '6.2373-0.11357*His-0.20366*Ile-0.03768*Tyr-0.0027037*Met+0.032838*Pro+0.1137*Leu' | 0.8948 |
| 79 | '3.947-0.11689*His-0.19322*Ile+0.026813*Pro+0.089458*Leu+0.0025035*Thr+0.011854*Lys' | 0.8974 |
| 80 | '4.2804-0.11347*His-0.19098*Ile+0.027125*Pro-0.0049206*Arg+0.087831*Leu+0.012885*Lys' | 0.897 |
| 81 | '5.6814-0.12257*His-0.20472*Ile-0.044898*Tyr+0.032507*Pro+0.11624*Leu+0.013393*Thr' | 0.904 |
| 82 | '5.7102-0.1143*His-0.19118*Ile-0.10383*Met+0.02825*Pro+0.10444*Leu+0.014274*Thr' | 0.8944 |
| 83 | '4.9206-0.11689*His-0.19178*Ile+0.029641*Pro+0.091343*Leu+0.054565*a-ABA' | 0.8927 |
| 84 | '5.9225-0.10861*His-0.19267*Ile-0.067334*Met+0.028577*Pro+0.0032612*Arg+0.10138*Leu' | 0.8896 |
| 85 | '5.8086-0.11393*His-0.18888*Ile+0.028905*Pro-0.014616*Val+0.1136*Leu+0.010043*Phe' | 0.894 |
| 86 | '5.4767-0.11571*His-0.043212*Cit-0.19512*Ile+0.027277*Pro+0.089822*Leu+0.03485*Trp' | 0.89 |
| 87 | '2.5671-0.13054*His-0.18116*Ile+0.010147*Ala+0.091074*Leu+0.0075718*Gln' | 0.8887 |
| 88 | '7.5425-0.12072*His-0.20442*Ile+0.027409*Pro+0.086448*Leu-0.0067821*Gly+0.036911*Trp' | 0.8966 |
| 89 | '5.6816-0.11331*His-0.19795*Ile+0.027993*Pro-0.0020146*Arg+0.098614*Leu' | 0.884 |
| 90 | '2.954-0.12787*His-0.17919*Ile-0.025664*Tyr+0.010954*Ala+0.098006*Leu+0.0077416*Gln' | 0.8953 |
| 91 | '5.4483-0.11082*His-0.18644*Ile-0.062639*Met+0.030363*Pro+0.094005*Leu+0.055706*a-ABA' | 0.8948 |
| 92 | '5.4958-0.11659*His-0.18404*Ile+0.031308*Pro-0.01446*Val+0.10907*Leu+0.053193*a-ABA' | 0.8992 |
| 93 | '1.5223-0.13298*His-0.17859*Ile+0.0097799*Ala+0.083628*Leu+0.0073015*Gln+0.01074*Lys' | 0.8983 |
| 94 | '4.8211-0.12641*His-0.19433*Ile+0.028094*Pro+0.082988*Leu+0.049215*a-ABA+0.039213*Trp' | 0.8957 |
| 95 | '7.7262-0.10515*His-0.042736*Cit-0.19956*Ile+0.029246*Pro+0.095723*Leu-0.0066485*Gly' | 0.8931 |
| 96 | '1.9873-0.13267*His-0.18867*Ile+0.010393*Ala+0.086047*Leu+0.0073984*Gln+0.028015*Phe' | 0.8883 |
| 97 | '5.2424-0.11766*His-0.19859*Ile+0.027376*Pro+0.099198*Leu+0.0054643*Thr' | 0.8861 |
| 98 | '6.2831-0.11317*His-0.19011*Ile+0.02974*Pro-0.014337*Val-0.0030176*Arg+0.11652*Leu' | 0.8922 |
| 99 | '5.3883-0.12446*His-0.20065*Ile+0.026514*Pro+0.088734*Leu+0.00087135*Phe+0.041355*Trp' | 0.8927 |
| 100 | '5.6771-0.12079*His-0.18751*Ile+0.028816*Pro-0.017607*Val+0.12023*Leu+0.010315*Thr' | 0.8953 |

FIG.104

| NO. | FORMULA | ROC_AUC |
|---|---|---|
| 1 | 'His+1.4024*Ile-0.15742*Pro-0.05371*Ala-0.74438*Leu-0.049608*Gln' | 0.9092 |
| 2 | 'His+1.4506*Ile+0.29684*Tyr-0.19439*Pro-0.061354*Ala-0.88168*Leu' | 0.9053 |
| 3 | 'His+1.4096*Ile-0.37788*Glu-0.20229*Pro-0.75107*Leu' | 0.897 |
| 4 | 'His+1.3683*Ile-0.38809*Glu+0.25709*Tyr-0.22707*Pro-0.80779*Leu' | 0.907 |
| 5 | 'His+1.4948*Ile-0.17341*Pro-0.053439*Ala-0.81667*Leu' | 0.8961 |
| 6 | 'His+1.4311*Ile-0.30432*Glu-0.16099*Pro-0.043522*Ala-0.75046*Leu' | 0.9013 |
| 7 | 'His+1.3375*Ile-0.33934*Glu-0.17417*Pro-0.61958*Leu-0.34351*Trp' | 0.9057 |
| 8 | 'His+1.366*Ile+0.34522*Tyr-0.24779*Pro-0.76174*Leu-0.16681*Lys' | 0.9048 |
| 9 | 'His+1.4069*Ile-0.17958*Pro-0.057716*Ala+0.14416*Val-0.99907*Leu' | 0.9027 |
| 10 | 'His+1.3417*Ile+0.27852*Tyr-0.21883*Pro-0.72211*Leu-0.44081*Trp' | 0.904 |
| 11 | 'His+1.369*Ile-0.36367*Glu-0.19219*Pro-0.65486*Leu-0.10648*Lys' | 0.9057 |
| 12 | 'His+1.2503*Ile-0.3516*Glu-0.064275*Ala-0.66468*Leu-0.054864*Gln' | 0.9083 |
| 13 | 'His+1.4558*Ile-0.16799*Pro-0.049325*Ala-0.73066*Leu-0.093829*Lys' | 0.9022 |
| 14 | 'His+1.4869*Ile-0.23097*Pro-0.83826*Leu' | 0.884 |
| 15 | 'His+1.4309*Ile-0.15963*Pro-0.043746*Ala-0.71108*Leu-0.26796*Trp' | 0.8957 |
| 16 | 'His+1.4484*Ile+0.25209*Tyr-0.25604*Pro-0.89618*Leu' | 0.8931 |
| 17 | 'His+1.4025*Ile-0.19826*Pro-0.69031*Leu-0.36203*Trp' | 0.8948 |
| 18 | 'His+0.38783*Cit+1.4327*Ile-0.3802*Glu-0.21491*Pro-0.77568*Leu' | 0.9018 |
| 19 | 'His+1.5316*Ile-0.17864*Pro-0.055101*Ala-0.8081*Leu+0.038646*Gly' | 0.8974 |
| 20 | 'His+1.3421*Ile-0.37503*Glu-0.20515*Pro-0.68567*Leu-0.34484*a-ABA' | 0.8996 |
| 21 | 'His+1.4003*Ile-0.3934*Glu-0.18975*Pro-0.076365*Arg-0.7393*Leu' | 0.8979 |
| 22 | 'His+1.4409*Ile-0.21915*Pro-0.733*Leu-0.11266*Lys' | 0.8948 |
| 23 | 'His+1.4292*Ile-0.17652*Pro-0.052913*Ala-0.75344*Leu-0.33115*a-ABA' | 0.8983 |
| 24 | 'His+1.3604*Ile-0.37883*Glu-0.18654*Pro-0.72702*Leu-0.054524*Thr' | 0.8996 |
| 25 | 'His+1.4292*Ile-0.36428*Glu-0.20654*Pro-0.75058*Leu+0.017736*Gly' | 0.897 |
| 26 | 'His+1.5067*Ile-0.1673*Pro-0.055039*Ala-0.78198*Leu-0.13843*Phe' | 0.8953 |
| 27 | 'His+0.2368*Cit+1.5088*Ile-0.18389*Pro-0.050964*Ala-0.83302*Leu' | 0.8979 |
| 28 | 'His+1.5057*Ile+0.25305*Met-0.18457*Pro-0.054102*Ala-0.84909*Leu' | 0.897 |
| 29 | 'His+1.4156*Ile-0.37698*Glu-0.20018*Pro-0.73438*Leu-0.068697*Phe' | 0.8987 |
| 30 | 'His+1.4136*Ile-0.37458*Glu+0.076358*Met-0.20612*Pro-0.76169*Leu' | 0.897 |
| 31 | 'His+1.4753*Ile-0.16838*Pro-0.052376*Ala-0.80771*Leu-0.021476*Thr' | 0.8953 |
| 32 | 'His+1.4476*Ile+0.90416*Met-0.25336*Pro-0.77669*Leu-0.19091*Lys' | 0.8992 |
| 33 | 'His+1.4928*Ile-0.17094*Pro-0.052558*Ala-0.022933*Arg-0.81456*Leu' | 0.8966 |

FIG.105

| NO. | FORMULA | ROC_AUC |
|---|---|---|
| 34 | 'His+0.65581*Cit+1.4657*Ile-0.23695*Pro-0.74128*Leu-0.14932*Lys' | 0.9013 |
| 35 | 'His+1.3222*Ile-0.078103*Ala-0.74613*Leu-0.051793*Gln' | 0.8892 |
| 36 | 'His+1.2201*Ile-0.083174*Ala+0.14658*Val-0.92344*Leu-0.057493*Gln' | 0.8935 |
| 37 | 'His+0.4908*Cit+1.5167*Ile-0.24718*Pro-0.87008*Leu' | 0.8883 |
| 38 | 'His+1.3785*Ile-0.19359*Pro-0.62923*Leu-0.08695*Lys-0.3127*Trp' | 0.8992 |
| 39 | 'His+1.343*Ile-0.35628*Glu-0.066544*Ala-0.74415*Leu' | 0.8931 |
| 40 | 'His+1.5247*Ile-0.23822*Pro-0.83011*Leu+0.039901*Gly' | 0.8818 |
| 41 | 'His+1.3622*Ile+0.29283*Tyr-0.23451*Pro-0.86668*Leu-0.088944*Thr' | 0.8966 |
| 42 | 'His+1.4338*Ile+0.29561*Tyr-0.24568*Pro-0.098673*Arg-0.8956*Leu' | 0.897 |
| 43 | 'His+0.39819*Cit+1.4262*Ile-0.21117*Pro-0.7151*Leu-0.36456*Trp' | 0.8848 |
| 44 | 'His+1.4349*Ile-0.20375*Pro-0.6763*Leu+0.037874*Gly-0.37738*Trp' | 0.8918 |
| 45 | ABA' | 0.8966 |
| 46 | 'His+1.4216*Ile-0.23351*Pro-0.77498*Leu-0.33029*a-ABA' | 0.8909 |
| 47 | 'His+1.2463*Ile-0.38184*Glu-0.070847*Ala+0.14582*Val-0.92327*Leu' | 0.8948 |
| 48 | 'His+1.3*Ile-0.36025*Glu+0.2306*Tyr-0.075075*Ala-0.7943*Leu' | 0.9061 |
| 49 | 'His+1.4794*Ile-0.22618*Pro-0.71112*Leu+0.046357*Gly-0.12594*Lys' | 0.9005 |
| 50 | 'His+1.5012*Ile+0.33394*Met-0.24664*Pro-0.88139*Leu' | 0.8853 |
| 51 | 'His+0.34948*Cit+1.4722*Ile+0.23551*Tyr-0.26593*Pro-0.91504*Leu' | 0.8922 |
| 52 | 'His+1.3427*Ile-0.20096*Pro-0.63294*Leu-0.30754*a-ABA-0.35824*Trp' | 0.8966 |
| 53 | 'His+1.2914*Ile+0.18981*Tyr-0.085358*Ala-0.79158*Leu-0.049441*Gln' | 0.8948 |
| 54 | 'His+1.4123*Ile+0.33751*Met-0.21226*Pro-0.72561*Leu-0.38234*Trp' | 0.894 |
| 55 | 'His+1.4596*Ile+0.27325*Tyr-0.25274*Pro-0.85911*Leu-0.1705*Phe' | 0.897 |
| 56 | 'His+1.4762*Ile+0.23758*Tyr-0.2595*Pro-0.88733*Leu+0.027011*Gly' | 0.8935 |
| 57 | 'His+1.4841*Ile-0.22579*Pro-0.034826*Arg-0.83452*Leu' | 0.8844 |
| 58 | 'His+1.4609*Ile-0.22266*Pro-0.82563*Leu-0.028899*Thr' | 0.8861 |
| 59 | 'His+1.493*Ile-0.22871*Pro-0.82064*Leu-0.071647*Phe' | 0.8861 |
| 60 | 'His+1.2953*Ile+0.31116*Tyr-0.084192*Ala-0.75285*Leu-0.15039*Lys' | 0.8961 |
| 61 | 'His+1.3548*Ile-0.080932*Ala-0.72668*Leu-0.057883*Gln+0.048408*Gly' | 0.8957 |
| 62 | 'His+1.2821*Ile-0.33499*Glu-0.053923*Ala-0.62834*Leu-0.30449*Trp' | 0.8905 |
| 63 | 'His+1.2258*Ile-0.079041*Ala+0.19477*Val-0.92189*Leu-0.16*Lys' | 0.8918 |
| 64 | 'His+1.3056*Ile-0.34818*Glu-0.061547*Ala-0.65358*Leu-0.10056*Lys' | 0.8948 |
| 65 | 'His+1.3805*Ile-0.1913*Pro-0.68163*Leu-0.026373*Thr-0.35507*Trp' | 0.8931 |
| 66 | 'His+1.4105*Ile-0.080417*Ala-0.82213*Leu' | 0.8796 |
| 67 | 'His+1.4475*Ile+0.25369*Tyr-0.015605*Met-0.25547*Pro-0.89453*Leu' | 0.8931 |

FIG.106

| NO. | FORMULA | ROC_AUC |
|---|---|---|
| 68 | 'His+1.4028*Ile-0.19649*Pro-0.015989*Arg-0.69137*Leu-0.35523*Trp' | 0.8948 |
| 69 | 'His+0.80476*Cit+1.5244*Ile-0.23658*Pro-0.14086*Arg-0.87534*Leu' | 0.89 |
| 70 | 'His+1.4017*Ile-0.19836*Pro-0.69143*Leu+0.0064393*Phe-0.36316*Trp' | 0.8957 |
| 71 | 'His+1.3948*Ile-0.22179*Pro-0.6921*Leu-0.24792*a-ABA-0.10561*Lys' | 0.8979 |
| 72 | 'His+1.3014*Ile-0.074427*Ala-0.68531*Leu-0.047311*Gln-0.073389*Lys' | 0.8948 |
| 73 | 'His+1.4463*Ile-0.2457*Pro+0.11694*Val-0.98091*Leu+0.032906*Gly' | 0.8909 |
| 74 | 'His+1.4383*Ile-0.22254*Pro+0.031574*Arg-0.72477*Leu-0.12509*Lys' | 0.8948 |
| 75 | 'His+1.3685*Ile+0.2294*Tyr-0.089057*Ala-0.87288*Leu' | 0.8848 |
| 76 | 'His+1.4594*Ile-0.22536*Pro-0.7339*Leu+0.025641*Thr-0.12369*Lys' | 0.8935 |
| 77 | 'His+1.4426*Ile-0.21869*Pro-0.72956*Leu-0.01705*Phe-0.11185*Lys' | 0.8957 |
| 78 | 'His+1.2927*Ile-0.069939*Ala-0.68016*Leu-0.045086*Gln-0.19161*Trp' | 0.8914 |
| 79 | 'His+1.2829*Ile-0.35855*Glu-0.059981*Ala-0.7117*Leu-0.075313*Thr' | 0.8957 |
| 80 | 'His+1.2871*Ile+0.24812*Tyr-0.073615*Ala-0.73238*Leu-0.36556*Trp' | 0.8887 |
| 81 | 'His+0.59453*Cit+1.4555*Ile-0.22899*Pro-0.84398*Leu-0.07514*Thr' | 0.8896 |
| 82 | 'His+0.61361*Cit+1.5421*Ile-0.24454*Pro-0.82609*Leu-0.21128*Phe' | 0.8896 |
| 83 | 'His+1.3426*Ile-0.078916*Ala-0.71235*Leu-0.049245*Gln-0.1489*Phe' | 0.89 |
| 84 | 'His+0.43272*Cit+1.5444*Ile-0.25124*Pro-0.85959*Leu+0.032919*Gly' | 0.8874 |
| 85 | 'His+1.3676*Ile-0.34613*Glu-0.067926*Ala-0.69336*Leu-0.21041*Phe' | 0.8931 |
| 86 | 'His+1.2742*Ile-0.078062*Ala-0.70101*Leu-0.23486*a-ABA-0.052034*Gln' | 0.8883 |
| 87 | 'His+1.3706*Ile-0.07498*Ala-0.7276*Leu-0.10293*Lys' | 0.884 |
| 88 | 'His+0.45393*Cit+1.4546*Ile-0.24829*Pro-0.80964*Leu-0.30306*a-ABA' | 0.8918 |
| 89 | 'His+1.3368*Ile-0.37508*Glu-0.061589*Ala-0.07657*Arg-0.73276*Leu' | 0.8957 |
| 90 | 'His+1.331*Ile-0.084998*Ala+0.12609*Val-0.98184*Leu' | 0.8844 |
| 91 | 'His+0.20143*Cit+1.3244*Ile-0.077244*Ala-0.7557*Leu-0.054947*Gln' | 0.8914 |
| 92 | 'His+1.3461*Ile-0.067085*Ala-0.70271*Leu-0.30182*Trp' | 0.8805 |
| 93 | 'His+1.3046*Ile-0.075894*Ala-0.73793*Leu-0.026816*Thr-0.049631*Gln' | 0.8892 |
| 94 | 'His+1.2407*Ile-0.069328*Ala+0.14431*Val-0.85862*Leu-0.36973*Trp' | 0.8883 |
| 95 | 'His+1.3221*Ile+0.14112*Met-0.079358*Ala-0.7617*Leu-0.053644*Gln' | 0.89 |
| 96 | 'His+1.4583*Ile-0.24048*Pro-0.76737*Leu-0.32908*a-ABA+0.038398*Gly' | 0.8905 |
| 97 | 'His+1.4171*Ile+0.72147*Met-0.23261*Pro-0.8825*Leu-0.11203*Thr' | 0.8896 |
| 98 | 'His+1.3228*Ile-0.077528*Ala-0.010907*Arg-0.74597*Leu-0.0512*Gln' | 0.8892 |
| 99 | 'His+0.45069*Cit+1.521*Ile+0.15684*Met-0.25321*Pro-0.88774*Leu' | 0.8874 |
| 100 | 'His+1.2966*Ile-0.35564*Glu-0.066539*Ala-0.70048*Leu-0.22985*a-ABA' | 0.8931 |

FIG.108

| NO. | FORMULA | CORRELATION COEFFICIENT |
|---|---|---|
| 1 | (Glu+Pro+Lys+Leu)/(Val+His) | 0.6521 |
| 2 | (Leu)/(Met+His)+(Pro+Lys)/(Val) | 0.6501 |
| 3 | (Leu)/(Ile+His)+(Pro+Lys)/(Val) | 0.659 |
| 4 | (Lys)/(Val)+(Pro+Leu)/(Ile+His) | 0.6559 |
| 5 | (Pro+Orn+Lys+Leu)/(Val+His) | 0.6444 |
| 6 | (Pro+Lys+Leu)/(Val+Met+His) | 0.6394 |
| 7 | (Pro+Lys+Leu)/(Val+Cit+His) | 0.627 |
| 8 | (Pro+Lys+Leu)/(Val+Ile+His) | 0.6348 |
| 9 | (Glu+Pro+Lys)/(Val+Cit+His) | 0.6152 |
| 10 | (Glu)/(Gly)+(Pro+Lys)/(Val+His) | 0.6273 |
| 11 | (Leu)/(Ile+His)+(Glu+Pro)/(Val) | 0.6108 |
| 12 | (Pro+Lys+Leu)/(Val+His) | 0.6202 |
| 13 | (Leu)/(Arg+His)+(Pro+Lys)/(Val) | 0.6103 |
| 14 | (Pro+Lys+Leu)/(Val+Cys2+His) | 0.6326 |
| 15 | (Pro)/(Arg+His)+(Lys+Leu)/(Val) | 0.599 |
| 16 | (Leu)/(Ile+His)+(Pro+Orn)/(Val) | 0.6068 |
| 17 | (Pro+Lys+Leu)/(ABA+Val+His) | 0.6055 |
| 18 | (Pro+Lys+Leu)/(Arg+Val+His) | 0.6023 |
| 19 | (Pro+Lys+Tau+Leu)/(Val+His) | 0.6243 |
| 20 | (Glu+Pro+Lys+Phe)/(Val+His) | 0.61 |
| 21 | (Pro+Lys+Leu+Phe)/(Val+His) | 0.5989 |
| 22 | (Glu+Pro+Lys)/(Val+Met+His) | 0.6198 |
| 23 | (Glu+Pro+Lys)/(Val+Cys2+His) | 0.6249 |
| 24 | (Pro+Lys+Trp+Leu)/(Val+His) | 0.6225 |
| 25 | (Pro)/(Ile+His)+(Lys+Leu)/(Val) | 0.617 |
| 26 | (Pro+Lys+Leu)/(Ile+Met+His) | 0.668 |
| 27 | (Pro)/(Val)+(Glu+Leu)/(Ile+His) | 0.609 |
| 28 | (Glu+Pro+Lys)/(Val+His) | 0.607 |
| 29 | (Glu+Pro+Lys+Leu)/(Ile+His) | 0.6642 |
| 30 | (Glu+Pro+Orn+Lys)/(Val+His) | 0.6272 |
| 31 | (Glu+Pro+Lys)/(Arg+Val+His) | 0.6114 |
| 32 | (Glu+Pro+Lys)/(Thr+Val+His) | 0.5866 |
| 33 | (Pro+Lys+Phe)/(Arg+Val+His) | 0.5902 |
| 34 | (Leu)/(Val)+(Pro+Lys)/(Ile+His) | 0.6452 |
| 35 | (Pro)/(His)+(Lys+Leu)/(Ile+Met) | 0.6587 |
| 36 | (Pro+Orn+Lys)/(Thr+Val+His) | 0.5903 |
| 37 | (Leu)/(Ser+His)+(Pro+Lys)/(Val) | 0.6146 |
| 38 | (Lys)/(Val)+(Glu+Pro)/(Ile+His) | 0.6226 |
| 39 | (Glu+Pro+Lys+Trp)/(Val+His) | 0.6215 |
| 40 | (Leu)/(Ile)+(Pro+Lys)/(Met+His) | 0.6689 |
| 41 | (Pro)/(Arg+His)+(Lys+Phe)/(Val) | 0.5897 |
| 42 | (Pro+Orn+Lys)/(Val+Cit+His) | 0.6248 |
| 43 | (Glu+Pro+Lys)/(ABA+Val+His) | 0.6058 |
| 44 | (Pro)/(Val)+(Lys+Leu)/(Ile+His) | 0.6662 |
| 45 | (Pro)/(Arg+His)+(Glu+Lys)/(Val) | 0.5927 |
| 46 | (Glu+Pro+Lys)/(Val+Ile+His) | 0.6208 |
| 47 | (Glu)/(His)+(Pro+Lys+Leu)/(Val) | 0.6284 |
| 48 | (Pro)/(Ile)+(Lys+Leu)/(Met+His) | 0.6444 |
| 49 | (Glu+Lys)/(His)+(Pro+Leu)/(Ile) | 0.6672 |
| 50 | (Tau)/(Gly)+(Pro+Lys)/(Val+His) | 0.6111 |

FIG.109

| NO. | FORMULA | CORRELATION COEFFICIENT |
|---|---|---|
| 51 | (Leu)/(His)+(Pro+Lys)/(Ile+Met) | 0.6699 |
| 52 | (Pro+Lys+Leu)/(Ser+Val+His) | 0.6117 |
| 53 | (Pro+Lys+Leu+Phe)/(Ile+His) | 0.6526 |
| 54 | (Pro)/(Val)+(Orn+Leu)/(Ile+His) | 0.6117 |
| 55 | (Pro+Lys+Leu)/(Thr+Val+His) | 0.5556 |
| 56 | (Leu)/(Cys2+His)+(Pro+Lys)/(Val) | 0.6291 |
| 57 | (Glu+Lys)/(Ile)+(Pro+Leu)/(His) | 0.6656 |
| 58 | (Glu+Pro+Lys)/(Ser+Val+His) | 0.6196 |
| 59 | (Leu)/(Thr+His)+(Pro+Lys)/(Val) | 0.5791 |
| 60 | (Pro+Orn+Lys+Leu)/(Ile+His) | 0.6603 |
| 61 | (Lys)/(Ile+His)+(Pro+Leu)/(Val) | 0.6374 |
| 62 | (Leu)/(Gly)+(Pro+Lys)/(Ile+His) | 0.6327 |
| 63 | (Pro)/(Val+Cit)+(Leu)/(Ile+His) | 0.578 |
| 64 | (Pro)/(Ile+His)+(Glu+Lys)/(Val) | 0.6104 |
| 65 | (Phe)/(Arg)+(Pro+Lys)/(Ile+His) | 0.6354 |
| 66 | (Glu+Pro+Lys+Phe)/(Ile+His) | 0.6502 |
| 67 | (Glu+Pro)/(His)+(Leu+Phe)/(Ile) | 0.6101 |
| 68 | (Leu)/(Ile)+(Glu+Pro)/(Cys2+His) | 0.6306 |
| 69 | (Leu)/(Cit+His)+(Pro+Lys)/(Val) | 0.6191 |
| 70 | (Glu+Pro+Lys+Tau)/(Val+His) | 0.608 |
| 71 | (Pro+Orn+Lys+Phe)/(Val+His) | 0.5964 |
| 72 | (Pro)/(Val+Met)+(Leu)/(Ile+His) | 0.5814 |
| 73 | (Pro+Orn+Lys)/(Ser+Val+His) | 0.6105 |
| 74 | (Pro+Lys+Leu)/(Ile+His) | 0.6532 |
| 75 | (Glu)/(Cit+His)+(Pro+Lys)/(Val) | 0.6122 |
| 76 | (Glu)/(Gly)+(Pro+Lys)/(Ile+His) | 0.6418 |
| 77 | (Pro+Orn+Lys)/(Val+Met+His) | 0.6158 |
| 78 | (Pro)/(His)+(Glu+Leu+Phe)/(Ile) | 0.6111 |
| 79 | (Glu)/(Cys2+His)+(Pro+Lys)/(Val) | 0.6206 |
| 80 | (Orn)/(Gly)+(Pro+Lys)/(Val+His) | 0.6088 |
| 81 | (Glu)/(Gly)+(Pro+Lys+Leu)/(Val) | 0.5863 |
| 82 | (Phe)/(His)+(Glu+Pro+Lys)/(Val) | 0.5814 |
| 83 | (Pro+Lys+Asn+Leu)/(Val+His) | 0.6061 |
| 84 | (Lys)/(Ile+Cys2)+(Glu+Pro)/(His) | 0.6482 |
| 85 | (Lys)/(His)+(Glu+Pro+Leu)/(Ile) | 0.6654 |
| 86 | (Glu+Pro+Lys+Asn)/(Val+His) | 0.6013 |
| 87 | (Glu+Pro+Lys+Leu)/(Val+Cit) | 0.5963 |
| 88 | (Glu+Pro+Leu+Phe)/(Ile+His) | 0.5928 |
| 89 | (Leu)/(Arg+Ile)+(Pro+Lys)/(Val) | 0.5905 |
| 90 | (Pro)/(Arg+Cys2+His)+(Lys)/(Val) | 0.5881 |
| 91 | (Pro)/(Arg+His)+(Orn+Lys)/(Val) | 0.5933 |
| 92 | (Pro+Orn+Lys)/(Arg+Val+His) | 0.6078 |
| 93 | (Orn)/(Thr)+(Pro+Lys)/(Ile+His) | 0.6366 |
| 94 | (Lys)/(Val)+(Pro+Phe)/(Ile+His) | 0.5934 |
| 95 | (Orn)/(Gly)+(Pro+Lys+Leu)/(Val) | 0.5928 |
| 96 | (Pro+Lys+Phe)/(Val+Cit+His) | 0.5919 |
| 97 | (Glu+Pro+Lys)/(Tyr+Val+His) | 0.6377 |
| 98 | (Pro)/(His)+(Orn+Leu+Phe)/(Ile) | 0.6079 |
| 99 | (Lys)/(Ile)+(Glu+Pro+Leu)/(His) | 0.6587 |
| 100 | (Pro+Orn+Lys)/(Val+Cys2+His) | 0.6162 |

FIG.111

| NO. | FORMULA | CORRELATION COEFFICIENT |
|---|---|---|
| 1 | 'Ala/His-15.532*Ile/Leu-7.5011*Val/Lys+1.8478*Glu/Cys2' | 0.6344 |
| 2 | 'Ala/His-15.3882*Ile/Leu+14.8069*Orn/Val+1.3264*Glu/Cys2' | 0.6498 |
| 3 | 'Ala/His-2.815*Cys2/Glu-9.2745*Val/Leu-3.0985*Ile/Orn' | 0.6627 |
| 4 | 'His/Lys-1.6618*Leu/Val-0.028736*Gln/Ile-0.0033504*Glu' | -0.6143 |
| 5 | 'His/Lys+0.17383*Val/Pro+0.04206*Ile/Glu-0.0015024*Asn' | -0.5906 |
| 6 | 'Ala/His-8.8864*Val/Leu-7.7073*Cys2/Orn-37.7855*Met/Lys' | 0.6805 |
| 7 | 'Ala/His-7.7915*Val/Lys+0.0056228*Gln+1.872*Glu/Cys2' | 0.5877 |
| 8 | 'Ala/His-3.7904*Cys2/Glu-6.9037*Val/Lys-14.447*Ile/Leu' | 0.61 |
| 9 | 'His/Lys-1.8289*Glu/Val-0.0057672*Gln/Cys2-0.10423*Pro/Tyr' | -0.6132 |
| 10 | 'Ala/His-8.7822*Val/Lys-3.8302*Cys2/Glu+0.0018751*Gln' | 0.5826 |
| 11 | 'Glu/His-2.931*Cys2/Pro+1.0477*Tau/Val-0.41617*Tyr/Leu' | 0.5585 |
| 12 | 'Ala/His-14.9111*Ile/Leu-5.4302*Cys2/Tau-7.4147*Val/Lys' | 0.6265 |
| 13 | 'Ala/His-4.7365*Cys2/Tau-9.2683*Val/Leu-3.3397*Ile/Orn' | 0.6358 |
| 14 | 'Ala/His-11.8423*Val/Leu+7.1814*Orn/Ile-22.0579*Cys2/Lys' | 0.6071 |
| 15 | 'Ala/His+3.0103*Glu/Cys2-9.8419*Val/Lys+1.1387*Leu/Tyr' | 0.5899 |
| 16 | 'Ala/His-18.7257*Ile/Leu-6.3625*Cys2/Orn-0.75522*Val/Arg' | 0.6138 |
| 17 | 'His/Orn-0.67262*Ala/Val+6.2224*Cys2/Lys+4.0596*Ile/Leu' | -0.6349 |
| 18 | 'Ala/His+4.7068*Leu/Ile-0.73141*Val/Orn-2.4234*Cys2/Tau' | 0.6343 |
| 19 | 'Ala/His-4.2089*Cys2/Glu-0.86292*Val/Asn-13.4986*Ile/Leu' | 0.5808 |
| 20 | 'Ala/His+3.9808*Leu/Ile-6.2879*Cys2/Orn-2.099*Val/Phe' | 0.6267 |
| 21 | 'His/Lys-0.097778*Ala/Val-0.03345*Tau/Cys2-0.0021518*Glu' | -0.6006 |
| 22 | 'His/Lys+0.30077*Val/Ala+0.082308*Cys2/Glu-0.055583*Pro/Tyr' | -0.6631 |
| 23 | 'Ala/His+57.1016*Leu/Val-9.0275*Cys2/Orn+3.4921*Pro/Ile' | 0.6389 |
| 24 | 'His/Lys-0.11466*Ala/Val-0.076041*Glu/Cys2+0.62514*Ile/Leu' | -0.6107 |
| 25 | 'Ala/His-9.8626*Val/Leu-4.2814*Ile/Orn-8.4206*Cys2/Arg' | 0.6279 |
| 26 | 'Ala/His+0.75357*Tau/Cys2+55.8432*Leu/Val-5.3508*Ile/Orn' | 0.6087 |
| 27 | 'His/Lys-0.10313*Glu/Cys2-0.098429*Ala/Val-0.064697*Leu/Tyr' | -0.5925 |
| 28 | 'His/Lys-0.07816*Glu/Cys2-0.4454*Pro/Val+0.64947*Ile/Leu' | -0.6263 |
| 29 | 'His/Lys-0.12575*Ala/Val-0.065442*Glu/Cys2-0.1376*Leu/Ile' | -0.6475 |
| 30 | 'Ala/His-2.7317*Cys2/Glu-6.9469*Val/Lys+3.419*Leu/Ile' | 0.617 |
| 31 | 'Ala/His+0.82761*Tau/Cys2-9.3915*Val/Leu-2.687*Ile/Orn' | 0.6014 |
| 32 | 'His/Lys-0.58638*Pro/Val-0.05593*Glu/Cys2-0.19011*Leu/Ile' | -0.622 |
| 33 | 'His/Lys-0.13756*Ala/Val+0.25035*Cys2/Tau-0.055407*Leu/Tyr' | -0.5961 |
| 34 | 'Ala/His+10.3389*Lys/Val-7.042*Cys2/Orn+2.6576*Leu/Ile' | 0.6537 |
| 35 | 'His/Lys+0.55359*Val/Leu+0.12323*Ile/Orn-0.08058*Glu/Cys2' | -0.6597 |
| 36 | 'His/Lys+0.35637*Val/Ala+0.31444*Cys2/Orn+0.12214*Tyr/Leu' | -0.6427 |
| 37 | 'His/Lys-0.64782*Pro/Val+0.86516*Ile/Leu-0.0032697*Glu' | -0.6015 |
| 38 | 'Ala/His-10.6598*Val/Leu-8.4936*Cys2/Orn-17.1469*Ile/Lys' | 0.6356 |
| 39 | 'Ala/His-8.3302*Val/Leu+0.5854*Gln/Ile+0.076466*Glu' | 0.6192 |
| 40 | 'Ala/His-7.4421*Val/Leu-2.3406*Ile/Orn+1.1709*Glu/Cys2' | 0.6568 |
| 41 | 'Ala/His-8.6924*Val/Lys+2.3327*Glu/Cys2+1.3154*Leu/Tyr' | 0.6461 |
| 42 | 'Ala/His+4.307*Leu/Ile-5.9301*Cys2/Orn+8.0252*Lys/Val' | 0.6682 |
| 43 | 'His/Lys-0.10732*Glu/Cys2-0.11061*Ala/Val+0.12957*Tyr/Leu' | -0.6246 |
| 44 | 'His/Lys-0.15819*Ala/Val+0.34718*Cys2/Orn-0.058762*Leu/Tyr' | -0.6188 |
| 45 | 'His/Lys-0.073881*Glu/Cys2+0.46257*Val/Leu-0.15727*Pro/Ile' | -0.66 |
| 46 | 'Ala/His+10.2519*Lys/Val+0.70566*Tau/Cys2-1.6871*Tyr/Leu' | 0.6256 |
| 47 | 'Ala/His+39.6683*Leu/Val-7.7653*Cys2/Orn+1.7684*Lys/Ile' | 0.6366 |
| 48 | 'Ala/His-14.3241*Ile/Leu-7.7479*Cys2/Orn-2.167*Val/Phe' | 0.6192 |
| 49 | 'Ala/His+4.4025*Leu/Ile-5.8611*Cys2/Orn+19.2124*Phe/Val' | 0.6339 |
| 50 | 'His/Lys-0.098153*Glu/Cys2-0.090646*Gln/Val-0.015294*Ala/Ile' | -0.5939 |

FIG.112

| NO. | FORMULA | CORRELATION COEFFICIENT |
|---|---|---|
| 51 | 'Ala/His-2.9807*Cys2/Glu-9.2367*Val/Leu-3.264*Ile/Orn' | 0.6071 |
| 52 | 'Ala/His-8.6652*Val/Lys-3.7934*Cys2/Glu-1.535*Tyr/Leu' | 0.5852 |
| 53 | 'Ala/His-6.8279*Val/Lys-6.2284*Tyr/Leu+1.8435*Pro/Ile' | 0.6262 |
| 54 | 'Ala/His-13.8541*Ile/Leu-6.9825*Cys2/Orn+10.8607*Tau/Val' | 0.6179 |
| 55 | 'Ala/His+2.2058*Glu/Cys2-11.0511*Val/Leu-3.1507*Ile/Orn' | 0.63 |
| 56 | 'His/Lys-0.098908*Glu/Cys2-0.094658*Ala/Val-0.18365*Leu/Ile' | -0.6241 |
| 57 | 'Ala/His-19.0341*Ile/Leu-0.8978*Val/Orn+0.017851*Arg' | 0.6077 |
| 58 | 'His/Lys+0.016807*Val/Glu-0.20534*Leu/Ile-0.018747*Pro/Cys2' | -0.6453 |
| 59 | 'His/Lys+0.15119*Cys2/Glu-0.089266*Ala/Val+0.031126*Tyr/Leu' | -0.5994 |
| 60 | 'His/Lys+0.30796*Val/Ala-0.070098*Leu/Tyr+0.098822*Cys2/Glu' | -0.6515 |
| 61 | 'Gln/His+2.1374*Glu/Cys2-14.1273*Ile/Leu+11.1139*Lys/Val' | 0.6493 |
| 62 | 'Ala/His-30.8376*Ile/Leu+17.0209*Pro/Val+0.57745*Tau/Cys2' | 0.6005 |
| 63 | 'His/Lys-0.12201*Ala/Val-0.081578*Glu/Cys2+0.21054*Ile/Phe' | -0.6133 |
| 64 | 'Ala/His-7.1004*Val/Lys+3.9109*Leu/Ile+0.003335*Gln' | 0.5871 |
| 65 | 'Ala/His+48.5992*Leu/Val-10.269*Cys2/Orn+3.5508*Tau/Ile' | 0.6434 |
| 66 | 'His/Lys-0.13228*Ala/Val-0.099327*Glu/Cys2-0.26084*Asn/Tyr' | -0.6239 |
| 67 | 'Ala/His-8.7045*Val/Leu-2.6895*Ile/Orn-8.5945*Cys2/Arg' | 0.6538 |
| 68 | 'Ala/His+1.9969*Glu/Cys2-7.7165*Val/Lys+1.5939*Leu/Tyr' | 0.6282 |
| 69 | 'Ala/His-16.9348*Ile/Leu-6.6524*Cys2/Orn-0.96203*Val/Arg' | 0.651 |
| 70 | 'Ala/His-8.5709*Val/Lys+2.7509*Glu/Cys2+5.6466*Leu/Ile' | 0.6162 |
| 71 | 'Ala/His+2.281*Glu/Cys2+4.8987*Leu/Ile+1.8857*Gln/Val' | 0.6458 |
| 72 | 'Ala/His-15.2149*Ile/Leu-3.2018*Cys2/Glu+11.6071*Lys/Val' | 0.6193 |
| 73 | 'Ala/His+33.5806*Leu/Val-7.2184*Cys2/Orn-13.3068*Ile/Lys' | 0.6483 |
| 74 | 'His/Lys-0.52864*Pro/Val+0.15226*Cys2/Glu+0.6209*Ile/Leu' | -0.6213 |
| 75 | 'His/Lys-1.3394*Glu/Val+3.2945*Cys2/Gln+0.26691*Met/Asn' | -0.6342 |
| 76 | 'Ala/His+1.4776*Glu/Cys2-9.43*Val/Leu+4.9096*Orn/Ile' | 0.6248 |
| 77 | 'Ala/His+0.66313*Tau/Cys2-9.6611*Val/Leu-3.1926*Ile/Orn' | 0.6143 |
| 78 | 'Ala/His-5.8199*Val/Lys-2.1092*Cys2/Glu-10.0567*Ile/Leu' | 0.6273 |
| 79 | 'His/Orn-0.04048*Ala/Cys2+2.0151*Val/Leu+0.33469*Ile/Tau' | -0.6382 |
| 80 | 'Ala/His-10.6701*Val/Leu+5.4252*Orn/Ile-20.9337*Cys2/Lys' | 0.595 |
| 81 | 'His/Lys+0.68343*Ile/Leu-0.48673*Pro/Val-0.0030348*Glu' | -0.6323 |
| 82 | 'His/Lys-0.088364*Glu/Cys2-0.086682*Ala/Val-0.15097*Asn/Tyr' | -0.6049 |
| 83 | 'Ala/His-12.8018*Ile/Leu+0.62652*Tau/Cys2-4.8293*Val/Lys' | 0.6224 |
| 84 | 'His/Lys-0.18513*Leu/Ile-0.93013*Glu/Val-0.0026457*Gln/Cys2' | -0.6424 |
| 85 | 'Ala/His-13.3835*Ile/Leu+12.8864*Lys/Val+0.092872*Glu' | 0.6177 |
| 86 | 'His/Lys-0.12783*Ala/Val-0.00023274*Gln-0.076286*Glu/Cys2' | -0.5799 |
| 87 | 'His/Lys-0.12407*Ala/Val-0.00026888*Gln-0.081091*Glu/Cys2' | -0.6022 |
| 88 | 'His/Lys+0.76369*Ile/Pro-1.9524*Leu/Val-0.0039055*Glu' | -0.6459 |
| 89 | 'Ala/His+4.1788*Leu/Ile-7.536*Cys2/Orn-2.1523*Val/Phe' | 0.6268 |
| 90 | 'His/Lys-1.2338*Glu/Val-0.0351*Tau/Cys2-0.016264*Ala/Ile' | -0.6147 |
| 91 | 'Ala/His+2.2956*Glu/Cys2+13.7882*Lys/Val+1.0404*Leu/Tyr' | 0.6396 |
| 92 | 'Ala/His+2.6951*Glu/Cys2+12.7397*Lys/Val-15.3557*Ile/Leu' | 0.6446 |
| 93 | 'Ala/His+3.0672*Glu/Cys2+15.1458*Lys/Val+1.005*Leu/Tyr' | 0.6092 |
| 94 | 'His/Lys+0.14796*Cys2/Glu-0.076891*Gln/Val+0.53294*Ile/Leu' | -0.6114 |
| 95 | 'His/Lys-1.7699*Leu/Val-0.12377*Pro/Ile-0.10935*Tau/Tyr' | -0.6292 |
| 96 | 'His/Lys-0.083888*Glu/Cys2+0.19179*Val/Pro-0.25568*Leu/Ile' | -0.6621 |
| 97 | 'Ala/His-8.5835*Val/Lys-3.7953*Cys2/Glu-13.8465*Ile/Leu' | 0.5918 |
| 98 | 'His/Lys-1.4633*Glu/Val-0.0034269*Gln/Cys2+0.065637*Tyr/Asn' | -0.6256 |
| 99 | 'His/Lys-0.10749*Ala/Val-0.074444*Glu/Cys2+0.64961*Ile/Leu' | -0.6059 |
| 100 | 'Ala/His-9.533*Val/Leu+3.8198*Tau/Ile+0.68034*Orn/Cys2' | 0.6399 |

FIG.114

| NO. | FORMULA | CORRELATION COEFFICIENT |
|---|---|---|
| 1 | 'Pro-2.7346*His-0.12911*Gly-0.94775*Val-2.7103*Ile+3.113*Leu' | 0.6342 |
| 2 | 'Pro-2.6799*His+0.85294*Lys-0.16956*Gly-1.5826*Val+1.776*Leu' | 0.6419 |
| 3 | 'Pro-2.9899*His+0.047406*Ala-1.0278*Val-2.7207*Ile+3.3495*Leu' | 0.6348 |
| 4 | 'Pro-3.0255*His+0.84405*Lys+0.065557*Ala-1.692*Val+2.0937*Leu' | 0.6467 |
| 5 | 'Pro-2.9508*His+0.7533*Lys-0.79078*Ser-4.1569*Ile+2.0013*Leu' | 0.6673 |
| 6 | 'Pro-2.1784*His+1.5519*Glu+1.0837*Lys-0.17256*Gly-1.1047*Val' | 0.6454 |
| 7 | 'Pro-3.3589*His+1.231*Glu+0.63736*Lys-4.1546*Ile+1.9802*Leu' | 0.6898 |
| 8 | 'Pro-2.8875*His+0.75939*Lys-3.496*Met-3.4741*Ile+2.0743*Leu' | 0.6727 |
| 9 | 'Pro-2.8038*His+0.72478*Lys-0.55742*Thr-3.8096*Ile+1.841*Leu' | 0.6468 |
| 10 | 'Pro-2.9832*His+1.5948*Glu+0.05273*Ala-1.5878*Val+2.4617*Leu' | 0.6169 |
| 11 | 'Pro-2.8157*His+1.5511*Glu-0.019255*Gly-1.5098*Val+2.334*Leu' | 0.6098 |
| 12 | 'Pro-2.3216*His+1.7892*Glu+1.0828*Lys+0.016676*Ala-1.0834*Val' | 0.6495 |
| 13 | 'Pro+1.0885*Lys-0.19961*Gly-1.4449*Val-5.411*Met+1.5429*Leu' | 0.6321 |
| 14 | 'Pro-3.1369*His+0.66132*Lys-0.2156*Gly-4.1*Ile+1.9202*Leu' | 0.663 |
| 15 | 'Pro-1.7557*His+1.226*Lys-0.22957*Gly-0.97605*Val-0.68835*Arg' | 0.6248 |
| 16 | 'Pro-3.3539*His+0.61048*Lys-4.0568*Ile+2.1301*Leu' | 0.6515 |
| 17 | 'Pro-3.182*His+1.2118*Orn+0.10048*Ala-1.8526*Val+2.9382*Leu' | 0.6106 |
| 18 | 'Pro-2.7675*His+1.1187*Orn-0.13657*Gly-1.672*Val+2.5623*Leu' | 0.6077 |
| 19 | 'Pro-1.7267*His+1.1819*Lys-0.25031*Gly-0.80476*Val-3.3239*Met' | 0.6367 |
| 20 | 'Pro-3.4136*His+0.64013*Orn+0.56221*Lys-4.4423*Ile+2.3097*Leu' | 0.6731 |
| 21 | 'Pro-3.6056*His+1.5197*Glu-3.9425*Ile-2.1927*Cys2+2.557*Leu' | 0.6586 |
| 22 | 'Pro-3.3273*His+1.2155*Glu-3.9179*Ile+2.4181*Leu' | 0.6317 |
| 23 | 'Pro-3.5029*His+0.61563*Lys-4.0603*Ile-1.1761*Cys2+2.2185*Leu' | 0.6583 |
| 24 | 'Pro-3.1325*His+0.70912*Lys-3.8315*Ile-0.31142*Arg+1.9346*Leu' | 0.6569 |
| 25 | 'Pro-3.0893*His+0.90353*Orn-0.62097*Ser-4.4375*Ile+2.7305*Leu' | 0.6436 |
| 26 | 'Pro-2.3359*His+1.0739*Lys-0.36577*Gly+0.88939*Tau-1.0497*Val' | 0.6297 |
| 27 | 'Pro-3.2682*His+0.62256*Lys-4.1765*Ile+2.2341*Leu-0.9509*a-ABA' | 0.647 |
| 28 | 'Pro-1.9618*His+1.1362*Lys-0.17707*Gly-0.61091*Ser-0.98216*Val' | 0.618 |
| 29 | 'Pro-2.1666*His+1.0507*Lys-0.26944*Gly-0.96556*Val' | 0.6118 |
| 30 | 'Pro-1.8811*His+1.0911*Lys-0.22652*Gly-0.92056*Val-0.46083*Thr' | 0.6114 |
| 31 | 'Pro-3.4348*His+0.60629*Lys+0.22375*Tau-4.0923*Ile+2.1551*Leu' | 0.6569 |
| 32 | 'Pro-3.4044*His+0.83215*Orn-4.3554*Ile+2.7385*Leu' | 0.6306 |
| 33 | 'Pro-3.2704*His+0.6186*Lys-0.54622*Cit-3.9332*Ile+2.06*Leu' | 0.6545 |

FIG.115

| NO. | FORMULA | CORRELATION COEFFICIENT |
|---|---|---|
| 34 | 'Pro-3.3774*His+0.9794*Glu+0.52318*Orn-4.2306*Ile+2.5631*Leu' | 0.6443 |
| 35 | 'Pro-2.1017*His+0.68942*Orn+1.0453*Lys-0.28887*Gly-1.0819*Val' | 0.6302 |
| 36 | 'Pro-2.9433*His+0.96937*Orn-0.47587*Thr-4.1947*Ile+2.5899*Leu' | 0.6308 |
| 37 | 'Pro-3.3731*His+0.61202*Lys+0.0055731*Ala-4.0716*Ile+2.1378*Leu' | 0.6537 |
| 38 | 'Pro+1.057*Lys+0.0049816*Ala-1.4628*Val-5.6712*Met+1.7628*Leu' | 0.6265 |
| 39 | 'Pro-3.1604*His+1.0423*Glu-0.32092*Ser-3.9247*Ile+2.424*Leu' | 0.6344 |
| 40 | 'Pro-3.2113*His+0.85411*Orn-0.19181*Gly-4.3909*Ile+2.5878*Leu' | 0.6422 |
| 41 | 'Pro+0.85063*Lys-0.26802*Gly-1.2728*Val-2.4274*Ile+2.0114*Leu' | 0.6135 |
| 42 | 'Pro-3.2208*His+1.085*Glu-0.10419*Gly-3.9204*Ile+2.3474*Leu' | 0.6327 |
| 43 | 'Pro-3.6509*His+0.97922*Orn-4.4505*Ile-1.8355*Cys2+2.9156*Leu' | 0.6549 |
| 44 | 'Pro-1.9534*His+1.0518*Lys-0.23894*Gly-0.92391*Val-1.6808*Cit' | 0.6259 |
| 45 | 'Pro-2.059*His+1.0624*Lys-0.2891*Gly-0.69983*Val-0.97768*Ile' | 0.6444 |
| 46 | 'Pro-3.4978*His+1.3303*Glu-4.1229*Ile+0.23421*Arg+2.5021*Leu' | 0.6357 |
| 47 | 'Pro+1.2211*Glu+1.2586*Lys-0.19511*Gly-1.2744*Val-0.729*Arg' | 0.6155 |
| 48 | 'Pro-3.1334*His+1.1204*Glu-0.19421*Thr-3.8102*Ile+2.3548*Leu' | 0.6258 |
| 49 | 'Pro-2.9837*His-0.2176*Gly+0.93701*Tau-1.4651*Val+2.3378*Leu' | 0.5883 |
| 50 | 'Pro-3.3237*His-3.8312*Ile+2.5479*Leu' | 0.6082 |
| 51 | 'Pro-2.2922*His+1.0734*Lys-0.31552*Gly-0.9436*Val-1.4428*Cys2' | 0.6309 |
| 52 | 'Pro-1.9436*His+1.2397*Lys+0.033483*Ala-0.92372*Val-0.7509*Arg' | 0.6127 |
| 53 | 'Pro-3.2642*His+1.148*Glu-0.4645*Met-3.8283*Ile+2.4314*Leu' | 0.6307 |
| 54 | 'Pro-3.3716*His+1.1929*Glu+0.12251*Tau-3.9365*Ile+2.4327*Leu' | 0.6305 |
| 55 | 'Pro-3.2879*His+1.2148*Glu-0.25642*Cit-3.8584*Ile+2.3879*Leu' | 0.632 |
| 56 | 'Pro-3.3156*His+1.2035*Glu-3.9327*Ile+2.4346*Leu-0.1291*a-ABA' | 0.6278 |
| 57 | 'Pro-3.3189*His+1.2151*Glu-0.0024486*Ala-3.9116*Ile+2.4143*Leu' | 0.6302 |
| 58 | 'Pro-2.3058*His+1.2435*Glu+0.9758*Lys-0.56699*Thr-2.1884*Ile' | 0.6441 |
| 59 | 'Pro-3.1383*His+0.82026*Orn-1.9556*Met-3.9912*Ile+2.7616*Leu' | 0.6355 |
| 60 | 'Pro+1.6513*Glu+0.94037*Lys-0.16005*Gly-1.8258*Val+1.2584*Leu' | 0.6137 |
| 61 | 'Pro-3.1569*His+0.089847*Ala-1.5011*Val+2.5857*Leu' | 0.578 |
| 62 | 'Pro-3.0624*His-0.50389*Ser-3.8613*Ile+2.5281*Leu' | 0.6137 |
| 63 | 'Pro-2.7877*His-0.12015*Gly-1.363*Val+2.2744*Leu' | 0.5752 |
| 64 | 'Pro-2.076*His+1.1763*Lys+0.039055*Ala-0.82565*Ser-0.96814*Val' | 0.6183 |
| 65 | 'Pro+1.1434*Lys-0.21084*Gly-1.5598*Val-0.84395*Arg+1.0606*Leu' | 0.5948 |
| 66 | 'Pro-2.7834*His+0.071667*Ala-1.3578*Val-2.5324*Met+2.6626*Leu' | 0.589 |
| 67 | 'Pro-2.5057*His-0.096775*Gly-1.254*Val-2.3938*Met+2.407*Leu' | 0.5911 |

FIG.116

| NO. | FORMULA | CORRELATION COEFFICIENT |
|---|---|---|
| 68 | 'Pro+1.6162*Glu+1.0829*Lys-0.16845*Gly-1.2464*Val-2.5904*Cit' | 0.6158 |
| 69 | 'Pro-3.2108*His+0.98961*Orn-1.3605*Cit-4.1393*Ile+2.614*Leu' | 0.6276 |
| 70 | 'Pro-3.1505*His-0.17011*Gly-3.8504*Ile+2.4098*Leu' | 0.6177 |
| 71 | 'Pro+1.3282*Lys-0.25074*Gly-0.97588*Val-3.082*Met-0.62337*Arg' | 0.6116 |
| 72 | 'Pro+1.3432*Orn+1.0396*Lys-0.27548*Gly-1.2623*Val-3.9108*Cit' | 0.6157 |
| 73 | 'Pro-2.4792*His+1.2057*Glu+1.0008*Lys-0.64581*Ser-2.3215*Ile' | 0.6507 |
| 74 | 'Pro-2.7917*His+1.562*Glu+0.90012*Lys-2.2052*Ile' | 0.6481 |
| 75 | 'Pro-2.2822*His+1.0847*Lys+0.050973*Ala-0.2783*Gly-1.0099*Val' | 0.6272 |
| 76 | 'Pro-3.3759*His+0.092681*Ala+0.69109*Tau-1.5899*Val+2.7137*Leu' | 0.5844 |
| 77 | 'Pro+0.7679*Orn+1.2624*Lys-0.28079*Gly-1.2788*Val-0.86757*Arg' | 0.607 |
| 78 | 'Pro-2.6244*His+1.2635*Glu+0.92158*Lys-0.21559*Gly-2.4013*Ile' | 0.6554 |
| 79 | 'Pro-2.9481*His-0.16667*Gly-1.3562*Val-1.6022*Cys2+2.349*Leu' | 0.5913 |
| 80 | 'Pro-3.3196*His-0.22022*Gly-3.8584*Ile-1.7394*Cys2+2.505*Leu' | 0.6264 |
| 81 | 'Pro-3.0173*His+1.8652*Glu+0.93099*Lys-2.1168*Ile-2.0389*Cys2' | 0.6564 |
| 82 | 'Pro-3.3532*His+0.81412*Orn-4.4102*Ile+2.7987*Leu-0.5453*a-ABA' | 0.6227 |
| 83 | 'Pro-3.0833*His-1.7743*Met-3.5075*Ile+2.5713*Leu' | 0.6118 |
| 84 | 'Pro-2.177*His+1.0485*Lys-0.26852*Gly-0.96546*Val+0.089295*a-ABA' | 0.6154 |
| 85 | 'Pro+1.0934*Glu+1.1984*Lys-0.22675*Gly-1.0953*Val-3.2459*Met' | 0.6218 |
| 86 | 'Pro-3.4914*His+0.84931*Orn+0.024899*Ala-4.4298*Ile+2.7818*Leu' | 0.63 |
| 87 | 'Pro-3.4455*His+0.80729*Orn+0.12006*Tau-4.3596*Ile+2.7447*Leu' | 0.6298 |
| 88 | 'Pro-3.4484*His+0.83533*Orn-4.408*Ile+0.060161*Arg+2.7639*Leu' | 0.63 |
| 89 | 'Pro-3.3242*His-0.2449*Gly+0.68919*Tau-3.973*Ile+2.4174*Leu' | 0.6225 |
| 90 | 'Pro-3.4804*His-3.8328*Ile-1.2386*Cys2+2.6447*Leu' | 0.6158 |
| 91 | 'Pro+0.7583*Orn+1.2127*Lys-0.30444*Gly-1.0484*Val-4.3337*Met' | 0.6273 |
| 92 | 'Pro-3.0413*His-0.28327*Thr-3.6841*Ile+2.4407*Leu' | 0.6008 |
| 93 | 'Pro+1.8618*Glu+0.91365*Lys+0.0023117*Ala-1.8657*Val+1.4142*Leu' | 0.6159 |
| 94 | 'Pro-2.0552*His+0.99899*Lys-0.24194*Gly-0.59898*Thr-2.2265*Ile' | 0.624 |
| 95 | 'Pro-1.956*His+1.1776*Lys+0.031342*Ala-0.73884*Val-3.3723*Met' | 0.6307 |
| 96 | 'Pro+1.4051*Orn-0.24335*Gly-1.3766*Val-2.8649*Ile+2.991*Leu' | 0.6185 |
| 97 | 'Pro-3.2122*His-0.52752*Ser-3.8644*Ile-1.2809*Cys2+2.6273*Leu' | 0.6268 |
| 98 | 'Pro-3.3659*His+0.10004*Ala-1.5144*Val-1.4165*Cys2+2.7158*Leu' | 0.6022 |
| 99 | 'Pro+1.7757*Glu+1.0243*Lys-0.072271*Ala-1.1245*Val-3.0371*Cit' | 0.594 |
| 100 | 'Pro-2.9653*His+0.082676*Ala-0.35699*Ser-1.4722*Val+2.5205*Leu' | 0.5795 |

FIG.118

| NO. | FORMULA | CORRELATION COEFFICIENT |
|---|---|---|
| 1 | (Pro)/(Gln)+(Tyr+Leu+Cys2)/(Val) | 0.619 |
| 2 | (Pro)/(Gln)+(Tyr+Leu)/(Val+Tau) | 0.6077 |
| 3 | (Pro)/(Tau+Gln)+(Leu+Cys2)/(Val) | 0.5945 |
| 4 | (Pro)/(Gln)+(Tyr+Cys2)/(Tau+Ser) | 0.6487 |
| 5 | (Pro)/(Gln)+(Tyr+Cys2)/(Tau+Thr) | 0.6019 |
| 6 | (Pro)/(Gln)+(Leu+Cys2)/(Val+Tau) | 0.6042 |
| 7 | (Tyr)/(Trp+Tau+ABA)+(Cys2)/(Ser) | 0.6509 |
| 8 | (Tyr)/(Trp)+(Leu+Cys2)/(Tau+Ser) | 0.6451 |
| 9 | (Pro)/(Trp+Gln)+(Leu+Cys2)/(Val) | 0.5777 |
| 10 | (Pro)/(Tau+Gln)+(Tyr+Leu)/(Val) | 0.5974 |
| 11 | (Tyr+Leu)/(Val)+(Pro+Cys2)/(Gln) | 0.5997 |
| 12 | (Pro)/(Gln)+(Tyr+Cys2)/(Trp+Tau) | 0.6016 |
| 13 | (Pro)/(Tau+Ala)+(Leu+Cys2)/(Val) | 0.6777 |
| 14 | (Tyr)/(Trp+Tau)+(Cys2)/(ABA+Ser) | 0.5993 |
| 15 | (Leu)/(Tau+Thr)+(Tyr+Pro)/(Val) | 0.5787 |
| 16 | (Pro)/(Ala+Thr)+(Leu+Cys2)/(Val) | 0.6525 |
| 17 | (Tyr+Cys2)/(Trp)+(Pro+Leu)/(Val) | 0.64 |
| 18 | (Pro)/(Gln)+(Tyr+Leu)/(Trp+Val) | 0.6367 |
| 19 | (Pro)/(Gln)+(Tyr+Leu+Ile)/(Val) | 0.5871 |
| 20 | (Pro)/(Gln+Thr)+(Leu+Cys2)/(Val) | 0.5842 |
| 21 | (Pro)/(Trp+Gln)+(Tyr+Leu)/(Val) | 0.599 |
| 22 | (Tyr+Leu+Cys2)/(Val+Tau+Thr) | 0.6264 |
| 23 | (Pro)/(Gln+Ser)+(Leu+Cys2)/(Val) | 0.5748 |
| 24 | (Pro)/(Gln)+(Leu+Cys2+Cit)/(Val) | 0.5913 |
| 25 | (Tyr)/(Trp)+(Pro+Leu+Cys2)/(Val) | 0.6338 |
| 26 | (Tyr)/(Trp+Tau)+(Cys2)/(Ser) | 0.6042 |
| 27 | (Pro)/(His+Gln)+(Leu+Cys2)/(Val) | 0.5652 |
| 28 | (Pro)/(Gln)+(Leu+Ile+Cys2)/(Val) | 0.5871 |
| 29 | (Tyr+Pro+Leu)/(Val+Tau+Thr) | 0.6026 |
| 30 | (Tyr)/(Tau+Thr)+(Pro+Leu)/(Val) | 0.588 |
| 31 | (Leu)/(Tau+Ser)+(Tyr+Cys2)/(Trp) | 0.6509 |
| 32 | (Tyr)/(Tau+Thr)+(Leu+Cys2)/(Val) | 0.619 |
| 33 | (Pro)/(Gln+Thr)+(Tyr+Leu)/(Val) | 0.5864 |
| 34 | (Tyr)/(Tau+Ser)+(Cys2)/(Trp+Thr) | 0.6309 |
| 35 | (Leu)/(Gln)+(Tyr+Cys2)/(Tau+Ser) | 0.6242 |
| 36 | (Tyr+Pro)/(Gln)+(Leu+Cys2)/(Val) | 0.6177 |
| 37 | (Tyr)/(Trp)+(Pro+Phe+Leu)/(Val) | 0.6032 |
| 38 | (Pro)/(Trp+Ala)+(Leu+Cys2)/(Val) | 0.6393 |
| 39 | (Pro)/(Tau+Ala)+(Tyr+Leu)/(Val) | 0.6232 |
| 40 | (Pro)/(Gln+Ala)+(Leu+Cys2)/(Val) | 0.5758 |
| 41 | (Pro)/(Ala+Ser)+(Leu+Cys2)/(Val) | 0.6483 |
| 42 | (Pro)/(Ala)+(Tyr+Leu+Cys2)/(Val) | 0.6387 |
| 43 | (Pro)/(Gln+Ser)+(Tyr+Leu)/(Val) | 0.5732 |
| 44 | (Pro)/(Met+Gln)+(Leu+Cys2)/(Val) | 0.5658 |
| 45 | (Tyr)/(Trp+Tau)+(Cys2)/(ABA+Thr) | 0.5942 |
| 46 | (Tyr)/(Trp)+(Pro+Leu+Ile)/(Val) | 0.6261 |
| 47 | (Pro)/(Gln)+(Leu+Cys2)/(Val) | 0.5761 |
| 48 | (Pro)/(Gln+ABA)+(Leu+Cys2)/(Val) | 0.5684 |
| 49 | (Tyr)/(Trp)+(Pro+Leu)/(Val+Tau) | 0.58 |
| 50 | (Pro)/(Ala+Thr)+(Tyr+Leu)/(Val) | 0.6242 |

FIG.119

| NO. | FORMULA | CORRELATION COEFFICIENT |
|---|---|---|
| 51 | (Pro)/(Asn+Gln)+(Leu+Cys2)/(Val) | 0.5674 |
| 52 | (Leu)/(Trp+ABA)+(Tyr+Pro)/(Val) | 0.619 |
| 53 | (Pro+Cit)/(Gln)+(Leu+Cys2)/(Val) | 0.6122 |
| 54 | (Pro)/(Gln+ABA)+(Tyr+Leu)/(Val) | 0.5793 |
| 55 | (Leu)/(Val)+(Pro+Cys2)/(Tau+Gln) | 0.5674 |
| 56 | (Leu)/(Val)+(Tyr+Cys2)/(Tau+Thr) | 0.6138 |
| 57 | (Tyr)/(Trp)+(Pro+Leu)/(Val+ABA) | 0.6064 |
| 58 | (Pro)/(Gln)+(Tyr+Leu)/(Val) | 0.5871 |
| 59 | (Pro)/(Met+Gln)+(Tyr+Leu)/(Val) | 0.5871 |
| 60 | (Pro)/(His+Gln)+(Tyr+Leu)/(Val) | 0.5716 |
| 61 | (Tyr+Leu)/(Trp+Val+Tau+Thr) | 0.6061 |
| 62 | (Pro)/(Gln)+(Tyr+Leu)/(Val+ABA) | 0.6084 |
| 63 | (Tyr+Leu)/(Val)+(Pro+Phe)/(Gln) | 0.6096 |
| 64 | (Tyr)/(Trp)+(Leu)/(Tau+ABA+Ser) | 0.6316 |
| 65 | (Leu)/(Val)+(Tyr+Cys2)/(Tau+Ser) | 0.6042 |
| 66 | (Pro)/(Gln+Gly)+(Tyr+Leu)/(Val) | 0.5539 |
| 67 | (Pro)/(His+Ala)+(Leu+Cys2)/(Val) | 0.6277 |
| 68 | (Pro)/(Arg+Gln)+(Leu+Cys2)/(Val) | 0.5658 |
| 69 | (Tyr)/(Trp+Tau)+(Pro+Leu)/(Val) | 0.6158 |
| 70 | (Tyr)/(Ala)+(Pro+Leu)/(Val+Thr) | 0.6464 |
| 71 | (Pro)/(Gln+Gly)+(Leu+Cys2)/(Val) | 0.5445 |
| 72 | (Pro)/(Arg+Ala)+(Leu+Cys2)/(Val) | 0.6058 |
| 73 | (Tyr+Pro+Leu+Cys2)/(Val+Thr) | 0.598 |
| 74 | (Pro)/(Gln)+(Tyr+Phe)/(Tau+Thr) | 0.6174 |
| 75 | (Pro)/(Ala)+(Tyr+Cys2)/(Tau+Thr) | 0.6551 |
| 76 | (Tyr+Leu)/(Val)+(Pro+Cit)/(Gln) | 0.5974 |
| 77 | (Pro)/(Ala+Ser)+(Tyr+Leu)/(Val) | 0.609 |
| 78 | (Phe)/(Gln)+(Tyr+Cys2)/(Tau+Ser) | 0.6019 |
| 79 | (Pro)/(Trp+Ala)+(Tyr+Leu)/(Val) | 0.619 |
| 80 | (Tyr)/(Trp+Tau+Thr)+(Cys2)/(Val) | 0.6516 |
| 81 | (Pro)/(Asn+Gln)+(Tyr+Leu)/(Val) | 0.5652 |
| 82 | (Pro+Phe)/(Gln)+(Leu+Cys2)/(Val) | 0.5987 |
| 83 | (Pro+Orn)/(Gln)+(Leu+Cys2)/(Val) | 0.6358 |
| 84 | (Tyr)/(Trp)+(Pro+Leu)/(Val) | 0.6138 |
| 85 | (Leu)/(Ala)+(Tyr+Pro)/(Val+Thr) | 0.6532 |
| 86 | (Pro)/(Arg+Gln)+(Tyr+Leu)/(Val) | 0.5664 |
| 87 | (Pro)/(Gln)+(Tyr+Leu+Cit)/(Val) | 0.5777 |
| 88 | (Leu)/(Val)+(Tyr+Pro)/(Tau+Gln) | 0.6113 |
| 89 | (Pro)/(Ala)+(Tyr+Leu)/(Val+Tau) | 0.6351 |
| 90 | (Tyr+Leu)/(Val)+(Pro+Ile)/(Gln) | 0.6026 |
| 91 | (Tyr)/(Tau+Ser)+(Leu)/(Val+Thr) | 0.6038 |
| 92 | (Tyr)/(Trp+ABA)+(Pro+Leu)/(Val) | 0.5997 |
| 93 | (Leu)/(Trp+Thr)+(Tyr+Pro)/(Val) | 0.5748 |
| 94 | (Tyr+Pro+Phe+Leu)/(Val+Thr) | 0.5877 |
| 95 | (Tyr)/(Tau+Ser)+(Leu+Cys2)/(Val) | 0.5784 |
| 96 | (Tyr)/(Trp)+(Leu)/(Tau+Ser) | 0.6042 |
| 97 | (Leu)/(Met+Trp)+(Tyr+Pro)/(Val) | 0.6074 |
| 98 | (Pro)/(Ala)+(Tyr+Cys2)/(Trp+Tau) | 0.6242 |
| 99 | (Tyr)/(Trp+Tau+ABA)+(Leu)/(Val) | 0.5929 |
| 100 | (Tyr)/(Trp)+(Phe+Leu)/(Tau+Ser) | 0.6219 |

FIG.121

| NO. | FORMULA | CORRELATION COEFFICIENT |
|---|---|---|
| 1 | 'Gln/Pro-7.0703*Met/Thr-8.6143*Leu/Val' | -0.5884 |
| 2 | 'Tyr/Trp-0.013725*Ser-0.090704*Ala/Asn' | 0.6812 |
| 3 | 'Pro/Ala-0.059011*Val/Met+0.34394*Trp/Thr' | 0.5439 |
| 4 | 'Ser/Tyr-9.9049*Asn/Ala+0.0038308*Val' | -0.7412 |
| 5 | 'Ser/Tyr-11.7394*Asn/Ala+0.004736*Val' | -0.7328 |
| 6 | 'Ser/Tyr-11.1586*Asn/Ala+0.0042126*Val' | -0.7283 |
| 7 | 'Tyr/Trp-0.014255*Ser+9.7504*Asn/Ala' | 0.697 |
| 8 | 'Tyr/Trp-0.080419*Ala/Phe-0.001235*Lys' | 0.6222 |
| 9 | 'Tyr/Trp-0.013966*Ser+9.6207*Asn/Ala' | 0.6938 |
| 10 | 'Ser/Tyr+0.228*Val/Asn+0.0042374*Thr' | -0.6277 |
| 11 | 'Thr/Pro-9.0976*Asn/Ala+0.0094995*Ser' | -0.6561 |
| 12 | 'Ser/Tyr+0.10299*Ala/Asn+0.0037247*Val' | -0.7096 |
| 13 | 'Thr/Tyr+0.026576*Ser+0.16501*Ala/Asn' | -0.648 |
| 14 | 'Pro/Ala+1.6406*Leu/Val-0.0037776*Ser' | 0.658 |
| 15 | 'Ser/Tyr-10.3073*Asn/Ala+0.0038924*Val' | -0.738 |
| 16 | 'Pro/Ala-0.13759*Val/Phe-0.093894*Thr/Asn' | 0.6306 |
| 17 | 'Pro/Ala-0.43293*Val/Leu-0.0028612*Ser' | 0.6886 |
| 18 | 'Tyr/Trp-0.014569*Ser+10.0113*Asn/Ala' | 0.6857 |
| 19 | 'Pro/Ala-0.0064015*Ser-0.03712*Gln/Asn' | 0.6938 |
| 20 | 'Ser/Tyr-6.7684*Asn/Val+0.0046251*Thr' | -0.6138 |
| 21 | 'Ser/Tyr-6.9053*Asn/Val+0.0047637*Thr' | -0.6138 |
| 22 | 'Pro/Ala-0.059484*Val/Met-0.1297*Thr/Trp' | 0.5429 |
| 23 | 'Pro/Ala-0.14161*Thr/Phe-0.2809*Tau/Tyr' | 0.6741 |
| 24 | 'Ser/Tyr+0.11532*Ala/Asn+0.0050596*Val' | -0.6993 |
| 25 | 'Ser/Tyr+0.0051381*Val-9.8348*Asn/Ala' | -0.7057 |
| 26 | 'Pro/Ala-0.4243*Val/Leu-0.0028473*Ser' | 0.6886 |
| 27 | 'Ser/Tyr-11.3974*Asn/Ala+0.0043599*Val' | -0.7354 |
| 28 | 'Gln/Pro+0.51396*Val/Met+0.01641*Thr' | -0.6512 |
| 29 | 'Pro/Ala-0.0071712*Ser-0.031073*Gln/Asn' | 0.6796 |
| 30 | 'Ser/Tyr-10.9411*Asn/Ala+0.0041527*Val' | -0.7363 |
| 31 | 'Ser/Tyr-11.6109*Asn/Ala+0.0047336*Val' | -0.7328 |
| 32 | 'Tyr/Trp+8.3861*Asn/Ala-0.0097465*Ser' | 0.6851 |
| 33 | 'Ser/Tyr-6.7233*Asn/Val+0.0063313*Thr' | -0.6187 |
| 34 | 'Pro/Ala-0.39785*Val/Leu-0.0027516*Ser' | 0.6832 |
| 35 | 'Pro/Ala-0.30125*Trp/Phe-0.0013453*Thr' | 0.6067 |
| 36 | 'Ser/Tyr-6.7021*Asn/Val+0.0048073*Thr' | -0.6145 |
| 37 | 'Gln/Pro-1.7202*Phe/Tau+0.035456*Ser' | -0.5916 |
| 38 | 'Thr/Tyr-1.2499*Cys2/Tau+0.010622*Ser' | -0.5997 |
| 39 | 'Gln/Pro+2.6452*Tau/Phe+0.29087*Thr/Cys2' | -0.6661 |
| 40 | 'Pro/Ala-0.0077429*Ser-0.034553*Gln/Met' | 0.6709 |
| 41 | 'Ser/Tyr+0.087584*Ala/Asn+0.0031913*Val' | -0.7122 |
| 42 | 'Ser/Tyr-11.1635*Asn/Ala+0.0043656*Val' | -0.7322 |
| 43 | 'Ser/Tyr-10.2001*Asn/Ala+0.0038034*Val' | -0.738 |
| 44 | 'Pro/Ala+0.85494*Cys2/Tau-0.26698*Ser/Tyr' | 0.6045 |
| 45 | 'Thr/Pro+0.002836*Lys+0.03476*Ala/Asn' | -0.443 |
| 46 | 'Ser/Tyr-10.3319*Asn/Ala+0.003816*Val' | -0.738 |
| 47 | 'Ser/Tyr-10.5193*Asn/Ala+0.0038989*Val' | -0.7363 |
| 48 | 'Thr/Pro-9.0976*Asn/Ala+0.0094995*Ser' | -0.6561 |
| 49 | 'Ser/Tyr+0.094573*Ala/Asn+0.0038697*Val' | -0.7118 |
| 50 | 'Tyr/Trp-0.26993*Thr/Met-0.0077251*Ser' | 0.6032 |

FIG.122

| NO. | FORMULA | CORRELATION COEFFICIENT |
|---|---|---|
| 51 | Tyr/Trp-0.012943*Ser-0.080336*Ala/Asn' | 0.706 |
| 52 | 'Ser/Tyr-10.9589*Asn/Ala+0.0044993*Val' | -0.7202 |
| 53 | 'Pro/Ala-0.38031*Val/Leu-0.097958*Thr/Trp' | 0.6 |
| 54 | 'Ser/Tyr-11.2773*Asn/Ala+0.004654*Val' | -0.7241 |
| 55 | 'Pro/Ala-0.27081*Tau/Phe+0.56173*Cys2/Trp' | 0.5748 |
| 56 | 'Gln/Pro+0.021991*Thr+0.20188*Ala/Asn' | -0.6267 |
| 57 | 'Pro/Ala-0.0080941*Ser-0.035852*Gln/Met' | 0.6683 |
| 58 | 'Pro/Ala+1.4572*Leu/Val-0.00283*Ser' | 0.6761 |
| 59 | 'Ser/Tyr-10.0927*Asn/Ala+0.0039612*Val' | -0.7363 |
| 60 | 'Gln/Pro-12.0555*Met/Thr-4.2568*His/Lys' | -0.5565 |
| 61 | 'Ser/Tyr+0.11097*Ala/Asn+0.0051902*Val' | -0.6993 |
| 62 | 'Pro/Ala-0.15073*Thr/Phe+0.14313*Tyr/Tau' | 0.648 |
| 63 | 'Tyr/Trp-0.079034*Ala/Asn-0.0089429*Ser' | 0.6735 |
| 64 | 'Thr/Tyr+0.026655*Ser-18.9392*Asn/Ala' | -0.6828 |
| 65 | 'Pro/Ala-0.43293*Val/Leu-0.0028612*Ser' | 0.6886 |
| 66 | 'Pro/Ala+0.32891*Phe/Trp-0.30058*Val/Leu' | 0.6657 |
| 67 | 'Ser/Tyr-10.7976*Asn/Ala+0.0045841*Val' | -0.717 |
| 68 | 'Tyr/Trp-0.77592*Tau/Phe+1.2994*Orn/Ala' | 0.5242 |
| 69 | 'Gln/Pro-7.1559*Met/Thr+2.3002*Val/Leu' | -0.5916 |
| 70 | 'Pro/Ala-0.0094707*Ser+18.3787*Met/Gln' | 0.6938 |
| 71 | 'Ser/Tyr-10.8614*Asn/Ala+0.0074144*Thr' | -0.6777 |
| 72 | 'Thr/Pro-8.0884*Asn/Ala+0.008874*Ser' | -0.657 |
| 73 | 'Pro/Ala+1.5551*Leu/Val-0.0027824*Ser' | 0.6886 |
| 74 | 'Tyr/Trp-0.014511*Ser+10.3799*Asn/Ala' | 0.6857 |
| 75 | 'Gln/Pro+0.017651*Thr-19.4927*Asn/Ala' | -0.638 |
| 76 | 'Pro/Ala+0.17958*Phe/Tau+0.58619*Cys2/Trp' | 0.5616 |
| 77 | 'Pro/Ala+1.0442*Leu/Val-0.0021747*Ser' | 0.6754 |
| 78 | 'Ser/Tyr-11.9*Asn/Ala+0.0040837*Val' | -0.7418 |
| 79 | 'Ser/Tyr-11.6691*Asn/Ala+0.0047672*Val' | -0.7328 |
| 80 | 'Ser/Tyr-10.0236*Asn/Ala+0.0037714*Val' | -0.7412 |
| 81 | 'Tyr/Trp+4.7003*Phe/Ala-0.0083525*Ser' | 0.6854 |
| 82 | 'Gln/Pro-3.857*Cys2/Tau+0.25689*Ala/Phe' | -0.5664 |
| 83 | 'Tyr/Trp-0.91993*Val/Leu-0.007775*Ser' | 0.667 |
| 84 | 'Thr/Pro-9.4602*Asn/Ala+0.010498*Ser' | -0.6735 |
| 85 | 'Thr/Tyr+0.22765*Tau/Cys2+0.010137*Ser' | -0.6261 |
| 86 | 'Ser/Tyr+0.11095*Ala/Asn+0.0048522*Val' | -0.7002 |
| 87 | 'Ser/Tyr+0.11042*Ala/Asn+0.0046532*Val' | -0.7057 |
| 88 | 'Ser/Tyr-10.0284*Asn/Ala+0.0041425*Val' | -0.7363 |
| 89 | 'Gln/Pro+0.024943*Thr+0.40053*Val/Met' | -0.7015 |
| 90 | 'Ser/Tyr-9.5502*Asn/Ala+0.0034035*Val' | -0.7596 |
| 91 | 'Tyr/Trp-0.0019761*Lys-0.17839*Gly/Leu' | 0.6267 |
| 92 | 'Ser/Tyr-9.9824*Asn/Ala+0.0041024*Val' | -0.7363 |
| 93 | 'Ser/Tyr+0.10715*Ala/Asn+0.0043534*Val' | -0.7077 |
| 94 | 'Gln/Pro-35.5567*Cys2/Ala+3.5682*Tau/Leu' | -0.6096 |
| 95 | 'Gln/Pro+0.40117*Ala/Asn+0.050923*Ser' | -0.717 |
| 96 | 'Ser/Tyr-11.9213*Asn/Ala+0.0040921*Val' | -0.7418 |
| 97 | 'Ser/Tyr-10.176*Asn/Ala+0.0040405*Val' | -0.7363 |
| 98 | 'Tyr/Trp-0.01356*Ser-0.089738*Ala/Asn' | 0.6861 |
| 99 | 'Pro/Ala-0.13344*Val/Phe-0.096045*Thr/Asn' | 0.6322 |
| 100 | 'Tyr/Trp-0.016207*Ser+15.2616*Asn/Ala' | 0.6815 |

FIG.124

| NO. | FORMULA | CORRELATION COEFFICIENT |
|---|---|---|
| 1 | 'Gln+3.8752*Ser-1.1059*Pro-5.227*Tyr-8.4117*Cys2+5.0966*Tau' | -0.7296 |
| 2 | 'Pro-0.30534*Ala-0.53504*Gly-2.3558*Trp-1.7847*Val+2.7569*Leu' | 0.7276 |
| 3 | 'Pro-0.34395*Ala-0.48331*Gly-1.852*Val+2.2057*Leu' | 0.6899 |
| 4 | 'Pro+2.6647*Tyr-0.92643*Gly-6.5594*Trp-2.8013*Val+4.2079*Leu' | 0.7086 |
| 5 | 'Gln+4.7231*Ser-5.6344*Tyr-7.5839*Cys2+5.3209*Tau-1.8438*Leu' | -0.7347 |
| 6 | 'Gln+6.6415*Ser-9.5843*Tyr+10.3625*Trp+5.6646*Tau-4.3529*Leu' | -0.7354 |
| 7 | 'Gln-5.4058*Pro+1.5946*Ala+2.6145*Gly+9.4264*Val-12.0094*Leu' | -0.7077 |
| 8 | 'Gln-2.1608*Pro+2.9887*Val-9.4181*Cys2+3.0938*Tau-4.7725*Leu' | -0.7247 |
| 9 | 'Pro-0.34029*Ala-0.43245*Gly-1.8871*Val+1.8048*Cys2+2.1879*Leu' | 0.6928 |
| 10 | 'Gln-3.5479*Pro+2.2609*Gly+11.1279*Trp+6.5939*Val-11.3222*Leu' | -0.7031 |
| 11 | 'Pro-0.36329*Ala-0.47149*Gly-1.8767*Val-1.2439*His+2.5238*Leu' | 0.7035 |
| 12 | 'Gln+4.8622*Ser-7.7461*Tyr-8.5786*Cys2+5.5562*Tau' | -0.7315 |
| 13 | 'Thr-2.3264*Pro+0.73865*Ala+1.1334*Gly+4.1802*Val-5.2171*Leu' | -0.7325 |
| 14 | 'Gln+3.8914*Ser-5.1059*Tyr-6.7246*Cys2+4.7548*Tau-2.3654*Ile' | -0.7241 |
| 15 | 'Gln+6.5195*Ser-8.9064*Tyr-0.99652*Gly-10.1468*Cys2+6.4634*Tau' | -0.7434 |
| 16 | 'Ser-0.80854*Pro+0.30691*Ala+1.3161*Val-1.8498*Leu' | -0.7051 |
| 17 | 'Pro-1.5607*a-ABA-0.3435*Ala-0.49563*Gly-1.8466*Val+2.2204*Leu' | 0.6993 |
| 18 | 'Gln+3.0713*Ser-1.3394*Pro-7.1722*Cys2+3.6883*Tau-2.1891*Leu' | -0.6928 |
| 19 | 'Gln-3.9361*Pro+1.1414*Ala+6.3381*Val-11.4464*Cys2-8.1256*Leu' | -0.7173 |
| 20 | 'Pro-0.35738*Ala-0.46603*Gly-1.7391*Val-1.3848*Cit+2.1348*Leu' | 0.6967 |
| 21 | 'Pro-0.67114*Gly-3.4864*Trp-2.096*Val+3.3208*Leu' | 0.6693 |
| 22 | 'Gln-1.3004*Pro+2.1799*Val-6.3093*Cys2+2.3601*Tau-6.2448*Ile' | -0.6989 |
| 23 | 'Pro+0.57293*Tyr-0.35993*Ala-0.52169*Gly-2.0164*Val+2.2364*Leu' | 0.7012 |
| 24 | 'Ser-0.73471*Pro+0.27194*Ala+1.0355*Val+0.60017*Tau-1.6698*Leu' | -0.7218 |
| 25 | 'Gln+6.0322*Ser-4.7834*Pro+1.5523*Ala+7.1962*Val-11.0519*Leu' | -0.7138 |
| 26 | 'Gln-2.7676*Pro+1.3708*Gly+5.5019*Val-8.1194*Cys2-6.8107*Leu' | -0.7031 |
| 27 | 'Ser-0.90525*Pro+0.33599*Ala+1.5346*Val-1.8997*Cys2-2.0467*Leu' | -0.7183 |
| 28 | 'Ser-1.9486*Pro+0.68945*Ala+0.75156*Gly+3.5021*Val-4.4315*Leu' | -0.7083 |
| 29 | 'Pro-0.34123*Ala-0.44988*Gly-1.7534*Val-0.32911*Tau+2.1785*Leu' | 0.7196 |
| 30 | 'Ser-0.84343*Pro+0.29441*Ala+1.6494*Trp+1.3138*Val-2.2949*Leu' | -0.7363 |
| 31 | 'Pro-0.34844*Ala-0.48352*Gly-1.8292*Val-0.17524*Arg+2.2176*Leu' | 0.7096 |
| 32 | 'Gln+5.1211*Ser-9.8066*Tyr+4.1787*Trp-9.4814*Cys2+5.7386*Tau' | -0.7147 |
| 33 | 'Pro-0.3558*Ala-0.46785*Gly-1.9987*Val+0.60807*Ile+2.0857*Leu' | 0.6964 |

FIG.125

| NO. | FORMULA | CORRELATION COEFFICIENT |
|---|---|---|
| 34 | 'Gln+4.2631*Ser-6.2103*Tyr-2.4105*Phe-7.4112*Cys2+5.1262*Tau' | -0.7157 |
| 35 | 'Gln+5.2818*Ser+1.4561*Thr-9.5769*Tyr-9.9516*Cys2+6.7118*Tau' | -0.7251 |
| 36 | 'Gln+5.0738*Ser-1.0299*Pro-4.6769*Tyr+5.0655*Tau-1.9351*Leu' | -0.7083 |
| 37 | 'Ser-1.6808*Tyr+2.0023*Trp+0.43992*Val+0.65015*Tau-1.0711*Leu' | -0.698 |
| 38 | 'Ser-0.37739*Pro-1.4201*Tyr+2.7664*Trp+1.0269*Val-1.7799*Leu' | -0.6967 |
| 39 | 'Pro-0.34395*Ala-0.48331*Gly+5.3822e-006*Phe-1.852*Val+2.2057*Leu' | 0.6899 |
| 40 | 'Gln+6.1726*Ser-1.8911*Pro-7.645*Tyr+0.78448*Ala+6.1633*Tau' | -0.7141 |
| 41 | 'Gln-3.194*Pro+1.869*Gly+6.3294*Val-8.0013*Leu' | -0.6806 |
| 42 | 'Gln+5.236*Ser-1.2088*Pro-6.6914*Tyr+5.2635*Tau' | -0.6628 |
| 43 | 'Pro-0.32714*Ala-2.0776*Trp-1.6668*Val+2.3748*Cys2+2.5137*Leu' | 0.7102 |
| 44 | 'Pro-0.60849*Gly-3.4357*Trp-2.1348*Val+2.1355*Cys2+3.2843*Leu' | 0.6864 |
| 45 | 'Gln-2.7034*Pro+7.5157*Trp+4.5724*Val-9.771*Cys2-7.8494*Leu' | -0.7273 |
| 46 | 'Gln+4.6422*Ser-7.0833*Tyr-7.8536*Cys2-0.80649*Arg+5.1804*Tau' | -0.7048 |
| 47 | 'Gln+4.1677*Ser-2.4143*Pro+3.1054*Val+3.2948*Tau-6.2599*Leu' | -0.7002 |
| 48 | 'Pro-0.3595*Ala-1.7388*Val+2.2315*Cys2+2.0429*Leu' | 0.6793 |
| 49 | 'Gln-3.0897*Pro+1.0131*Ala+6.5529*Val-7.8665*Ile-4.9154*Leu' | -0.6999 |
| 50 | 'Ser-0.63549*Pro-0.64824*Tyr+0.26355*Ala+1.1965*Val-1.5164*Leu' | -0.7102 |
| 51 | 'Gln+5.3592*Ser-8.5962*Tyr+0.30113*Ala-9.1743*Cys2+5.9965*Tau' | -0.7457 |
| 52 | 'Pro-0.36703*Ala-1.6721*Val+2.0438*Leu' | 0.657 |
| 53 | 'Pro-0.33505*Ala-2.0842*Trp-1.5955*Val+2.5161*Leu' | 0.6915 |
| 54 | 'Pro+1.645*Tyr-0.35916*Ala-3.8466*Trp-1.9616*Val+2.967*Leu' | 0.7102 |
| 55 | 'Pro-0.6687*Gly-3.6317*Trp-2.1411*Val-1.356*His+3.7211*Leu' | 0.6931 |
| 56 | 'Gln+4.6102*Ser+4.3303*a-ABA-8.4151*Tyr-8.5276*Cys2+6.4387*Tau' | -0.7386 |
| 57 | 'Pro-2.2676*a-ABA-0.69005*Gly-3.5675*Trp-2.0835*Val+3.3591*Leu' | 0.689 |
| 58 | 'Gln+3.2118*Ser-2.4577*Pro+4.3482*Val-8.3779*Cys2-6.3363*Leu' | -0.6706 |
| 59 | 'Tyr-0.2204*Gly-1.8705*Trp-0.51762*Val+0.8939*Leu' | 0.6458 |
| 60 | 'Gln+5.989*Ser-6.8244*Tyr+5.4716*Tau-2.1185*Leu' | -0.6732 |
| 61 | 'Pro-0.34835*Ala-1.5519*Val+2.5968*Cys2-0.75599*Tau+2.0061*Leu' | 0.687 |
| 62 | 'Ser-0.82058*Pro+0.32404*Ala+1.2288*Val+1.3968*Cit-1.8087*Leu' | -0.6951 |
| 63 | 'Gln+5.0257*Ser-7.4118*Tyr-1.4618*His-8.3988*Cys2+5.3005*Tau' | -0.7118 |
| 64 | 'Pro-0.37888*Ala-1.5756*Val+2.6646*Cys2-2.2904*Cit+1.9351*Leu' | 0.6828 |
| 65 | 'Gln+6.3464*Ser-9.4819*Tyr+5.7705*Tau' | -0.6345 |
| 66 | 'Gln-5.0098*Pro+1.5741*Ala+7.7908*Val-10.3242*Leu' | -0.6748 |
| 67 | 'Pro-0.35661*Ala-2.1708*Trp-1.6277*Val-1.5165*His+2.9285*Leu' | 0.7057 |
| 68 | 'Thr-2.0117*Pro+1.32*Gly+6.0318*Trp+4.0619*Val-6.4891*Leu' | -0.6977 |

FIG.126

| NO. | FORMULA | CORRELATION COEFFICIENT |
|---|---|---|
| 69 | 'Ser-0.94401*Pro+0.37052*Ala+1.5641*Val+0.92033*His-2.365*Leu' | -0.7289 |
| 70 | 'Pro-0.38875*Ala-1.7057*Val-1.4393*His+2.4165*Leu' | 0.6931 |
| 71 | 'Pro-0.38367*Ala-1.4843*Val-1.8712*His-0.88423*Tau+2.4854*Leu' | 0.7099 |
| 72 | 'Gln+4.7057*Ser-7.4213*Tyr+5.8064*Trp+4.5997*Tau-4.0617*Ile' | -0.687 |
| 73 | 'Gln-1.8544*Pro+4.548*Val-6.7085*Cys2-5.2159*Ile-3.3433*Leu' | -0.6825 |
| 74 | 'Ser-1.7107*Tyr+2.7441*Trp+0.66291*Val-1.38*Leu' | -0.6757 |
| 75 | 'Gln+4.798*Ser-7.335*Tyr-0.20669*Val-8.2914*Cys2+5.5046*Tau' | -0.7293 |
| 76 | 'Gln+4.3856*Ser-1.0497*Pro-4.8543*Tyr-2.9988*Phe+4.759*Tau' | -0.6861 |
| 77 | 'Gln-2.3406*Pro+1.2513*Gly+5.7501*Val-5.1129*Ile-4.908*Leu' | -0.7025 |
| 78 | 'Gln+4.8676*Ser-7.7561*Tyr-8.5909*Cys2+5.5602*Tau+0.033682*Cit' | -0.7315 |
| 79 | 'Gln-5.1428*Pro+1.4627*Ala+10.4427*Trp+7.6294*Val-12.9627*Leu' | -0.7205 |
| 80 | 'Ser+0.27124*Thr-0.87856*Pro+0.31604*Ala+1.3975*Val-2.0154*Leu' | -0.7073 |
| 81 | 'Gln-2.0176*Pro+0.6569*Ala+3.8334*Val-6.2141*Cys2-8.6146*Ile' | -0.698 |
| 82 | 'Gln+4.7814*Ser-5.828*Tyr+4.7433*Tau-2.8663*Ile' | -0.6709 |
| 83 | 'Gln-4.1535*Pro+1.2162*Ala+5.4876*Val+3.3285*Tau-8.4126*Leu' | -0.678 |
| 84 | 'Pro-0.3785*Ala-1.7625*Val-1.2226*His+2.0673*Cys2+2.3596*Leu' | 0.6925 |
| 85 | 'Ser-0.85098*Pro+0.33632*Ala+1.577*Val-0.75728*Ile-1.7936*Leu' | -0.6948 |
| 86 | 'Gln-2.2061*Pro+0.77732*Ala+4.3109*Val-10.186*Ile' | -0.6638 |
| 87 | 'Gln+4.6454*Ser-1.333*Pro+7.9096*a-ABA-7.6077*Tyr+6.8211*Tau' | -0.6899 |
| 88 | 'Gln+4.3163*Ser-0.86602*Pro-4.6003*Tyr+4.597*Tau-2.2611*Ile' | -0.7096 |
| 89 | 'Gln+5.8176*Ser+1.8058*Thr-1.4629*Pro-8.7199*Tyr+6.6326*Tau' | -0.6886 |
| 90 | 'Gln+7.8128*Ser-7.6322*Tyr-0.98801*Gly+6.3359*Tau-2.6423*Leu' | -0.6622 |
| 91 | 'Gln-2.5382*Pro+4.6094*Val-8.9394*Cys2-5.8623*Leu' | -0.6551 |
| 92 | 'Gln+6.1188*Ser-5.9495*Tyr-0.98842*Gly+5.304*Tau-3.9207*Ile' | -0.6899 |
| 93 | 'Gln+5.322*Ser-9.4405*Tyr+7.0158*Trp-5.18*Phe+5.1278*Tau' | -0.6854 |
| 94 | 'Gln+4.3127*Ser-3.0143*Pro+8.3921*Trp+4.8036*Val-9.7032*Leu' | -0.7025 |
| 95 | 'Pro-3.1616*a-ABA-0.35325*Ala-1.3716*Val-1.0706*Tau+2.0134*Leu' | 0.6864 |
| 96 | 'Gln+6.6131*Ser-8.1747*Tyr+1.8026*Val+5.6755*Tau-4.3042*Leu' | -0.6725 |
| 97 | 'Gln-1.9781*Pro+0.63744*Ala+3.238*Val+2.1731*Tau-8.999*Ile' | -0.6767 |
| 98 | 'Gln-2.9064*Pro+1.48*Gly+5.053*Val+2.02*Tau-7.0795*Leu' | -0.6851 |
| 99 | 'Thr-2.2147*Pro+0.73478*Ala+3.7223*Val-5.0377*Cys2-4.6073*Leu' | -0.6973 |
| 100 | 'Pro-0.6623*Gly-3.5387*Trp-2.016*Val-1.1079*Cit+3.2866*Leu' | 0.6596 |

FIG.128

| ROC_AUC RANK | 0.85 | | 0.8 | | 0.75 | | 0.7 | |
|---|---|---|---|---|---|---|---|---|
| | AMINO ACID | FREQUENCY OF APPEARANCE | AMINO ACID | FREQUENCY OF APPEARANCE | AMINO ACID | FREQUENCY OF APPEARANCE | AMINO ACID | FREQUENCY OF APPEARANCE |
| 1 | His | 342 | His | 3419 | His | 7858 | His | 9109 |
| 2 | Glu | 224 | Glu | 1920 | Glu | 5012 | Glu | 9079 |
| 3 | Ile | 170 | Lys | 1554 | Ile | 4607 | Ile | 7417 |
| 4 | Lys | 162 | Ile | 1214 | Lys | 4115 | Pro | 6929 |
| 5 | Gln | 149 | Pro | 1101 | Pro | 3582 | Cit | 6925 |
| 6 | Pro | 106 | Gln | 818 | Cit | 3490 | Lus | 6846 |
| 7 | Leu | 88 | Leu | 777 | Met | 3179 | Met | 6297 |
| 8 | Tyr | 55 | Ala | 775 | Ala | 3115 | Ala | 6206 |
| 9 | ABA | 42 | Cit | 679 | Val | 2916 | Val | 5969 |
| 10 | Ala | 40 | Val | 627 | Orn | 2778 | Orn | 5789 |
| 11 | Met | 38 | Met | 615 | Leu | 2717 | Leu | 5376 |
| 12 | Cit | 37 | Tyr | 588 | Gln | 2629 | Gly | 5307 |
| 13 | Asn | 36 | Gly | 528 | Gly | 2375 | Tyr | 5274 |
| 14 | Val | 35 | Orn | 525 | Tyr | 2362 | Gln | 5116 |
| 15 | Tau | 25 | ABA | 522 | Tau | 2285 | Phe | 4902 |
| 16 | Ser | 24 | Tau | 495 | Trp | 2228 | Trp | 4887 |
| 17 | Gly | 19 | Phe | 463 | ABA | 2194 | Tau | 4870 |
| 18 | Phe | 19 | Trp | 447 | Asn | 2187 | ABA | 4849 |
| 19 | Thr | 18 | Thr | 443 | Phe | 2155 | Thr | 4806 |
| 20 | Trp | 18 | Arg | 442 | Thr | 2115 | Ser | 4794 |
| 21 | Orn | 18 | Cys | 439 | Ser | 1993 | Asn | 4767 |
| 22 | Arg | 16 | Asn | 437 | Arg | 1989 | Arg | 4756 |
| 23 | Cys | 14 | Ser | 430 | Cys | 1903 | Cys | 4751 |

LUNG CANCER EVALUATING APPARATUS, METHOD, SYSTEM, AND PROGRAM AND RECORDING MEDIUM THEREFOR

This application is a Continuation of PCT/JP2007/065179, filed Aug. 2, 2007, which claims priority to Japanese patent application JP 2006-213919 filed Aug. 4, 2006 and JP 2006-265973, filed Sep. 28, 2006. The contents of each of the aforementioned applications are incorporated herein by reference in their entirety.

BACKGROUND OF THE INVENTION

1. Field of the Invention

The present invention relates to a method of evaluating lung cancer, a lung cancer-evaluating apparatus, a lung cancer-evaluating method, a lung cancer-evaluating system, a lung cancer-evaluating program and recording medium, which utilize the concentration of amino acids in blood (plasma).

2. Description of the Related Art

The number of deaths from lung cancer in Japan in 2003 is 41634 males and 15086 females, which account for 18.3% of deaths from all cancers, and the number of deaths from lung cancer ranks first in males. The number of deaths from lung cancer ranks third in females, but is increasing year by year and is currently presumed to rank first in the near future.

At present, lung cancer is a hardly curable cancer, and more than half of cases when detected have already been advanced and are inoperable. On the other hand, the five year survival rate in early lung cancer (stage I to II) is 50% or more, and particularly the five year survival rate in lung cancer at stage IA (tumor of 3 cm or less in size with no lymph node metastasis and with no infiltration into surrounding organs) is about 90%, and early detection is important for cure of lung cancer.

Diagnosis of lung cancer includes diagnosis by imaging with X-ray picture, CT (computer tomography), MRI (magnetic resonance imaging), PET (positron emission computerized-tomography) and the like, sputum cytodiagnosis, lung biopsy with a bronchoscope, lung biopsy with a percutaneous needle, and lung biopsy by exploratory thoracotomy or with a thoracoscope.

However, diagnosis by imaging does not serve as definitive diagnosis. In chest X-ray examination (indirect roentgenography) for example, the positive-finding rate is 20% but the specificity is 0.1%, and almost all of persons with positive-finding are false-positive. The detection sensitivity is low, and some examination results according to Ministry of Health, Labour and Welfare, Japan, showed that in the case of indirect roentgenographic examination, about 80% of patients with onset of lung cancer were overlooked in chest X-ray examination. There is a concern that these methods are poor in both detection sensitivity and detection specificity, particularly in early lung cancer. In chest X-ray examination, there is also a problem of exposure of subjects to radiation. Carrying out the mass screening by CT, MRI, PET and the like, on the other hand, is problematic from the viewpoint of facilities and costs.

Patients who can be definitely diagnosed in sputum cytodiagnosis are only 20 to 30%. Lung biopsy using a bronchoscope, a percutaneous needle, exploratory thoracotomy or a thoracoscope serves as definitive diagnosis but is a highly invasive examination, and thus lung biopsy of all patients suspected of having lung cancer in diagnostic imaging is not practical. Such invasive diagnosis is accompanied by a burden such as suffering in patients, and there can also be a risk such as bleeding upon examination. For reducing a physical burden on patients and for cost-benefit performance, it is desired that subjects with high possibility of onset of lung cancer are selected by a less-invasive method and then diagnosed definitively as those with lung cancer by lung biopsy, followed by treatment.

On the other hand, the amino acid concentration in blood is known to change due to the onset of cancer. For example, Cynober ("Cynober, L. ed., Metabolic and therapeutic aspects of amino acids in clinical nutrition. 2nd ed., CRC Press.") has reported that for example, the amount of glutamine consumed mainly as an oxidation energy source, the amount of arginine consumed as a precursor of nitrogen oxide and polyamine, and the amount of methionine consumed by activation of the ability of cancer cells to incorporate methionine are increased respectively in cancer cells. Proenza ("Proenza, A. M., J. Oliver, A. Palou and P. Roca, Breast and lung cancer are associated with a decrease in blood cell amino acid content. J Nutr Biochem, 2003. 14(3): p. 133-8.") and Cascino ("Cascino, A., M. Muscaritoli, C. Cangiano, L. Conversano, A. Laviano, S. Ariemma, M. M. Meguid and F. Rossi Fanelli, Plasma amino acid imbalance in patients with lung and breast cancer. Anticancer Res, 1995. 15(2): p. 507-10.") have reported that the amino acid composition in plasma in lung cancer patients is different from that of healthy individuals. Rodriguez ("Rodriguez, P. C., C. P. Hernandez, D. Quiceno, S. M. Dubinett, J. Zabaleta, J. B. Ochoa, J. Gilbert and A. C. Ochoa, Arginase I in myeloid suppressor cells is induced by COX-2 in lung carcinoma. J Exp Med, 2005. 202(7): p. 931-9.") has reported that an increase in the gene expression and enzyme activity of arginase I is recognized in bone marrow cells contacted with cancer cells, and as a result, the concentration of arginine in plasma is reduced.

However, there is a problem that the development of techniques of diagnosing the presence or absence of onset of lung cancer with a plurality of amino acids as variables is not conducted from the viewpoint of time and cost and is not practically used.

SUMMARY OF THE INVENTION

It is an object of the present invention to at least partially solve the problems in the conventional technology. The present invention is made in view of the problem described above, and for example, an object of the present invention is to provide a method of evaluating lung cancer, a lung cancer-evaluating apparatus, a lung cancer-evaluating method, a lung cancer-evaluating system, a lung cancer-evaluating program and a recording medium, which are capable of evaluating a lung cancer state accurately by utilizing the concentration of amino acids related to a lung cancer state among amino acids in blood.

The present inventors have made extensive study for solving the problem described above, and as a result they have identified amino acid variables fluctuating with a statistically significant difference between 2 groups, which are useful in discrimination of lung cancer by the amino acid concentration in blood, and have found that a correlation equation (index) using amino acid variables correlates significantly with the progress of a morbid state of early lung cancer, and the present invention was thereby completed. The present invention encompasses the following.

To solve the problem and achieve the object described above, a method of evaluating lung cancer according to one aspect of the present invention includes a measuring step of measuring amino acid concentration data on the concentration value of amino acid in blood collected from a subject to be evaluated, and a concentration value criterion evaluating step of evaluating a lung cancer state in the subject, based on the concentration value of at least one of Orn, Lys, ABA (ABA is α-aminobutyric acid), Arg, Glu, His, Tau, Pro, Ala, Cit and Ile contained in the amino acid concentration data of the subject measured at the measuring step.

Another aspect of the present invention is the method of evaluating lung cancer, wherein the concentration value criterion evaluating step further includes a concentration value criterion discriminating step of discriminating between lung cancer and non-lung cancer in the subject, based on the concentration value of at least one of Orn, Lys, ABA, Arg, Glu, His, Tau, Pro, Ala, Cit and Ile contained in the amino acid concentration data of the subject measured at the measuring step.

Still another aspect of the present invention is the method of evaluating lung cancer, wherein the concentration value criterion evaluating step further includes a concentration value criterion discriminating step of discriminating between lung cancer with a certain disease stage and non-lung cancer in the subject, based on the concentration value of at least one of Orn, Lys, ABA, Arg, Glu, His, Tau, Pro, Ala, Cit and Ile contained in the amino acid concentration data of the subject measured at the measuring step.

Still another aspect of the present invention is the method of evaluating lung cancer, wherein the concentration value criterion evaluating step further includes a concentration value criterion discriminating step of discriminating between adenocarcinoma in lung cancer and non-lung cancer in the subject, based on the concentration value of at least one of Orn, Lys, ABA, Arg, Glu, His, Tau, Pro, Ala, Cit and Ile contained in the amino acid concentration data of the subject measured at the measuring step.

Still another aspect of the present invention is the method of evaluating lung cancer, wherein the concentration criterion evaluating step further includes a discriminant value calculating step of calculating a discriminant value that is a value of multivariate discriminant, based on both the concentration value of at least one of Orn, Lys, ABA, Arg, Glu, His, Tau, Pro, Ala, Cit and Ile contained in the amino acid concentration data of the subject measured at the measuring step and a previously established multivariate discriminant with the concentration of the amino acid as variable, and a discriminant value criterion evaluating step of evaluating the lung cancer state in the subject, based on the discriminant value calculated at the discriminant value calculating step, wherein the multivariate discriminant contains at least one of Orn, Lys, ABA, Arg, Glu, His, Tau, Pro, Ala, Cit and Ile as the variable.

Still another aspect of the present invention is the method of evaluating lung cancer, wherein the multivariate discriminant further contains age as the variable.

Still another aspect of the present invention is the method of evaluating lung cancer, wherein the discriminant value criterion evaluating step further includes a discriminant value criterion discriminating step of discriminating between lung cancer and non-lung cancer in the subject based on the discriminant value calculated at the discriminant value calculating step.

Still another aspect of the present invention is the method of evaluating lung cancer, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the method of evaluating lung cancer, wherein the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

Still another aspect of the present invention is the method of evaluating lung cancer, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating lung cancer, wherein the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

Still another aspect of the present invention is the method of evaluating lung cancer, wherein the discriminant value criterion evaluating step further includes a discriminant value criterion discriminating step of discriminating between lung cancer with a certain disease stage and non-lung cancer in the subject based on the discriminant value calculated at the discriminant value calculating step.

Still another aspect of the present invention is the method of evaluating lung cancer, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the method of evaluating lung cancer, wherein the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

Still another aspect of the present invention is the method of evaluating lung cancer, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating lung cancer, wherein the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

Still another aspect of the present invention is the method of evaluating lung cancer, wherein the discriminant value criterion evaluating step further includes a discriminant value criterion discriminating step of discriminating between adenocarcinoma in lung cancer and non-lung cancer in the subject based on the discriminant value calculated at the discriminant value calculating step.

Still another aspect of the present invention is the method of evaluating lung cancer, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the method of evaluating lung cancer, wherein the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

Still another aspect of the present invention is the method of evaluating lung cancer, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating lung cancer, wherein the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

The present invention also relates to a lung cancer-evaluating apparatus, the lung cancer-evaluating apparatus according to one aspect of the present invention includes a control unit and a memory unit to evaluate a lung cancer state in a subject to be evaluated. The control unit includes a discriminant value-calculating unit that calculates a discriminant value that is a value of multivariate discriminant, based on both the concentration value of at least one of Orn, Lys, ABA, Arg, Glu, His, Tau, Pro, Ala, Cit and Ile contained in previously obtained amino acid concentration data on the concentration value of amino acid in the subject and a multivariate discriminant with the concentration of the amino acid as variable stored in the memory unit, and a discriminant value criterion-evaluating unit that evaluates the lung cancer state in the subject, based on the discriminant value calculated by the discriminant value-calculating unit, and the multivariate discriminant contains at least one of Orn, Lys, ABA, Arg, Glu, His, Tau, Pro, Ala, Cit and Ile as the variable.

Another aspect of the present invention is the lung cancer-evaluating apparatus, wherein the multivariate discriminant further contains age as the variable.

Still another aspect of the present invention is the lung cancer-evaluating apparatus, wherein the discriminant value criterion-evaluating unit further includes a discriminant value criterion-discriminating unit that discriminates between lung cancer and non-lung cancer in the subject based on the discriminant value calculated by the discriminant value-calculating unit.

Still another aspect of the present invention is the lung cancer-evaluating apparatus, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating apparatus, wherein the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

Still another aspect of the present invention is the lung cancer-evaluating apparatus, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating apparatus, wherein the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

Still another aspect of the present invention is the lung cancer-evaluating apparatus, wherein the discriminant value criterion-evaluating unit further includes a discriminant value criterion-discriminating unit that discriminates between lung cancer with a certain disease stage and non-lung cancer in the subject based on the discriminant value calculated by the discriminant value-calculating unit.

Still another aspect of the present invention is the lung cancer-evaluating apparatus, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating apparatus, wherein the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

Still another aspect of the present invention is the lung cancer-evaluating apparatus, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating apparatus, wherein the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

Still another aspect of the present invention is the lung cancer-evaluating apparatus, wherein the discriminant value criterion-evaluating unit further includes a discriminant value criterion-discriminating unit that discriminates between adenocarcinoma in lung cancer and non-lung cancer in the subject based on the discriminant value calculated by the discriminant value-calculating unit.

Still another aspect of the present invention is the lung cancer-evaluating apparatus, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating apparatus, wherein the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

Still another aspect of the present invention is the lung cancer-evaluating apparatus, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating apparatus, wherein the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Still another aspect of the present invention is the lung cancer-evaluating apparatus, wherein the control unit further includes a multivariate discriminant-preparing unit that prepares the multivariate discriminant stored in the memory unit, based on lung cancer state information containing the amino acid concentration data and lung cancer state index data on an index for indicating the lung cancer state, stored in the memory unit. The multivariate discriminant-preparing unit further includes a candidate multivariate discriminant-preparing unit that prepares a candidate multivariate discriminant that is a candidate of the multivariate discriminant, based on a predetermined discriminant-preparing method from the lung cancer state information, a candidate multivariate discriminant-verifying unit that verifies the candidate multivariate discriminant prepared by the candidate multivariate discriminant-preparing unit, based on a predetermined verifying method, and a variable-selecting unit that selects a variable of the candidate multivariate discriminant based on a predetermined variable-selecting method from the verification result obtained by the candidate multivariate discriminant-verifying unit, thereby selecting a combination of the amino acid concentration data contained in the lung cancer state information used in preparing the candidate multivariate discriminant, and the multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the variable-selecting unit.

The present invention also relates to a lung cancer-evaluating method, one aspect of the present invention is the lung cancer-evaluating method of evaluating a lung cancer state in a subject to be evaluated which is carried out with an information processing apparatus including a control unit and a memory unit. The method includes a discriminant value calculating step of calculating a discriminant value that is a value of multivariate discriminant, based on both the concentration value of at least one of Orn, Lys, ABA, Arg, Glu, His, Tau, Pro, Ala, Cit and Ile contained in previously obtained amino acid concentration data on the concentration value of amino acid in the subject and a multivariate discriminant with the concentration of the amino acid as variable stored in the memory unit, and a discriminant value criterion evaluating step of evaluating the lung cancer state in the subject, based on the discriminant value calculated at the discriminant value calculating step, that are executed by the control unit, and the multivariate discriminant contains at least one of Orn, Lys, ABA, Arg, Glu, His, Tau, Pro, Ala, Cit and Ile as the variable.

Another aspect of the present invention is the lung cancer-evaluating method, wherein the multivariate discriminant further contains age as the variable.

Still another aspect of the present invention is the lung cancer-evaluating method, wherein the discriminant value criterion evaluating step further includes a discriminant value criterion discriminating step of discriminating between lung cancer and non-lung cancer in the subject based on the discriminant value calculated at the discriminant value calculating step.

Still another aspect of the present invention is the lung cancer-evaluating method, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating method, wherein the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

Still another aspect of the present invention is the lung cancer-evaluating method, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating method, wherein the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

Still another aspect of the present invention is the lung cancer-evaluating method, wherein the discriminant value criterion evaluating step further includes a discriminant value criterion discriminating step of discriminating between lung cancer with a certain disease stage and non-lung cancer in the subject based on the discriminant value calculated at the discriminant value calculating step.

Still another aspect of the present invention is the lung cancer-evaluating method, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating method, wherein the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

Still another aspect of the present invention is the lung cancer-evaluating method, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating method, wherein the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

Still another aspect of the present invention is the lung cancer-evaluating method, wherein the discriminant value criterion evaluating step further includes a discriminant value criterion discriminating step of discriminating between adenocarcinoma in lung cancer and non-lung cancer in the subject based on the discriminant value calculated at the discriminant value calculating step.

Still another aspect of the present invention is the lung cancer-evaluating method, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating method, wherein the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

Still another aspect of the present invention is the lung cancer-evaluating method, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating method, wherein the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Still another aspect of the present invention is the lung cancer-evaluating method, wherein the method further includes a multivariate criterion preparing step of preparing the multivariate discriminant stored in the memory unit, based on lung cancer state information containing the amino acid concentration data and lung cancer state index date on an index for indicating the lung cancer state, stored in the memory unit that is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the lung cancer state information, a candidate multivariate discriminant verifying step of verifying the candidate multivariate discriminant prepared at the candidate multivariate preparing step, based on a predetermined verifying method, and a variable selecting step of selecting variable of the candidate multivariate discriminant based on a predetermined variable-selecting method from the verification result obtained at the candidate multivariate discriminant verifying step, thereby selecting a combination of the amino acid concentration data contained in the lung cancer state information used in preparing the candidate multivariate discriminant, and at the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the variable selecting step.

The present invention also relates to a lung cancer-evaluating system, the lung cancer-evaluating system according to one aspect of the present invention includes a lung cancer-evaluating apparatus including a control unit and a memory unit to evaluate a lung cancer state in a subject to be evaluated and an information communication terminal apparatus that provides amino acid concentration data on the concentration value of amino acid in the subject connected to each other communicatively via a network. The information communication terminal apparatus includes an amino acid concentration data-sending unit that transmits the amino acid concentration data of the subject to the lung cancer-evaluating apparatus, and an evaluation result-receiving unit that receives the evaluation result of the lung cancer state of the subject transmitted from the lung cancer-evaluating apparatus. The control unit of the lung cancer-evaluating apparatus includes an amino acid concentration data-receiving unit that receives the amino acid concentration data of the subject transmitted from the information communication terminal apparatus, a discriminant value-calculating unit that calculates a discriminant value that is a value of multivariate discriminant, based on both the concentration value of at least one of Orn, Lys, ABA, Arg, Glu, His, Tau, Pro, Ala, Cit and Ile contained in the amino acid concentration data of the subject received by the amino acid concentration data-receiving unit and a multivariate discriminant with the concentration of the amino acid as variable stored in the memory unit, a discriminant value criterion-evaluating unit that evaluates the lung cancer state in the subject, based on the discriminant value calculated by the discriminant value-calculating unit, and an evaluation result-sending unit that transmits the evaluation result of the subject obtained by the discriminant value criterion-evaluating unit to the information communication terminal apparatus, and the multivariate discriminant contains at least one of Orn, Lys, ABA, Arg, Glu, His, Tau, Pro, Ala, Cit and Ile as the variable.

Another aspect of the present invention is the lung cancer-evaluating system, wherein the multivariate discriminant further contains age as the variable.

Still another aspect of the present invention is the lung cancer-evaluating system, wherein the discriminant value criterion-evaluating unit further includes a discriminant value criterion-discriminating unit that discriminates between lung cancer and non-lung cancer in the subject based on the discriminant value calculated by the discriminant value-calculating unit.

Still another aspect of the present invention is the lung cancer-evaluating system, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating system, wherein the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

Still another aspect of the present invention is the lung cancer-evaluating system, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating system, wherein the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

Still another aspect of the present invention is the lung cancer-evaluating system, wherein the discriminant value criterion-evaluating unit further includes a discriminant value criterion-discriminating unit that discriminates between lung cancer with a certain disease stage and non-lung cancer in the subject based on the discriminant value calculated by the discriminant value-calculating unit.

Still another aspect of the present invention is the lung cancer-evaluating system, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating system, wherein the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

Still another aspect of the present invention is the lung cancer-evaluating system, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating system, wherein the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gin, Glu, Ala, His, Cys and ABA as the variables.

Still another aspect of the present invention is the lung cancer-evaluating system, wherein the discriminant value criterion-evaluating unit further includes a discriminant value criterion-discriminating unit that discriminates between adenocarcinoma in lung cancer and non-lung cancer in the subject based on the discriminant value calculated by the discriminant value-calculating unit.

Still another aspect of the present invention is the lung cancer-evaluating system, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating system, wherein the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

Still another aspect of the present invention is the lung cancer-evaluating system, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating system, wherein the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Still another aspect of the present invention is the lung cancer-evaluating system, wherein the control unit of the lung cancer-evaluating apparatus further includes a multivariate discriminant-preparing unit that prepares the multivariate discriminant stored in the memory unit, based on lung cancer state information containing the amino acid concentration data and lung cancer state index data on an index for indicating the lung cancer state, stored in the memory unit. The multivariate discriminant-preparing unit further includes a candidate multivariate discriminant-preparing unit that prepares a candidate multivariate discriminant that is a candidate of the multivariate discriminant, based on a predetermined discriminant-preparing method from the lung cancer state information, a candidate multivariate discriminant-verifying unit that verifies the candidate multivariate discriminant prepared by the candidate multivariate discriminant-preparing unit, based on a predetermined verifying method, and a variable-selecting unit that selects a variable of the candidate multivariate discriminant based on a predetermined variable-selecting method from the verification result obtained by the candidate multivariate discriminant-verifying unit, thereby selecting a combination of the amino acid concentration data contained in the lung cancer state information used in preparing the candidate multivariate discriminant, and the multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the variable-selecting unit.

The present invention also relates to a lung cancer-evaluating program, one aspect of the present invention is the lung cancer-evaluating program that makes an information processing apparatus including a control unit and a memory unit execute a method of evaluating a lung cancer state in a subject to be evaluated. The method includes a discriminant value calculating step of calculating a discriminant value that is a value of multivariate discriminant, based on both the concentration value of at least one of Orn, Lys, ABA, Arg, Glu, His, Tau, Pro, Ala, Cit and Ile contained in previously obtained amino acid concentration data on the concentration value of amino acid in the subject and a multivariate discriminant with the concentration of the amino acid as variable stored in the memory unit, and a discriminant value criterion evaluating step of evaluating the lung cancer state in the subject, based on the discriminant value calculated at the discriminant value calculating step, that are executed by the control unit, and the multivariate discriminant contains at least one of Orn, Lys, ABA, Arg, Glu, His, Tau, Pro, Ala, Cit and Ile as the variable.

Another aspect of the present invention is the lung cancer-evaluating program, wherein the multivariate discriminant further contains age as the variable.

Still another aspect of the present invention is the lung cancer-evaluating program, wherein the discriminant value criterion evaluating step further includes a discriminant value criterion discriminating step of discriminating between lung cancer and non-lung cancer in the subject based on the discriminant value calculated at the discriminant value calculating step.

Still another aspect of the present invention is the lung cancer-evaluating program, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating program, wherein the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

Still another aspect of the present invention is the lung cancer-evaluating program, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating program, wherein the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

Still another aspect of the present invention is the lung cancer-evaluating program, wherein the discriminant value criterion evaluating step further includes a discriminant value criterion discriminating step of discriminating between lung cancer with a certain disease stage and non-lung cancer in the subject based on the discriminant value calculated at the discriminant value calculating step.

Still another aspect of the present invention is the lung cancer-evaluating program, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating program, wherein the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

Still another aspect of the present invention is the lung cancer-evaluating program, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating program, wherein the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

Still another aspect of the present invention is the lung cancer-evaluating program, wherein the discriminant value criterion evaluating step further includes a discriminant value criterion discriminating step of discriminating between adenocarcinoma in lung cancer and non-lung cancer in the subject based on the discriminant value calculated at the discriminant value calculating step.

Still another aspect of the present invention is the lung cancer-evaluating program, wherein the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant.

Still another aspect of the present invention is the lung cancer-evaluating program, wherein the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

Still another aspect of the present invention is the lung cancer-evaluating program, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the lung cancer-evaluating program, wherein the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Still another aspect of the present invention is the lung cancer-evaluating program, wherein the method further includes a multivariate criterion preparing step of preparing the multivariate discriminant stored in the memory unit, based on lung cancer state information containing the amino acid concentration data and lung cancer state index date on an index for indicating the lung cancer state, stored in the memory unit that is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the lung cancer state information, a candidate multivariate discriminant verifying step of verifying the candidate multivariate discriminant prepared at the candidate multivariate preparing step, based on a predetermined verifying method, and a variable selecting step of selecting variable of the candidate multivariate discriminant based on a predetermined variable-selecting method from the verification result obtained at the candidate multivariate discriminant verifying step, thereby selecting a combination of the amino acid concentration data contained in the lung cancer state information used in preparing the candidate multivariate discriminant, and at the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the variable selecting step.

The present invention also relates to a recording medium, the recording medium according to one aspect of the present invention includes the lung cancer-evaluating program described above.

According to the method of evaluating lung cancer of the present invention, amino acid concentration data on the concentration value of amino acid in blood collected from a subject to be evaluated is measured, and a lung cancer state in the subject is evaluated based on the concentration value of at least one of Orn, Lys, ABA, Arg, Glu, His, Tau, Pro, Ala, Cit and Ile contained in the measured amino acid concentration data of the subject. Thus, the concentrations of the amino acids which among amino acids in blood, are related to a lung cancer state can be utilized to bring about an effect of enabling accurate evaluation of a lung cancer state.

According to the method of evaluating lung cancer of the present invention, between lung cancer and non-lung cancer in the subject is discriminated based on the concentration value of at least one of Orn, Lys, ABA, Arg, Glu, His, Tau, Pro, Ala, Cit and Ile contained in the measured amino acid concentration data of the subject. Thus, the concentrations of the amino acids which among amino acids in blood, are useful for discriminating between the 2 groups of lung cancer and non-lung cancer can be utilized to bring about an effect of enabling accurate discrimination between the 2 groups of lung cancer and non-lung cancer.

According to the method of evaluating lung cancer of the present invention, between lung cancer with a certain disease stage and non-lung cancer in the subject is discriminated based on the concentration value of at least one of Orn, Lys, ABA, Arg, Glu, His, Tau, Pro, Ala, Cit and Ile contained in the measured amino acid concentration data of the subject. Thus, the concentrations of the amino acids which among amino acids in blood, are useful for discriminating between the 2 groups of early lung cancer and non-lung cancer can be utilized to bring about an effect of enabling accurate discrimination between the 2 groups of early lung cancer and non-lung cancer.

According to the method of evaluating lung cancer of the present invention, between adenocarcinoma in lung cancer and non-lung cancer in the subject is discriminated based on the concentration value of at least one of Orn, Lys, ABA, Arg, Glu, His, Tau, Pro, Ala, Cit and Ile contained in the measured amino acid concentration data of the subject. Thus, the concentrations of the amino acids which among amino acids in blood, are useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

According to the method of evaluating lung cancer of the present invention, a discriminant value that is a value of multivariate discriminant is calculated based on both the concentration value of at least one of Orn, Lys, ABA, Arg, Glu, His, Tau, Pro, Ala, Cit and Ile contained in the measured amino acid concentration data of the subject and a previously established multivariate discriminant with the concentration of the amino acid as variable, where the concentration value of at least one of Orn, Lys, ABA, Arg, Glu, His, Tau, Pro, Ala, Cit and Ile is contained as the variable, and the lung cancer state in the subject is evaluated based on the calculated discriminant value. Thus, a discriminant value obtained in a multivariate discriminant (multivariate discriminant correlated significantly with a lung cancer state) wherein the concentrations of amino acids which among amino acids in blood, are related to a lung cancer state are variables can be utilized to bring about an effect of enabling accurate evaluation of a lung cancer state.

According to the method of evaluating lung cancer of the present invention, the multivariate discriminant further contains age as the variable. Thus, a discriminant value obtained in a multivariate discriminant (multivariate discriminant correlated significantly with a lung cancer state) wherein not only the concentrations of amino acids which among amino acids in blood, are related to a lung cancer state but also the age of a subject are variables can be utilized to bring about an effect of enabling more accurate evaluation of a lung cancer state.

According to the method of evaluating lung cancer of the present invention, between lung cancer and non-lung cancer in the subject is discriminated based on the calculated discriminant value. Thus, a discriminant value obtained in a multivariate discriminant using amino acid variables useful for discriminating between the 2 groups of lung cancer and non-lung cancer can be utilized to bring about an effect of enabling accurate discrimination between the 2 groups of lung cancer and non-lung cancer.

According to the method of evaluating lung cancer of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of lung cancer and non-lung cancer can be utilized to bring about an effect of enabling more accurate discrimination between the 2 groups of lung cancer and non-lung cancer.

According to the method of evaluating lung cancer of the present invention, the multivariate discriminant is formula 1, 2 or 3:

$$a_1 \times \mathrm{Orn}/\mathrm{Trp} + b_1 \times (\mathrm{Tau}+\mathrm{ABA})/\mathrm{Arg} + c_1 \quad \text{(formula 1)}$$

$$a_2 \times \mathrm{Glu}/\mathrm{Tyr} + b_2 \times (\mathrm{Pro}+\mathrm{Lys})/(\mathrm{Ile}+\mathrm{His}) + c_2 \quad \text{(formula 2)}$$

$$a_3 \times \mathrm{His}/\mathrm{Lys} + b_3 \times \mathrm{Glu}/\mathrm{Ile} + c_3 \times \mathrm{Tyr}/\mathrm{Pro} + d_3 \times \mathrm{Val}/\mathrm{Leu} + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

According to the method of evaluating lung cancer of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of lung cancer and non-lung cancer can be utilized to bring about an effect of enabling more accurate discrimination between the 2 groups of lung cancer and non-lung cancer.

According to the method of evaluating lung cancer of the present invention, the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

According to the method of evaluating lung cancer of the present invention, between lung cancer with a certain disease stage and non-lung cancer in the subject is discriminated based on the calculated discriminant value. Thus, a discriminant value obtained in a multivariate discriminant using amino acid variables useful for discriminating between the 2 groups of early lung cancer and non-lung cancer can be utilized to bring about an effect of enabling accurate discrimination between the 2 groups of early lung cancer and non-lung cancer.

According to the method of evaluating lung cancer of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of early lung cancer and non-lung cancer can be utilized to bring about an effect of enabling more accurate discrimination between the 2 groups of early lung cancer and non-lung cancer.

According to the method of evaluating lung cancer of the present invention, the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the method of evaluating lung cancer of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of early lung cancer and non-lung cancer can be utilized to bring about an effect of enabling more accurate discrimination between the 2 groups of early lung cancer and non-lung cancer.

According to the method of evaluating lung cancer of the present invention, the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the method of evaluating lung cancer of the present invention, between adenocarcinoma in lung cancer and non-lung cancer in the subject is discriminated based on the calculated discriminant value. Thus, a discriminant value obtained in a multivariate discriminant using amino acid variables useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

According to the method of evaluating lung cancer of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the method of evaluating lung cancer of the present invention, the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the method of evaluating lung cancer of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the method of evaluating lung cancer of the present invention, the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating apparatus, the lung cancer-evaluating method and the lung cancer-evaluating program of the present invention, a discriminant value that is a value of multivariate discriminant is calculated based on both the concentration value of at least one of Orn, Lys, ABA, Arg, Glu, His, Tau, Pro, Ala, Cit and Ile contained in previously obtained amino acid concentration data on the concentration value of amino acid in the subject and a multivariate discriminant with the concentration of the amino acid as variable stored in the memory unit, where the concentration value of at least one of Orn, Lys, ABA, Arg, Glu, His, Tau, Pro, Ala, Cit and Ile is contained as the variable, and the lung cancer state in the subject is evaluated based on the calculated discriminant value. Thus, a discriminant value obtained in a multivariate discriminant (multivariate discriminant correlated significantly with a lung cancer state) wherein the concentrations of amino acids which among amino acids in blood, are related to a lung cancer state are variables can be utilized to bring about an effect of enabling accurate evaluation of a lung cancer state.

According to the lung cancer-evaluating apparatus, the lung cancer-evaluating method and the lung cancer-evaluating program of the present invention, the multivariate discriminant further contains age as the variable. Thus, a discriminant value obtained in a multivariate discriminant (multivariate discriminant correlated significantly with a lung cancer state) wherein not only the concentrations of amino acids which among amino acids in blood, are related to a lung cancer state but also the age of a subject are variables can be utilized to bring about an effect of enabling more accurate evaluation of a lung cancer state.

According to the lung cancer-evaluating apparatus, the lung cancer-evaluating method and the lung cancer-evaluating program of the present invention, between lung cancer and non-lung cancer in the subject is discriminated based on the calculated discriminant value. Thus, a discriminant value obtained in a multivariate discriminant using amino acid variables useful for discriminating between the 2 groups of lung cancer and non-lung cancer can be utilized to bring about an effect of enabling accurate discrimination between the 2 groups of lung cancer and non-lung cancer.

According to the lung cancer-evaluating apparatus, the lung cancer-evaluating method and the lung cancer-evaluating program of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of lung cancer and non-lung cancer can be utilized to bring about an effect of enabling more accurate discrimination between the 2 groups of lung cancer and non-lung cancer.

According to the lung cancer-evaluating apparatus, the lung cancer-evaluating method and the lung cancer-evaluating program of the present invention, the multivariate discriminant is formula 1, 2 or 3:

$$a_1\times Orn/Trp+b_1\times(Tau+ABA)/Arg+c_1 \quad \text{(formula 1)}$$

$$a_2\times Glu/Tyr+b_2\times(Pro+Lys)/(Ile+His)+c_2 \quad \text{(formula 2)}$$

$$a_3\times His/Lys+b_3\times Glu/Ile+c_3\times Tyr/Pro+d_3\times Val/Leu+e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

According to the lung cancer-evaluating apparatus, the lung cancer-evaluating method and the lung cancer-evaluating program of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of lung cancer and non-lung cancer can be utilized to bring about an effect of enabling more accurate discrimination between the 2 groups of lung cancer and non-lung cancer.

According to the lung cancer-evaluating apparatus, the lung cancer-evaluating method and the lung cancer-evaluating program of the present invention, the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

According to the lung cancer-evaluating apparatus, the lung cancer-evaluating method and the lung cancer-evaluating program of the present invention, between lung cancer with a certain disease stage and non-lung cancer in the subject is discriminated based on the calculated discriminant value. Thus, a discriminant value obtained in a multivariate discriminant using amino acid variables useful for discriminating between the 2 groups of early lung cancer and non-lung cancer can be utilized to bring about an effect of enabling accurate discrimination between the 2 groups of early lung cancer and non-lung cancer.

According to the lung cancer-evaluating apparatus, the lung cancer-evaluating method and the lung cancer-evaluating program of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of early lung cancer and non-lung cancer can be utilized to bring about an effect of enabling more accurate discrimination between the 2 groups of early lung cancer and non-lung cancer.

According to the lung cancer-evaluating apparatus, the lung cancer-evaluating method and the lung cancer-evaluating program of the present invention, the multivariate discriminant is formula 4, 5 or 6:

$$a_4\times Tau/Arg+b_4\times(Orn+ABA)/Trp+c_4 \quad \text{(formula 4)}$$

$$a_5\times Gln/(Cit+His)+b_5\times(Glu+ABA)/(Cys2)+c_5 \quad \text{(formula 5)}$$

$$a_6\times Gln/His+b_6\times Glu+c_6\times ABA/Cys+d_6\times Lys/Val+e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the lung cancer-evaluating apparatus, the lung cancer-evaluating method and the lung cancer-evaluating program of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of early lung cancer and non-lung cancer can be utilized to bring about an effect of enabling more accurate discrimination between the 2 groups of early lung cancer and non-lung cancer.

According to the lung cancer-evaluating apparatus, the lung cancer-evaluating method and the lung cancer-evaluating program of the present invention, the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the lung cancer-evaluating apparatus, the lung cancer-evaluating method and the lung cancer-evaluating program of the present invention, between adenocarcinoma in lung cancer and non-lung cancer in the subject is discriminated based on the calculated discriminant value. Thus, a discriminant value obtained in a multivariate discriminant using amino acid variables useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

According to the lung cancer-evaluating apparatus, the lung cancer-evaluating method and the lung cancer-evaluating program of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating apparatus, the lung cancer-evaluating method and the lung cancer-evaluating program of the present invention, the multivariate discriminant is formula 7, 8 or 9:

$$a_7\times Orn/Trp+b_7\times Tau/Arg+c_7 \quad \text{(formula 7)}$$

$$a_8\times(Glu+Pro)/His+b_8\times(ABA+Lys)/Ile+c_8 \quad \text{(formula 8)}$$

$$a_9\times Glu/Cit+b_9\times His/Gln+c_9\times Ile/Leu+d_9\times Tyr/Ala+e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating apparatus, the lung cancer-evaluating method and the lung cancer-evaluating program of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating apparatus, the lung cancer-evaluating method and the lung cancer-evaluating program of the present invention, the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating apparatus, the lung cancer-evaluating method and the lung cancer-evaluating program of the present invention, a multivariate discriminant stored in a memory unit is prepared based on the lung cancer state information stored in the memory unit, including amino acid concentration data and lung cancer state index data on an index for indicating a lung cancer state. Specifically, (1) a candidate multivariate discriminant that is a candidate of multivariate discriminant is prepared from the lung cancer state information, according to a predetermined discriminant-preparing method, (2) the prepared candidate multivariate discriminant is verified based on a predetermined verification method, (3) based on a predetermined variable-selecting method, variables in the candidate multivariate discriminant are selected from the verification results in (2), thereby selecting a combination of amino acid concentration data contained in the lung cancer state information used in preparing of a candidate multivariate discriminant, and (4) based on verification results accumulated by executing (1), (2) and (3) repeatedly, a candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a lung cancer state (specifically a multivariate discriminant correlating significantly with a lung cancer state (more specifically, a multivariate discriminant useful for discrimination of the 2 groups of lung cancer and non-lung cancer, a multivariate discriminant useful for discrimination of the 2 groups of early lung cancer and non-lung cancer, or a multivariate discriminant useful for discrimination of the 2 groups of adenocarcinoma in lung cancer and non-lung cancer).

According to the lung cancer-evaluating system of the present invention, the information communication terminal apparatus first transmits amino acid concentration data of a subject to be evaluated to the lung cancer-evaluating apparatus. The lung cancer-evaluating apparatus receives the amino acid concentration data of the subject transmitted from the information communication terminal apparatus, calculates a discriminant value that is the value of the multivariate discriminant based on both the concentration value of at least one of Orn, Lys, ABA, Arg, Glu, His, Tau, Pro, Ala, Cit and Ile contained in the received amino acid concentration data of the subject and the multivariate discriminant with amino acid concentration as variable stored in the memory unit, where the concentration value of at least one of Orn, Lys, ABA, Arg, Glu, His, Tau, Pro, Ala, Cit and Ile is contained as a variable, and evaluates the lung cancer state in the subject based on the calculated discriminant value, and transmits the evaluation result of the subject to the information communication terminal apparatus. Then, the information communication terminal apparatus receives the evaluation result of the subject concerning the lung cancer state transmitted from the lung cancer-evaluating apparatus. Thus, a discriminant value obtained in a multivariate discriminant (multivariate discriminant correlated significantly with a lung cancer state) wherein the concentrations of amino acids which among amino acids in blood, are related to a lung cancer state are variables can be utilized to bring about an effect of enabling accurate evaluation of a lung cancer state.

According to the lung cancer-evaluating system of the present invention, the multivariate discriminant further contains age as the variable. Thus, a discriminant value obtained in a multivariate discriminant (multivariate discriminant correlated significantly with a lung cancer state) wherein not only the concentrations of amino acids which among amino acids in blood, are related to a lung cancer state but also the age of a subject are variables can be utilized to bring about an effect of enabling more accurate evaluation of a lung cancer state.

According to the lung cancer-evaluating system of the present invention, between lung cancer and non-lung cancer in the subject is discriminated based on the calculated discriminant value. Thus, a discriminant value obtained in a multivariate discriminant using amino acid variables useful for discriminating between the 2 groups of lung cancer and non-lung cancer can be utilized to bring about an effect of enabling accurate discrimination between the 2 groups of lung cancer and non-lung cancer.

According to the lung cancer-evaluating system of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of lung cancer and non-lung cancer can be utilized to bring about an effect of enabling more accurate discrimination between the 2 groups of lung cancer and non-lung cancer.

According to the lung cancer-evaluating system of the present invention, the multivariate discriminant is formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

According to the lung cancer-evaluating system of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of lung cancer and non-lung cancer can be utilized to bring about an effect of enabling more accurate discrimination between the 2 groups of lung cancer and non-lung cancer.

According to the lung cancer-evaluating system of the present invention, the multivariate discriminant is the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

According to the lung cancer-evaluating system of the present invention, between lung cancer with a certain disease stage and non-lung cancer in the subject is discriminated based on the calculated discriminant value. Thus, a discriminant value obtained in a multivariate discriminant using amino acid variables useful for discriminating between the 2 groups of early lung cancer and non-lung cancer can be utilized to bring about an effect of enabling accurate discrimination between the 2 groups of early lung cancer and non-lung cancer.

According to the lung cancer-evaluating system of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of early lung cancer and non-lung cancer can be utilized to bring about an effect of enabling more accurate discrimination between the 2 groups of early lung cancer and non-lung cancer.

According to the lung cancer-evaluating system of the present invention, the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the lung cancer-evaluating system of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of early lung cancer and non-lung cancer can be utilized to bring about an effect of enabling more accurate discrimination between the 2 groups of early lung cancer and non-lung cancer.

According to the lung cancer-evaluating system of the present invention, the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

According to the lung cancer-evaluating system of the present invention, between adenocarcinoma in lung cancer and non-lung cancer in the subject is discriminated based on the calculated discriminant value. Thus, a discriminant value obtained in a multivariate discriminant using amino acid variables useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

According to the lung cancer-evaluating system of the present invention, the multivariate discriminant is expressed by one fractional expression or the sum of a plurality of the fractional expressions and contains at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating system of the present invention, the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating system of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating system of the present invention, the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating system of the present invention, a multivariate discriminant stored in a memory unit is prepared based on the lung cancer state information stored in the memory unit, including amino acid concentration data and lung cancer state index data on an index for indicating a lung cancer state. Specifically, (1) a candidate multivariate discriminant that is a candidate of multivariate discriminant is prepared from the lung cancer state information, according to a predetermined discriminant-preparing method, (2) the prepared candidate multivariate discriminant is verified based on a predetermined verification method, (3) based on a predetermined variable-selecting method, variables in the candidate multivariate discriminant are selected from the verification results in (2), thereby selecting a combination of amino acid concentration data contained in the lung cancer state information used in preparing of a candidate multivariate discriminant, and (4) based on verification results accumulated by executing (1), (2) and (3) repeatedly, a candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a lung cancer state (specifically a multivariate discriminant correlating significantly with a lung cancer state (more specifically, a multivariate discriminant useful for discrimination of the 2 groups of lung cancer and non-lung cancer, a multivariate discriminant useful for discrimination of the 2 groups of early lung cancer and non-lung cancer, or a multivariate discriminant useful for discrimination of the 2 groups of adenocarcinoma in lung cancer and non-lung cancer).

According to the recording medium of the present invention, the lung cancer-evaluating program recorded on the recording medium is read and executed by the computer, thereby allowing the computer to execute the lung cancer-evaluating program, thus bringing about an effect of obtaining the same effect as in the lung cancer-evaluating program.

When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used in addition to the amino acid concentration data. When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used as variables in the multivariate discriminant in addition to the amino acid concentration.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a block diagram showing an example of the configuration of the lung cancer-evaluating apparatus 100 in the present system;

FIG. 7 is a chart showing an example of the information stored in the user information file 106*a;*

FIG. 8 is a chart showing an example of the information stored in the amino acid concentration data file 106*b;*

FIG. 9 is a chart showing an example of the information stored in the lung cancer state information file 106*c;*

FIG. 10 is a chart showing an example of the information stored in the designated lung cancer state information file 106*d;*

FIG. 11 is a chart showing an example of the information stored in the candidate multivariable discriminant file 106*e*1;

FIG. 12 is a chart showing an example of the information stored in the verification result file 106*e*2;

FIG. 13 is a chart showing an example of the information stored in the selected lung cancer state information file 106*e*3;

FIG. 14 is a chart showing an example of the information stored in the multivariable discriminant file 106_e_4;

FIG. 15 is a chart showing an example of the information stored in the discriminant value file 106_f;_

FIG. 24 is a graph showing the AUC of the ROC curve of amino acid variables for discrimination between 2 groups of non-lung cancer and lung cancer, non-lung cancer and early lung cancer, or non-lung cancer and adenocarcinoma in lung cancer;

FIG. 25 is a chart showing a list of indices having the same diagnostic performance as that of index 1;

FIG. 26 is a chart showing a list of indices having the same diagnostic performance as that of index 1;

FIG. 28 is a chart showing the cutoff value, sensitivity, specificity, positive predictive value, negative predictive value, and correct diagnostic rate in discrimination of 2 groups;

FIG. 29 is a chart showing a list of indices having the same diagnostic performance as that of index 2;

FIG. 30 is a chart showing a list of indices having the same diagnostic performance as that of index 2;

FIG. 32 is a chart showing a list of indices having the same diagnostic performance as that of index 3;

FIG. 33 is a chart showing a list of indices having the same diagnostic performance as that of index 3;

FIG. 35 is a chart showing a list of indices having the same diagnostic performance as that of index 4;

FIG. 36 is a chart showing a list of indices having the same diagnostic performance as that of index 4;

FIG. 37 is a chart showing a list of indices having the same diagnostic performance as that of index 4;

FIG. 39 is a chart showing the cutoff value, sensitivity, specificity, positive predictive value, negative predictive value, and correct diagnostic rate in discrimination of 2 groups;

FIG. 40 is a chart showing a list of indices having the same diagnostic performance as that of index 5;

FIG. 41 is a chart showing a list of indices having the same diagnostic performance as that of index 5;

FIG. 42 is a chart showing a list of indices having the same diagnostic performance as that of index 5;

FIG. 44 is a chart showing a list of indices having the same diagnostic performance as that of index 6;

FIG. 45 is a chart showing a list of indices having the same diagnostic performance as that of index 6;

FIG. 46 is a chart showing a list of indices having the same diagnostic performance as that of index 6;

FIG. 48 is a chart showing a list of indices having the same diagnostic performance as that of index 7;

FIG. 49 is a chart showing a list of indices having the same diagnostic performance as that of index 7;

FIG. 50 is a chart showing a list of indices having the same diagnostic performance as that of index 7;

FIG. 52 is a chart showing the cutoff value, sensitivity, specificity, positive predictive value, negative predictive value, and correct diagnostic rate in discrimination of 2 groups;

FIG. 53 is a chart showing a list of indices having the same diagnostic performance as that of index 8;

FIG. 54 is a chart showing a list of indices having the same diagnostic performance as that of index 8;

FIG. 55 is a chart showing a list of indices having the same diagnostic performance as that of index 8;

FIG. 57 is a chart showing a list of indices having the same diagnostic performance as that of index 9;

FIG. 58 is a chart showing a list of indices having the same diagnostic performance as that of index 9;

FIG. 59 is a chart showing a list of indices having the same diagnostic performance as that of index 9;

FIG. 61 is a graph showing a list of amino acids extracted based on the AUC of the ROC curve;

FIG. 65 is a graph showing the AUC of the ROC curve of amino acid variables for discrimination between 2 groups of non-lung cancer and lung cancer, non-lung cancer and early lung cancer, or non-lung cancer and adenocarcinoma in lung cancer;

FIG. 66 is a chart showing a list of formulae having the same diagnostic performance as that of index 10;

FIG. 67 is a chart showing a list of formulae having the same diagnostic performance as that of index 10;

FIG. 69 is a chart showing a list of formulae having the same diagnostic performance as that of index 11;

FIG. 70 is a chart showing a list of formulae having the same diagnostic performance as that of index 11;

FIG. 72 is a chart showing a list of formulae having the same diagnostic performance as that of index 12;

FIG. 73 is a chart showing a list of formulae having the same diagnostic performance as that of index 12;

FIG. 74 is a chart showing a list of formulae having the same diagnostic performance as that of index 12;

FIG. 76 is a chart showing a list of formulae having the same diagnostic performance as that of index 13;

FIG. 77 is a chart showing a list of formulae having the same diagnostic performance as that of index 13;

FIG. 78 is a chart showing a list of formulae having the same diagnostic performance as that of index 13;

FIG. 80 is a chart showing a list of formulae having the same diagnostic performance as that of index 14;

FIG. 81 is a chart showing a list of formulae having the same diagnostic performance as that of index 14;

FIG. 83 is a chart showing a list of formulae having the same diagnostic performance as that of index 15;

FIG. 84 is a chart showing a list of formulae having the same diagnostic performance as that of index 15;

FIG. 86 is a chart showing a list of formulae having the same diagnostic performance as that of index 16;

FIG. 87 is a chart showing a list of formulae having the same diagnostic performance as that of index 16;

FIG. 88 is a chart showing a list of formulae having the same diagnostic performance as that of index 16;

FIG. 90 is a chart showing a list of formulae having the same diagnostic performance as that of index 17;

FIG. 91 is a chart showing a list of formulae having the same diagnostic performance as that of index 17;

FIG. 92 is a chart showing a list of formulae having the same diagnostic performance as that of index 17;

FIG. 94 is a chart showing a list of formulae having the same diagnostic performance as that of index 18;

FIG. 95 is a chart showing a list of formulae having the same diagnostic performance as that of index 18;

FIG. 97 is a chart showing a list of formulae having the same diagnostic performance as that of index 19;

FIG. 98 is a chart showing a list of formulae having the same diagnostic performance as that of index 19;

FIG. 100 is a chart showing a list of formulae having the same diagnostic performance as that of index 20;

FIG. 101 is a chart showing a list of formulae having the same diagnostic performance as that of index 20;

FIG. 102 is a chart showing a list of formulae having the same diagnostic performance as that of index 20;

FIG. 104 is a chart showing a list of formulae having the same diagnostic performance as that of index 21;

FIG. 105 is a chart showing a list of formulae having the same diagnostic performance as that of index 21;

FIG. 106 is a chart showing a list of formulae having the same diagnostic performance as that of index 21;

FIG. 108 is a chart showing a list of formulae having the same diagnostic performance as that of index 22;

FIG. 109 is a chart showing a list of formulae having the same diagnostic performance as that of index 22;

FIG. 111 is a chart showing a list of formulae having the same diagnostic performance as that of index 23;

FIG. 112 is a chart showing a list of formulae having the same diagnostic performance as that of index 23;

FIG. 114 is a chart showing a list of formulae having the same diagnostic performance as that of index 24;

FIG. 115 is a chart showing a list of formulae having the same diagnostic performance as that of index 24;

FIG. 116 is a chart showing a list of formulae having the same diagnostic performance as that of index 24;

FIG. 118 is a chart showing a list of formulae having the same diagnostic performance as that of index 25;

FIG. 119 is a chart showing a list of formulae having the same diagnostic performance as that of index 25;

FIG. 120 is a diagram showing Spearman's rank-correlation coefficient between groups 1 to 4, and values in index 25;

FIG. 121 is a chart showing a list of formulae having the same diagnostic performance as that of index 26;

FIG. 122 is a chart showing a list of formulae having the same diagnostic performance as that of index 26;

FIG. 123 is a diagram showing Spearman's rank-correlation coefficient between groups 1 to 4, and values in index 26;

FIG. 124 is a chart showing a list of formulae having the same diagnostic performance as that of index 27;

FIG. 125 is a chart showing a list of formulae having the same diagnostic performance as that of index 27;

FIG. 126 is a chart showing a list of formulae having the same diagnostic performance as that of index 27;

FIG. 127 is a diagram showing Spearman's rank-correlation coefficient between groups 1 to 4, and values in index 27; and FIG. 128 is a graph showing a list of amino acids extracted based on the AUC of the ROC curve.

DETAILED DESCRIPTION OF THE PREFERRED EMBODIMENTS

Hereinafter, an embodiment (first embodiment) of the method of evaluating lung cancer of the present invention and an embodiment (second embodiment) of the lung cancer-evaluating apparatus, the lung cancer-evaluating method, the lung cancer-evaluating system, the lung cancer-evaluating program and the recording medium of the present invention are described in detail with reference to the drawings. The present invention is not limited to these embodiments.

First Embodiment 1-1. Outline of the Invention

Figure 1:
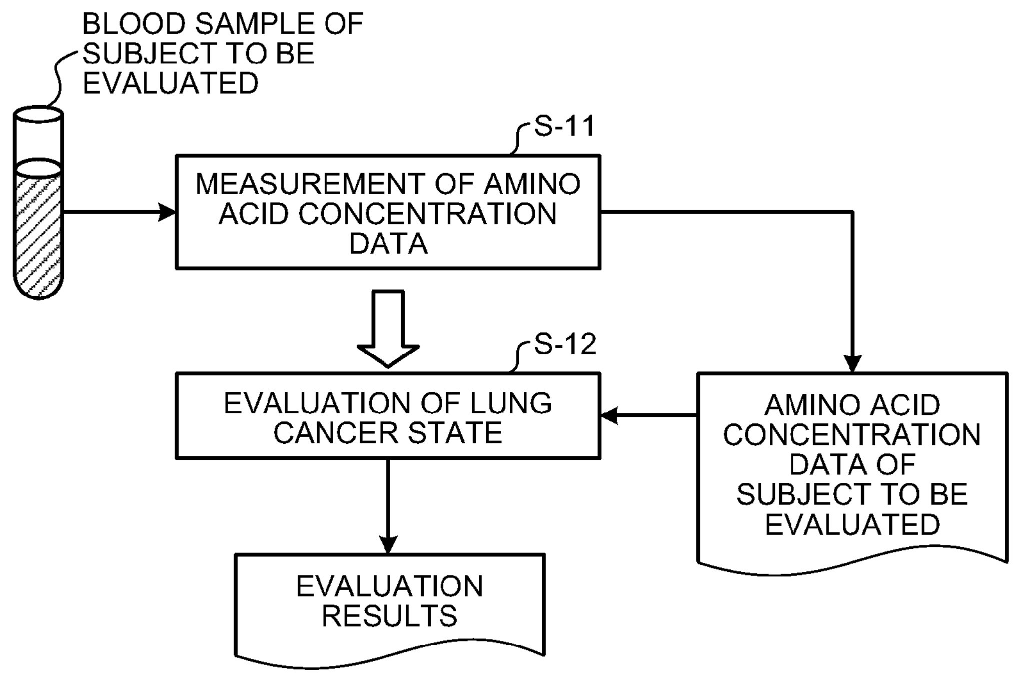
FIG. 1 is a principle configurational diagram showing the basic principle of the present invention.

Here, an outline of the method of evaluating lung cancer of the present invention will be described with reference to FIG. 1. FIG. 1 is a principle configurational diagram showing the basic principle of the present invention.

In the present invention, the amino acid concentration data on concentration values of amino acids in blood collected from a subject (for example, an individual such as animal or human) to be evaluated are first measured (step S-11). The concentrations of amino acids in blood were analyzed in the following manner. A blood sample is collected in a heparin-treated tube, and then the blood plasma is separated by centrifugation of the collected blood sample. All blood plasma samples separated were frozen and stored at −70° C. before measurement of amino acid concentration. Before measurement of amino acid concentration, the blood plasma sample was deproteinized by adding sulfosalicylic acid to a concentration of 3%. An amino acid analyzer by high-performance liquid chromatography (HPLC) by using ninhydrin reaction in the post column was used for measurement of amino acid concentration. The unit of amino acid concentration is for example molar concentration or weight concentration, which may be subjected to addition, subtraction, multiplication and division by an arbitrary constant.

In the present invention, the lung cancer state in a subject to be evaluated is evaluated based on at least one concentration value of Orn, Lys, ABA, Arg, Glu, His, Tau, Pro, Ala, Cit and Ile contained in the amino acid concentration data of the subject to be evaluated measured in the step S-11 (step S-12).

According to the present invention described above, amino acid concentration data on the concentration value of amino acid in blood collected from a subject to be evaluated is measured, and a lung cancer state in the subject is evaluated based on the concentration value of at least one of Orn, Lys, ABA, Arg, Glu, His, Tau, Pro, Ala, Cit and Ile contained in the measured amino acid concentration data of the subject. Thus, the concentrations of the amino acids which among amino acids in blood, are related to a lung cancer state can be utilized to bring about an effect of enabling accurate evaluation of a lung cancer state.

Before step S-12 is executed, data such as defective and outliers may be removed from the amino acid concentration data of the subject to be evaluated measured in step S-11. Thereby, the state of lung cancer can be more accurately evaluated.

In step S-12, between lung cancer and non-lung cancer in the subject may be discriminated based on the concentration value of at least one of Orn, Lys, ABA, Arg, Glu, His, Tau, Pro, Ala, Cit and Ile contained in the amino acid concentration data of the subject measured in step S-11. Specifically, at least one concentration value of Orn, Lys, ABA, Arg, Glu, His, Tau, Pro, Ala, Cit and Ile may be compared with a previously established threshold (cutoff value), thereby discriminating between lung cancer and non-lung cancer in the subject. Thus, the concentrations of the amino acids which among amino acids in blood, are useful for discriminating between the 2 groups of lung cancer and non-lung cancer can be utilized to bring about an effect of enabling accurate discrimination between the 2 groups of lung cancer and non-lung cancer.

In step S-12, between lung cancer with a certain disease stage and non-lung cancer in the subject may be discriminated based on the concentration value of at least one of Orn, Lys, ABA, Arg, Glu, His, Tau, Pro, Ala, Cit and Ile contained in the amino acid concentration data of the subject measured in step S-11. Specifically, at least one concentration value of Orn, Lys, ABA, Arg, Glu, His, Tau, Pro, Ala, Cit and Ile may be compared with a previously established threshold (cutoff value), thereby discriminating between lung cancer with a certain disease stage and non-lung cancer in the subject. Thus, the concentrations of the amino acids which among amino acids in blood, are useful for discriminating between the 2 groups of early lung cancer and non-lung cancer can be utilized to bring about an effect of enabling accurate discrimination between the 2 groups of early lung cancer and non-lung cancer.

In step S-12, between adenocarcinoma in lung cancer and non-lung cancer in the subject may be discriminated based on the concentration value of at least one of Orn, Lys, ABA, Arg, Glu, His, Tau, Pro, Ala, Cit and Ile contained in the amino acid concentration data of the subject measured in step S-11. Specifically, at least one concentration value of Orn, Lys, ABA, Arg, Glu, His, Tau, Pro, Ala, Cit and Ile may be compared with a previously established threshold (cutoff value), thereby discriminating between adenocarcinoma in lung cancer and non-lung cancer in the subject. Thus, the concentrations of the amino acids which among amino acids in blood, are useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

In step S-12, a discriminant value that is a value of multivariate discriminant may be calculated based on both the concentration value of at least one of Orn, Lys, ABA, Arg, Glu, His, Tau, Pro, Ala, Cit and Ile contained in the amino acid concentration data of the subject measured in step S-11 and a previously established multivariate discriminant with the concentration of the amino acid as variable, where the concentration value of at least one of Orn, Lys, ABA, Arg, Glu, His, Tau, Pro, Ala, Cit and Ile is contained as the variable, and the lung cancer state in the subject may be evaluated based on the calculated discriminant value. Thus, a discriminant value obtained in a multivariate discriminant (multivariate discriminant correlated significantly with a lung cancer state) wherein the concentrations of amino acids which among amino acids in blood, are related to a lung cancer state are variables can be utilized to bring about an effect of enabling accurate evaluation of a lung cancer state.

In step S-12, the multivariate discriminant may further contain age as the variable. Thus, a discriminant value obtained in a multivariate discriminant (multivariate discriminant correlated significantly with a lung cancer state) wherein not only the concentrations of amino acids which among amino acids in blood, are related to a lung cancer state but also the age of a subject are variables can be utilized to bring about an effect of enabling more accurate evaluation of a lung cancer state.

In step S-12, between lung cancer and non-lung cancer in the subject may be discriminated based on the calculated discriminant value. Specifically, the discriminant value may be compared with a previously established threshold (cutoff value), thereby discriminating between lung cancer and non-lung cancer in the subject. Thus, a discriminant value obtained in a multivariate discriminant using amino acid variables useful for discriminating between the 2 groups of lung cancer and non-lung cancer can be utilized to bring about an effect of enabling accurate discrimination between the 2 groups of lung cancer and non-lung cancer.

The multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, a discriminant value obtained in a multivariate discriminant (fractional expression) using amino acid variables useful for discriminating between the 2 groups of lung cancer and non-lung cancer can be utilized to bring about an effect of enabling more accurate discrimination between the 2 groups of lung cancer and non-lung cancer. Specifically, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful for discriminating between the 2 groups of lung cancer and non-lung cancer can be utilized to bring about an effect of enabling more accurate discrimination between the 2 groups of lung cancer and non-lung cancer. Specifically, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

In step S-12, between lung cancer with a certain disease stage and non-lung cancer in the subject may be discriminated based on the calculated discriminant value. Specifically, the discriminant value may be compared with a previously established threshold (cutoff value), thereby discriminating between lung cancer with a certain disease stage and non-lung cancer in the subject. Thus, a discriminant value obtained in a multivariate discriminant using amino acid variables useful for discriminating between the 2 groups of early lung cancer and non-lung cancer can be utilized to bring about an effect of enabling accurate discrimination between the 2 groups of early lung cancer and non-lung cancer.

The multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, a discriminant value obtained in a multivariate discriminant (fractional expression) using amino acid variables useful for discriminating between the 2 groups of early lung cancer and non-lung cancer can be utilized to bring about an effect of enabling more accurate discrimination between the 2 groups of early lung cancer and non-lung cancer. Specifically, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful for discriminating between the 2 groups of early lung cancer and non-lung cancer can be utilized to bring about an effect of enabling more accurate discrimination between the 2 groups of early lung cancer and non-lung cancer. Specifically, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

In step S-12, between adenocarcinoma in lung cancer and non-lung cancer in the subject may be discriminated based on the calculated discriminant value. Specifically, the discriminant value may be compared with a previously established threshold (cutoff value), thereby discriminating between adenocarcinoma in lung cancer and non-lung cancer in the subject. Thus, a discriminant value obtained in a multivariate discriminant using amino acid variables useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

The multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, a discriminant value obtained in a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer. Specifically, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus,a discriminant value obtained in a multivariate discriminant using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer. Specifically, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a lung cancer state, regardless of the unit of amino acid concentration in the amino acid concentration data as input data.

In a fractional expression, the numerator of the fractional expression is expressed by the sum of amino acids A, B, C etc. and/or the denominator of the fractional expression is expressed by the sum of amino acids a, b, c etc. The fractional expression also includes the sum of fractional expressions α, β, γ etc. (for example, α+β) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each variable and the value for a constant term may be any real numbers. In combinations where variables in the numerator and variables in the denominator in the fractional expression are switched with each other, the positive (or negative) sign is generally reversed in correlation with objective variables, but because their correlation is maintained, such combinations can be assumed to be equivalent to one another in discrimination, and thus the fractional expression also includes combinations where variables in the numerator and variables in the denominator in the fractional expression are switched with each other.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used in addition to the amino acid concentration data. When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used as variables in the multivariate discriminant in addition to the amino acid concentration.

1-2. Method of Evaluating Lung Cancer in Accordance with the First Embodiment

Figure 2:
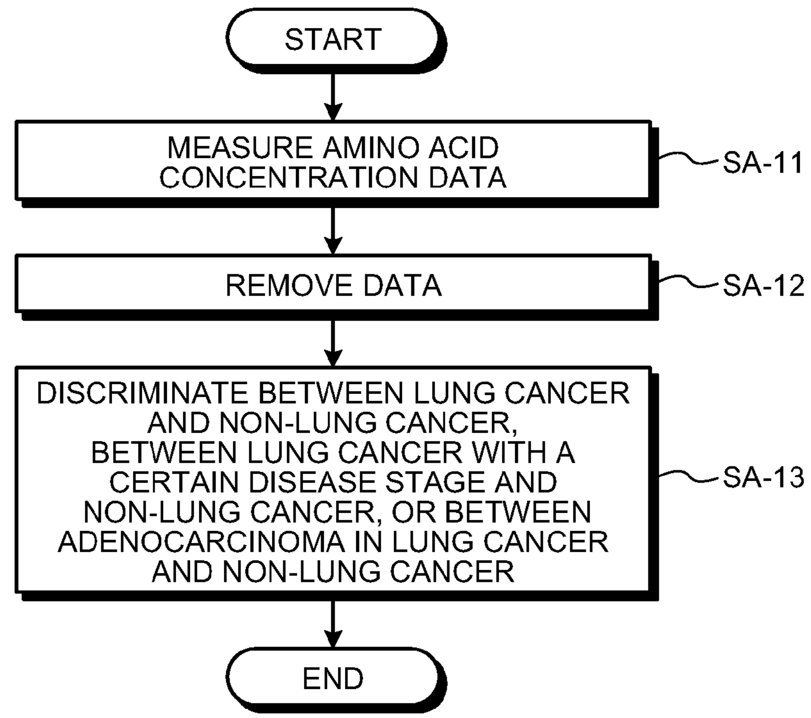
FIG. 2 is a flowchart showing one example of the method of evaluating lung cancer according to the first embodiment.

Herein, the method of evaluating lung cancer according to the first embodiment is described with reference to FIG. 2. FIG. 2 is a flowchart showing one example of the method of evaluating lung cancer according to the first embodiment.

From blood collected from an individuals such as animal or human, amino acid concentration data on the concentration values of amino acids are measured (step SA-11). Measurement of the concentration values of amino acids is conducted by the method described above.

From the amino acid concentration data measured in step SA-11, data such as defective and outliers are then removed (step SA-12).

Then, at least one concentration value of Orn, Lys, ABA, Arg, Glu, His, Tau, Pro, Ala, Cit and Ile contained in the amino acid concentration data of the individual from which defective and outliers have been removed is compared with a previously established threshold (cutoff value), thereby discriminating between lung cancer and non-lung cancer, between lung cancer with a certain disease stage and non-lung cancer, and between adenocarcinoma in lung cancer and non-lung cancer, in the individual (step SA-13).

1-3. Summary of the First embodiment and Other Embodiments

In the method of evaluating lung cancer as described above in detail, (1) amino acid concentration data are measured from blood collected from an individual, (2) data such as defective and outliers are removed from the measured amino acid concentration data of the individual, and (3) at least one concentration value of Orn, Lys, ABA, Arg, Glu, His, Tau, Pro, Ala, Cit and Ile contained in the amino acid concentration data of the individual from which defective and outliers have been removed is compared with a previously established threshold (cutoff value), thereby discriminating between lung cancer and non-lung cancer, between lung cancer with a certain disease stage and non-lung cancer, and between adenocarcinoma in lung cancer and non-lung cancer, in the individual. Thus, the concentrations of the amino acids which among amino acids in blood, are useful for discriminating between the 2 groups of lung cancer and non-lung cancer, the concentrations of the amino acids which among amino acids in blood, are useful for discriminating between the 2 groups of early lung cancer and non-lung cancer, and the concentrations of the amino acids which among amino acids in blood, are useful for discriminating between the 2 groups of adenocarcinoma in lung cancer and non-lung cancer can be utilized to bring about an effect of enabling accurate discrimination between the 2 groups of lung cancer and non-lung cancer, between the 2 groups of early lung cancer and non-lung cancer, and between the 2 groups of adenocarcinoma in lung cancer and non-lung cancer.

According to the method of evaluating lung cancer, a discriminant value may be calculated based on both the concentration value of at least one of Orn, Lys, ABA, Arg, Glu, His, Tau, Pro, Ala, Cit and Ile contained in the amino acid concentration data of the individual from which defective and outliers have been removed and the previously established multivariate discriminant with the concentrations of at least one of Orn, Lys, ABA, Arg, Glu, His, Tau, Pro, Ala, Cit and Ile as variables, and the calculated discriminant value may be compared with a previously established threshold (cutoff value), thereby discriminating between lung cancer and non-lung cancer, between lung cancer with a certain disease stage and non-lung cancer, and between adenocarcinoma in lung cancer and non-lung cancer, in the individual. Thus, a discriminant value obtained in a multivariate discriminant using amino acid variables useful for discriminating between the 2 groups of lung cancer and non-lung cancer, a multivariate discriminant using amino acid variables useful for discriminating between the 2 groups of early lung cancer and non-lung cancer, and a multivariate discriminant using amino acid variables useful for discriminating between the 2 groups of adenocarcinoma in lung cancer and non-lung cancer can be utilized to bring about an effect of enabling accurate discrimination between the 2 groups of lung cancer and non-lung cancer, between the 2 groups of early lung cancer and non-lung cancer, and between the 2 groups of adenocarcinoma in lung cancer and non-lung cancer.

According to the method of evaluating lung cancer, the multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of lung cancer and non-lung cancer, a multivariate discriminant (fractional expression) using amino acid variables useful for discriminating between the 2 groups of early lung cancer and non-lung cancer, and a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of lung cancer and non-lung cancer, between the 2 groups of early lung cancer and non-lung cancer, and between the 2 groups of adenocarcinoma in lung cancer and non-lung cancer.

Specifically, when between lung cancer and non-lung cancer is discriminated in step SA-13,the multivariate discriminant may be formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

When between lung cancer with a certain disease stage and non-lung cancer is discriminated in step SA-13,the multivariate discriminant may be formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

When between adenocarcinoma in lung cancer and non-lung cancer is discriminated in step SA-13, the multivariate discriminant may be formula 7, 8 or 9:

$$a_7\times Orn/Trp+b_7\times Tau/Arg+c_7 \quad \text{(formula 7)}$$

$$a_8\times(Glu+Pro)/His+b_8\times(ABA+Lys)/Ile+c_8 \quad \text{(formula 8)}$$

$$a_9\times Glu/Cit+b_9\times His/Gln+c_9\times Ile/Leu+d_9\times Tyr/Ala+e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the method of evaluating lung cancer, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of lung cancer and non-lung cancer, a multivariate discriminant using amino acid variables useful for discriminating between the 2 groups of early lung cancer and non-lung cancer, and a multivariate discriminant using amino acid variables useful for discriminating between the 2 groups of adenocarcinoma in lung cancer and non-lung cancer can be utilized to bring about an effect of enabling more accurate discrimination between the 2 groups of lung cancer and non-lung cancer, between the 2 groups of early lung cancer and non-lung cancer, and between the 2 groups of adenocarcinoma in lung cancer and non-lung cancer.

Specifically, when between lung cancer and non-lung cancer is discriminated in step SA-13,the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

When between lung cancer with a certain disease stage and non-lung cancer is discriminated in step SA-13, the multivariate discriminant is the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

When between adenocarcinoma in lung cancer and non-lung cancer is discriminated in step SA-13, the multivariate discriminant is the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a lung cancer state, regardless of the unit of amino acid concentration in the amino acid concentration data as input data.

Second Embodiment 2-1. Outline of the Invention

Figure 3:
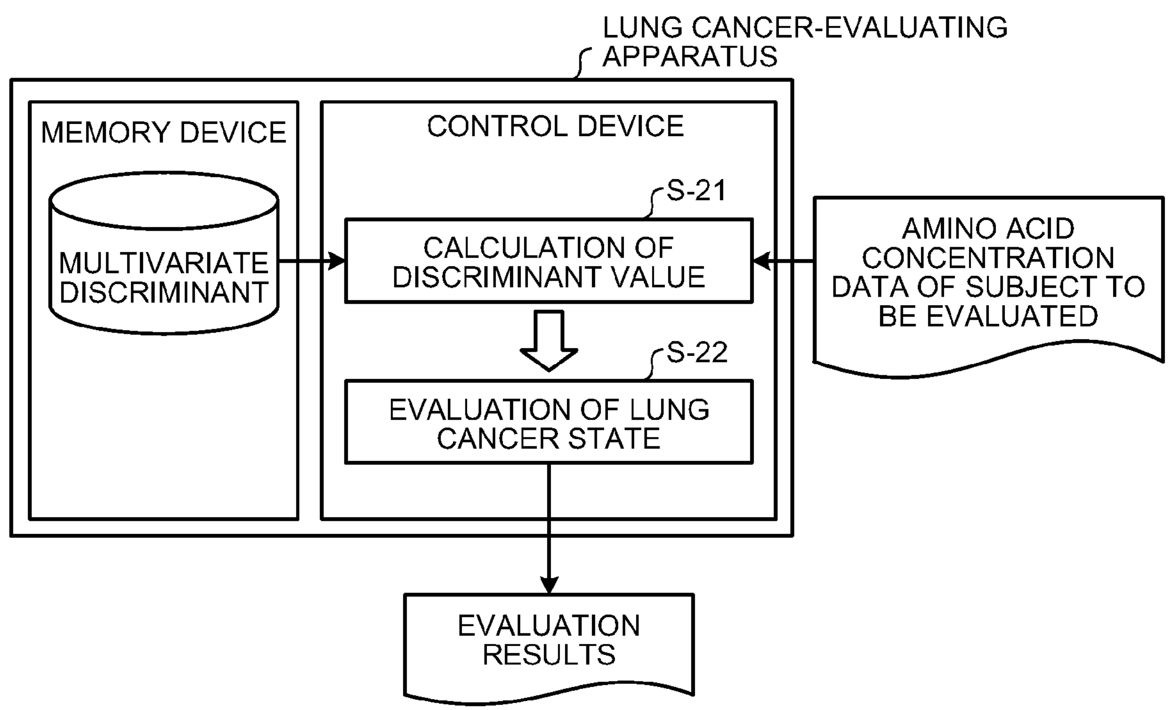
FIG. 3 is a principle configurational diagram showing the basic principle of the present invention.

Herein, an outline of the lung cancer-evaluating apparatus, the lung cancer-evaluating method, the lung cancer-evaluating system, the lung cancer-evaluating program and the recording medium of the present invention are described in detail with reference to FIG. 3. FIG. 3 is a principle configurational diagram showing the basic principle of the present invention.

In the present invention, a discriminant value that is the value of multivalent discriminant is calculated in a control device based on both the previously obtained concentration value of at least one of Orn, Lys, ABA, Arg, Glu, His, Tau, Pro, Ala, Cit and Ile contained in the amino acid concentration data of a subject to be evaluated (for example, an individual such as animal or human) and the previously established multivariate discriminant with the concentration value of at least one of Orn, Lys, ABA, Arg, Glu, His, Tau, Pro, Ala, Cit and Ile as variables, stored in the memory device (step S-21).

In the present invention, lung cancer state in the subject to be evaluated is evaluated in the control device based on the discriminant value calculated in step S-21 (step S-22).

According to the present invention described above, a discriminant value that is a value of multivariate discriminant is calculated based on both the concentration value of at least one of Orn, Lys, ABA, Arg, Glu, His, Tau, Pro, Ala, Cit and Ile contained in previously obtained amino acid concentration data on the concentration value of amino acid in the subject and a multivariate discriminant with the concentration of the amino acid as variable stored in the memory device, where the concentration value of at least one of Orn, Lys, ABA, Arg, Glu, His, Tau, Pro, Ala, Cit and Ile is contained as the variable, and the lung cancer state in the subject is evaluated based on the calculated discriminant value. Thus, a discriminant value obtained in a multivariate discriminant (multivariate discriminant correlated significantly with a lung cancer state) wherein the concentrations of amino acids which among amino acids in blood, are related to a lung cancer state are variables can be utilized to bring about an effect of enabling accurate evaluation of a lung cancer state.

In step S-21, the multivariate discriminant may further contain age as the variable. Thus, a discriminant value obtained in a multivariate discriminant (multivariate discriminant correlated significantly with a lung cancer state) wherein not only the concentrations of amino acids which among amino acids in blood, are related to a lung cancer state but also the age of a subject are variables can be utilized to bring about an effect of enabling more accurate evaluation of a lung cancer state.

In step S-22, between lung cancer and non-lung cancer in the subject may be discriminated based on the discriminant value calculated in step S-21. Specifically, the discriminant value may be compared with a previously established threshold (cutoff value), thereby discriminating between lung cancer and non-lung cancer in the subject. Thus, a discriminant value obtained in a multivariate discriminant using amino acid variables useful for discriminating between the 2 groups of lung cancer and non-lung cancer can be utilized to bring about an effect of enabling accurate discrimination between the 2 groups of lung cancer and non-lung cancer.

In step S-21, the multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 1, 2 or 3:

$$a_1\times Orn/Trp+b_1\times(Tau+ABA)/Arg+c_1 \quad \text{(formula 1)}$$

$$a_2\times Glu/Tyr+b_2\times(Pro+Lys)/(Ile+His)+c_2 \quad \text{(formula 2)}$$

$$a_3\times His/Lys+b_3\times Glu/Ile+c_3\times Tyr/Pro+d_3\times Val/Leu+e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, a discriminant value obtained in a multivariate discriminant (fractional expression) using amino acid variables useful for discriminating between the 2 groups of lung cancer and non-lung cancer can be utilized to bring about an effect of enabling more accurate discrimination between the 2 groups of lung cancer and non-lung cancer. Specifically, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

In step S-21, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful for discriminating between the 2 groups of lung cancer and non-lung cancer can be utilized to bring about an effect of enabling more accurate discrimination between the 2 groups of lung cancer and non-lung cancer. Specifically, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

In step S-22, between lung cancer with a certain disease stage and non-lung cancer in the subject may be discriminated based on the discriminant value calculated in step S-21. Specifically, the discriminant value may be compared with a previously established threshold (cutoff value), thereby discriminating between lung cancer with a certain disease stage and non-lung cancer in the subject. Thus, a discriminant value obtained in a multivariate discriminant using amino acid variables useful for discriminating between the 2 groups of early lung cancer and non-lung cancer can be utilized to bring about an effect of enabling accurate discrimination between the 2 groups of early lung cancer and non-lung cancer.

In step S-21, the multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 4, 5 or 6:

$$a_4\times Tau/Arg+b_4\times(Orn+ABA)/Trp+c_4 \quad \text{(formula 4)}$$

$$a_5\times Gln/(Cit+His)+b_5\times(Glu+ABA)/(Cys2)+c_5 \quad \text{(formula 5)}$$

$$a_6\times Gln/His+b_6\times Glu+c_6\times ABA/Cys+d_6\times Lys/Val+e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, a discriminant value obtained in a multivariate discriminant (fractional expression) using amino acid variables useful for discriminating between the 2 groups of early lung cancer and non-lung cancer can be utilized to bring about an effect of enabling more accurate discrimination between the 2 groups of early lung cancer and non-lung cancer. Specifically, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

In step S-21, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful for discriminating between the 2 groups of early lung cancer and non-lung cancer can be utilized to bring about an effect of enabling more accurate discrimination between the 2 groups of early lung cancer and non-lung cancer. Specifically, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

In step S-22, between adenocarcinoma in lung cancer and non-lung cancer in the subject may be discriminated based on the discriminant value calculated in step S-21. Specifically, the discriminant value may be compared with a previously established threshold (cutoff value), thereby discriminating between adenocarcinoma in lung cancer and non-lung cancer in the subject. Thus, a discriminant value obtained in a multivariate discriminant using amino acid variables useful for discriminating between the 2 groups of adenocarcinoma in lung cancer and non-lung cancer can be utilized to bring about an effect of enabling accurate discrimination between the 2 groups of adenocarcinoma in lung cancer and non-lung cancer.

In step S-21, the multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Specifically, the multivariate discriminant may be formula 7, 8 or 9:

$$a_7 \times Orn/Trp+b_7 \times Tau/Arg+c_7 \quad \text{(formula 7)}$$

$$a_8 \times (Glu+Pro)/His+b_8 \times (ABA+Lys)/Ile+c_8 \quad \text{(formula 8)}$$

$$a_9 \times Glu/Cit+b_9 \times His/Gln+c_9 \times Ile/Leu+d_9 \times Tyr/Ala+e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, a discriminant value obtained in a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer. Specifically, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

In step S-21, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus,a discriminant value obtained in a multivariate discriminant using amino acid variables useful for discriminating between the 2 groups of adenocarcinoma in lung cancer and non-lung cancer can be utilized to bring about an effect of enabling more accurate discrimination between the 2 groups of adenocarcinoma in lung cancer and non-lung cancer. Specifically, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

The multivariate discriminants described above can be prepared by a method described in International Publication WO 2004/052191 that is an international application filed by the present applicant or by a method (multivariate discriminant-preparing processing described later) described in International Publication PCT/JP2006/304398 that is an international application filed by the present applicant. Any multivariate discriminants obtained by these methods can be preferably used in evaluation of a lung cancer state, regardless of the unit of amino acid concentration in the amino acid concentration data as input data.

In a fractional expression, the numerator of the fractional expression is expressed by the sum of amino acids A, B, C etc. and/or the denominator of the fractional expression is expressed by the sum of amino acids a, b, c etc. The fractional expression also includes the sum of fractional expressions $\alpha$, $\beta$, $\gamma$ etc. (for example, $\alpha+\beta$) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each variable and the value for a constant term may be any real numbers. In combinations where variables in the numerator and variables in the denominator in the fractional expression are switched with each other, the positive (or negative) sign is generally reversed in correlation with objective variables, but because their correlation is maintained, such combinations can be assumed to be equivalent to one another in discrimination, and thus the fractional expression also includes combinations where variables in the numerator and variables in the denominator in the fractional expression are switched with each other.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used in addition to the amino acid concentration data. When lung cancer state is evaluated (specifically discrimination between lung cancer and non-lung cancer, discrimination between lung cancer with a certain disease stage and non-lung cancer or discrimination between adenocarcinoma in lung cancer and non-lung cancer is conducted) in the present invention, the concentrations of other metabolites (biological metabolites), the protein expression level, the age and sex of the subject, biological indices or the like may be used as variables in the multivariate discriminant in addition to the amino acid concentration.

Here, the summary of the multivariate discriminant-preparing processing (steps 1 to 4) is described in detail.

First, from lung cancer state information including amino acid concentration data and lung cancer state index data concerning an index showing a lung cancer state stored in a memory device, a candidate multivariate discriminant that is a candidate for a multivariate discriminant (e.g., $y=a_1x_1+a_2x_2+ \ldots +a_nx_n$, y: lung cancer state index data, $x_i$: amino acid concentration data, $a_i$: constant, $i=1,2, \ldots, n$) is prepared by a predetermined discriminant-preparing method at the control device (step 1). Data containing defective and outliers may be removed in advance from the lung cancer state information.

In step 1, a plurality of candidate multivariate discriminants may be prepared from the lung cancer state information by using a plurality of different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of candidate multivariate discriminant groups may be prepared simultaneously and concurrently by using a plurality of different algorithms with lung cancer state information which is multivariate data composed of amino acid concentration data and lung cancer state index data obtained by analyzing blood samples from a large number of non-lung groups and lung cancer patient groups. For example, two different candidate multivariate discriminants may be formed by performing discriminant analysis and logistic regression analysis simultaneously with different algorithms. Alternatively, a candidate multivariate discriminant may be formed by converting lung cancer state information with the candidate multivariate discriminant prepared by performing principal component analysis and then performing discriminant analysis of the converted lung cancer state information. In this way, it is possible to finally prepare a candidate multivariate discriminant suitable for diagnostic condition.

The candidate multivariate discriminant prepared by principal component analysis is a linear expression consisting of amino acid variables maximizing the variance of all amino acid concentration data. The candidate multivariate discriminant prepared by discriminant analysis is a high-powered expression (including exponential and logarithmic expressions) consisting of amino acid variables minimizing the ratio of the sum of the variances in respective groups to the variance of all amino acid concentration data. The candidate multivariate discriminant prepared by using support vector machine is a high-powered expression (including kernel function) consisting of amino acid variables maximizing the boundary between groups. The candidate multivariate discriminant prepared by multiple regression analysis is a high-powered expression consisting of amino acid variables minimizing the sum of the distances from all amino acid concentration data. The candidate multivariate discriminant prepared by logistic regression analysis is a fraction expression having, as a component, the natural logarithm having a linear expression consisting of amino acid variables maximizing the likelihood as the exponent. The k-means method is a method of searching k pieces of neighboring amino acid concentration data in various groups designating the group containing the greatest number of the neighboring points as its data-belonging group, and selecting an amino acid variable that makes the group to which input amino acid concentration data belong agree well with the designated group. The cluster analysis is a method of clustering the points closest in entire amino acid concentration data. The decision tree is a method of ordering amino acid variables and predicting the group of amino acid concentration data from the pattern possibly held by the higher-ordered amino acid variable.

Returning to the description of the multivariate discriminant-preparing processing, the candidate multivariate discriminant prepared in step 1 is verified (mutually verified) in the control device by a particular verification method (step 2). Verification of the candidate multivariate discriminant is performed on each other to each candidate multivariate discriminant prepared in step 1.

In step 2, at least one of the discrimination rate, sensitivity, specificity, information criterion, and the like of the candidate multivariate discriminant may be verified by at least one of the bootstrap method, holdout method, leave-one-out method, and the like. In this way, it is possible to prepare a candidate multivariate discriminant higher in predictability or reliability, by taking the lung cancer state information and the diagnostic condition into consideration.

The discrimination rate is the rate of the data wherein the lung cancer state evaluated according to the present invention is correct in all input data. The sensitivity is the rate of the lung cancer states judged correct according to the present invention in the lung cancer states declared lung cancer in the input data. The specificity is the rate of the lung cancer states judged correct according to the present invention in the lung cancer states described non-lung cancer in the input data. The information criterion is the sum of the number of the amino acid variables in the candidate multivariate discriminant prepared in step 1 and the difference in number between the lung cancer states evaluated according to the present invention and those described in input data. The predictability is the average of the discrimination rate, sensitivity, or specificity obtained by repeating verification of the candidate multivariate discriminant. Alternatively, the reliability is the variance of the discrimination rate, sensitivity, or specificity obtained by repeating verification of the candidate multivariate discriminant.

Returning to the description of the multivariate discriminant-preparing processing, a combination of amino acid concentration data contained in the lung cancer state information used in preparing the candidate multivariate discriminant is selected by selecting a variable of the candidate multivariate discriminant from the verification result in step 2 according to a predetermined variable selection method in the control device (step 3). The selection of amino acid variable is performed on each candidate multivariate discriminant prepared in step 1. In this way, it is possible to select the amino acid variable of the candidate multivariate discriminant properly. The step 1 is executed once again by using the lung cancer state information including the amino acid concentration data selected in step 3.

From the verification result in step 2, an amino acid variable of the candidate multivariate discriminant may be selected in step 3, based on at least one of stepwise method, best path method, local search method, and genetic algorithm.

The best path method is a method of selecting an amino acid variable by optimizing the evaluation index of the candidate multivariate discriminant while eliminating the variables contained in the candidate multivariate discriminant one by one.

Returning to the description of the multivariate discriminant-preparing processing, the steps 1, 2 and 3 are repeatedly performed in the control device, and based on verification results thus accumulated, a candidate multivariate discriminant used as multivariate discriminant is selected from a plurality of candidate multivariate discriminants, thereby preparing the multivariate discriminant (step 4). In selection of the candidate multivariate discriminants, there are cases where the optimum multivariate discriminant is selected from candidate multivariate discriminants prepared in the same method or the optimum multivariate discriminant is selected from all candidate multivariate discriminants.

As described above, processing for preparation of candidate multivariate discriminants based on lung cancer state information, verification of the candidate multivariate discriminants, and selection of variables in the candidate multivariate discriminants are performed in a series of operations in a systematized manner in the multivariate discriminant-preparing processing, whereby the optimum multivariate discriminant for evaluation of lung cancer state can be prepared. In other words, in the multivariate discriminant-preparing processing, amino acid concentration is used in multivariate statistical analysis, and for selecting the optimum and robust combination of variables, the variable selection method is combined with cross-validation to extract a multivariate discriminant having high diagnosis performance. Logistic regression equation, linear discriminant function, support vector machine, Mahalanobis' generalized distance, multiple regression analysis, cluster analysis and the like can be used in the multivariate discriminant.

2-2. System Configuration

Hereinafter, the configuration of the lung cancer-evaluating system according to the second embodiment (hereinafter referred to sometimes as the present system) will be described with reference to FIGS. 4 to 20. This system is merely one example, and the present invention is not limited thereto.

Figure 4:
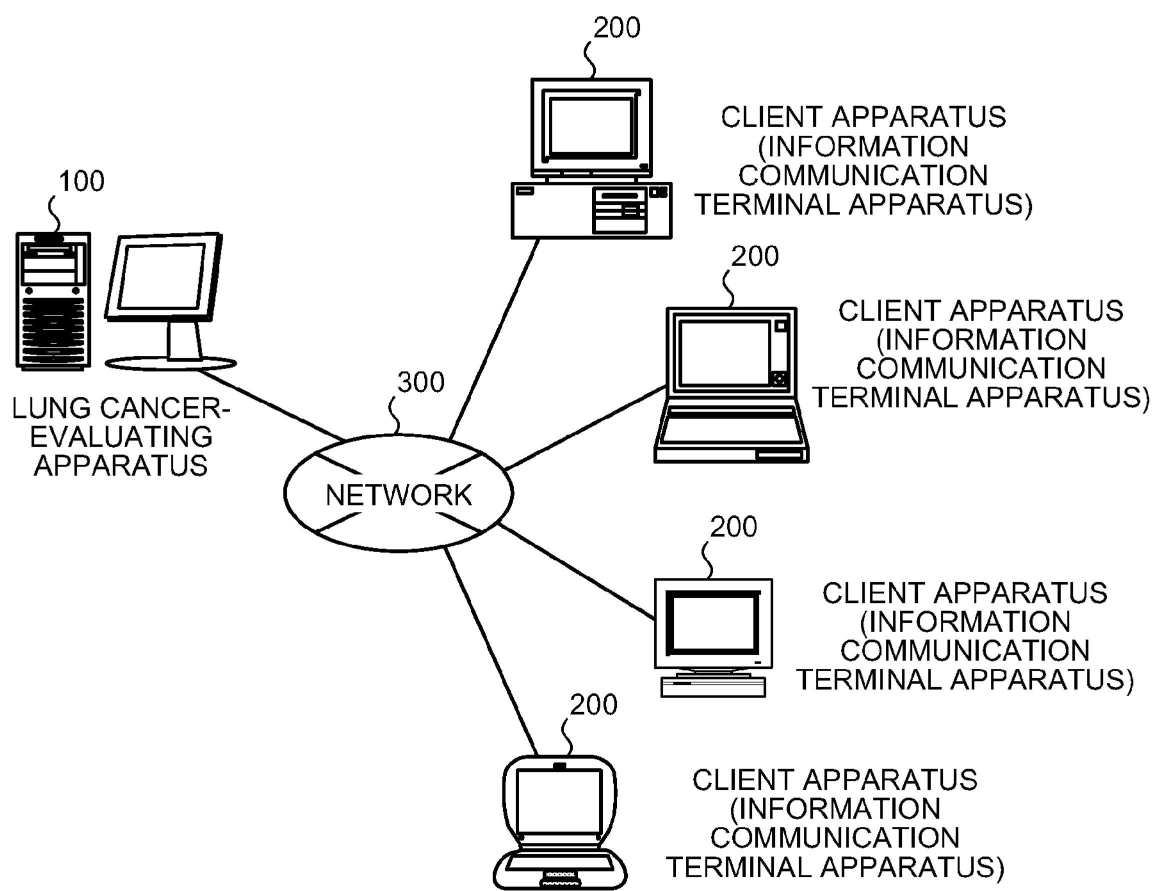
FIG. 4 is a diagram showing an example of the entire configuration of the present system.
Figure 5:
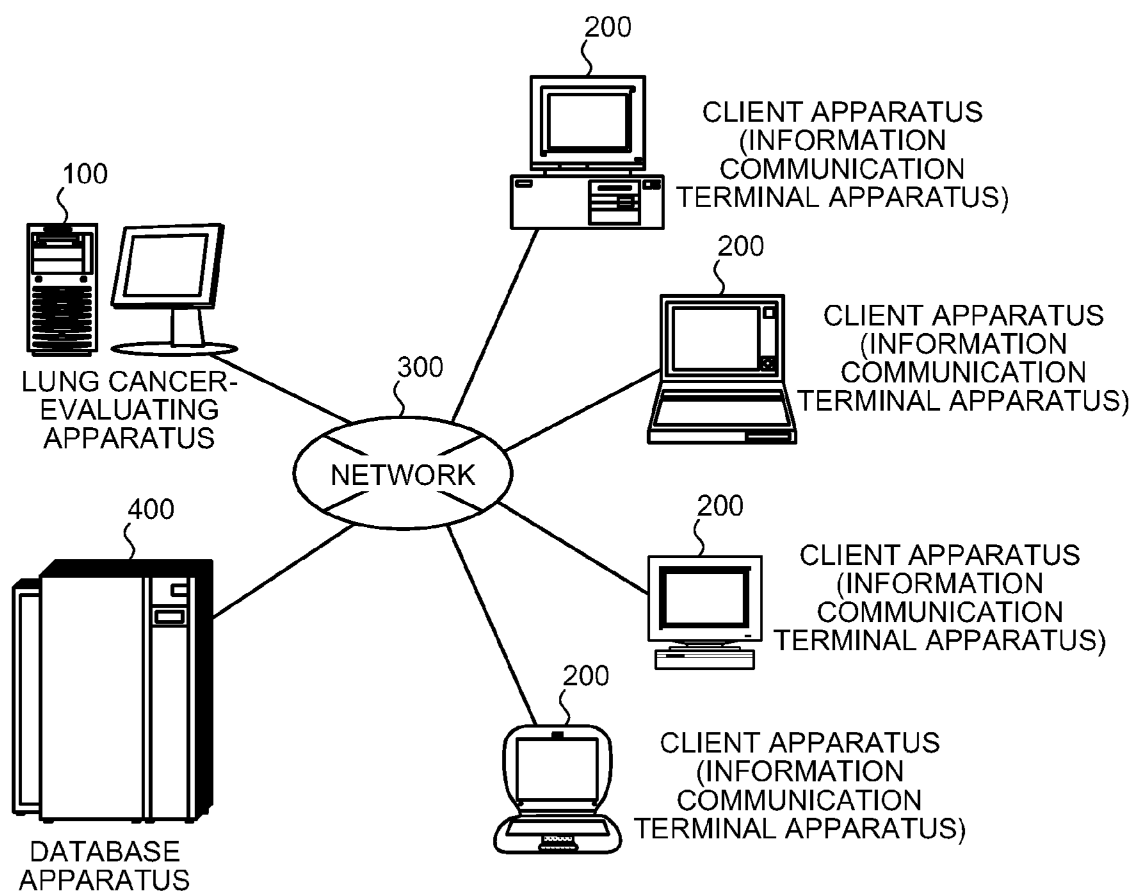
FIG. 5 is a diagram showing another example of the entire configuration of the present system.

First, the entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which a lung cancer-evaluating apparatus 100 that evaluates a lung cancer state in a subject to be evaluated, and a client apparatus 200 (corresponding to the information communication terminal apparatus of the present invention) which provides the amino acid concentration data on the concentration values of amino acids in the subject, are communicatively connected to each other via a network 300.

In the present system as shown in FIG. 5, in addition to the lung cancer-evaluating apparatus 100 and the client apparatus 200, a database apparatus 400 storing, for example, the lung cancer state information used in preparing a multivariate discriminant and the multivariate discriminant used in evaluating a lung cancer state in the lung cancer-evaluating apparatus 100, may be communicatively connected via the network 300. In this configuration, the information on a lung cancer state etc. are provided via the network 300 from the lung cancer-evaluating apparatus 100 to the client apparatuses 200 and the database apparatus 400, or from the client apparatuses 200 and the database apparatus 400 to the lung cancer-evaluating apparatus 100. The "information on a lung cancer state" is information on the measured values of particular items of the lung cancer state of organisms including human. The information on a lung cancer state is generated in the lung cancer-evaluating apparatus 100, client apparatus 200, and other apparatuses (e.g., various measuring apparatuses) and stored mainly in the database apparatus 400.

Now, the configuration of the lung cancer-evaluating apparatus 100 in the present system will be described with reference to FIGS. 6 to 18. FIG. 6 is a block diagram showing an example of the configuration of the lung cancer-evaluating apparatus 100 in the present system, showing conceptually only the region relevant to the present invention.

The lung cancer-evaluating apparatus 100 includes a control device 102, such as CPU (Central Processing Unit), that integrally controls the lung cancer-evaluating apparatus 100, a communication interface 104 that connects the lung cancer-evaluating apparatus 100 to the network 300 communicatively via communication apparatuses such as router and a wired or wireless communication line such as private line, a memory device 106 that stores various databases, tables, files and others, and an input/output interface 108 connected to an input device 112 and an output device 114, that are connected to each other communicatively via any communication channel. The lung cancer-evaluating apparatus 100 may be present together with various analyzers (e.g., amino acid analyzer) in a same housing. Typical configuration of disintegration/integration of the lung cancer-evaluating apparatus 100 is not limited to that shown in the figure, and all or a part of it may be disintegrated or integrated functionally or physically in any unit, for example, according to various loads applied. For example, a part of the processing may be performed via a CGI (Common Gateway Interface).

The memory device 106 is a storage means, and examples thereof include memory apparatuses such as RAM (Random Access Memory) and ROM (Read Only Memory), fixed disk drives such as hard disk, flexible disk, optical disk, and the like. The memory device 106 stores computer programs giving instructions to CPU for various processing, together with OS (Operating System). As shown in the figure, the memory device 106 stores a user information file 106*a*, an amino acid concentration data file 106*b*, a lung cancer state information file 106*c*, a designated lung cancer state information file 106*d*, a multivariate discriminant-related information database 106*e*, a discriminant value file 106*f* and an evaluation result file 106*g*.

The user information file 106*a* stores a user information on users. FIG. 7 is a chart showing an example of the information stored in the user information file 106*a*. As shown in FIG. 7, the information stored in the user information file 106*a* includes user ID (identification) for identifying the user uniquely, user password for authentication of the user, user name, organization ID uniquely identifying the organization of the user, department ID for uniquely identifying the department of the user organization, department name, and electronic mail address of the user that are correlated to one another.

Returning to FIG. 6, the amino acid concentration data file 106*b* stores amino acid concentration data on amino acid concentration values. FIG. 8 is a chart showing an example of the information stored in the amino acid concentration data file 106*b*. As shown in FIG. 8, the information stored in the amino acid concentration data file 106*b* includes individual number for uniquely identifying an individual (sample) as a subject to be evaluated and amino acid concentration data that are correlated to one another. In FIG. 8, the amino acid concentration data are assumed to be numerical values, i.e., on continuous scale, but the amino acid concentration data may be expressed on nominal scale or ordinal scale. In the case of nominal or ordinal scale, any number may be allocated to each state for analysis. The amino acid concentration data may be combined with other biological information (e.g., sex difference, age, height, weight, BMI index, abdominal circumference, insulin resistance index, uric acid level, blood glucose level, triglyceride, body fat percentage, total cholesterol, HDL cholesterol, LDL cholesterol, systolic pressure, diastolic pressure, hemoglobin Alc, arteriosclerosis index, smoking, smoking index, digitalized electrocardiogram waveform, protein concentration, antibody concentration, tumor marker amount, enzyme concentration, gene expression level, and the concentrations of metabolites other than amino acids).

Returning to FIG. 6, the lung cancer state information file 106*c* stores the lung cancer state information used in preparing a multivariate discriminant. FIG. 9 is a chart showing an example of the information stored in the lung cancer state information file 106*c*. As shown in FIG. 9, the information stored in the lung cancer state information file 106*c* includes individual (sample) number, lung cancer state index data (T) corresponding to the lung cancer state index (index $T_1$, index $T_2$, index $T_3$ . . . ), and amino acid concentration data that are correlated to one another. In FIG. 9, the lung cancer state index data and the amino acid concentration data are assumed to be numerical values, i.e., on continuous scale, but the lung cancer state index data and the amino acid concentration data may be expressed on nominal scale or ordinal scale. In the case of nominal or ordinal scale, any number may be allocated to each state for analysis. The lung cancer state index data is a single known state index serving as a marker of lung cancer state, and numerical data may be used.

Returning to FIG. 6, the designated lung cancer state information file 106*d* stores the lung cancer state information designated in the lung cancer state information-designating part 102*g* described below. FIG. 10 is a chart showing an example of the information stored in the designated lung cancer state information file 106*d*. As shown in FIG. 10, the information stored in the designated lung cancer state information file 106*d* includes individual number, designated lung cancer state index data, and designated amino acid concentration data that are correlated to one another.

Returning to FIG. 6, the multivariate discriminant-related information database 106*e* is composed of a candidate multivariate discriminant file 106*e*1 storing the candidate multivariate discriminant prepared in the candidate multivariate discriminant-preparing part 102*h*1 described below; a verification result file 106*e*2 storing the verification results in the candidate multivariate discriminant-verifying part 102*h*2 described below; a selected lung cancer state information file 106*e*3 storing the lung cancer state information containing the combination of amino acid concentration data selected in the variable-selecting part 102*h*3 described below; and a multivariate discriminant file 106*e*4 storing the multivariate discriminant prepared in the multivariate discriminant-preparing part 102*h* described below.

The candidate multivariate discriminant file 106*e*1 stores the candidate multivariate discriminant prepared in the candidate multivariate discriminant-preparing part 102*h*1 described below. FIG. 11 is a chart showing an example of the information stored in the candidate multivariate discriminant file 106*e*1. As shown in FIG. 11, the information stored in the candidate multivariate discriminant file 106*e*1 includes rank, and candidate multivariate discriminant (e.g., $F_1$ (Gly, Leu, Phe, . . . ), $F_2$ (Gly, Leu, Phe, . . . ), or $F_3$ (Gly, Leu, Phe, . . . ) in FIG. 11) that are correlated to each other.

Returning to FIG. 6, the verification result file 106*e*2 stores the verification results verified in the candidate multivariate discriminant-verifying part 102*h*2 described below. FIG. 12 is a chart showing an example of the information stored in the verification result file 106*e*2. As shown in FIG. 12, the information stored in the verification result file 106*e*2 includes rank, candidate multivariate discriminant (e.g., $F_k$ (Gly, Leu, Phe, . . . ), $F_m$ (Gly, Leu, Phe, . . . ), $F_l$ (Gly, Leu, Phe, . . . ) in FIG. 12), and the verification results of each candidate multivariate discriminant (e.g., evaluation value of each candidate multivariate discriminant) that are correlated to one another.

Returning to FIG. 6, the selected lung cancer state information file 106*e*3 stores the lung cancer state information including the combination of amino acid concentration data corresponding to the variable selected in the variable-selecting part 102*h*3 described below. FIG. 13 is a chart showing an example of the information stored in the selected lung cancer state information file 106*e*3. As shown in FIG. 13, the information stored in the selected lung cancer state information file 106*e*3 includes individual number, the lung cancer state index data designated in the lung cancer state information-designating part 102*g* described below, and the amino acid concentration data selected in the variable-selecting part 102*h*3 described below that are correlated to one another.

Returning to FIG. 6, the multivariate discriminant file 106*e*4 stores the multivariate discriminant prepared in the multivariate discriminant-preparing part 102*h* described below. FIG. 14 is a chart showing an example of the information stored in the multivariate discriminant file 106*e*4. As shown in FIG. 14, the information stored in the multivariate discriminant file 106*e*4 includes rank, multivariate discriminant (e.g., $F_p$ (Phe, . . . ), $F_p$ (Gly, Leu, Phe), $F_k$ (Gly, Leu, Phe, . . . ) in FIG. 14), a threshold corresponding to each discriminant-preparing method, and verification results of each multivariate discriminant (e.g., evaluation value of each multivariate discriminant) that are correlated to one another.

Returning to FIG. 6, the discriminant value file 106*f* stores the discriminant value calculated in the discriminant value-calculating part 102*i* described below. FIG. 15 is a chart showing an example of the information stored in the discriminant value file 106*f*. As shown in FIG. 15, the information stored in the discriminant value file 106*f* includes individual number for uniquely identifying an individual (sample) as a subject to be evaluated, rank (number for uniquely identifying the multivariate discriminant), and discriminant value that are correlated to one another.

Figures 16, 17:
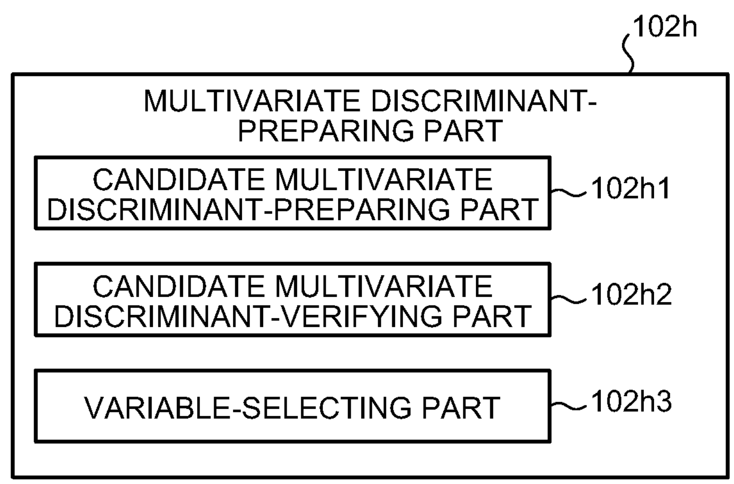
FIG. 16 is a chart showing an example of the information stored in the evaluation result file 106_g;_
FIG. 17 is a block diagram showing the configuration of the multivariable discriminant-preparing part 102_h;_

Returning to FIG. 6, the evaluation result file 106*g* stores the evaluation results obtained in the discriminant value criterion-evaluating part 102*j* described below (specifically the discrimination results obtained in the discriminant value criterion-discriminating part 102*j*1). FIG. 16 is a chart showing an example of the information stored in the evaluation result file 106*g*. The information stored in the evaluation result file 106*g* includes individual number for uniquely identifying an individual (sample) as a subject to be evaluated, the previously obtained amino acid concentration data on a subject to be evaluated, the discriminant value calculated in the multivariate discriminant, and the evaluation results on the lung cancer state (specifically, discrimination results as to discrimination between lung cancer and non-lung cancer, discrimination results as to discrimination between lung cancer with a certain disease stage and non-lung cancer, or discrimination results as to discrimination between adenocarcinoma in lung cancer and non-lung cancer) that are correlated to one another.

Returning to FIG. 6, the memory device 106 stores various Web data, CGI programs, and others for providing the client apparatuses 200 with web site information as information other than the information described above. The Web data include various data for displaying the Web page described below and others, and the data are generated as, for example, a HTML (HyperText Markup Language) or XML (Extensible Markup Language) text file. Other temporary files such as files for the components for generation of Web data and for operation, and others are also stored in the memory device 106. In addition, it may store as needed sound files in the WAVE or AIFF (Audio Interchange File Format) format for transmission to the client apparatuses 200 and image files of still image or motion picture in the JPEG (Joint Photographic Experts Group) or MPEG2 (Moving Picture Experts Group phase 2) format.

The communication interface 104 allows communication between the lung cancer-evaluating apparatus 100 and the network 300 (or communication apparatus such as router). Thus, the communication interface 104 has a function to communicate data via a communication line with other terminals.

The input/output interface 108 is connected to the input device 112 and the output device 114. A monitor (including home television), a speaker, or a printer may be used as the output device 114 (hereinafter, the output device 114 may be described as monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs information processing according to these programs. As shown in the figure, the control device 102 includes mainly the request-interpreting part 102*a*, a browsing processing part 102*b*, an authentication-processing part 102*c*, an electronic mail-generating part 102*d*, a Web page-generating part 102*e*, a receiving part 102*f*, a lung cancer state information-designating part 102*g*, a multivariate discriminant-preparing part 102*h*, a discriminant value-calculating part 102*i*, a discriminant value criterion-evaluating part 102*j*, a result outputting part 102*k* and a sending part 102*m*. The control device 102 performs data processing such as removal of data including defective or many outliers and of variables for the defective value-including data in the lung cancer state information transmitted from the database apparatus 400 and in the amino acid concentration data transmitted from the client apparatus 200.

The request-interpreting part 102*a* interprets the request from the client apparatus 200 or the database apparatus 400 and sends the request to other parts in the control device 102 according to the analytical result. Upon receiving browsing request for various screens from the client apparatus 200, the browsing processing part 102*b* generates and transmits the web data for these screens. Upon receiving authentication request from the client apparatus 200 or the database apparatus 400, the authentication-processing part 102*c* performs authentication. The electronic mail-generating part 102*d* generates an electronic mail including various kinds of information. The Web page-generating part 102*e* generates a Web page for a user to browse with the client apparatus 200.

The receiving part 102*f* receives, via the network 300, the information (specifically, the amino acid concentration data, lung cancer state information, multivariate discriminant etc.) transmitted from the client apparatus 200 and the database apparatus 400. The lung cancer state information-designating part 102*g* designates the objective lung cancer state index data and amino acid concentration data in preparing the multivariate discriminant.

The multivariate discriminant-preparing part 102*h* generates a multivariate discriminant based on the lung cancer state information received in the receiving part 102*f* and the lung cancer state information designated in the lung cancer state information-designating part 102*g*. Specifically, the multivariate discriminant-preparing part 102*h* generates a multivariate discriminant by selecting a candidate multivariate discriminant to be used as the multivariate discriminant from a plurality of candidate multivariate discriminants, according to the verification results accumulated by repeating the processings in the candidate multivariate discriminant-preparing part 102*h*1, the candidate multivariate discriminant-verifying part 102*h*2 and the variable-selecting part 102*h*3 from the lung cancer state information.

If a previously generated multivariate discriminant is stored in a predetermined region of the memory device 106, the multivariate discriminant-preparing part 102*h* may generate a multivariate discriminant by selecting a desired multivariate discriminant out of the memory device 106. Alternatively, the multivariate discriminant-preparing part 102*h* may generate the multivariate discriminant by selecting and downloading a desired multivariate discriminant from the multivariate discriminants previously stored in another computer apparatus (e.g., database apparatus 400).

Hereinafter, the configuration of the multivariate discriminant-preparing part 102*h* will be described with reference to FIG. 17. FIG. 17 is a block diagram showing the configuration of the multivariate discriminant-preparing part 102*h*, and only a part in the configuration related to the present invention is shown conceptually. The multivariate discriminant-preparing part 102*h* has a candidate multivariate discriminant-preparing part 102*h*1, a candidate multivariate discriminant-verifying part **102*h*2, and a variable-selecting part 102*h*3, additionally. The candidate multivariate discriminant-preparing part 102*h*1 generates a candidate multivariate discriminant that is a candidate of the multivariate discriminant from the lung cancer state information according to a predetermined discriminant-preparing method. Specifically, the candidate multivariate discriminant-preparing part 102*h*1 may generate a plurality of candidate multivariate discriminants from the lung cancer state information, by using a plurality of different discriminant-preparing methods. The candidate multivariate discriminant-verifying part 102*h*2 verifies the candidate multivariate discriminants prepared in the candidate multivariate discriminant-preparing part 102*h*1 according to a particular verification method. Specifically, the candidate multivariate discriminant-verifying part 102*h*2 may verify at least one of the discrimination rate, sensitivity, specificity, and information criterion of the candidate multivariate discriminants according to at least one of bootstrap method, holdout method, and leave-one-out method. The variable-selecting part 102*h*3 selects the combination of the amino acid concentration data contained in the lung cancer state information to be used in preparing the candidate multivariate discriminant, by selecting a variable of the candidate multivariate discriminant from the verification results in the candidate multivariate discriminant-verifying part 102*h*2 according to a particular variable selection method. The variable-selecting part 102*h*3** may select the variable of the candidate multivariate discriminant from the verification results according to at least one of stepwise method, best path method, local search method, and genetic algorithm.

Returning to FIG. 6, the discriminant value-calculating part **102*i* calculates a discriminant value that is the value of the multivariate discriminant, based on at least one concentration value of Orn, Lys, ABA, Arg, Glu, His, Tau, Pro, Ala, Cit and Ile contained in the amino acid concentration data of a subject to be evaluated received in the receiving part 102*f* and the multivariate discriminant containing at least one of Orn, Lys, ABA, Arg, Glu, His, Tau, Pro, Ala, Cit and Ile as variables prepared in the multivariate discriminant-preparing part 102*h***.

The multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant.

Specifically, the multivariate discriminant may be formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

The multivariate discriminant may be formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

The multivariate discriminant may be formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

The multivariate discriminant may be the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

The multivariate discriminant may be the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Figure 18:
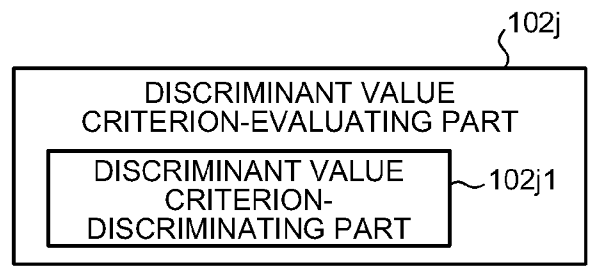
FIG. 18 is a block diagram showing the configuration of the discriminant criterion-evaluating part 102_j;_

Returning to FIG. 6, the discriminant value criterion-evaluating part **102*j* evaluates a lung cancer state in the subject to be evaluated, based on the discriminant value calculated in the discriminant value-calculating part 102*i*. The discriminant value criterion-evaluating part 102*j* further includes a discriminant value criterion-discriminating part 102*j*1. Now, the configuration of the discriminant value criterion-evaluating part 102*j* will be described with reference to FIG. 18. FIG. 18 is a block diagram showing the configuration of the discriminant value criterion-evaluating part 102*j*, and only a part in the configuration related to the present invention is shown conceptually. Based on the discriminant value, the discriminant value criterion-discriminating part 102*j*1 discriminates between lung cancer and non-lung cancer, between lung cancer with a certain disease stage and non-lung cancer, and between adenocarcinoma in lung cancer and non-lung cancer, in the subject to be evaluated. Specifically, the discriminant value criterion-discriminating part 102*j*1** compares the discriminant value with a predetermined threshold value (cutoff value), thereby discriminating between lung cancer and non-lung cancer, between lung cancer with a certain disease stage and non-lung cancer, and between adenocarcinoma in lung cancer and non-lung cancer, in the subject to be evaluated.

Returning to FIG. 6, the result outputting part 102*k* outputs, into the output device 114, the processing results in each processing part in the control device 102 (the evaluation results in the discriminant value criterion-evaluating part 102*j* (specifically the discrimination results in the discriminant value criterion-discriminating part 102*j*1)) etc.

The sending part 102*m* sends the evaluation results to the client apparatus 200 that is the sender of the amino acid concentration data of the subject to be evaluated or sends the multivariate discriminant prepared in the lung cancer-evaluating apparatus 100, and the evaluation results, to the database apparatus 400.

Figure 19:
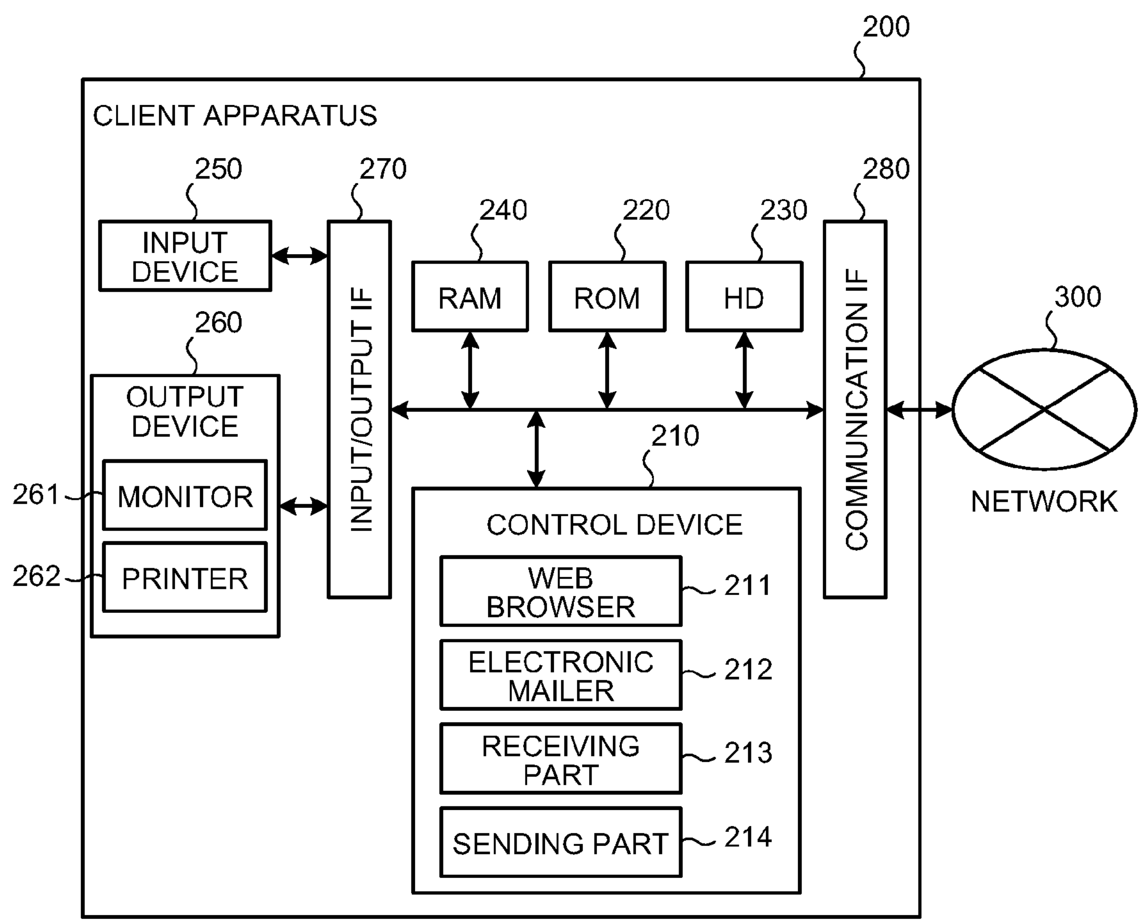
FIG. 19 is a block diagram showing an example of the configuration of the client apparatus 200 in the present system.

Hereinafter, the configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, input/output IF 270, and communication IF 280 that are connected communicatively to one another through a communication channel.

The control device 210 has a Web browser 211, an electronic mailer 212, a receiving part 213, and a sending part 214. The Web browser 211 performs browsing processing of interpreting Web data and displaying the interpreted Web data on a monitor 261 described below. The Web browser 211 may have various plug-in software, such as stream player, having functions to receive, display and feedback streaming screen image. The electronic mailer 212 sends and receives electronic mails using a particular protocol (e.g., SMTP (Simple Mail Transfer Protocol) or POP3 (Post Office Protocol version 3)). The receiving part 213 receives various information, such as the evaluation results transmitted from the lung cancer-evaluating apparatus 100, via the communication IF 280. The sending part 214 sends various information such as the amino acid concentration data on the subject to be evaluated, via communication IF 280, to the lung cancer-evaluating apparatus 100.

The input device 250 is for example a keyboard, a mouse or a microphone. The monitor 261 described below also functions as a pointing device together with a mouse. The output device 260 is an output means for outputting the information received via the communication IF 280, and includes the monitor (including home television) 261 and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as router) communicatively. In other words, the client apparatuses 200 are connected to the network 300 via a communication apparatus such as modem, TA (Terminal Adapter) or router, and a telephone line, or a private line. In this way, the client apparatuses 200 can access to the lung cancer-evaluating apparatus 100 by using a particular protocol.

The client apparatus 200 may be realized by installing software (including programs, data and others) for Web data-browsing function and electronic mail-processing function to information processing apparatus (for example, information processing terminal such as known personal computer, workstation, family computer, Internet TV (Television), PHS (Personal Handyphone System) terminal, mobile phone terminal, mobile unit communication terminal or PDA (Personal Digital Assistants)) connected as needed with peripheral devices such as printer, monitor, and image scanner.

All or a part of processings of the control device 210 in the client apparatus 200 may be performed by a CPU and programs read and executed by the CPU. Thus, computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in an application program server connected via any network to the client apparatus 200, and the client apparatus 200 may download all or a part of them as needed. All or any part of processings of the control device 210 may be realized by hardware such as wired-logic.

Hereinafter, the network 300 in the present system will be described with reference to FIGS. 4 and 5. The network 300 has a function to connect the lung cancer-evaluating apparatus 100, the client apparatuses 200, and the database apparatus 400 mutually, communicatively to one another, and is for example the Internet, intranet, or LAN (Local Area Network (both wired/wireless)). The network 300 may be VAN (Value Added Network), personal computer communication network, public telephone network (including both analog and digital), leased line network (including both analog and digital), CATV (Community Antenna Television) network, portable switched network or portable packet-switched network (including IMT2000 (International Mobile Telecommunication 2000) system, GSM (Global System for Mobile Communications) system, or PDC (Personal Digital Cellular)/PDC-P system), wireless calling network, local wireless network such as Bluetooth (registered trademark), PHS network, satellite communication network (including CS (Communication Satellite), BS (Broadcasting Satellite), and ISDB (Integrated Services Digital Broadcasting)), or the like.

Figure 20:
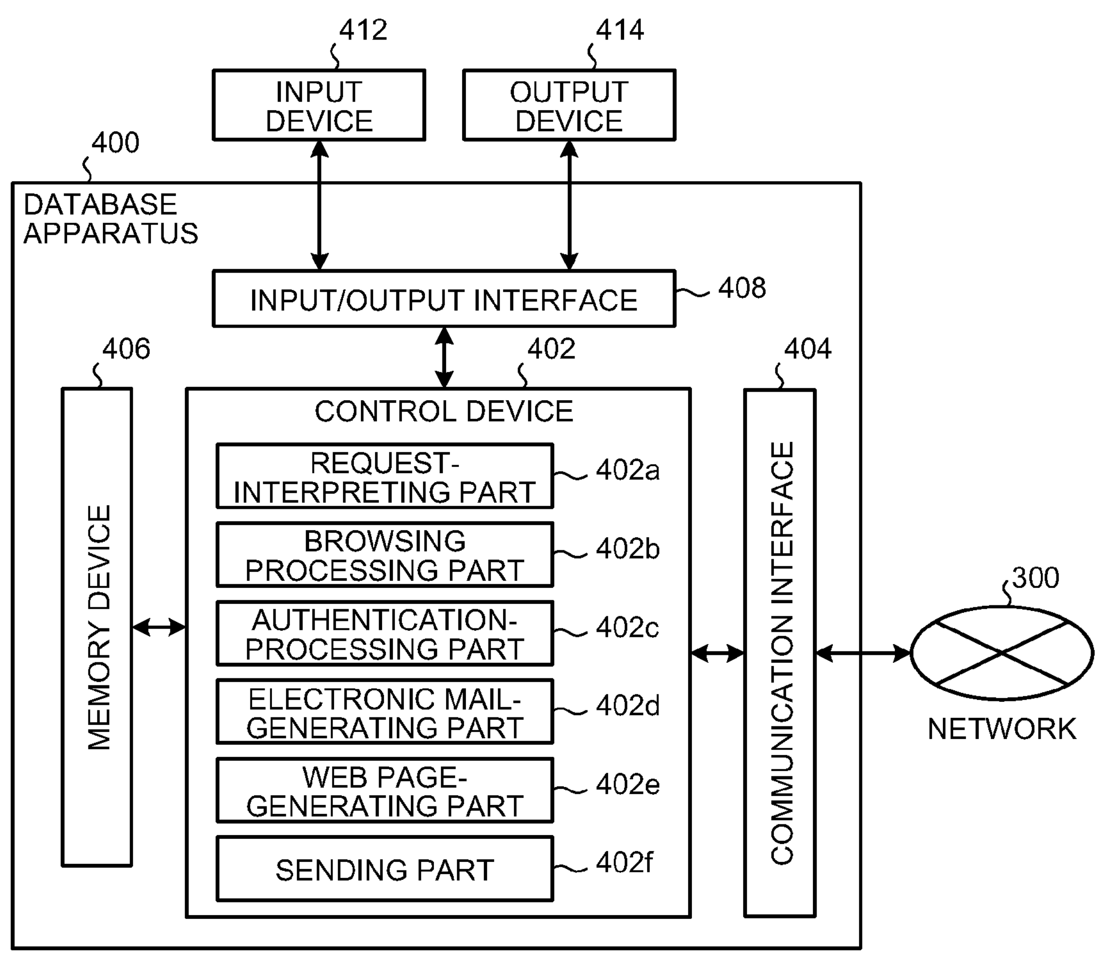
FIG. 20 is a block diagram showing an example of the configuration of the database apparatus 400 in the present system.

Hereinafter, the configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the lung cancer state information used in preparing a multivariate discriminant in the lung cancer-evaluating apparatus 100 or in the database apparatus, the multivariate discriminant prepared in the lung cancer-evaluating apparatus 100, and the evaluation results in the lung cancer-evaluating apparatus 100. As shown in FIG. 20, the database apparatus 400 includes a control device 402, such as CPU, which controls the entire database apparatus 400 integrally, a communication interface 404 connecting the database apparatus to the network 300 communicatively via a communication apparatus such as router and via a wired or wireless communication circuit such as private line, a memory device 406 storing various data, tables and files (for example, file for Web page), and an input/output interface 408 connected to an input device 412 and an output device 414, and these parts are connected communicatively to each other via any communication channel.

The memory device 406 is a storage means, and may be, for example, memory apparatus such as RAM or ROM, fixed disk drive such as harddisk, flexible disk, optical disk, or the like. Various programs used in various processings are stored in the memory device 406. The communication interface 404 allows communication between the database apparatus 400 and the network 300 (or communication apparatus such as router). Thus, the communication interface 404 has a function to communicate data with other terminal via a communication line. The input/output interface 408 is connected to the input device 412 and the output device 414. A monitor (including home television), a speaker, or a printer may be used as the output device 414 (hereinafter, the output device 414 may be described as monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processing according to these programs. As shown in the figure, the control device 402 includes mainly the request-interpreting part 402*a*, a browsing processing part 402*b*, an authentication-processing part 402*c*, an electronic mail-generating part 402*d*, a Web page-generating part 402*e*, and a sending part 402*f*.

The request-interpreting part 402*a* interprets the request from the lung cancer-evaluating apparatus 100 and sends the request to other parts in the control device 402 according to the analytical result. Upon receiving various screen-browsing request from the lung cancer-evaluating apparatus 100, the browsing processing part 402*b* generates and transmits web data for these screens. Upon receipt of authentication request from the lung cancer-evaluating apparatus 100, the authentication-processing part 402*c* performs authentication. The electronic mail-generating part 402*d* generates an electronic mail including various information. The Web page-generating part 402*e* generates a Web page for a user to browse with the client apparatus 200. The sending part 402*f* sends the information such as the lung cancer state information and the multivariate discriminant to the lung cancer-evaluating apparatus 100.

2-3. Processing in the Present System

Figure 21:
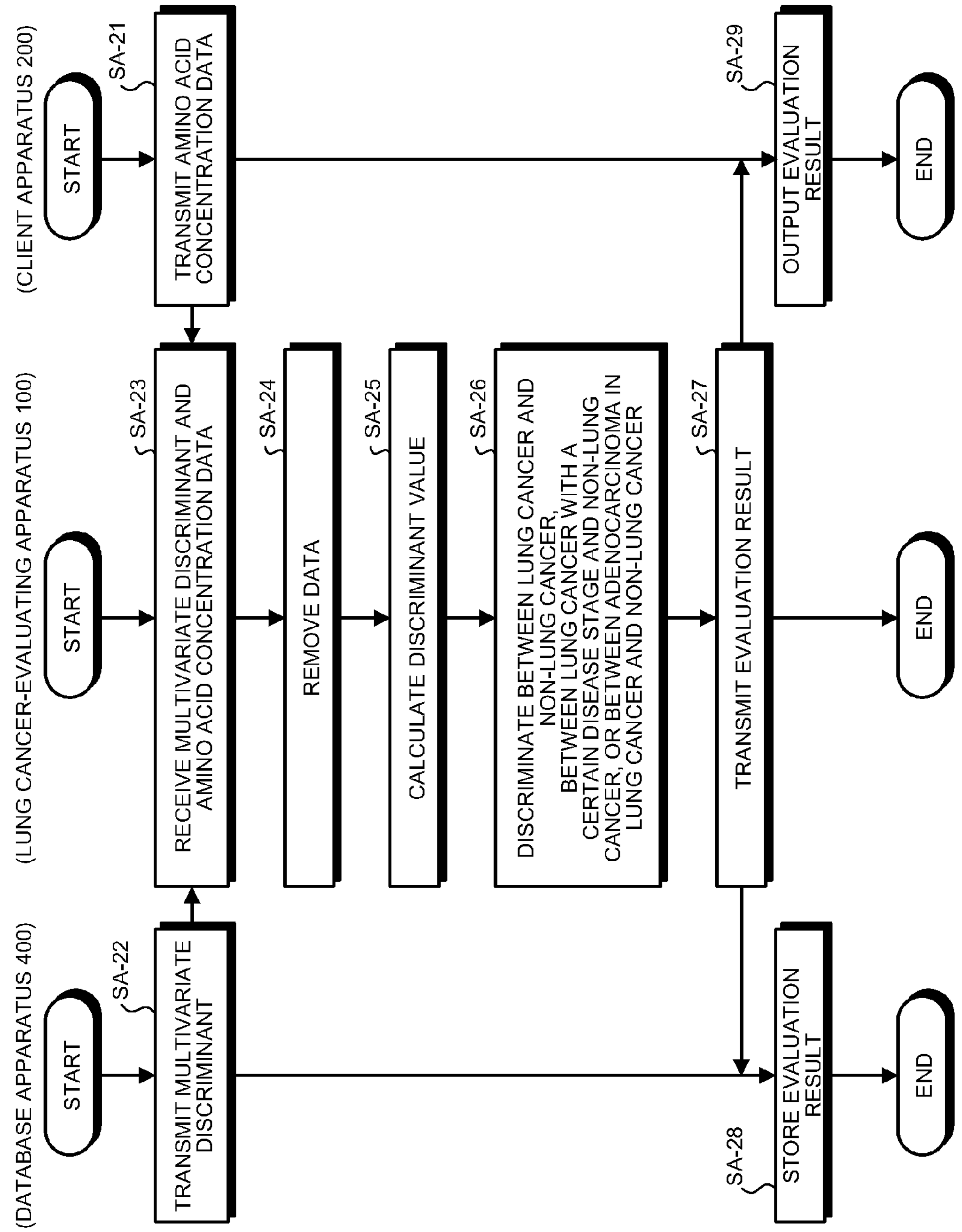
FIG. 21 is a flowchart showing an example of the lung cancer evaluation service processing performed in the present system.

Here, an example of the lung cancer evaluation service processing performed in the present system constituted as described above will be described with reference to FIG. 21. FIG. 21 is a flowchart showing an example of the lung cancer evaluation service processing.

The amino acid concentration data used in the present processing concerns amino acid concentration value obtained by analyzing blood previously collected from an individual. Hereinafter, the method of analyzing blood amino acid will be described briefly. First, a blood sample is collected in a heparin-treated tube, and then the blood plasma is separated by centrifugation of the tube. All blood plasma samples separated are frozen and stored at −70° C. before measurement of amino acid concentration. Before measurement of amino acid concentration, the blood plasma sample is deproteinized by adding sulfosalicylic acid to a concentration of 3%. An amino acid analyzer by high-performance liquid chromatography (HPLC) by using ninhydrin reaction in the post column was used for measurement of amino acid concentration.

First, the client apparatus 200 accesses the lung cancer-evaluating apparatus 100 when the user specifies the Web site address (such as URL) provided from the lung cancer-evaluating apparatus 100, via the input device 250 on the screen displaying Web browser 211. Specifically, when the user instructs update of the Web browser 211 screen on the client apparatus 200, the Web browser 211 sends the Web site's address provided from the lung cancer-evaluating apparatus 100 by a particular protocol, thereby transmitting a request demanding transmission of the Web page corresponding to the amino acid concentration data transmission screen to the lung cancer-evaluating apparatus 100 based on the routing of the address.

Then, upon receipt of the request from the client apparatus 200, the request-interpreting part 102*a* in the lung cancer-evaluating apparatus 100 analyzes the transmitted request and sends the request to other parts in the control device 102 according to the analytical result. Specifically, when the transmitted request is a request to send the Web page corresponding to the amino acid concentration data transmission screen, mainly the browsing processing part 102*b* in the lung cancer-evaluating apparatus 100 obtains the Web data for display of the Web page stored in a predetermined region of the memory device 106 and sends the obtained Web data to the client apparatus 200. More specifically, upon receiving the Web page transmission request corresponding to the amino acid concentration data transmission screen by the user, the control device 102 in the lung cancer-evaluating apparatus 100 demands input of user ID and user password from the user. If the user ID and password are input, the authentication-processing part 102*c* in the lung cancer-evaluating apparatus 100 examines the input user ID and password by comparing them with the user ID and user password stored in the user information file 106*a* for authentication. Only when the user is authenticated, the browsing processing part 102*b* in the lung cancer-evaluating apparatus 100 sends, to the client apparatus 200, the Web data for displaying the Web page corresponding to the amino acid concentration data transmission screen. The client apparatus 200 is identified with the IP (Internet Protocol) address transmitted from the client apparatus 200 together with the transmission request.

Then, the client apparatus 200 receives, in the receiving part 213, the Web data (for displaying the Web page corresponding to the amino acid concentration data transmission screen) transmitted from the lung cancer-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 sends an identifier for identifying input information and selected items to the lung cancer-evaluating apparatus 100, thereby transmitting the amino acid concentration data of the individual as the subject to be evaluated to the lung cancer-evaluating apparatus 100 (step SA-21). In step SA-21, transmission of the amino acid concentration data may be realized for example by using an existing file transfer technology such as FTP (File Transfer Protocol).

Then, the request-interpreting part 102*a* of the lung cancer-evaluating apparatus 100 interprets the identifier transmitted from the client apparatus 200 thereby analyzing the request from the client apparatus 200, and requests the database apparatus 400 to send the multivariate discriminant for lung cancer evaluation (specifically for discrimination of the 2 groups of lung cancer and non-lung cancer, for discrimination of the 2 groups of early lung cancer and non-lung cancer, and for discrimination of the 2 groups of adenocarcinoma in lung cancer and non-lung cancer)containing at least one of Orn, Lys, ABA, Arg, Glu, His, Tau, Pro, Ala, Cit and Ile as variables.

Then, the request-interpreting part 402*a* of the database apparatus 400 interprets the transmission request from the lung cancer-evaluating apparatus 100 and transmits, to the lung cancer-evaluating apparatus 100, the multivariate discriminant (for example, the updated newest multivariate discriminant) containing at least one of Orn, Lys, ABA, Arg, Glu, His, Tau, Pro, Ala, Cit and Ile as variables, stored in a predetermined region of the memory device 406 (step SA-22).

In step SA-22, the multivariate discriminant transmitted to the lung cancer-evaluating apparatus 100 may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant.

Specifically, when between lung cancer and non-lung cancer is discriminated in step SA-26 described below, the multivariate discriminant may be formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers.

When between lung cancer with a certain disease stage and non-lung cancer is discriminated in step SA-26 described below, the multivariate discriminant may be formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

When between adenocarcinoma in lung cancer and non-lung cancer is discriminated in step SA-26 described below, the multivariate discriminant may be formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

In step SA-22, the multivariate discriminant transmitted to the lung cancer-evaluating apparatus 100 may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, when between lung cancer and non-lung cancer is discriminated in step SA-26, the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables.

When between lung cancer with a certain disease stage and non-lung cancer is discriminated in step SA-26, the multivariate discriminant may be the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables.

When between adenocarcinoma in lung cancer and non-lung cancer is discriminated in step SA-26, the multivariate discriminant may be the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables.

Returning to FIG. 21, the lung cancer-evaluating apparatus 100 receives, in the receiving part 102*f*, the amino acid concentration data of the individual transmitted from the client apparatuses 200, receives the multivariate discriminant transmitted from the database apparatus 400, stores the received amino acid concentration data in a predetermined memory region of the amino acid concentration data file 106*b*, and stores the received multivariate discriminant in a predetermined memory region of a multivariate discriminant file 106*e*4 (step SA-23).

In the control device 102 of the lung cancer-evaluating apparatus 100, data such as defective and outliers are then removed from the amino acid concentration data of the individual received in step SA-23 (step SA-24).

Then, the lung cancer-evaluating apparatus 100 calculates a discriminant value in the discriminant value-calculating part 102*i*, based on the multivariate discriminant received in step SA-23 and at least one concentration of Orn, Lys, ABA, Arg, Glu, His, Tau, Pro, Ala, Cit and Ile contained in the amino acid concentration data of the individual from which defective and outliers have been removed in step SA-24 (step SA-25).

Then, the discriminant value criterion-discriminating part 102*j*1 of the lung cancer-evaluating apparatus 100 compares the discriminant value calculated in step SA-25 with a previously established threshold (cutoff value), thereby discriminating between lung cancer and non-lung cancer, between lung cancer with a certain disease stage and non-lung cancer, and between adenocarcinoma in lung cancer and non-lung cancer, in the subject to be evaluated, and the discrimination results are stored in a predetermined memory region of the evaluation result file 106*g* (step SA-26).

The sending part 102*m* of the lung cancer-evaluating apparatus 100 then sends the discrimination results (discrimination results as to discrimination between lung cancer and non-lung cancer, discrimination results as to discrimination between lung cancer with a certain disease stage and non-lung cancer, or discrimination results as to discrimination between adenocarcinoma in lung cancer and non-lung cancer) obtained in step SA-26 to the client apparatus 200 that has sent the amino acid concentration data and to the database apparatus 400 (step SA-27). Specifically, the lung cancer-evaluating apparatus 100 first generates a Web page for display of discrimination results in the Web page-generating part 102*e* and stores the Web data corresponding to the generated Web page, in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the lung cancer-evaluating apparatus 100. The lung cancer-evaluating apparatus 100 then examines the browsing request transmitted from the client apparatus 200 in the browsing processing part 102*b* and reads the Web data corresponding to the Web page for displaying the discrimination results, out of the predetermined memory region of the memory device 106. The sending part 102*m* of the lung cancer-evaluating apparatus 100 then sends the read-out Web data to the client apparatus 200 and simultaneously sends the Web data or the discrimination results to the database apparatus 400.

In step SA-27, the control device 102 of the lung cancer-evaluating apparatus 100 may notify the discrimination results to the user client apparatus 200 by electronic mail. Specifically, the lung cancer-evaluating apparatus 100 first acquires the user electronic mail address in the electronic mail-generating part 102*d* at the transmission timing for example based on the user ID, with reference to the user information stored in the user information file 106*a*. The lung cancer-evaluating apparatus 100 then generates electronic mail data including user name and discrimination result, with the electronic mail address obtained as its mail address in the electronic mail-generating part 102*d*. The sending part 102*m* of the lung cancer-evaluating apparatus 100 then sends the generated data to the user client apparatus 200.

Also in step SA-27, the lung cancer-evaluating apparatus 100 may send the discrimination results to the user client apparatus 200 by using an existing file transfer technology such as FTP.

Returning to FIG. 21, the control device 402 in the database apparatus 400 receives the discrimination results or the Web data transmitted from the lung cancer-evaluating apparatus 100 and stores (accumulates) the received discrimination results or Web data in a predetermined memory region of the memory device 406 (step SA-28).

The receiving part 213 of the client apparatus 200 receives the Web data transmitted from the lung cancer-evaluating apparatus 100, and the received Web data are interpreted with the Web browser 211, to display on the monitor 261 the Web page screen displaying the discrimination result of the individual (step SA-29). When the discrimination results are sent from the lung cancer-evaluating apparatus 100 by electronic mail, the electronic mail transmitted from the lung cancer-evaluating apparatus 100 is received at any timing, and the received electronic mail is displayed on the monitor 261 with the known function of the electronic mailer 212 of the client apparatus 200.

In this way, the user knows discrimination results as to discrimination of 2 groups of lung cancer and non-lung cancer, discrimination results as to discrimination of 2 groups of lung cancer with a certain disease stage and non-lung cancer, or discrimination results as to discrimination of 2 groups adenocarcinoma in lung cancer and non-lung cancer, in the individual, by browsing the Web page displayed on the monitor 261. The user can print out the content of the Web page displayed on the monitor 261 by a printer 262.

When the discrimination results are transmitted by electronic mail from the lung cancer-evaluating apparatus 100, the user reads the electronic mail displayed on the monitor 261, whereby the user can confirm discrimination results as to discrimination of 2 groups of lung cancer and non-lung cancer, discrimination results as to discrimination of 2 groups of lung cancer with a certain disease stage and non-lung cancer, or discrimination results as to discrimination of 2 groups adenocarcinoma in lung cancer and non-lung cancer, in the individual. The user may print out the content of the electronic mail displayed on the monitor 261 by the printer 262.

Given the foregoing description, the explanation of the lung cancer evaluation service processing is finished.

2-4. Summary of the Second Embodiment and Other Embodiments

According to the lung cancer-evaluating system described above in detail, the client apparatus 200 sends the amino acid concentration data of the individual to the lung cancer-evaluating apparatus 100, and upon receiving a request from the lung cancer-evaluating apparatus 100, the database apparatus 400 transmits the multivariate discriminant containing at least one of Orn, Lys, ABA, Arg, Glu, His, Tau, Pro, Ala, Cit and Ile as variables, to the lung cancer-evaluating apparatus 100. By the lung cancer-evaluating apparatus 100, (1) amino acid concentration data are received from the client apparatus 200, and simultaneously the multivariate discriminant is received from the database apparatus 400, (2) data such as defective and outliers are removed from the received amino acid concentration data of the individual, (3) a discriminant value is calculated based on at least one concentration value of Orn, Lys, ABA, Arg, Glu, His, Tau, Pro, Ala, Cit and Ile contained in the amino acid concentration data of the individual from which defective and outliers have been removed and the received multivariate discriminant containing at least one of Orn, Lys, ABA, Arg, Glu, His, Tau, Pro, Ala, Cit and Ile as variables, (4) the calculated discriminant value is compared with a previously established threshold, thereby discriminating between lung cancer and non-lung cancer, between lung cancer with a certain disease stage and non-lung cancer, and between adenocarcinoma in lung cancer and non-lung cancer, in the individual, and (5) this discrimination result is transmitted to the client apparatus 200 and database apparatus 400. Then, the client apparatus 200 receives and displays the discrimination result transmitted from the lung cancer-evaluating apparatus 100, and the database apparatus 400 receives and stores the discrimination result transmitted from the lung cancer-evaluating apparatus 100. Thus, a discriminant value obtained in a multivariate discriminant using amino acid variables useful for discriminating between the 2 groups of lung cancer and non-lung cancer, a multivariate discriminant using amino acid variables useful for discriminating between the 2 groups of early lung cancer and non-lung cancer, and a multivariate discriminant using amino acid variables useful for discriminating between the 2 groups of adenocarcinoma in lung cancer and non-lung cancer can be utilized to bring about an effect of enabling accurate discrimination between the 2 groups of lung cancer and non-lung cancer, between the 2 groups of early lung cancer and non-lung cancer, and between the 2 groups of adenocarcinoma in lung cancer and non-lung cancer.

According to the lung cancer-evaluating system, the multivariate discriminant may be expressed by one fractional expression or the sum of a plurality of the fractional expressions and may contain at least one of Orn, Lys, ABA, Arg, Glu, His, Tau, Pro, Ala, Cit and Ile as the variable in any one of the numerator and denominator or both in the fractional expression constituting the multivariate discriminant. Thus, a discriminant value obtained in a multivariate discriminant (fractional expression) using amino acid variables useful for discriminating between the 2 groups of lung cancer and non-lung cancer, a multivariate discriminant (fractional expression) using amino acid variables useful for discriminating between the 2 groups of early lung cancer and non-lung cancer, and a multivariate discriminant (fractional expression) using amino acid variables useful for discriminating between the 2 groups of adenocarcinoma in lung cancer and non-lung cancer can be utilized to bring about an effect of enabling more accurate discrimination between the 2 groups of lung cancer and non-lung cancer, between the 2 groups of early lung cancer and non-lung cancer, and between the 2 groups of adenocarcinoma in lung cancer and non-lung cancer.

Specifically, when between lung cancer and non-lung cancer is discriminated in step SA-26, the multivariate discriminant may be formula 1, 2 or 3:

$$a_1 \times Orn/Trp + b_1 \times (Tau+ABA)/Arg + c_1 \quad \text{(formula 1)}$$

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_1$, $b_1$ and $c_1$ in the formula 1 are arbitrary real numbers, $a_2$, $b_2$ and $c_2$ in the formula 2 are arbitrary real numbers, and $a_3$, $b_3$, $c_3$, $d_3$, and $e_3$ in the formula 3 are arbitrary real numbers. Thus, discriminant values obtained in multivariate discriminants (formulae 1, 2 and 3) using amino acid variables useful particularly for discriminating between the 2 groups of lung cancer and non-lung cancer can be utilized to bring about an effect of enabling more accurate discrimination between the 2 groups of lung cancer and non-lung cancer.

When between lung cancer with a certain disease stage and non-lung cancer is discriminated in step SA-26, the multivariate discriminant may be formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers. Thus, discriminant values obtained in multivariate discriminants (formulae 4, 5 and 6) using amino acid variables useful particularly for discriminating between the 2 groups of early lung cancer and non-lung cancer can be utilized to bring about an effect of enabling more accurate discrimination between the 2 groups of early lung cancer and non-lung cancer.

When between adenocarcinoma in lung cancer and non-lung cancer is discriminated in step SA-26, the multivariate discriminant may be formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers. Thus, discriminant values obtained in multivariate discriminants (formulae 7, 8 and 9) using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

According to the lung cancer-evaluating system, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of lung cancer and non-lung cancer, a multivariate discriminant using amino acid variables useful for discriminating between the 2 groups of early lung cancer and non-lung cancer, and a multivariate discriminant using amino acid variables useful for discriminating between the 2 groups of adenocarcinoma in lung cancer and non-lung cancer can be utilized to bring about an effect of enabling more accurate discrimination between the 2 groups of lung cancer and non-lung cancer, between the 2 groups of early lung cancer and non-lung cancer, and between the 2 groups of adenocarcinoma in lung cancer and non-lung cancer.

Specifically, when between lung cancer and non-lung cancer is discriminated in step SA-26, the multivariate discriminant may be the logistic regression equation with Tau, Orn, Arg, Ser, Glu, Pro and Asn as the variables, the linear discriminant with age and ABA, Arg, Gln, His, Leu, Orn, Pro, Tau, Trp and Val as the variables, the logistic regression equation with His, Glu, Pro, Ile, Gln and Lys as the variables, or the linear discriminant with His, Glu, Pro, Ile, Tyr and Lys as the variables. Thus, a discriminant value obtained in a multivariate discriminant using amino acid variables useful particularly for discriminating between the 2 groups of lung cancer and non-lung cancer can be utilized to bring about an effect of enabling more accurate discrimination between the 2 groups of lung cancer and non-lung cancer.

When between lung cancer with a certain disease stage and non-lung cancer is discriminated in step SA-26, the multivariate discriminant may be the logistic regression equation with Orn, Tau and Trp as the variables, the linear discriminant with Orn, Arg, Tau, ABA, Gly and His as the variables, the logistic regression equation with Gln, Glu, His, Lys, Cys and ABA as the variables, or the linear discriminant with Gln, Glu, Ala, His, Cys and ABA as the variables. Thus, a discriminant value obtained in a multivariate discriminant using amino acid variables useful particularly for discriminating between the 2 groups of early lung cancer and non-lung cancer can be utilized to bring about an effect of enabling more accurate discrimination between the 2 groups of early lung cancer and non-lung cancer.

When between adenocarcinoma in lung cancer and non-lung cancer is discriminated in step SA-26, the multivariate discriminant may be the logistic regression equation with Orn, ABA, Tau and Gly as the variables, the linear discriminant with Orn, ABA, Tau, His, Arg and Gly as the variables, the logistic regression equation with His, Ile, Glu, Pro, Leu and Gln as the variables, or the linear discriminant with His, Ile, Pro, Ala, Leu and Gln as the variables. Thus, a discriminant value obtained in a multivariate discriminant using amino acid variables useful particularly for discriminating between the 2 groups of adenocarcinoma in lung cancer and non-lung cancer can be utilized to bring about an effect of enabling more accurate discrimination between the 2 groups of adenocarcinoma in lung cancer and non-lung cancer.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a lung cancer state, regardless of the unit of amino acid concentration in the amino acid concentration data as input data.

In addition to the second embodiment described above, the lung cancer-evaluating apparatus, the lung cancer-evaluating method, the lung cancer-evaluating system, the lung cancer-evaluating program and the recording medium according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the lung cancer-evaluating apparatus 100 shown in the figures are conceptual and functional and may not be the same physically as those shown in the figure. In addition, all or a part of the operational function of each component and each device in the lung cancer-evaluating apparatus 100 (in particular, processings in control device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may not be configured singly, and may be operated together with plurality of modules and libraries or with a different program such as OS (Operating System) to achieve the function. The program is stored on a recording medium and read mechanically as needed by the lung cancer-evaluating apparatus 100. Any well-known configuration or procedure may be used for reading the programs recorded on the recording medium in each apparatus and for reading procedure and installation of the procedure after reading.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), and the like. Examples of the "fixed physical media" include various media installed in a computer system such as ROM, RAM, and HD. The "communication media" for example stores the program for a short period of time such as communication line and carrier wave when the program is transmitted via a network such as LAN (Local Area Network), WAN (Wide Area Network), or the Internet.

Figure 22:
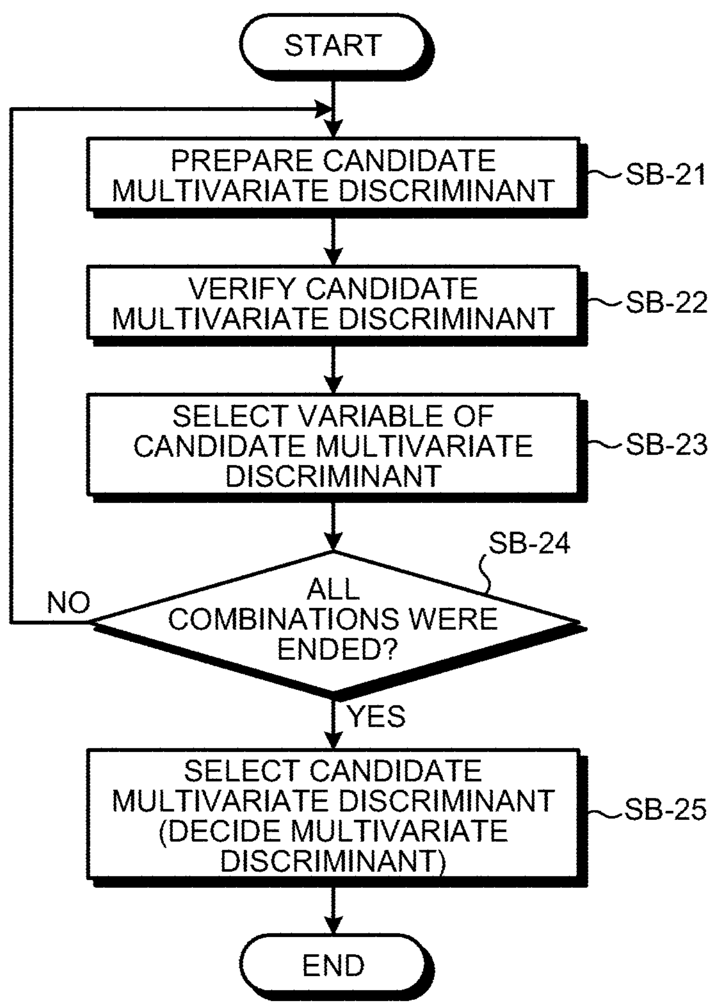
FIG. 22 is a flowchart showing an example of the multivariate discriminant-preparing processing performed in the lung cancer-evaluating apparatus 100 in the present system.

Finally, an example of the multivariate discriminant-preparing processing performed in the lung cancer-evaluating apparatus 100 is described in detail with reference to FIG. 22. FIG. 22 is a flowchart showing an example of the multivariate discriminant-preparing processing. The multivariate discriminant-preparing processing may be performed in the database apparatus 400 handling the lung cancer state information.

In the present description, the lung cancer-evaluating apparatus 100 stores the lung cancer state information previously obtained from the database apparatus 400 in a predetermined memory region of the lung cancer state information file 106*c*. The lung cancer-evaluating apparatus 100 shall store, in a predetermined memory region of the designated lung cancer state information file 106*d*, the lung cancer state information including the lung cancer state index data and amino acid concentration data designated previously in the lung cancer state information-designating part 102*g*.

According to a predetermined discriminant-preparing method, the candidate multivariate discriminant-preparing part 102*h*1 in the multivariate discriminant-preparing part 102*h* first prepares a candidate multivariate discriminant from the lung cancer state information stored in a predetermine memory region of the designated lung cancer state information file 106*d*, and the prepared candidate multivariate discriminate is stored in a predetermined memory region of the candidate multivariate discriminant file 106*e*1 (step SB-21). Specifically, the candidate multivariate discriminant-preparing part 102*h*1 in the multivariate discriminant-preparing part 102*h* first selects a desired method out of a plurality of different discriminant-preparing methods (including multivariate analysis methods such as principal component analysis, discriminant analysis, support vector machine, multiple regression analysis, logistic regression analysis, k-means method, cluster analysis, and decision tree and the like) and determines the form of the candidate multivariate discriminant to be prepared based on the selected discriminant-preparing method. The candidate multivariate discriminant-preparing part 102*h*1 in the multivariate discriminant-preparing part 102*h* then performs various calculation corresponding to the selected function-selecting method (e.g., average or variance), based on the lung cancer state information. The candidate multivariate discriminant-preparing part 102*h*1 in the multivariate discriminant-preparing part 102*h* then determines the parameters for the calculation result and the determined candidate multivariate discriminant. In this way, a candidate multivariate discriminant is generated based on the selected discriminant-preparing method. When candidate multivariate discriminants are generated simultaneously and concurrently (in parallel) by using a plurality of different discriminant-preparing methods in combination, the processings described above may be executed concurrently for each selected discriminant-preparing method. Alternatively when candidate multivariate discriminants are to be generated in series by using a plurality of different discriminant-preparing methods in combination, for example, candidate multivariate discriminants may be generated by converting lung cancer state information with a candidate multivariate discriminant prepared by performing principal component analysis and performing discriminant analysis of the converted lung cancer state information.

The candidate multivariate discriminant-verifying part 102*h*2 in the multivariate discriminant-preparing part 102*h* verifies (mutually verifies) the candidate multivariate discriminant prepared in step SB-21 according to a particular verification method and stores the verification result in a predetermined memory region of verification result file 106*e*2 (step SB-22). Specifically, the candidate multivariate discriminant-verifying part 102*h*2 in the multivariate discriminant-preparing part 102*h* first generates the verification data to be used in verification of the candidate multivariate discriminant, based on the lung cancer state information stored in a predetermined memory region of the designated lung cancer state information file 106*d*, and verifies the candidate multivariate discriminant according to the generated verification data. If a plurality of candidate multivariate discriminants are generated by using a plurality of different discriminant-preparing methods in step SB-21, the candidate multivariate discriminant-verifying part 102*h*2 in the multivariate discriminant-preparing part 102*h* verifies each candidate multivariate discriminant corresponding to each discriminant-preparing method according to a particular verification method. Here in step SB-22, at least one of the discrimination rate, sensitivity, specificity, information criterion, and the like of the candidate multivariate discriminant may be verified based on at least one method of the bootstrap, holdout, leave-one-out, and other methods. Thus, it is possible to select a candidate multivariate discriminant higher in predictability or reliability, based on the lung cancer state information and diagnostic condition.

Then, the variable-selecting part 102*h*3 in the multivariate discriminant-preparing part 102*h* selects the combination of amino acid concentration data contained in the lung cancer state information to be used in preparing the candidate multivariate discriminant by selecting a variable of the candidate multivariate discriminant from the verification results in step SB-22 according to a particular variable selection method, and stores the lung cancer state information including the selected combination of amino acid concentration data in a predetermined memory region of the selected lung cancer state information file 106*e*3 (step SB-23). When a plurality of candidate multivariate discriminants are generated by using a plurality of different discriminant-preparing methods in step SB-21 and each candidate multivariate discriminant corresponding to each discriminant-preparing method is verified according to a particular verification method in step SB-22, the variable-selecting part 102*h*3 in the multivariate discriminant-preparing part 102*h* selects the variable of the candidate multivariate discriminant for each candidate multivariate discriminant corresponding to the verification result obtained in step SB-22, according to a particular variable selection method in step SB-23. Here in step SB-23, the variable of the candidate multivariate discriminant may be selected from the verification results according to at least one of stepwise method, best path method, local search method, and genetic algorithm. The best path method is a method of selecting a variable by optimizing the evaluation index of the candidate multivariate discriminant while eliminating the variables contained in the candidate multivariate discriminant one by one. In step SB-23, the variable-selecting part 102*h*3 in the multivariate discriminant-preparing part 102*h* may select the combination of amino acid concentration data based on the lung cancer state information stored in a predetermined memory region of the designated lung cancer state information file 106*d*.

The multivariate discriminant-preparing part 102*h* then judges whether all combinations of the amino acid concentration data contained in the lung cancer state information stored in a predetermined memory region of the designated lung cancer state information file 106*d* are processed, and if the judgment result is "End" (Yes in step SB-24), the processing advances to the next step (step SB-25), and if the judgment result is not "End" (No in step SB-24), it returns to step SB-21. The multivariate discriminant-preparing part 102*h* judges whether the processing is performed a predetermined number of times, and if the judgment result is "End" (Yes in step SB-24), the processing may advance to the next step (step SB-25), and if the judgment result is not "End" (No in step SB-24), it returns to step SB-21. The multivariate discriminant-preparing part 102*h* may judge whether the combination of the amino acid concentration data selected in step SB-23 is the same as the combination of the amino acid concentration data contained in the lung cancer state information stored in a predetermined memory region of the designated lung cancer state information file 106*d* or the combination of the amino acid concentration data selected in the previous step SB-23, and if the judgment result is "the same" (Yes in step SB-24), the processing may advance to the next step (step SB-25) and if the judgment result is not "the same" (No in step SB-24), it may return to step SB-21. If the verification result is specifically the evaluation value for each multivariate discriminant, the multivariate discriminant-preparing part 102*h* may advance to step SB-25 or return to step SB-21, based on the comparison of the evaluation value with a particular threshold corresponding to each discriminant-preparing method.

Then, the multivariate discriminant-preparing part 102*h* determines the multivariate discriminant based on the verification results by selecting a candidate multivariate discriminant to be used as the multivariate discriminant among the candidate multivariate discriminants, and stores the determined multivariate discriminant (selected candidate multivariate discriminant) in particular memory region of the multivariate discriminant file 106*e*4 (step SB-25). Here, in step SB-25, for example, the optimal multivariate discriminant may be selected from the candidate multivariate discriminants prepared by the same discriminant-preparing method or from all candidate multivariate discriminants.

These are description of the multivariate discriminant-preparing processing.

Example 1

Figure 23:
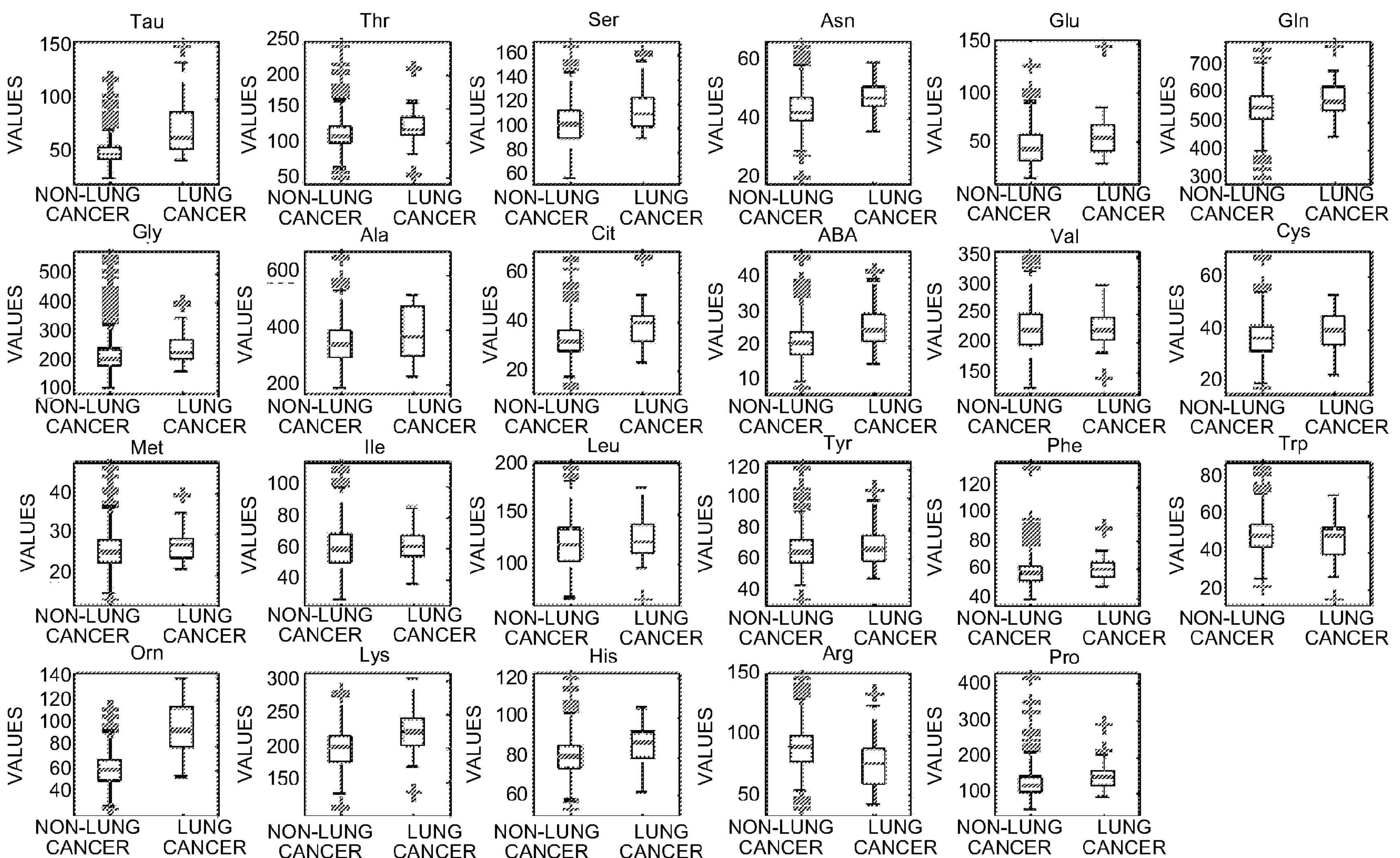
FIG. 23 is a boxplot showing the distribution of amino acid variables between 2 groups of non-lung cancer and lung cancer.

Blood samples of lung cancer patients diagnosed by lung biopsy, and blood samples of healthy subjects, were measured for their blood amino acid concentration by the amino acid analysis method described above. The unit of amino acid concentration is nmol/ml. FIG. 23 is a boxplot showing the distribution of amino acid variables in the lung cancer patients and healthy subjects (non-lung cancer group and lung cancer group on the abscissa; ABA is α-ABA (aminobutyric acid), and Cys is Cystine). For the purpose of discrimination between the lung cancer group and non-lung cancer group, t-test of the 2 groups was performed.

In the lung cancer group as compared with the non-lung caner group, Tau, Glu, ABA, Val, Leu, Orn, Lys and His were significantly increased (significant difference possibility $P<0.05$), and Arg was significantly reduced, and it was revealed that the amino acid variables Tau, Glu, ABA, Val, Leu, Orn, Lys, His and Arg have an ability to discriminate between the 2 groups of the lung cancer group and non-lung cancer group.

Example 2

Blood samples of lung cancer patients diagnosed by lung biopsy, and blood samples of healthy subjects, were measured for their blood amino acid concentration by the amino acid analysis method described above. In FIG. 24, discrimination of the 2 groups of lung cancer group and non-lung cancer group, early lung cancer group and non-lung-cancer group, or adenocarcinoma group in lung cancer group and non-lung cancer group was evaluated by the AUC (area under the curve) of the ROC (receiver operating characteristic) curve (FIG. 24) using the amino acid variables of the lung cancer patients and the healthy subjects.

A value of 0.65 or more was obtained by Orn, Tau, ABA, Asn, Lys, Cit, Arg, Ser, Thr, Gly, Glu, His and Pro in discrimination between the lung cancer group and the non-lung caner group, by Orn, Arg, Tau, ABA, Gly, Asn, Cit, Lys, Ser, His and Pro in discrimination between the early lung cancer group and the non-lung cancer group, and by Orn, Tau, ABA, Asn, Lys, Cit, His, Arg, Thr, Glu, Gly and Cys in discrimination between the adenocarcinoma group in the lung cancer group and the non-lung cancer group, and it was revealed that these amino acids have an ability to discriminate between the 2 groups mentioned above.

Example 3

The sample data used in Example 1 were used. Using a method described in International Publication WO 2004/052191 that is an international application filed by the present applicant, an index by which the performance of discriminating the 2 groups of lung cancer group and non-lung cancer group was maximized for discrimination of lung cancer was extensively studied to give index 1 in a plurality of indices having the same performance. Besides, a plurality of logistic regression equations having the same discrimination performance as that of the index 1 were obtained. These are shown in FIGS. 25 and 26.

(Orn)/(Trp)+(Tau+ABA)/(Arg) Index 1

Figure 27:
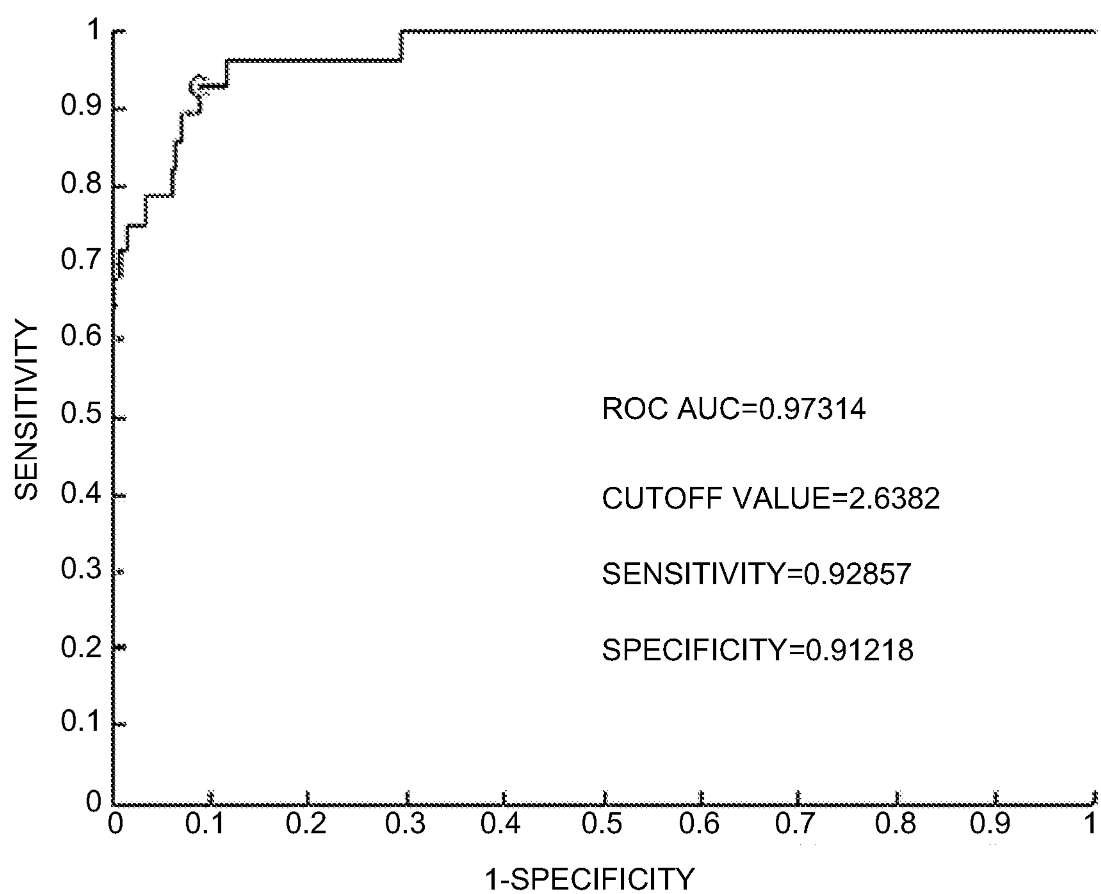
FIG. 27 is a graph showing an ROC curve for evaluation of diagnostic performance between 2 groups.

Discrimination of the 2 groups of lung cancer group and non-lung cancer group by the index 1 was evaluated by the AUC of the ROC curve (FIG. 27), to give an AUC of 0.973±0.020 (95% confidence interval: 0.936 to 0.986). When the optimum cutoff value for discrimination of the 2 groups of lung cancer group and non-lung cancer group by the index 1 was determined assuming that the incidence of lung cancer group was 0.038, the cutoff value was 2.64, and the sensitivity was 93%; the specificity, 91%; the positive predictive value, 29%; the negative predictive value, 99%, and the correct diagnostic rate, 96% (FIG. 28), and the index 1 was revealed to be an useful index with high diagnostic performance.

Example 4

The sample data used in Example 1 were used. Using a method described in International Publication WO 2004/052191 that is an international application filed by the present applicant, an index by which the performance of discriminating the 2 groups of early lung cancer group (pathological stages I and II) and non-lung cancer group was maximized for discrimination of lung cancer was extensively studied to give index 2 in a plurality of indices having the same performance. Besides, a plurality of logistic regression equations having the same discrimination performance as that of the index 2 were obtained. These are shown in FIGS. 29 and 30.

(Tau)/(Arg)+(Orn+ABA)/(Trp) Index 2

Figure 31:
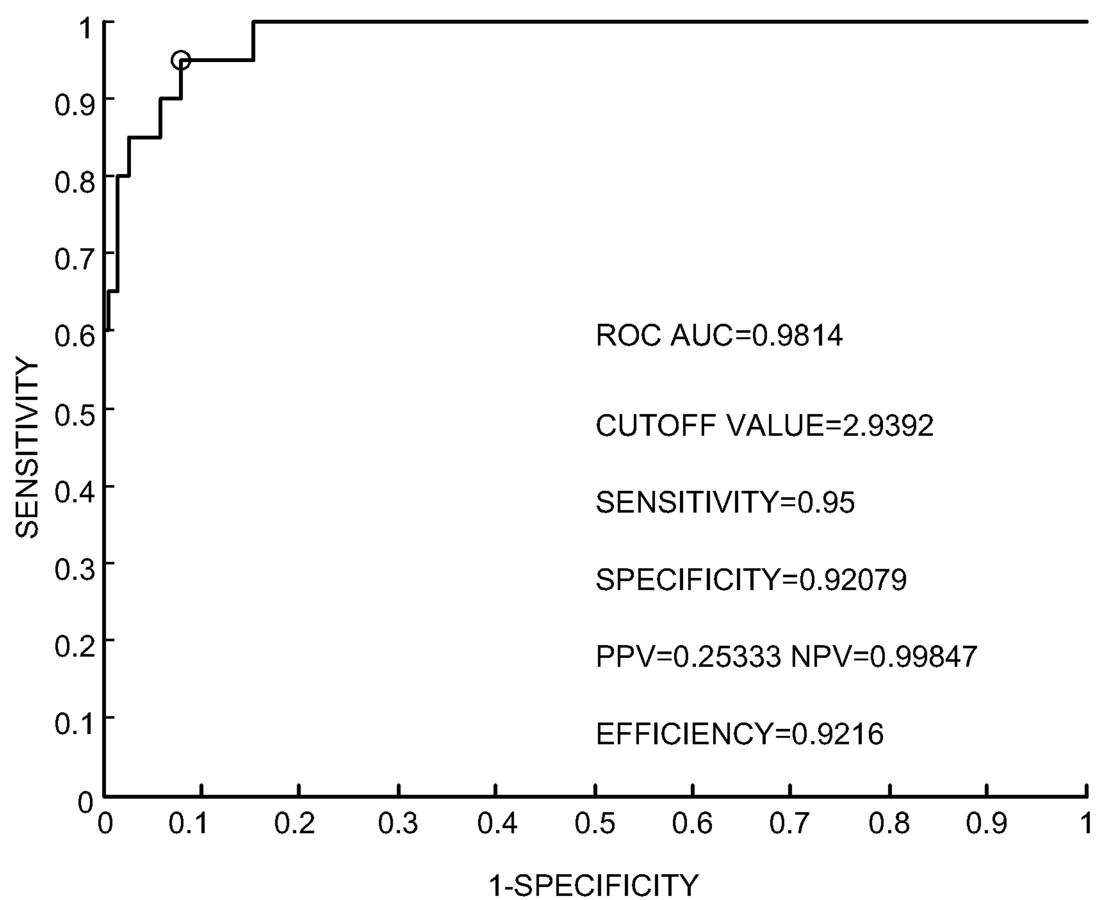
FIG. 31 is a graph showing an ROC curve for evaluation of diagnostic performance between 2 groups.

Discrimination of the 2 groups of early lung cancer group (pathological stages I and II) and non-lung cancer group by the index 2 was evaluated by the AUC of the ROC curve (FIG. 31), to give an AUC of 0.966±0.008 (95% confidence interval: 0.960 to 0.991). When the optimum cutoff value for discrimination of the 2 groups of early lung cancer group and non-lung cancer group by the index 2 was determined assuming that the incidence of early lung cancer group was 0.28, the cutoff value was 2.40, and the sensitivity was 91%; the specificity, 92%; the positive predictive value, 28%; the negative predictive value, 99%, and the correct diagnostic rate, 92% (FIG. 31), and the index 2 was revealed to be an useful index with high diagnostic performance.

Example 5

The sample data used in Example 1 were used. Using a method described in International Publication WO 2004/052191 that is an international application filed by the present applicant, an index by which the performance of discriminating the 2 groups of adenocarcinoma group and non-lung cancer group was maximized for discrimination of lung cancer was extensively studied to give index 3 in a plurality of indices having the same performance. Besides, a plurality of logistic regression equations having the same discrimination performance as that of the index 3 were obtained. These are shown in FIGS. 32 and 33.

(Orn)/(Trp)+(Tau)/(Arg) Index 3

Figure 34:
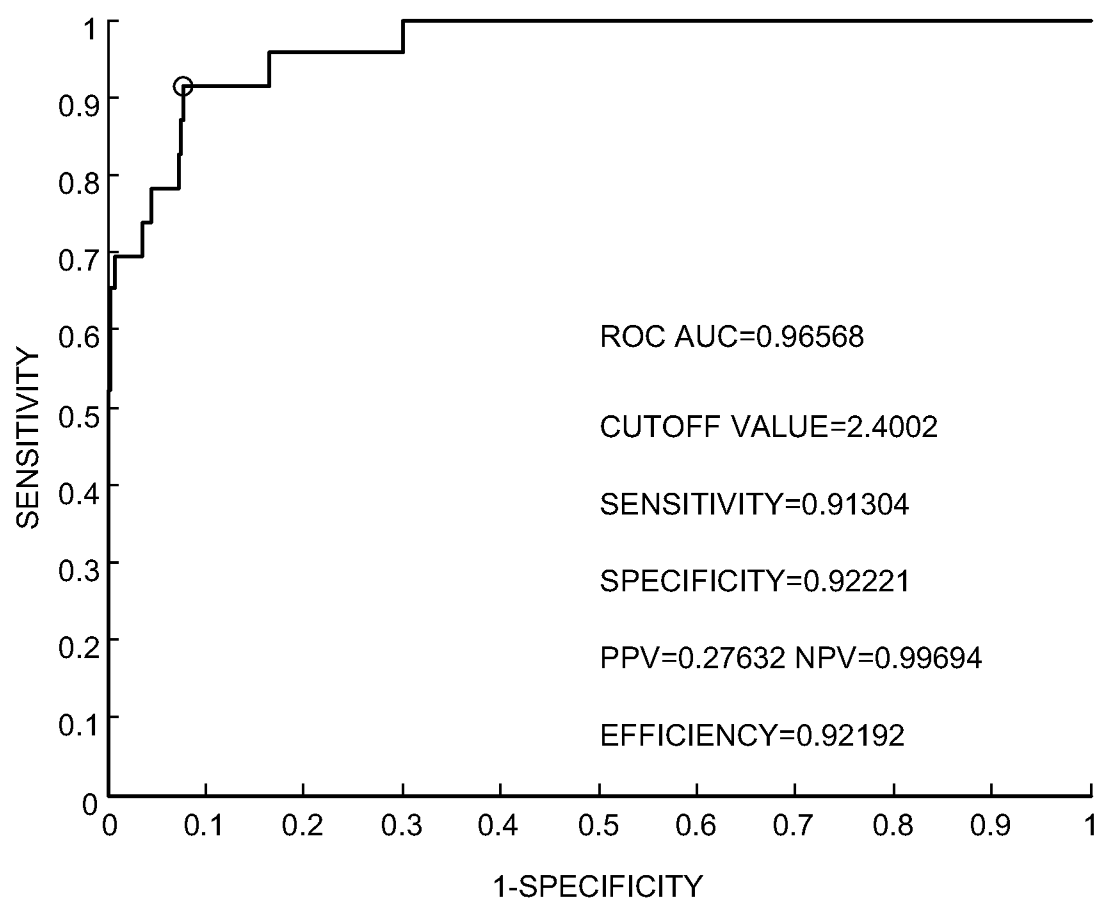
FIG. 34 is a graph showing an ROC curve for evaluation of diagnostic performance between 2 groups.

Discrimination of the 2 groups of adenocarcinoma group and non-lung cancer group by the index 3 was evaluated by the AUC of the ROC curve (FIG. 34), to give an AUC of 0.966±0.017 (95% confidence interval: 0.924 to 0.989). When the optimum cutoff value for discrimination of the 2 groups of adenocarcinoma group and non-lung cancer group by the index 3 was determined assuming that the incidence of adenocarcinoma group was 0.032, the cutoff value was 2.40, and the sensitivity was 91%; the specificity, 92%; the positive predictive value, 28%; the negative predictive value, 99%, and the correct diagnostic rate, 92% (FIG. 34), and the index 3 was revealed to be an useful index with high diagnostic performance.

Example 6

The sample data used in Example 1 were used. An index by which the performance of discriminating the 2 groups of lung cancer group and non-lung cancer group was maximized for discrimination of lung cancer was examined by logistic analysis (variable coverage method by BIC (bayesian information criterion) minimum criterion) to give a logistic regression equation composed of Tau, Orn, Arg, Ser, Glu, Pro and Asn as index 4 (numerical coefficients of amino acid variables Tau, Orn, Arg, Ser, Glu, Pro and Asn and the constant term were 0.086±0.020, 0.124±0.020, −0.046±0.018, 0.023±0.018, −0.016±0.019, 0.013±0.006, 0.003±0.054, and −17.61±3.437, respectively). Besides, a plurality of logistic regression equations having the same discrimination performance as that of the index 4 were obtained. These are shown in FIGS. 35, 36 and 37. The value of each coefficient or constant term in each index in FIGS. 35, 36 and 37, and 95% confidence interval thereof, may be those multiplied by a real number.

Figure 38:
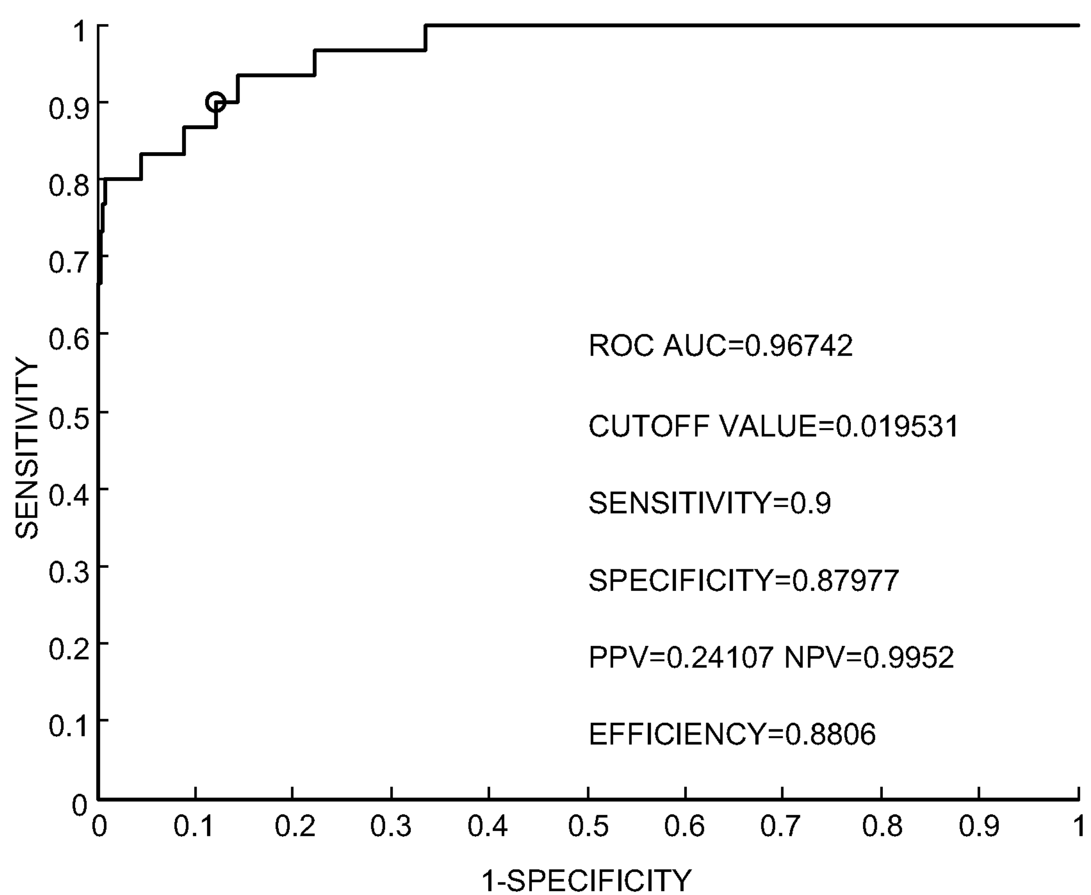
FIG. 38 is a graph showing an ROC curve for evaluation of diagnostic performance between 2 groups.

Discrimination of the 2 groups of lung cancer group and non-lung cancer group by the index 4 was evaluated by the AUC of the ROC curve (FIG. 38), to give an AUC of 0.967±0.014 (95% confidence interval: 0.923 to 0.988), and the index 4 was revealed to be an useful index with high diagnostic performance. When the optimum cutoff value for discrimination of the 2 groups of lung cancer group and non-lung cancer group by the index 4 was determined assuming that the incidence of lung cancer group was 0.038, the cutoff value was 0.019, and the sensitivity was 90%; the specificity, 88%; the positive predictive value, 24%; the negative predictive value, 99%, and the correct diagnostic rate, 88% (FIG. 39), and the index 4 was revealed to be an useful index with high diagnostic performance.

Example 7

The sample data used in Example 1 were used. An index by which the performance of discriminating the 2 groups of early lung cancer group and non-lung cancer group was maximized for discrimination of lung cancer was examined by logistic analysis (variable coverage method by BIC minimum criterion) to give a logistic regression equation composed of Orn, Tau and Trp as index 5 (numerical coefficients of amino acid variables Orn, Tau and Trp and the constant term were 0.178±0.032, 0.0780±0.0197, −0.201±0.0510, and −12.367±2.316, respectively). Besides, a plurality of logistic regression equations having the same discrimination performance as that of the index 5 were obtained. These are shown in FIGS. 40, 41 and 42. The value of each coefficient or constant term in each index in FIGS. 40, 41 and 42, and 95% confidence interval thereof, may be those multiplied by a real number.

Figure 43:
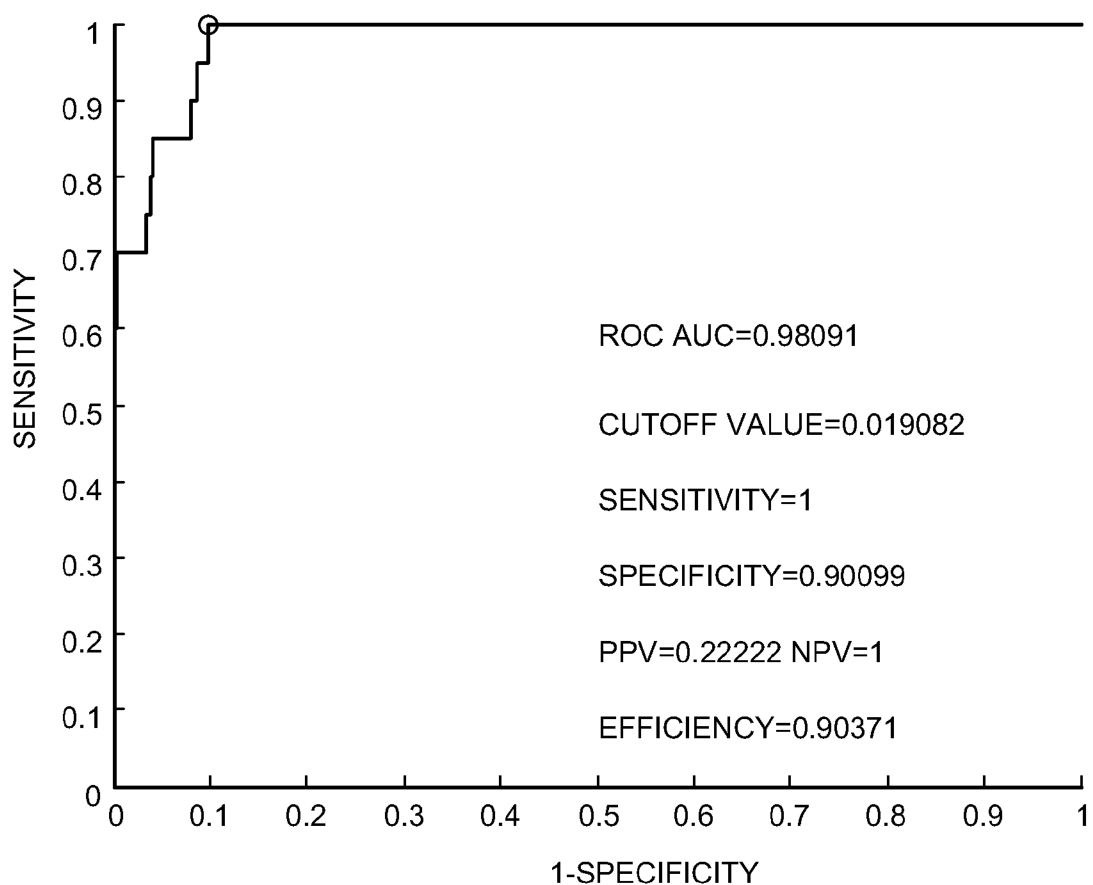
FIG. 43 is a graph showing an ROC curve for evaluation of diagnostic performance between 2 groups.

Discrimination of the 2 groups of early lung cancer group and non-lung cancer group by the index 5 was evaluated by the AUC of the ROC curve (FIG. 43), to give an AUC of 0.981±0.008 (95% confidence interval: 0.960 to 0.990), and the index 5 was revealed to be an useful index with high diagnostic performance. When the optimum cutoff value for discrimination of the 2 groups of early lung cancer group and non-lung cancer group by the index 5 was determined assuming that the incidence of early lung cancer group was 0.028, the cutoff value was 0.019, and the sensitivity was 100%; the specificity, 90%; the positive predictive value, 22%; the negative predictive value, 100%, and the correct diagnostic rate, 90% (FIG. 43), and the index 5 was revealed to be an useful index with high diagnostic performance.

Example 8

The sample data used in Example 1 were used. An index by which the performance of discriminating the 2 groups of adenocarcinoma group and non-lung cancer group was maximized for discrimination of lung cancer was examined by logistic analysis (variable coverage method by BIC minimum criterion) to give a logistic regression equation composed of Orn, ABA, Tau and Gly as index 6 (numerical coefficients of amino acid variables Orn, ABA, Tau and Gly and the constant term were 0.114±0.020, 0.120±0.051, 0.0654±0.0161, 0.00702±0.00469, and −20.62±2.90, respectively). Besides, a plurality of logistic regression equations having the same discrimination performance as that of the index 6 were obtained. These are shown in FIGS. 44, 45 and 46. The value of each coefficient or constant term in each index in FIGS. 44, 45 and 46, and 95% confidence interval thereof, may be those multiplied by a real number.

Figure 47:
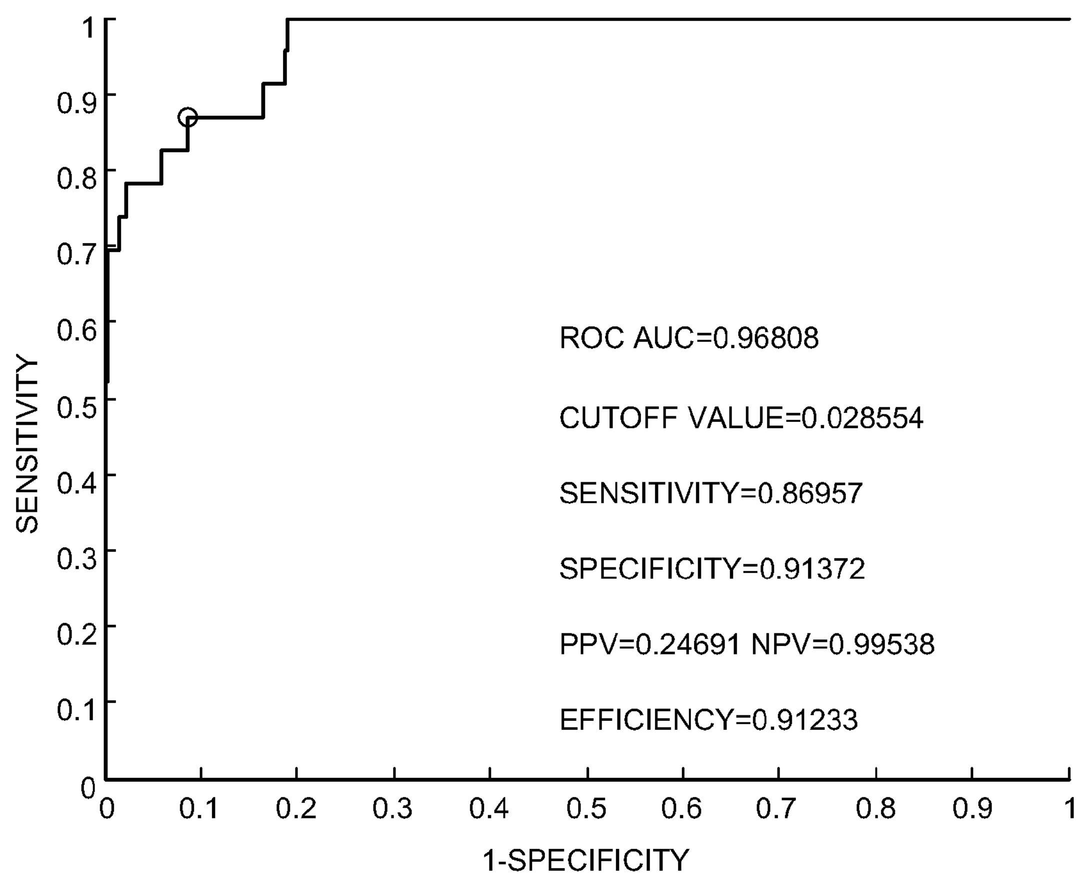
FIG. 47 is a graph showing an ROC curve for evaluation of diagnostic performance between 2 groups.

Discrimination of the 2 groups of adenocarcinoma group and non-lung cancer group by the index 6 was evaluated by the AUC of the ROC curve (FIG. 47), to give an AUC of 0.968±0.012 (95% confidence interval: 0.937 to 0.989), and the index 6 was revealed to be an useful index with high diagnostic performance. When the optimum cutoff value for discrimination of the 2 groups of adenocarcinoma group and non-lung cancer group by the index 6 was determined assuming that the incidence of adenocarcinoma group was 0.032, the cutoff value was 0.029, and the sensitivity was 87%; the specificity, 91%; the positive predictive value, 25%; the negative predictive value, 99%, and the correct diagnostic rate, 91% (FIG. 47), and the index 6 was revealed to be an useful index with high diagnostic performance.

Example 9

The sample data used in Example 1 were used. An index by which the performance of discriminating the 2 groups of lung cancer group and non-lung cancer group was maximized for discrimination of lung cancer was examined by linear discriminant analysis (variable coverage method) to give a linear discriminant function composed of age and ABA, Arg, Gln, His, Leu, Orn, Pro, Tau, Trp and Val as index 7 (numerical coefficients of age and amino acid variables ABA, Arg, Gln, His, Leu, Orn, Pro, Tau, Trp and Val were 0.0338±0.0177, 0.0332±0.0227, −0.0180±0.0073, −0.0030±0.0020, 0.0233±0.0151, 0.0136±0.0124, 0.0617±0.0092, 0.0031±0.0031, 0.0475±0.0099, −0.0268±0.0150, and −0.0134±0.0072, respectively). Besides, a plurality of linear discriminant functions having the same discrimination performance as that of the index 7 were obtained. These are shown in FIGS. 48, 49 and 50. The value of each coefficient or constant term in each index in FIGS. 48, 49 and 50, and 95% confidence interval thereof, may be those multiplied by a real number.

Figure 51:
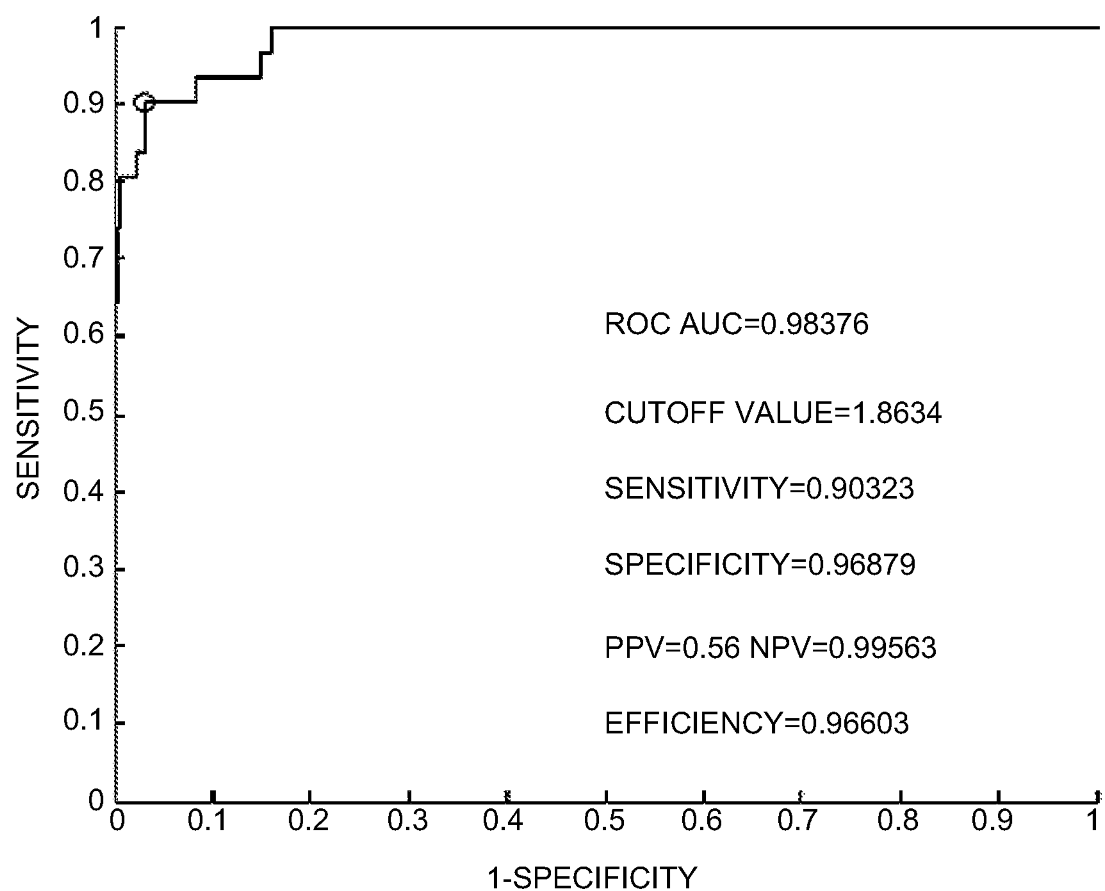
FIG. 51 is a graph showing an ROC curve for evaluation of diagnostic performance between 2 groups.

Discrimination of the 2 groups of lung cancer group and non-lung cancer group by the index 7 was evaluated by the AUC of the ROC curve (FIG. 51), to give an AUC of 0.984±0.008 (95% confidence interval: 0.962 to 0.995), and the index 7 was revealed to be an useful index with high diagnostic performance. When the optimum cutoff value for discrimination of the 2 groups of lung cancer group and non-lung cancer group by the index 7 was determined assuming that the incidence of lung cancer group was 0.038, the cutoff value was 1.863, and the sensitivity was 90%; the specificity, 97%; the positive predictive value, 56%; the negative predictive value, 99%, and the correct diagnostic rate, 97% (FIG. 52), and the index 7 was revealed to be an useful index with high diagnostic performance.

Example 10

The sample data used in Example 1 were used. An index by which the performance of discriminating the 2 groups of early lung cancer group and non-lung cancer group was maximized for discrimination of lung cancer was examined by linear discriminant analysis (variable coverage method) to give a linear discriminant function composed of Orn, Arg, Tau, ABA, Gly and His as index 8 (numerical coefficients of amino acid variables Orn, Arg, Tau, ABA, Gly and His and the constant term were 0.00412±0.00080, −0.00212±0.00063, 0.00316±0.00097, 0.00223±0.00202, 0.00020±0.00018, 0.00088±0.00123, and 0.634±0.123, respectively). Besides, a plurality of linear discriminant functions having the same discrimination performance as that of the index 8 were obtained. These are shown in FIGS. 53, 54 and 55. The value of each coefficient or constant term in each index in FIGS. 53, 54 and 55, and 95% confidence interval thereof, may be those multiplied by a real number.

Figure 56:
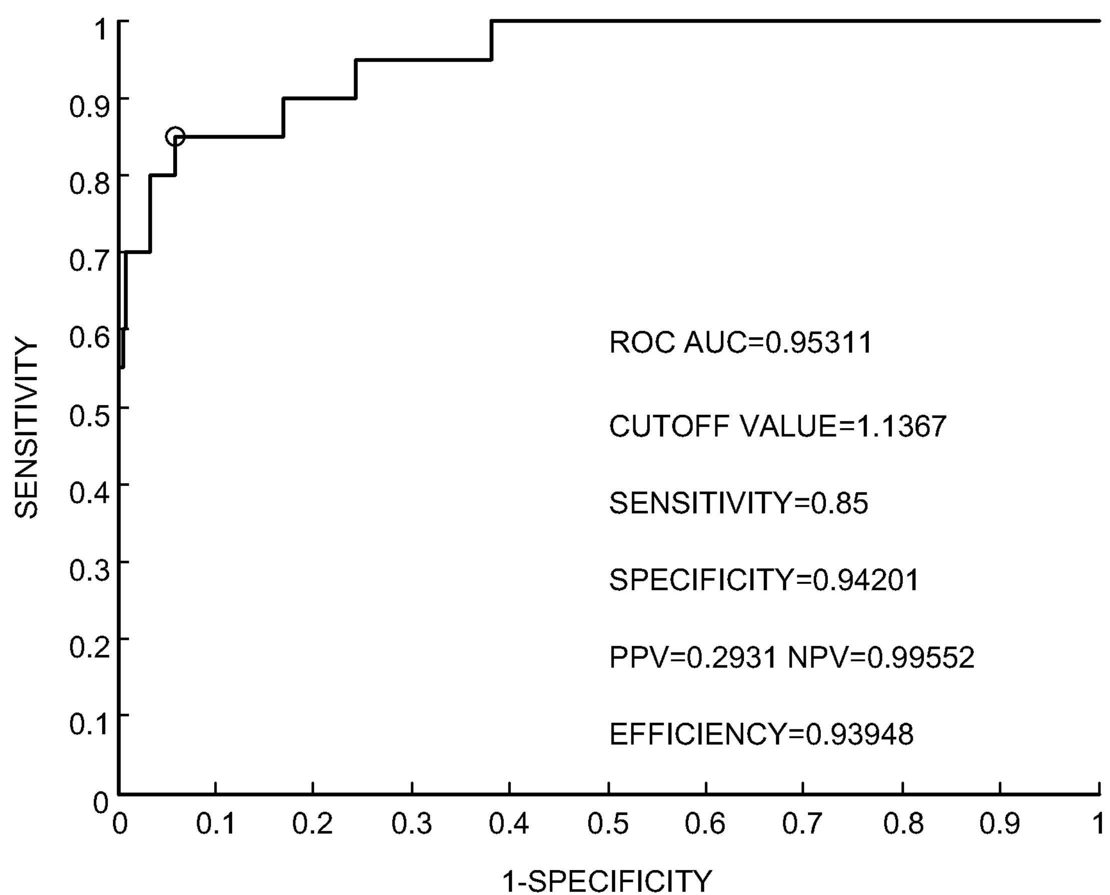
FIG. 56 is a graph showing an ROC curve for evaluation of diagnostic performance between 2 groups.

Discrimination of the 2 groups of early lung cancer group and non-lung cancer group by the index 8 was evaluated by the AUC of the ROC curve (FIG. 56), to give an AUC of 0.953±0.023 (95% confidence interval: 0.877 to 0.979), and the index 8 was revealed to be an useful index with high diagnostic performance. When the optimum cutoff value for discrimination of the 2 groups of early lung cancer group and non-lung cancer group by the index 8 was determined assuming that the incidence of early lung cancer group was 0.028, the cutoff value was 1.137, and the sensitivity was 85%; the specificity, 94%; the positive predictive value, 29%; the negative predictive value, 99%, and the correct diagnostic rate, 94% (FIG. 56), and the index 8 was revealed to be an useful index with high diagnostic performance.

Example 11

The sample data used in Example 1 were used. An index by which the performance of discriminating the 2 groups of adenocarcinoma group and non-lung cancer group was maximized for discrimination of lung cancer was examined by linear discriminant analysis (variable coverage method) to give a linear discriminant function composed of Orn, ABA, Tau, His, Arg and Gly as index 9 (numerical coefficients of amino acid variables Orn, ABA, Tau, His, Arg and Gly and the constant term were 0.00464±0.00080, 0.00222±0.0021, 0.00428±0.00091, 0.00065±0.00127, −0.00159±0.00065, 0.00012±0.00019, and 0.534±0.124, respectively). Besides, a plurality of linear discriminant functions having the same discrimination performance as that of the index 9 were obtained. These are shown in FIGS. 57, 58 and 59. The value of each coefficient or constant term in each index in FIGS. 57, 58 and 59, and 95% confidence interval thereof, may be those multiplied by a real number.

Figure 60:
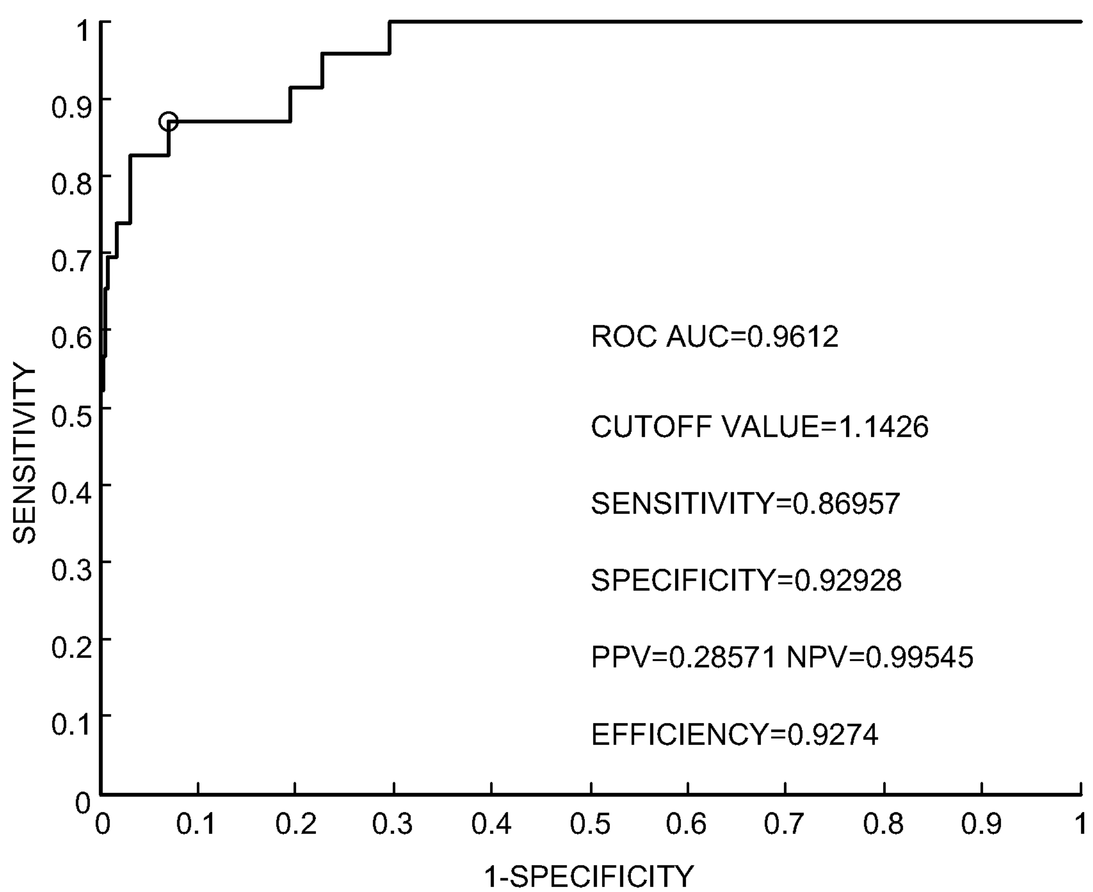
FIG. 60 is a graph showing an ROC curve for evaluation of diagnostic performance between 2 groups.

Discrimination of the 2 groups of adenocarcinoma group and non-lung cancer group by the index 9 was evaluated by the AUC of the ROC curve (FIG. 60), to give an AUC of 0.961±0.015 (95% confidence interval: 0.894 to 0.984), and the index 9 was revealed to be an useful index with high diagnostic performance. When the optimum cutoff value for discrimination of the 2 groups of adenocarcinoma group and non-lung cancer group by the index 9 was determined assuming that the incidence of adenocarcinoma group group was 0.032, the cutoff value was 1.143, and the sensitivity was 87%; the specificity, 93%; the positive predictive value, 29%; the negative predictive value, 99%, and the correct diagnostic rate, 93% (FIG. 60), and the index 9 was revealed to be an useful index with high diagnostic performance.

Example 12

The sample data used in Example 1 were used. All linear discriminants for discriminating the 2 groups of lung cancer group and non-lung cancer group were extracted by the variable coverage method for discrimination of lung cancer. Assuming that the maximum value of the amino acid variables in each discriminant was 6, the area under the ROC curve of every discriminant meeting this condition was calculated. As a result of measurement of the frequency of each amino acid appearing in the discriminant wherein the area under the ROC curve was not less than a certain threshold value, Arg, Lys, Orn, ABA, His, Gly, Glu, Tau, Ser and Cit were confirmed to be in top 10 amino acids extracted always at high frequency when areas of 0.7, 0.75, 0.8 and 0.85 under the ROC curve were respectively threshold values, and it was revealed that the multivariate discriminant using these amino acids as variables has an ability to discriminate the 2 groups of lung cancer group and non-lung cancer group (FIG. 61).

Example 13

Figures 62, 63:
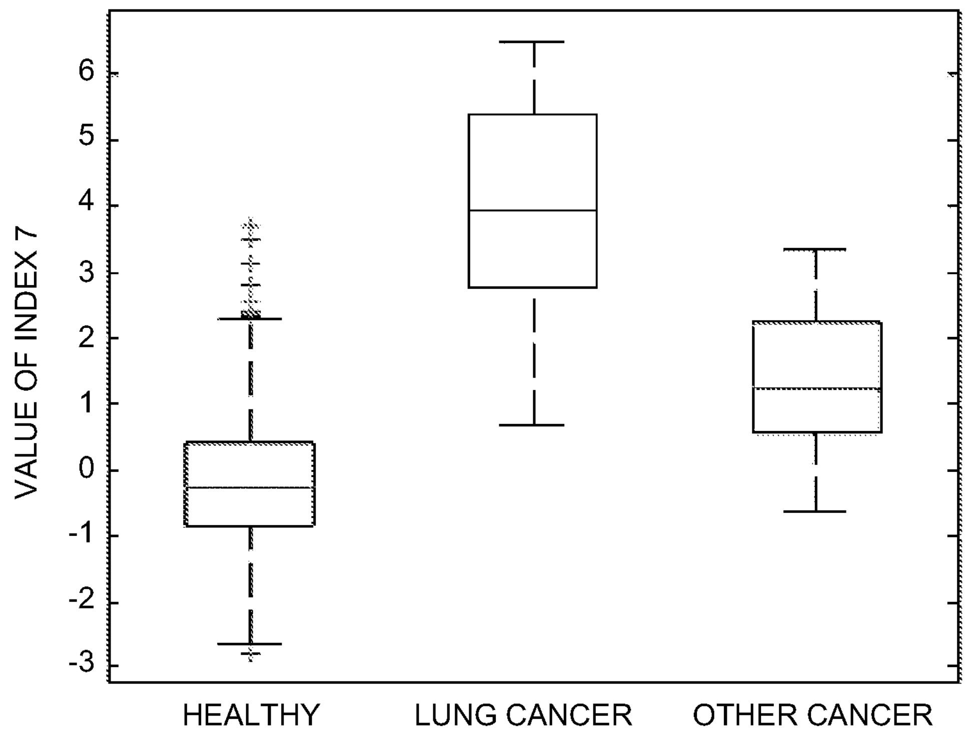
FIG. 62 is a diagram showing the average value and standard derivation of the calculation result, by index 7, of a healthy group, a lung cancer group and another cancer group.
FIG. 63 is a diagram showing a boxplot of the calculation result, by index 7, of a healthy group, a lung cancer group and another cancer group.

The sample data used in Example 1 were used. The index 7 for discriminating the 2 groups of lung cancer group and non-lung cancer group was used to calculate the distribution of each of the healthy group, lung cancer group and other cancer group. As shown in FIGS. 62 and 63, the lung cancer group and other cancer group are different in distribution, and the p value by t-test between the lung cancer group and other cancer group is 0, and it was revealed that there is a significant difference between both the groups. From this result, the index 7 was revealed to be a function specifically discriminating between lung cancer and non-lung cancer.

Example 14

Figure 64:
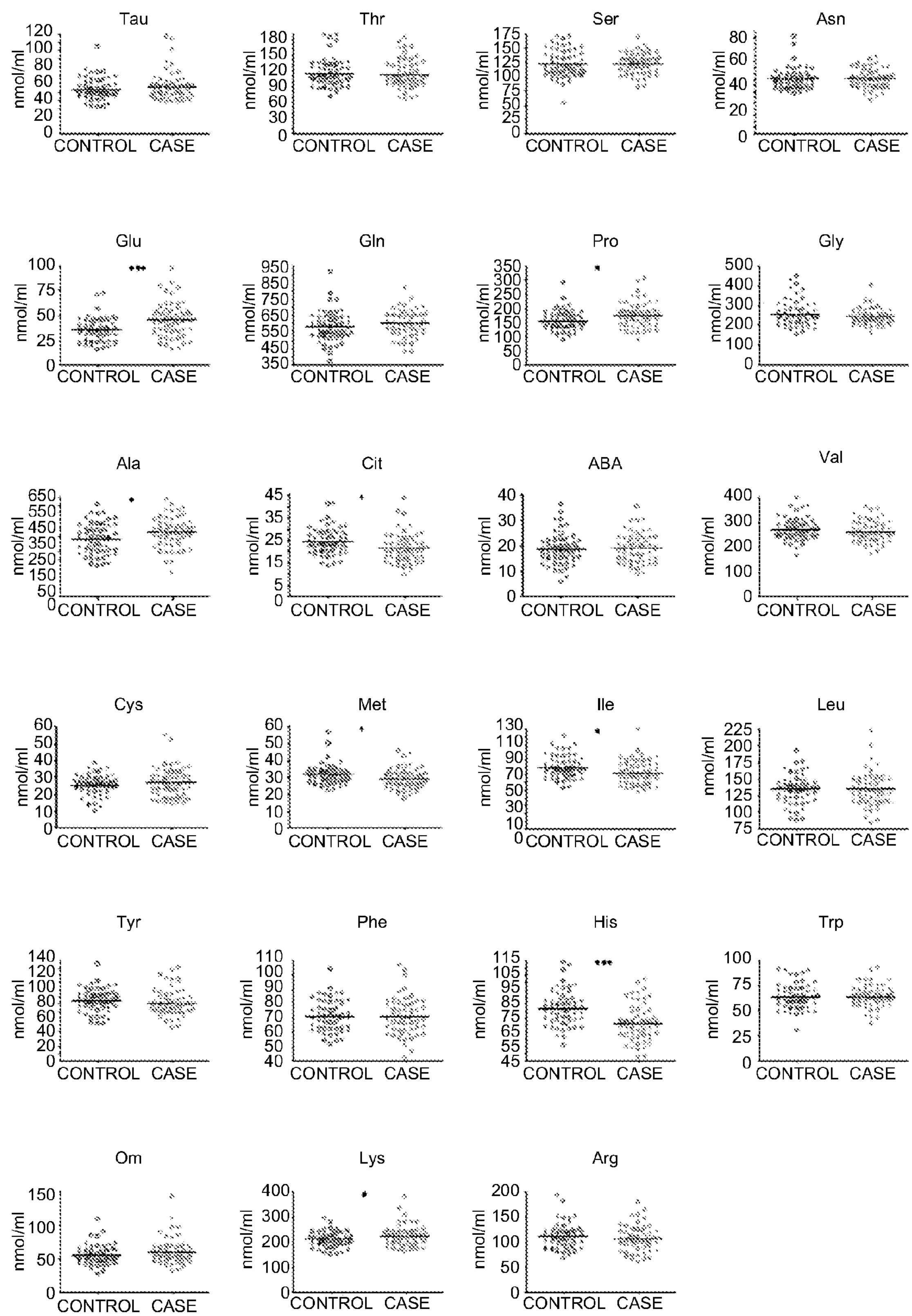
FIG. 64 is a diagram where the distribution of amino acid variables between 2 groups of non-lung cancer and lung cancer is shown by scatter plotting.

Blood samples of lung cancer patients diagnosed by lung biopsy, and blood samples of healthy subjects, were measured for their blood amino acid concentration by the amino acid analysis method described above. The unit of amino acid concentration is nmol/ml. FIG. 64 is a diagram where the distribution of amino acid variables in the lung cancer patients and healthy subjects is shown by scatter plotting (non-lung cancer group and lung cancer group on the abscissa; ABA is α-ABA (aminobutyric acid), and Cys is Cystine). For the purpose of discrimination of the lung cancer group and non-lung cancer group, t-test of the 2 groups was performed.

In the lung cancer group as compared with the non-lung caner group, Glu, Pro, Ala and Lys were significantly increased (significant difference possibility $P<0.05$), and Cit, Met, Ile and His were significantly reduced, and it was revealed that the amino acid variables Glu, Pro, Ala, Lys, Cit, Met, Ile and His have an ability to discriminate between the 2 groups of lung cancer group and non-lung cancer group.

Example 15

The sample data used in Example 14 were used. In FIG. 65, the discrimination between lung cancer group and non-lung cancer group, early lung cancer group and non-lung cancer group, or adenocarcinoma group in lung cancer group and non-lung cancer group was evaluated by the area under the curve (AUC) of the ROC curve using amino acid variables of lung cancer patients and healthy subjects.

A value of 0.625 or more was obtained by Glu, Pro, Cit, Ile and His in discrimination between lung cancer group and non-lung caner group, by Glu, Gln, Ala, His, Trp and Lys in discrimination between early lung cancer group and non-lung cancer group, and by Glu, Cit, Met, Ile, Tyr and His in discrimination between adenocarcinoma group in lung cancer group and non-lung cancer group, and it was revealed that these amino acids have an ability to discriminate between the 2 groups mentioned above.

Example 16

The sample data used in Example 14 were used. Using a method described in International Publication WO 2004/052191 that is an international application filed by the present applicant, an index by which the performance of discriminating the 2 groups of lung cancer group and non-lung cancer group was maximized for discrimination of lung cancer was extensively examined to give index 10 in a plurality of indices having the same performance. Besides, a plurality of multivariate discriminants having the same discrimination performance as that of the index 10 were obtained. These are shown in FIGS. 66 and 67.

$$(Glu)/(Tyr)+(Pro+Lys)/(Ile+His) \qquad \text{Index 10}$$

Figure 68:
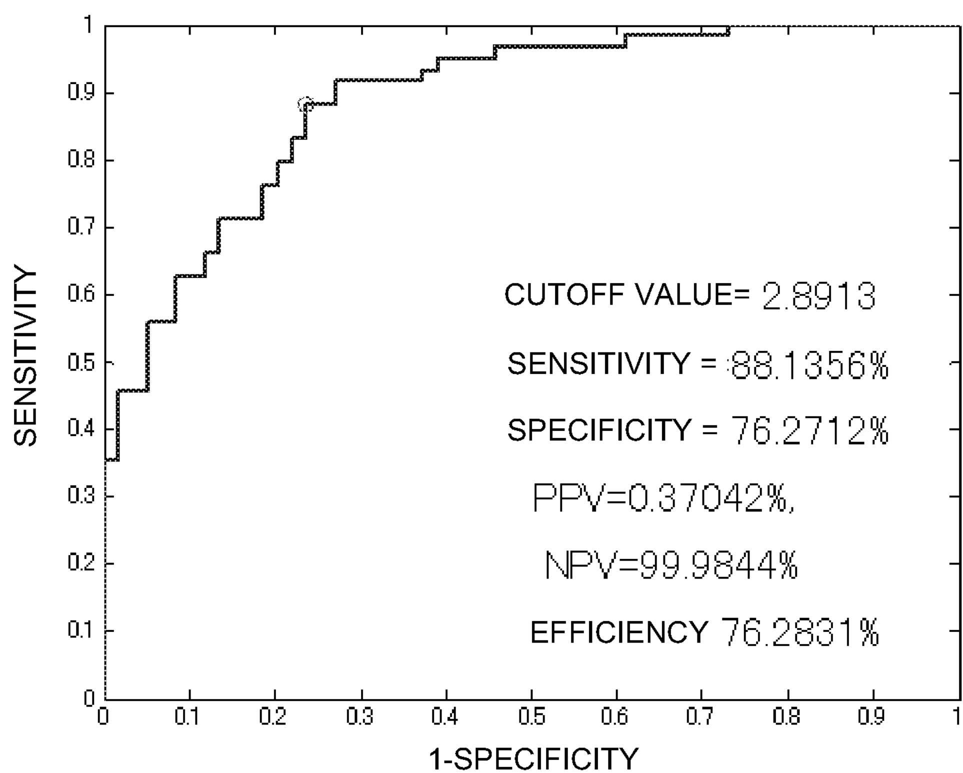
FIG. 68 is a graph showing an ROC curve for evaluation of diagnostic performance between 2 groups.

Discrimination of the 2 groups of lung cancer group and non-lung cancer group by the index 10 was evaluated by the area under the curve (AUC) of the ROC curve (FIG. 68), to give an AUC of 0.888±0.029 (95% confidence interval: 0.831 to 0.945). When the optimum cutoff value for discrimination of the 2 groups of lung cancer group and non-lung cancer group by the index 10 was determined assuming that the incidence of lung cancer group was 0.106%, the cutoff value was 2.891, and the sensitivity was 88.1%; the specificity, 76.3%; the positive predictive value, 0.37%; the negative predictive value, 99.98%, and the correct diagnostic rate, 76.28% (FIG. 68), and the index 10 was revealed to be an useful index with high diagnostic performance.

Example 17

The sample data used in Example 14 were used. Using a method described in International Publication WO 2004/052191 that is an international application filed by the present applicant, an index by which the performance of discriminating the 2 groups of lung cancer group and non-lung cancer group was maximized for discrimination of lung cancer was extensively examined to give index 11 in a plurality of indices having the same performance. Besides, a plurality of multivariate discriminants having the same discrimination performance as that of the index 11 were obtained. These are shown in FIGS. 69 and 70. The values of coefficients in the formulae in FIGS. 69 and 70 may be those multiplied by a real number or those to which an arbitrary constant term was added.

$$(His)/(Lys)-0.22205\times(Glu)(Ile)+0.38171\times(Tyr)/(Pro)+0.16513\times(Val)/(Leu) \quad \text{Index 11}$$

Figure 71:
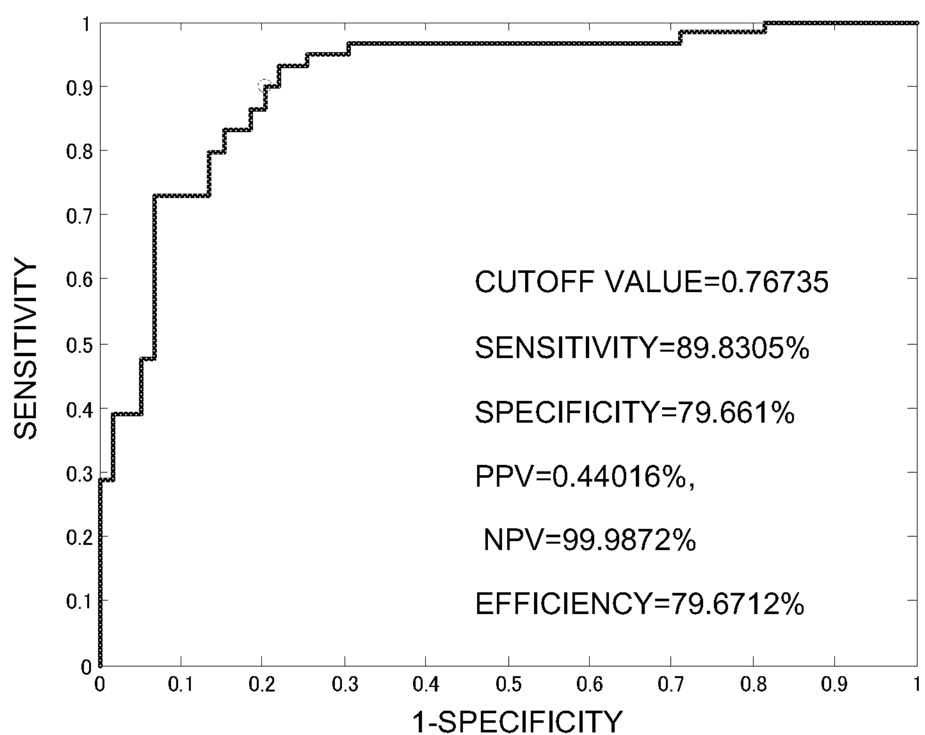
FIG. 71 is a graph showing an ROC curve for evaluation of diagnostic performance between 2 groups.

Discrimination of the 2 groups of lung cancer group and non-lung cancer group by the index 11 was evaluated by the area under the curve (AUC) of the ROC curve (FIG. 71), to give an AUC of 0.906±0.028 (95% confidence interval: 0.851 to 0.962). When the optimum cutoff value for discrimination of the 2 groups of lung cancer group and non-lung cancer group by the index 11 was determined assuming that the incidence of lung cancer group was 0.106%, the cutoff value was 0.767, and the sensitivity was 89.8%; the specificity, 79.7%; the positive predictive value, 0.44%; the negative predictive value, 99.99%, and the correct diagnostic rate, 79.68% (FIG. 71), and the index 11 was revealed to be an useful index with high diagnostic performance.

Example 18

The sample data used in Example 14 were used. An index by which the performance of discriminating the 2 groups of lung cancer group and non-lung cancer group was maximized for discrimination of lung cancer was examined by logistic analysis (variable coverage method by BIC minimum criterion) to give a logistic regression equation composed of His, Glu, Pro, Ile, Gln and Lys as index 12 (numerical coefficients of amino acid variables His, Glu, Pro, Ile, Gln and Lys and the constant term were −1.289±0.027, 0.070±0.014, 0.018±0.004, 0.092±0.018, 0.009±0.002, 0.031±0.006, and −0.926±0.185, respectively). Besides, a plurality of logistic regression equations having the same discrimination performance as that of the index 12 were obtained. These are shown in FIGS. 72, 73 and 74. The values of coefficients in the formulae in FIGS. 72, 73 and 74 may be those multiplied by a real number.

Figure 75:
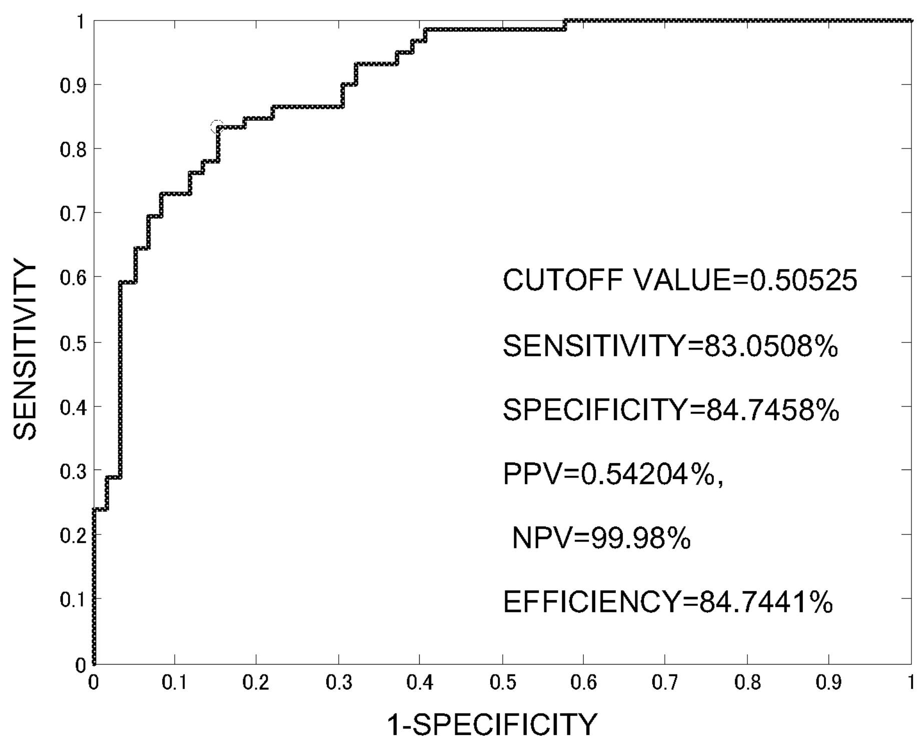
FIG. 75 is a graph showing an ROC curve for evaluation of diagnostic performance between 2 groups.

Discrimination of the 2 groups of lung cancer group and non-lung cancer group by the index 12 was evaluated by the area under the curve (AUC) of the ROC curve (FIG. 75), to give an AUC of 0.908±0.026 (95% confidence interval: 0.856 to 0.960), and the index 12 was revealed to be an useful index with high diagnostic performance. When the optimum cutoff value for discrimination of the 2 groups of lung cancer group and non-lung cancer group by the index 12 was determined assuming that the incidence of lung cancer group was 0.106%, the cutoff value was 0.505, and the sensitivity was 83.1%; the specificity, 84.7%; the positive predictive value, 0.54%; the negative predictive value, 99.98%, and the correct diagnostic rate, 84.74% (FIG. 75), and the index 12 was revealed to be an useful index with high diagnostic performance.

Example 19

The sample data used in Example 14 were used. An index by which the performance of discriminating the 2 groups of lung cancer group and non-lung cancer group was maximized for discrimination of lung cancer was examined by linear discriminant analysis (variable coverage method) to give a linear discriminant composed of His, Glu, Pro, Ile, Tyr and Lys as index 13 (numerical coefficients of amino acid variables His, Glu, Pro, Ile, Tyr and Lys were 1.000±0.197, −0.566±0.11, −0.253±0.076, 0.628±0.189, 0.437±0.130, and −0.368±0.110, respectively). Besides, a plurality of linear discriminant functions having the same discrimination performance as that of the index 13 were obtained. These are shown in FIGS. 76, 77 and 78. The values of coefficients in the formulae in FIGS. 76, 77 and 78 may be those multiplied by a real number or those to which an arbitrary constant term was added.

Figure 79:
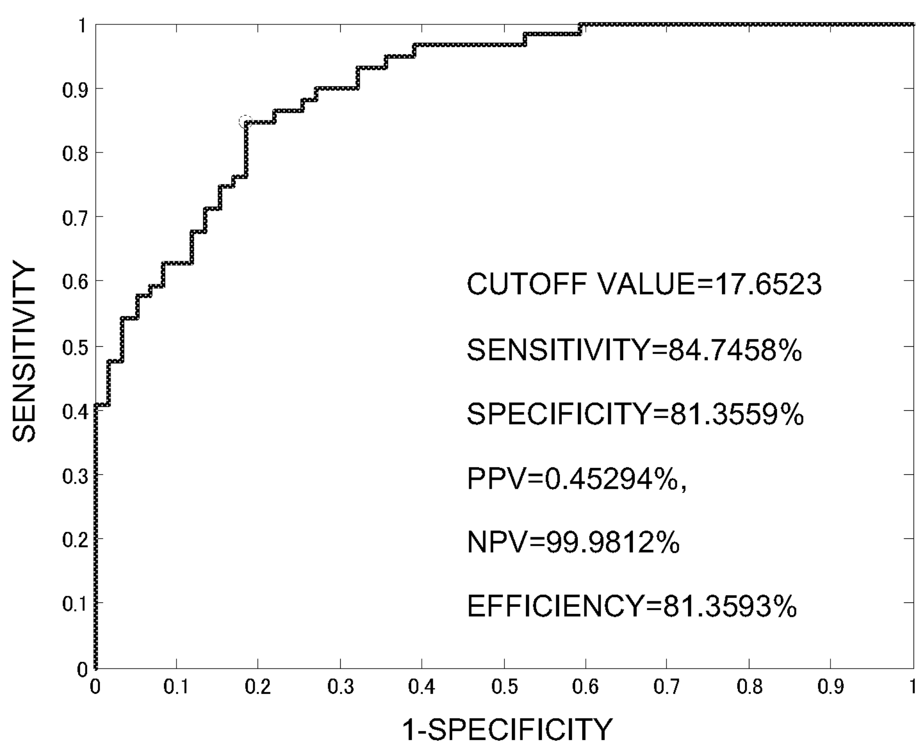
FIG. 79 is a graph showing an ROC curve for evaluation of diagnostic performance between 2 groups.

Discrimination of the 2 groups of lung cancer group and non-lung cancer group by the index 13 was evaluated by the area under the curve (AUC) of the ROC curve (FIG. 79), to give an AUC of 0.901±0.0267 (95% confidence interval: 0.849 to 0.954), and the index 13 was revealed to be an useful index with high diagnostic performance. When the optimum cutoff value for discrimination of the 2 groups of lung cancer group and non-lung cancer group by the index 13 was determined assuming that the incidence of lung cancer group was 0.106%, the cutoff value was 17.65, and the sensitivity was 84.8%; the specificity, 81.4%; the positive predictive value, 0.45%; the negative predictive value, 99.98%, and the correct diagnostic rate, 81.36% (FIG. 79), and the index 13 was revealed to be an useful index with high diagnostic performance.

Example 20

The sample data used in Example 14 were used. Using a method described in International Publication WO 2004/052191 that is an international application filed by the present applicant, an index by which the performance of discriminating the 2 groups of early lung cancer group (pathological stages I and II) and non-lung cancer group was maximized for discrimination of lung cancer was extensively studied to give index 14 in a plurality of indices having the same performance. Besides, a plurality of multivariate discriminants having the same discrimination performance as that of the index 14 were obtained. These are shown in FIGS. 80 and 81.

$$(Gln)/(Cit+His)+(Glu+ABA)/(Cys2) \quad \text{Index 14}$$

Figure 82:
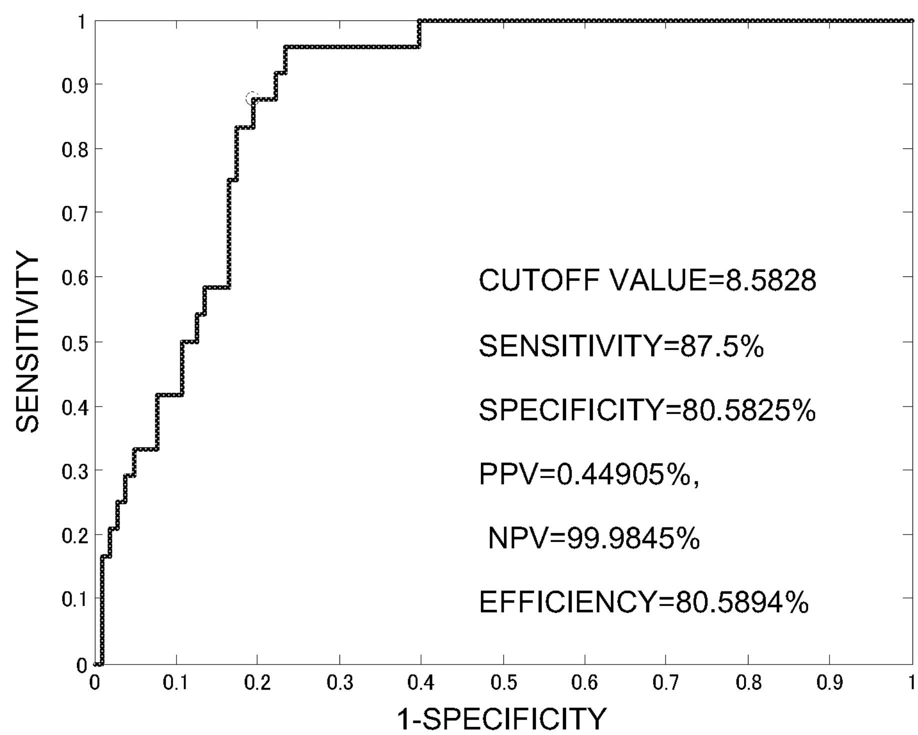
FIG. 82 is a graph showing an ROC curve for evaluation of diagnostic performance between 2 groups.

Discrimination of the 2 groups of early lung cancer and non-lung cancer group by the index 14 was evaluated by the area under the curve (AUC) of the ROC curve (FIG. 82), to give an AUC of 0.881±0.030 (95% confidence interval: 0.822 to 0.940). When the optimum cutoff value for discrimination of the 2 groups of early lung cancer group and non-lung cancer group by the index 14 was determined assuming that the incidence of early lung cancer group was 0.106%, the cutoff value was 8.58, and the sensitivity was 87.5%; the specificity, 80.6%; the positive predictive value, 0.45%; the negative predictive value, 99.98%, and the correct diagnostic rate, 80.58% (FIG. 82), and the index 14 was revealed to be an useful index with high diagnostic performance.

Example 21

The sample data used in Example 14 were used. Using a method described in International Publication WO 2004/052191 that is an international application filed by the present applicant, an index by which the performance of discriminating the 2 groups of early lung cancer group and non-lung cancer group was maximized for discrimination of lung cancer was extensively examined to give index 15 in a plurality of indices having the same performance. Besides, a plurality of multivariate discriminants having the same discrimination performance as that of the index 15 were obtained. These are shown in FIGS. 83 and 84. The values of coefficients in the formulae in FIGS. 83 and 84 may be those multiplied by a real number or those to which an arbitrary constant term was added.

(Gln)/(His)+0.091931×(Glu)+3.9043×(ABA)/(Cys2)+4.3541×(Lys)/(Val) Index 15

Figure 85:
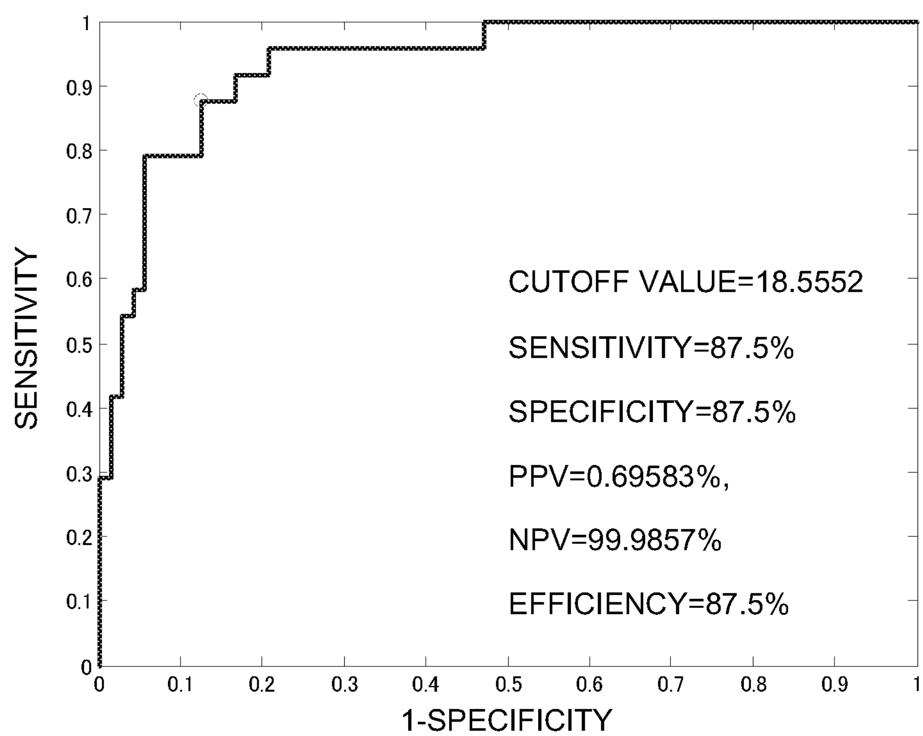
FIG. 85 is a graph showing an ROC curve for evaluation of diagnostic performance between 2 groups.

Discrimination of the 2 groups of early lung cancer group and non-lung cancer group by the index 15 was evaluated by the area under the curve (AUC) of the ROC curve (FIG. 85), to give an AUC of 0.936±0.026 (95% confidence interval: 0.884 to 0.987). When the optimum cutoff value for discrimination of the 2 groups of early lung cancer group and non-lung cancer group by the index 15 was determined assuming that the incidence of early lung cancer group was 0.106%, the cutoff value was 18.55, and the sensitivity was 87.5%; the specificity, 87.5%; the positive predictive value, 0.70%; the negative predictive value, 99.99%, and the correct diagnostic rate, 87.50% (FIG. 85), and the index 15 was revealed to be an useful index with high diagnostic performance.

Example 22

The sample data used in Example 14 were used. An index by which the performance of discriminating the 2 groups of early lung cancer group and non-lung cancer group was maximized for discrimination of lung cancer was examined by logistic analysis (variable coverage method by BIC minimum criterion) to give a logistic regression equation composed of Gln, Glu, His, Lys, Cys and ABA as index 16 (numerical coefficients of amino acid variables Gin, Glu, His, Lys, Cys and ABA and the constant term were 0.016±0.004, 0.0101±0.003, −0.141±0.428, 0.025±0.008, −0.168±0.050, 0.173±0.050, and −6.125±1.840, respectively). Besides, a plurality of logistic regression equations having the same discrimination performance as that of the index 16 were obtained. These are shown in FIGS. 86, 87 and 88. The values of coefficients in the formulae in FIGS. 86, 87 and 88 may be those multiplied by a real number.

Figure 89:
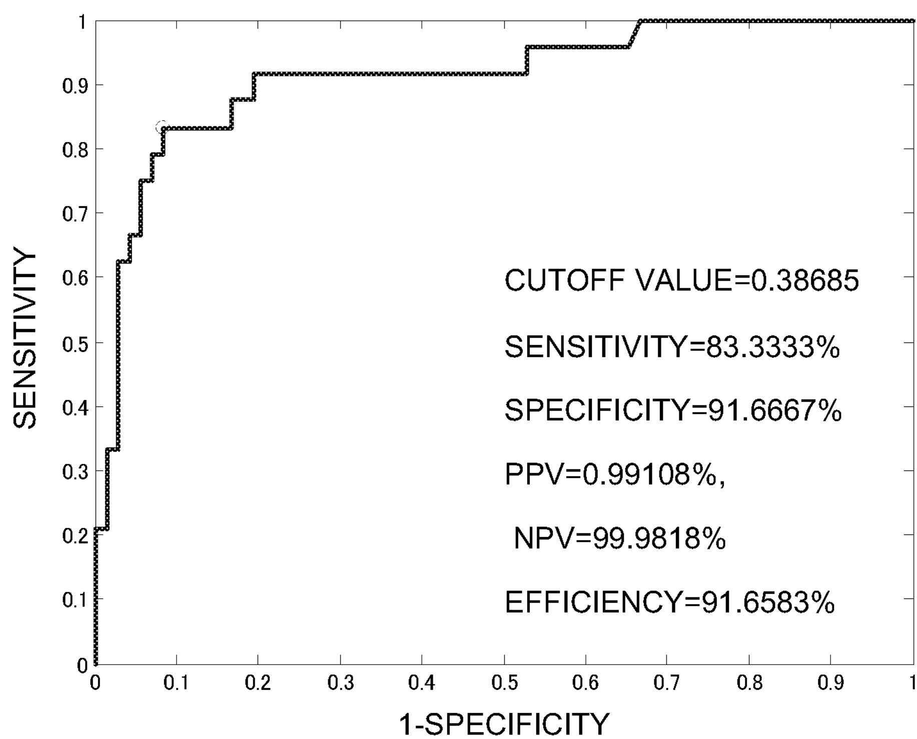
FIG. 89 is a graph showing an ROC curve for evaluation of diagnostic performance between 2 groups.

Discrimination of the 2 groups of early lung cancer group and non-lung cancer group by the index 16 was evaluated by the area under the curve (AUC) of the ROC curve (FIG. 89), to give an AUC of 0.913±0.037 (95% confidence interval: 0.841 to 0.985), and the index 16 was revealed to be an useful index with high diagnostic performance. When the optimum cutoff value for discrimination of the 2 groups of early lung cancer group and non-lung cancer group by the index 16 was determined assuming that the incidence of early lung cancer group was 0.106%, the cutoff value was 0.387, and the sensitivity was 83.3%; the specificity, 91.7%; the positive predictive value, 0.99%; the negative predictive value, 99.98%, and the correct diagnostic rate, 91.65% (FIG. 89), and the index 16 was revealed to be an useful index with high diagnostic performance.

Example 23

The sample data used in Example 14 were used. An index by which the performance of discriminating the 2 groups of early lung cancer group and non-lung cancer group was maximized for discrimination of lung cancer was examined by linear discriminant analysis (variable coverage method) to give a linear discriminant function composed of Gln, Glu, Ala, His, Cys and ABA as index 17 (numerical coefficients of amino acid variables Gln, Glu, Ala, His, Cys and ABA were 1.000±0.201, 7.251±1.450, 0.495±0.091, −9.07±1.82, −11.10±2.24, and 12.63±2.58, respectively). Besides, a plurality of linear discriminant functions having the same discrimination performance as that of the index 17 were obtained. These are shown in FIGS. 90, 91 and 92. The values of coefficients in the formulae in FIGS. 90, 91 and 92 may be those multiplied by a real number or those to which an arbitrary constant term was added.

Figure 93:
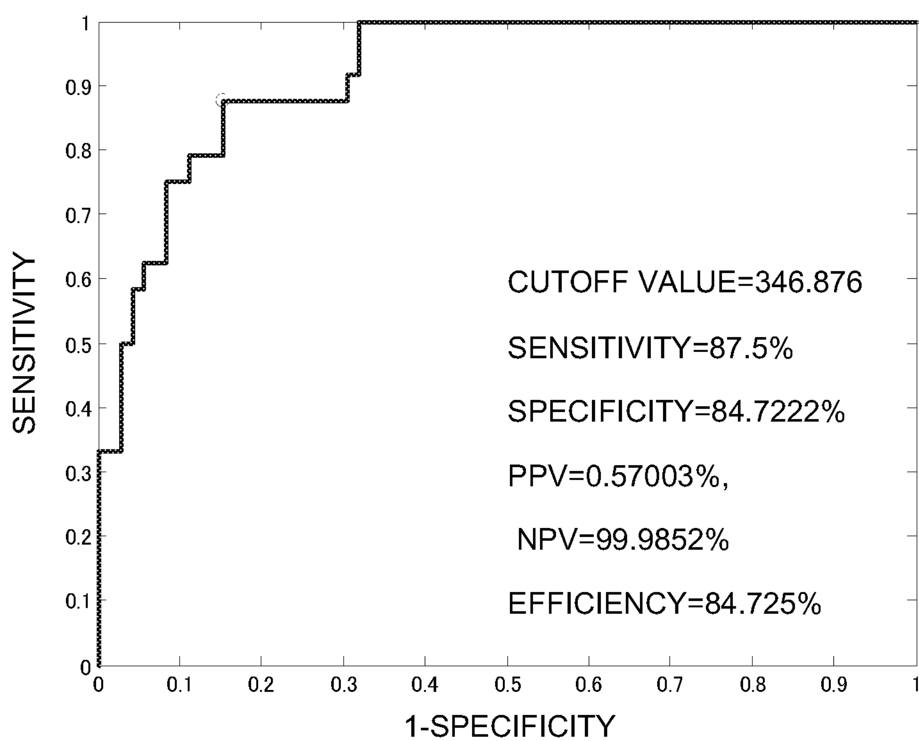
FIG. 93 is a graph showing an ROC curve for evaluation of diagnostic performance between 2 groups.

Discrimination of the 2 groups of early lung cancer group and non-lung cancer group by the index 17 was evaluated by the area under the curve (AUC) of the ROC curve (FIG. 93), to give an AUC of 0.923±0.027 (95% confidence interval: 0.869 to 0.976), and the index 17 was revealed to be an useful index with high diagnostic performance. When the optimum cutoff value for discrimination of the 2 groups of early lung cancer group and non-lung cancer group by the index 17 was determined assuming that the incidence of early lung cancer group was 0.106%, the cutoff value was 346.8, and the sensitivity was 87.5%; the specificity, 84.7%; the positive predictive value, 0.57%; the negative predictive value, 99.99%, and the correct diagnostic rate, 84.73% (FIG. 93), and the index 17 was revealed to be an useful index with high diagnostic performance.

Example 24

The sample data used in Example 14 were used. Using a method described in International Publication WO 2004/052191 that is an international application filed by the present applicant, an index by which the performance of discriminating the 2 groups of adenocarcinoma group (pathological stages I and II) and non-lung cancer group was maximized for discrimination of lung cancer was extensively studied to give index 18 in a plurality of indices having the same performance. Besides, a plurality of multivariate discriminants having the same discrimination performance as that of the index 18 were obtained. These are shown in FIGS. 94 and 95.

(Glu+Pro)/(His)+(ABA+Lys)/(Ile) Index 18

Figure 96:
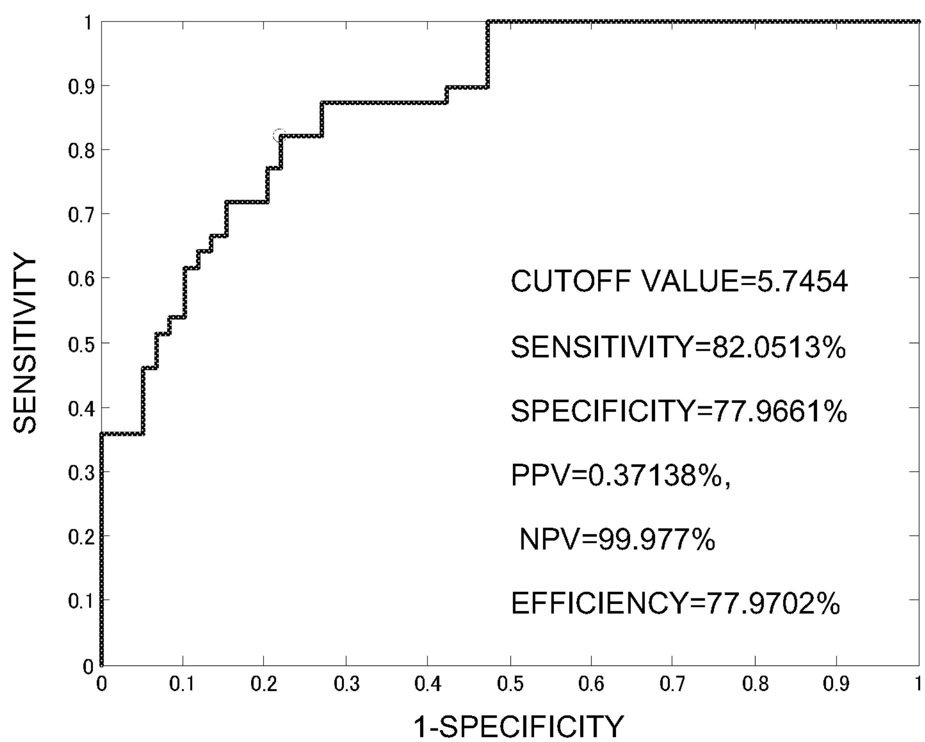
FIG. 96 is a graph showing an ROC curve for evaluation of diagnostic performance between 2 groups.

Discrimination of the 2 groups of adenocarcinoma group and non-lung cancer group by the index 18 was evaluated by the area under the curve (AUC) of the ROC curve (FIG. 96), to give an AUC of 0.872±0.034 (95% confidence interval: 0.804 to 0.939). When the optimum cutoff value for discrimination of the 2 groups of adenocarcinoma group and non-lung cancer group by the index 18 was determined assuming that the incidence of adenocarcinoma group was 0.106%, the cutoff value was 5.745, and the sensitivity was 82.1%; the specificity, 78.0%; the positive predictive value, 0.37%; the negative predictive value, 99.98%, and the correct diagnostic rate, 77.97% (FIG. 96), and the index 18 was revealed to be an useful index with high diagnostic performance.

Example 25

The sample data used in Example 14 were used. Using a method described in International Publication WO 2004/052191 that is an international application filed by the present applicant, an index by which the performance of discriminating the 2 groups of adenocarcinoma group and non-lung cancer group was maximized for discrimination of lung cancer was extensively examined to give index 19 in a plurality of indices having the same performance. Besides, a plurality of multivariate discriminants having the same discrimination performance as that of the index 19 were obtained. These are shown in FIGS. 97 and 98. The values of coefficients in the formulae in FIGS. 97 and 98 may be those multiplied by a real number or those to which an arbitrary constant term was added.

(Glu)/(Cit)−31.7927×(His)/(Gln)−11.3577×(Ile)/(Leu)−9.975×(Tyr)/(Ala) Index 19

Figure 99:
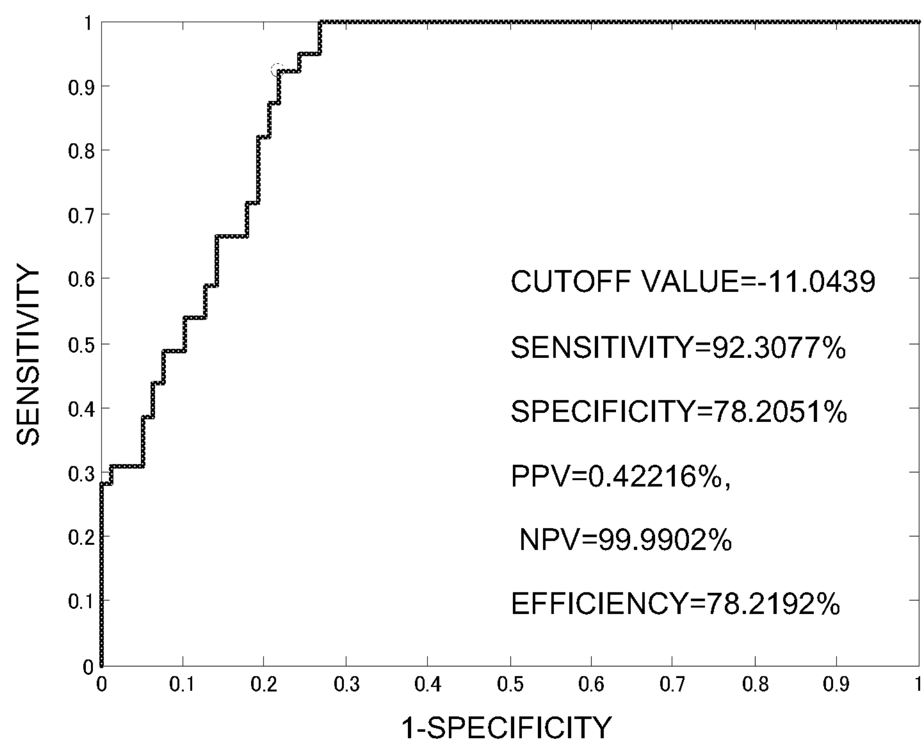
FIG. 99 is a graph showing an ROC curve for evaluation of diagnostic performance between 2 groups.

Discrimination of the 2 groups of adenocarcinoma group and non-lung cancer group by the index 19 was evaluated by the area under the curve (AUC) of the ROC curve (FIG. 99), to give an AUC of 0.895±0.028 (95% confidence interval: 0.841 to 0.950). When the optimum cutoff value for discrimination of the 2 groups of adenocarcinoma group and non-lung cancer group by the index 19 was determined assuming that the incidence of adenocarcinoma group was 0.106%, the cutoff value was −11.04, and the sensitivity was 92.3%; the specificity, 78.2%; the positive predictive value, 0.42%; the negative predictive value, 99.99%, and the correct diagnostic rate, 78.22% (FIG. 99), and the index 19 was revealed to be an useful index with high diagnostic performance.

Example 26

The sample data used in Example 14 were used. An index by which the performance of discriminating the 2 groups of adenocarcinoma group and non-lung cancer group was maximized for discrimination of lung cancer was examined by logistic analysis (variable coverage method by BIC minimum criterion) to give a logistic regression equation composed of His, Ile, Glu, Pro, Leu and Gln as index 20 (numerical coefficients of amino acid variables His, Ile, Glu, Pro, Leu and Gln and the constant term were −0.150±0.044, −0.210±0.041, 0.054±0.011, 0.025±0.008, 0.092±0.018, 0.008±0.002, and 3.577±0.714, respectively). Besides, a plurality of logistic regression equations having the same discrimination performance as that of the index 20 were obtained. These are shown in FIGS. 100, 101 and 102. The values of coefficients in the formulae in FIGS. 100, 101 and 102 may be those multiplied by a real number.

Figure 103:
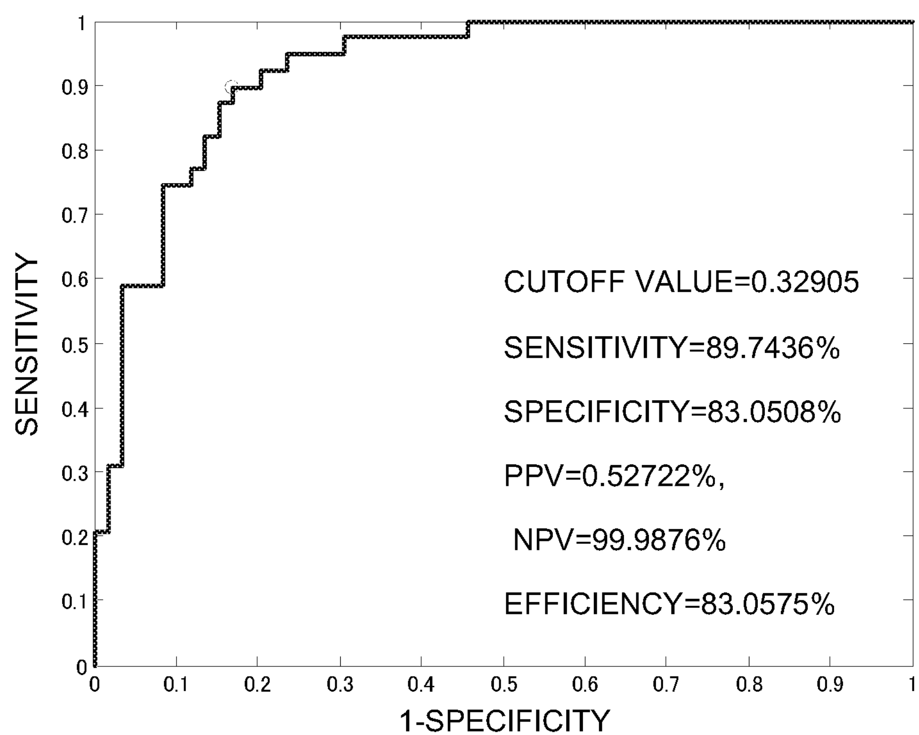
FIG. 103 is a graph showing an ROC curve for evaluation of diagnostic performance between 2 groups.

Discrimination of the 2 groups of adenocarcinoma group and non-lung cancer group by the index 20 was evaluated by the area under the curve (AUC) of the ROC curve (FIG. 103), to give an AUC of 0.909±0.028 (95% confidence interval: 0.855 to 0.964), and the index 20 was revealed to be an useful index with high diagnostic performance. When the optimum cutoff value for discrimination of the 2 groups of adenocarcinoma group and non-lung cancer group by the index 20 was determined assuming that the incidence of adenocarcinoma group was 0.106%, the cutoff value was 0.329, and the sensitivity was 89.7%; the specificity, 83.1%; the positive predictive value, 0.53%; the negative predictive value, 99.99%, and the correct diagnostic rate, 83.06% (FIG. 103), and the index 20 was revealed to be an useful index with high diagnostic performance.

Example 27

The sample data used in Example 14 were used. An index by which the performance of discriminating the 2 groups of adenocarcinoma group and non-lung cancer group was maximized for discrimination of lung cancer was examined by linear discriminant analysis (variable coverage method) to give a linear discriminant function composed of His, Ile, Pro, Ala, Leu and Gln as index 21 (numerical coefficients of amino acid variables His, Ile, Pro, Ala, Leu and Gln were 1.000±0.198, 1.402±0.28, −0.157±0.035, −0.053±0.011, −0.744±0.151, and −0.050±0.013, respectively). Besides, a plurality of liner discriminant functions having the same discrimination performance as that of the index 21 were obtained. These are shown in FIGS. 104, 105 and 106. The values of coefficients in the formulae in FIGS. 104, 105 and 106 may be those multiplied by a real number or those to which an arbitrary constant term was added.

Figure 107:
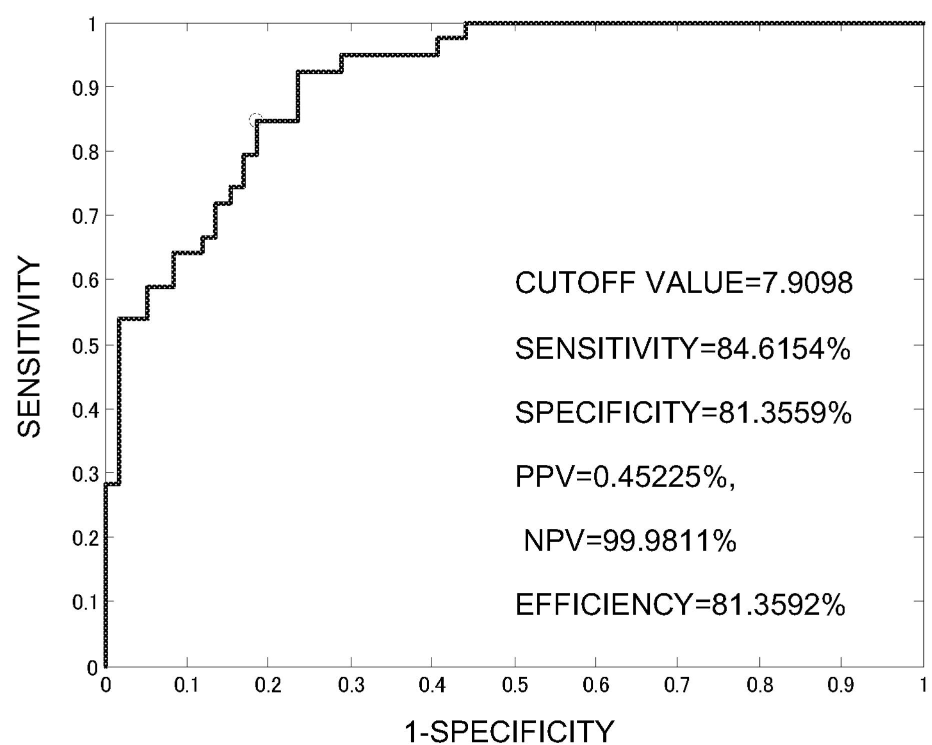
FIG. 107 is a graph showing an ROC curve for evaluation of diagnostic performance between 2 groups.

Discrimination of the 2 groups of adenocarcinoma group and non-lung cancer group by the index 21 was evaluated by the area under the curve (AUC) of the ROC curve (FIG. 107), to give an AUC of 0.923±0.026 (95% confidence interval: 0.871 to 0.974), and the index 21 was revealed to be an useful index with high diagnostic performance. When the optimum cutoff value for discrimination of the 2 groups of adenocarcinoma group and non-lung cancer group by the index 21 was determined assuming that the incidence of adenocarcinoma group was 0.106%, the cutoff value was 7.91, and the sensitivity was 84.6%; the specificity, 81.4%; the positive predictive value, 0.45%; the negative predictive value, 99.98%, and the correct diagnostic rate, 81.36% (FIG. 107), and the index 21 was revealed to be an useful index with high diagnostic performance.

Example 28

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). Using a method described in International Publication WO 2004/052191 that is an international application filed by the present applicant, the index most correlated with the first to fourth groups and the non-lung cancer group to discriminate the pathological stage of lung cancer was extensively studied to give index 22 in a plurality of indices having the same performance. Besides, a plurality of multivariate discriminants having the same discrimination performance as that of the index 22 were obtained. These are shown in FIGS. 108 and 109.

(Glu+Pro+Lys+Leu)/(Val+His) Index 22

Figure 110:
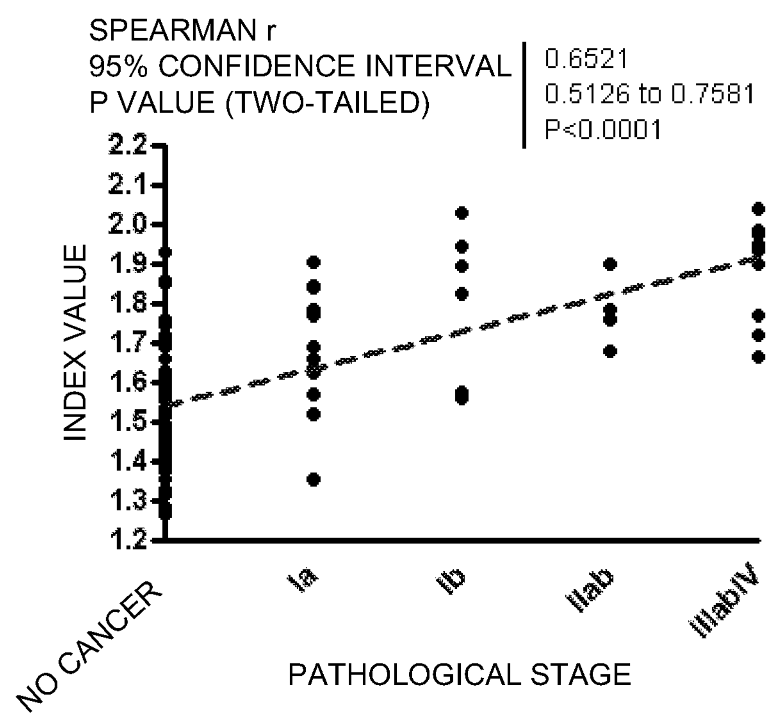
FIG. 110 is a diagram showing Spearman's rank-correlation coefficient between non-lung cancer group, groups 1 to 4, and values in index 22.

At this time, the Spearman's rank-correlation coefficient between the value of the index 22 and the non-lung cancer group and the first to fourth groups was 0.654 (95% confidence interval: 0.513 to 0.758), and the index 22 was revealed to be an useful index with high diagnostic performance (FIG. 110).

Example 29

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). Using a method described in International Publication WO 2004/052191 that is an international application filed by the present applicant, the index most correlated with the first to fourth groups and the non-lung cancer group to discriminate the pathological stage of lung cancer was extensively studied to give index 23 in a plurality of indices having the same performance. Besides, a plurality of multivariate discriminants having the same discrimination performance as that of the index 23 were obtained. These are shown in FIGS. 111 and 112.

(Ala)/(His)+33.5806×(Leu)/(Val)−7.2184×(Cys2)/(Orn)−13.3068×(Ile)/(Lys) Index 23

Figure 113:
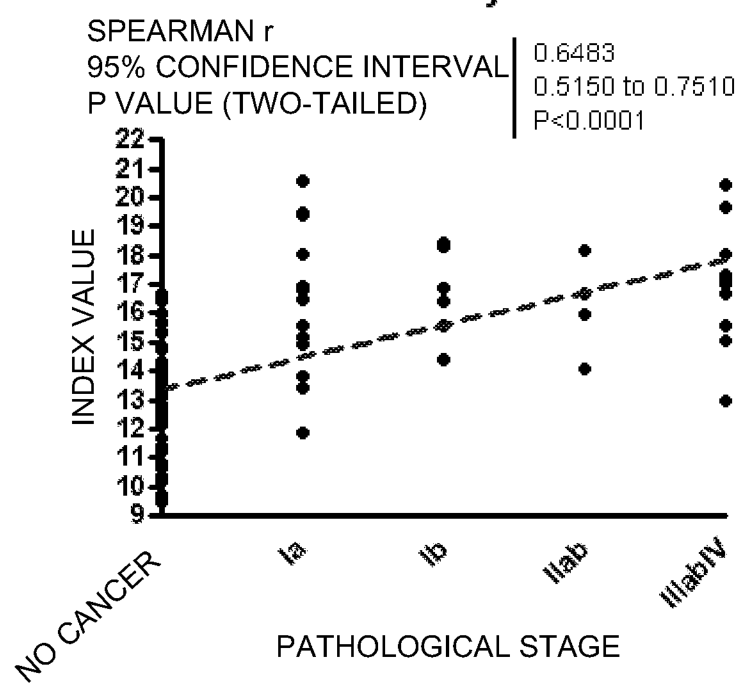
FIG. 113 is a diagram showing Spearman's rank-correlation coefficient between non-lung cancer group, groups 1 to 4, and values in index 23.

At this time, the Spearman's rank-correlation coefficient between the value of the index 23 and the non-lung cancer group and the first to fourth groups was 0.648 (95% confidence interval: 0.515 to 0.751), and the index 23 was revealed to be an useful index with high diagnostic performance (FIG. 113).

Example 30

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). The index most correlated with the non-lung cancer group and the first to fourth groups to discriminate the pathological stage of lung cancer was extensively studied by multiple regression analysis (variable selection method by AIC (Akaike's information criteria) minimum criterion) to give a multiple regression equation composed of Pro, His, Gly, Val, Ile and Leu as index 24 (numerical coefficients of amino acid variables Pro, His, Gly, Val, Ile and Leu were 1.000±0.200, −2.735±0.55, −0.129±0.025, −0.948±0.195, −2.710±0.584, and 3.113±0.659, respectively). Besides, a plurality of multiple regression equations having the same correlation as that of the index 24 were obtained. These are shown in FIGS. 114, 115 and 116. The values of coefficients in the formulae in FIGS. 114, 115 and 116 may be those multiplied by a real number or those to which an arbitrary constant term was added.

Figure 117:
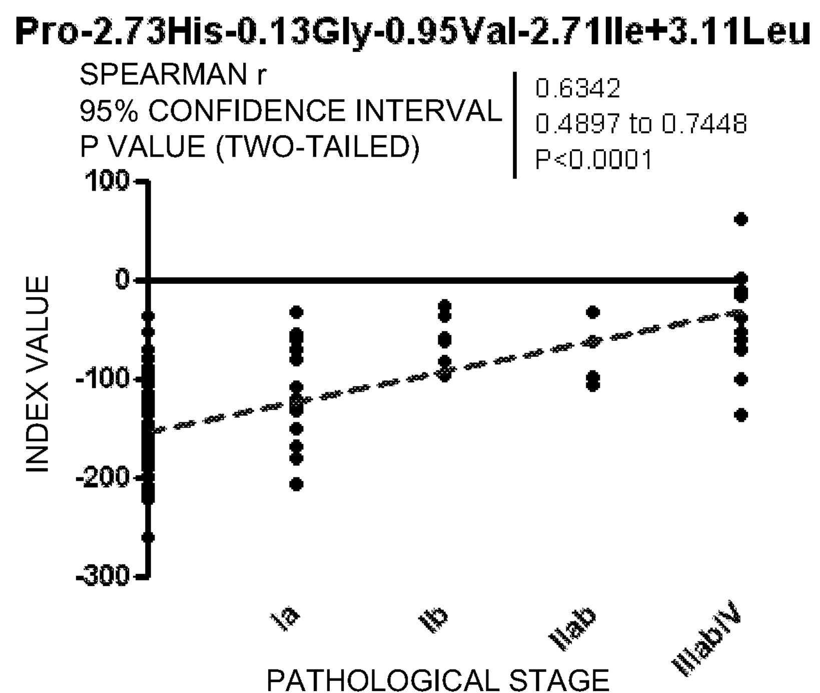
FIG. 117 is a diagram showing Spearman's rank-correlation coefficient between non-lung cancer group, groups 1 to 4, and values in index 24.

At this time, the Spearman's rank-correlation coefficient between the value of the index 24 and the non-lung cancer group and the first to fourth groups was 0.634 (95% confidence interval: 0.490 to 0.745), and the index 24 was revealed to be an useful index with high diagnostic performance (FIG. 117).

Example 31

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). Using a method described in International Publication WO 2004/052191 that is an international application filed by the present applicant, the index most correlated with the first to fourth groups to discriminate the pathological stage of lung cancer was extensively studied to give index 25 in a plurality of indices having the same performance. Besides, a plurality of multivariate discriminants having the same discrimination performance as that of the index 25 were obtained. These are shown in FIGS. 118 and 119.

(Pro)/(Gln)+(Tyr+Leu+Cys2)/(Val) Index 25

Figure 120:
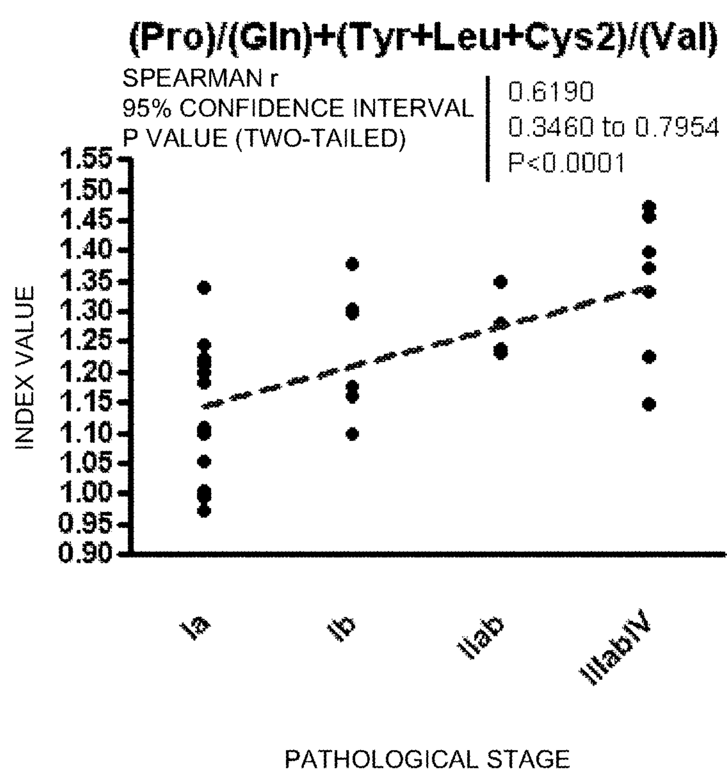

At this time, the Spearman's rank-correlation coefficient between the value of the index 25 and the first to fourth groups was 0.619 (95% confidence interval: 0.346 to 0.794), and the index 25 was revealed to be an useful index with high diagnostic performance (FIG. 120).

Example 32

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). Using a method described in International Publication WO 2004/052191 that is an international application filed by the present applicant, the index most correlated with the first to fourth groups to discriminate the pathological stage of lung cancer was extensively studied to give index 26 in a plurality of indices having the same performance. Besides, a plurality of multivariate discriminants having the same discrimination performance as that of the index 26 were obtained. These are shown in FIGS. 121 and 122.

(Tyr)/(Trp)−0.012943×(Ser)−0.080336×(Ala)/(Asn) Index 26

Figure 123:
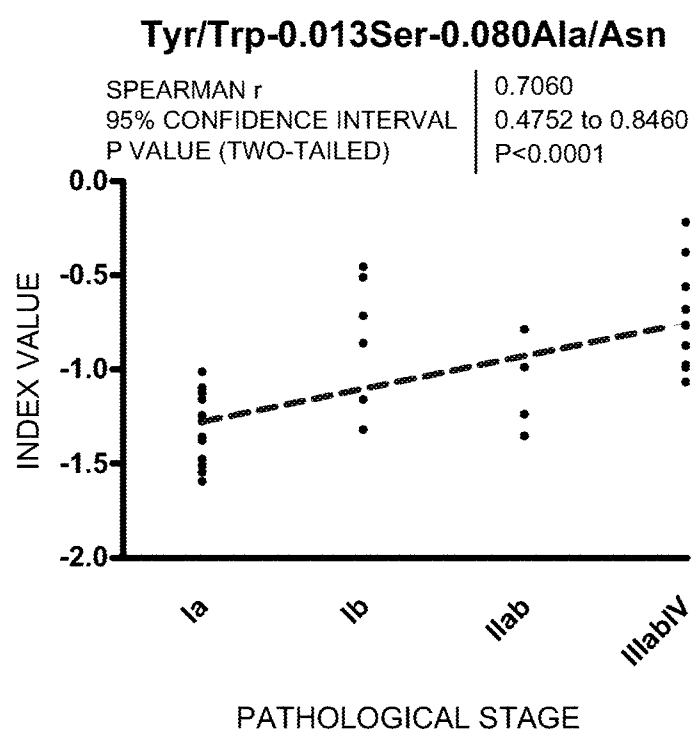

At this time, the Spearman's rank-correlation coefficient between the value of the index 26 and the first to fourth groups was 0.706 (95% confidence interval: 0.475 to 0.846), and the index 26 was revealed to be an useful index with high diagnostic performance (FIG. 123).

Example 33

The sample data used in Example 14 were used. Lung cancer with pathological stages (Ia, Ib, IIa, IIb, IIIa, IIIb and IV) was divided into a first group (Ia), a second group (Ib), a third group (IIa and IIb), and a fourth group (IIIa, IIIb and IV). The index most correlated with the first to fourth groups to discriminate the pathological stage of lung cancer was extensively studied by multiple regression analysis (variable selection method by AIC minimum criterion) to give a multiple regression equation composed of Gln, Ser, Pro, Tyr, Cys and Tau as index 27 (numerical coefficients of amino acid variables Gln, Ser, Pro, Tyr, Cys and Tau were 1.000±0.304, 3.875±1.289, −1.106±0.321, −5.227±1.583, −8.412±2.523, and 5.097±1.529, respectively). Besides, a plurality of multiple regression equations having the same correlation as that of the index 27 were obtained. These are shown in FIGS. 124, 125 and 126. The values of coefficients in the formulae in FIGS. 124, 125 and 126 may be those multiplied by a real number or those to which an arbitrary constant term was added.

Figure 127:
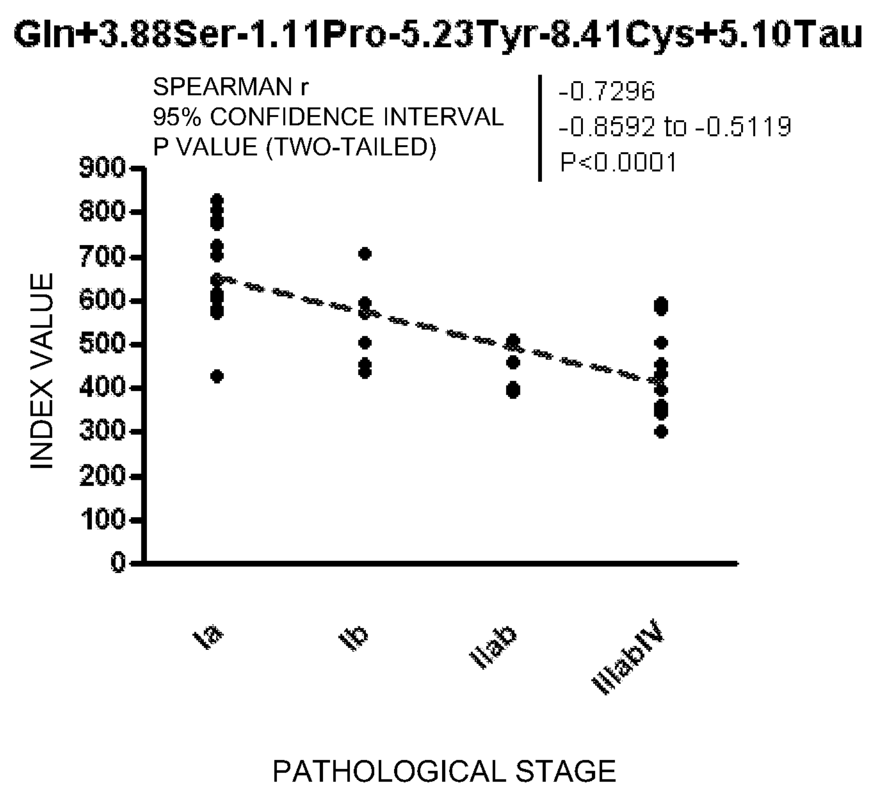

At this time, the Spearman's rank-correlation coefficient between the value of the index 27 and the first to fourth groups was −0.730 (95% confidence interval: −0.512 to −0.859), and the index 27 was revealed to be an useful index with high diagnostic performance (FIG. 127).

Example 34

The sample data used in Example 14 were used. All linear discriminants for discriminating the 2 groups of lung cancer group and non-lung cancer group were extracted by the variable coverage method for discrimination of lung cancer. Assuming that the maximum value of amino acid variables in each discriminant was 5, the area under the ROC curve of every discriminant meeting this condition was calculated. As a result of measurement of the frequency of each amino acid appearing in the discriminant wherein the area under the ROC curve is not less than a certain threshold value, Ala, Glu, His, Ile, Lys and Pro were confirmed to be in top 10 amino acids extracted always at high frequency when areas of 0.7, 0.75, 0.8 and 0.85 under the ROC curve were respectively threshold values, and it was revealed that the multivariate discriminant using these amino acids as variables has an ability to discriminate the 2 groups of lung cancer group and non-lung cancer group (FIG. 128).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating lung cancer, comprising:

a concentration value criterion evaluating step of evaluating, by a central processing unit (CPU) executing a lung cancer-evaluating program stored on a computer-readable recording medium, a lung cancer state in a subject to be evaluated, based on concentration values of at least Lys and His contained in amino acid concentration data on the concentration values of the at least two amino acids in blood of the subject, wherein the concentration value criterion evaluating step further includes a discriminant value calculating step of calculating, by the CPU, a discriminant value that is a value of a multivariate discriminant, based on both (i) the concentration values of at least Lys and His and (ii) the multivariate discriminant for evaluating the lung cancer state containing at least Lys and His explanatory variables.

2. The method of evaluating lung cancer according to claim 1, wherein the concentration value criterion evaluating step further includes:

a discriminant value criterion evaluating step of evaluating the lung cancer state in the subject by the CPU, based on the discriminant value calculated at the discriminant value calculating step.

3. The method of evaluating lung cancer according to claim 2, wherein the multivariate discriminant further contains age as an explanatory variable.

4. The method of evaluating lung cancer according to claim 2, wherein the discriminant value criterion evaluating step further includes a discriminant value criterion discriminating step of discriminating between lung cancer and non-lung cancer in the subject by the CPU, based on the discriminant value calculated at the discriminant value calculating step.

5. The method of evaluating lung cancer according to claim 4, wherein the multivariate discriminant is expressed by one fractional expression or the sum of a plurality of the fractional expressions and contains the concentration values of at least Lys and His as the explanatory variables in any one of the numerator and denominator or both in the fractional expression constituting the multivariate discriminant.

6. The method of evaluating lung cancer according to claim 5, wherein the multivariate discriminant is formula 2 or 3:

$$a_2 \times Glu/Tyr + b_2 \times (Pro+Lys)/Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_2$, $b_2$ and $c_2$ in the formula 2 are arbitrary real numbers, and $a_3$, $b_3$, $c_3$, $d_3$, and $e_3$ in the formula 3 are arbitrary real numbers.

7. The method of evaluating lung cancer according to claim 4, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

8. The method of evaluating lung cancer according to claim 7, wherein the multivariate discriminant is the logistic regression equation containing the concentration values of His, Glu, Pro, Ile, Gln and Lys as the explanatory variables, or the linear discriminant containing the concentration values of His, Glu, Pro, Ile, Tyr and Lys as the explanatory variables.

9. The method of evaluating lung cancer according to claim 2, wherein the discriminant value criterion evaluating step further includes a discriminant value criterion discriminating step of discriminating between lung cancer with a certain disease stage and non-lung cancer in the subject based on the discriminant value calculated at the discriminant value calculating step, and the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

10. The method of evaluating lung cancer according to claim 2, wherein the discriminant value criterion evaluating step further includes a discriminant value criterion discriminating step of discriminating between adenocarcinoma in lung cancer and non-lung cancer in the subject based on the discriminant value calculated at the discriminant value calculating step, and the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

11. The method of evaluating lung cancer according to claim 1, wherein the multivariate discriminant contains at least Lys and His as the explanatory variables.

12. A lung cancer-evaluating apparatus comprising at least one CPU executing a lung cancer-evaluating program stored on at least one computer-readable recording medium, wherein the CPU is configured to:

calculate a discriminant value that is a value of a multivariate discriminant, based on both (i) concentration values of at least Lys and His contained in amino acid concentration data on the concentration values of the amino acids in blood of a subject to be evaluated and (ii) the multivariate discriminant for evaluating a lung cancer state containing at least Lys and His as explanatory variables.

13. The lung cancer-evaluating apparatus according to claim 12, wherein the multivariate discriminant further contains age as an explanatory variable.

14. The lung cancer-evaluating apparatus according to claim 12, wherein the CPU is configured to evaluate the lung cancer state in the subject, based on the discriminant value, wherein the CPU is further configured to discriminate between lung cancer and non-lung cancer in the subject based on the discriminant value.

15. The lung cancer-evaluating apparatus according to claim 14, wherein the multivariate discriminant is expressed by one fractional expression or the sum of a plurality of the fractional expressions and contains the concentration values of at least Lys and His as the explanatory variables in any one of the numerator and denominator or both in the fractional expression constituting the multivariate discriminant.

16. The lung cancer-evaluating apparatus according to claim 15, wherein the multivariate discriminant is formula 2 or 3:

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_2$, $b_2$ and $c_2$ in the formula 2 are arbitrary real numbers, $a_3$, $b_3$, $c_3$, $d_3$, and $e_3$ in the formula 3 are arbitrary real numbers.

17. The lung cancer-evaluating apparatus according to claim 14, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

18. The lung cancer-evaluating apparatus according to claim 17, wherein the multivariate discriminant is the logistic regression equation containing the concentration values of His, Glu, Pro, Ile, Gln and Lys as the explanatory variables, or the linear discriminant containing the concentration values of His, Glu, Pro, Ile, Tyr and Lys as the explanatory variables.

19. The lung cancer-evaluating apparatus according to claim 12, wherein the discriminant value criterion-evaluating unit further includes a discriminant value criterion-discriminating unit that discriminates between lung cancer with a certain disease stage and non-lung cancer in the subject based on the discriminant value calculated by the discriminant value-calculating unit, and the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

20. The lung cancer-evaluating apparatus according to claim 12, wherein the discriminant value criterion-evaluating unit further includes a discriminant value criterion-discriminating unit that discriminates between adenocarcinoma in lung cancer and non-lung cancer in the subject based on the discriminant value calculated by the discriminant value-calculating unit, and the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

21. The lung cancer-evaluating apparatus according to claim 12, wherein the CPU is configured to prepare the multivariate discriminant, based on lung cancer state information containing the amino acid concentration data and lung cancer state index data on an index for indicating the lung cancer state, wherein the CPU is further configured to repeatedly:

prepare a candidate multivariate discriminant that is a candidate of the multivariate discriminant, based on a predetermined discriminant-preparing method from the lung cancer state information;

verify the candidate multivariate discriminant, based on a predetermined verifying method; and select an explanatory variable of the candidate multivariate discriminant based on a predetermined explanatory variable-selecting method, thereby selecting a combination of the amino acid concentration data contained in the lung cancer state information used in preparing the candidate multivariate discriminant, thereby preparing the multivariate discriminant by selecting the candidate multivariate discriminant used as the multivariate discriminant, from a plurality of the candidate multivariate discriminants, based on the verification results.

22. The lung cancer-evaluating apparatus according to claim 12, wherein the multivariate discriminant contains at least Lys and His as the explanatory variables.

23. The lung cancer-evaluating apparatus according to claim 12, wherein the CPU is further configured to evaluate the lung cancer state in the subject, based on the discriminant value.

24. A lung cancer-evaluating method carried out with an information processing apparatus comprising at least one CPU executing a lung cancer-evaluating program stored on at least one computer-readable recording medium, wherein the CPU is configured to:

calculate a discriminant value that is a value of a multivariate discriminant, based on both (1) concentration values of at least Lys and His contained in amino acid concentration data on the concentration values of the amino acids in blood of a subject to be evaluated and (2) the multivariate discriminant for evaluating a lung cancer state containing at least Lys and His as explanatory variables.

25. The lung cancer-evaluating method according to claim 24, wherein the multivariate discriminant further contains age as an explanatory variable.

26. The lung cancer-evaluating method according to claim 24, wherein the CPU is further configured to evaluate the lung cancer state in the subject, based on the discriminant value wherein the CPU is further configured to discriminate between lung cancer and non-lung cancer in the subject based on the discriminant value.

27. The lung cancer-evaluating method according to claim 26, wherein the multivariate discriminant is expressed by one fractional expression or the sum of a plurality of the fractional expressions and contains the concentration values of at least Lys and His as the explanatory variables in any one of the numerator and denominator or both in the fractional expression constituting the multivariate discriminant.

28. The lung cancer-evaluating method according to claim 27, wherein the multivariate discriminant is formula 2 or 3:

$$a_2 \times Glu/Tyr + b_2 \times (Pro+Lys)/(Ile+His) + c_2 \quad \text{(formula 2)}$$

$$a_3 \times His/Lys + b_3 \times Glu/Ile + c_3 \times Tyr/Pro + d_3 \times Val/Leu + e_3 \quad \text{(formula 3)}$$

wherein $a_2$, $b_2$ and $c_2$ in the formula 2 are arbitrary real numbers, and $a_3$, $b_3$, $c_3$, $d_3$, and $e_3$ in the formula 3 are arbitrary real numbers.

29. The lung cancer-evaluating method according to claim 26, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

30. The lung cancer-evaluating method according to claim 29, wherein the multivariate discriminant is the logistic regression equation containing the concentration values of His, Glu, Pro, Ile, Gln and Lys as the explanatory variables, or the linear discriminant containing the concentration values of His, Glu, Pro, Ile, Tyr and Lys as the explanatory variables.

31. The lung cancer-evaluating method according to claim 24, wherein the discriminant value criterion evaluating step further includes a discriminant value criterion discriminating step of discriminating between lung cancer with a certain disease stage and non-lung cancer in the subject based on the discriminant value calculated at the discriminant value calculating step, and the multivariate discriminant is formula 4, 5 or 6:

$$a_4 \times Tau/Arg + b_4 \times (Orn+ABA)/Trp + c_4 \quad \text{(formula 4)}$$

$$a_5 \times Gln/(Cit+His) + b_5 \times (Glu+ABA)/(Cys2) + c_5 \quad \text{(formula 5)}$$

$$a_6 \times Gln/His + b_6 \times Glu + c_6 \times ABA/Cys + d_6 \times Lys/Val + e_6 \quad \text{(formula 6)}$$

wherein $a_4$, $b_4$ and $c_4$ in the formula 4 are arbitrary real numbers, $a_5$, $b_5$ and $c_5$ in the formula 5 are arbitrary real numbers, and $a_6$, $b_6$, $c_6$, $d_6$, and $e_6$ in the formula 6 are arbitrary real numbers.

32. The lung cancer-evaluating method according to claim 24, wherein the discriminant value criterion evaluating step further includes a discriminant value criterion discriminating step of discriminating between adenocarcinoma in lung cancer and non-lung cancer in the subject based on the discriminant value calculated at the discriminant value calculating step, and the multivariate discriminant is formula 7, 8 or 9:

$$a_7 \times Orn/Trp + b_7 \times Tau/Arg + c_7 \quad \text{(formula 7)}$$

$$a_8 \times (Glu+Pro)/His + b_8 \times (ABA+Lys)/Ile + c_8 \quad \text{(formula 8)}$$

$$a_9 \times Glu/Cit + b_9 \times His/Gln + c_9 \times Ile/Leu + d_9 \times Tyr/Ala + e_9 \quad \text{(formula 9)}$$

wherein $a_7$, $b_7$ and $c_7$ in the formula 7 are arbitrary real numbers, $a_8$, $b_8$ and $c_8$ in the formula 8 are arbitrary real numbers, and $a_9$, $b_9$, $c_9$, $d_9$, and $e_9$ in the formula 9 are arbitrary real numbers.

33. The lung cancer-evaluating method according to claim 24, wherein the CPU is configured to prepare the multivariate discriminant, based on lung cancer state information containing the amino acid concentration data and lung cancer state index date on an index for indicating the lung cancer state, wherein the CPU is further configured to repeatedly:

prepare a candidate multivariate discriminant that is a candidate of the multivariate discriminant, based on a predetermined discriminant-preparing method from the lung cancer state information;

verify the candidate multivariate discriminant, based on a predetermined verifying method; and select an explanatory variable of the candidate multivariate discriminant based on a predetermined explanatory variable-selecting method, thereby selecting a combination of the amino acid concentration data contained in the lung cancer state information used in preparing the candidate multivariate discriminant, thereby preparing the multivariate discriminant by selecting the candidate multivariate discriminant used as the multivariate discriminant from a plurality of the candidate multivariate discriminants, based on the verification results.

34. The lung cancer-evaluating method according to claim 24, wherein the CPU is further configured to evaluate the lung cancer state in the subject, based on the discriminant value calculated at the discriminant value.

35. A lung cancer-evaluating system compromising a lung cancer-evaluating apparatus comprising at least one CPU executing a lung cancer-evaluating program stored on at least one computer-readable recording medium and a terminal apparatus comprising at least one CPU executing a computer program stored on at least one computer-readable recording medium to provide amino acid concentration data on a concentration value of at least one amino acid in blood of a subject to be evaluated, wherein the apparatuses are connected to each other communicatively via a network, wherein the CPU of the terminal apparatus is configured to:

transmit the amino acid concentration data of the subject to the lung cancer-evaluating apparatus; and receive a discriminant value that is a value of a multivariate discriminant or an evaluation result of a lung cancer state, transmitted from the lung cancer-evaluating apparatus, wherein the CPU of the lung cancer-evaluating apparatus is configured to:

receive the amino acid concentration data of the subject transmitted from the terminal apparatus;

calculate the discriminant value, based on both (i) the concentration values of at least Lys and His contained in the amino acid concentration data of the subject and (ii) the multivariate discriminant for evaluating a lunch cancer state containing at least Lys and His as explanatory variables or calculate a discriminant value that is a value of a multivariate discriminant, based on both the concentration values of at least Lys and His contained in the amino acid concentration data of the subject and the multivariate discriminant for evaluating the lung cancer state containing at least Lys and His as explanatory variables, and evaluate the lung cancer state in the subject based on at least the discriminant value; and transmit the discriminant value or the evaluation result of the subject to the terminal apparatus.

36. A non-transitory computer-readable recording medium, comprising a lung cancer-evaluating program that is executed by at least one CPU, wherein the CPU is configured to:

calculate a discriminant value that is a value of a multivariate discriminant, based on both (1) concentration values of at least Lys His contained in amino acid concentration data on the concentration values of the amino acids in blood of a subject to be evaluated and (2) the multivariate discriminant for evaluating a lung cancer state containing at least Lys and His as explanatory variables.

37. The non-transitory computer-readable recording medium according to claim 36, wherein the CPU is further configured to evaluate the lung cancer state in the subject, based on the discriminant value.

38. A terminal apparatus comprising at least one CPU executing a computer program stored on at least one computer-readable recording medium, wherein the CPU is configured to obtain a discriminant value that is a value of a multivariate discriminant or an evaluation result of a lung cancer state, wherein the discriminant value is calculated based on both (i) concentration values of at least Lys and His contained in amino acid concentration data on the concentration values of the amino acids in blood of a subject to be evaluated and (ii) the multivariate discriminant for evaluating a lung cancer state containing at least Lys and His as explanatory variables or the evaluation result is the result of evaluating the lung cancer state in a subject to be evaluated based on at least a discriminant value that is a value of a multivariate discriminant, wherein the discriminant value is calculated based on both concentration values of at least Lys and His contained in amino acid concentration data on the concentration values of the amino acids in blood of the subject and the multivariate discriminant for evaluating the lung cancer state containing at least Lys and His as explanatory variables.

39. The terminal apparatus according to claim 38, wherein the terminal apparatus is communicatively connected via a network to a lung cancer-evaluating apparatus comprising a CPU executing a lung cancer-evaluating program stored on a computer-readable recording medium to calculate the discriminant value or evaluate the lung cancer state, wherein the CPU of the terminal apparatus is further configured to receive the discriminant value or the evaluation result transmitted from the lung cancer evaluating apparatus.

40. A lung cancer-evaluating apparatus comprising at least one CPU executing a lung cancer-evaluating program stored on at least one computer-readable recording medium, wherein the apparatus is communicatively connected via a network to a terminal apparatus configured to provide amino acid concentration data on concentration values of amino acids in blood of a subject to be evaluated, wherein the CPU is configured to:

receive the amino acid concentration data of the subject transmitted from the terminal apparatus;

calculate a discriminant value that is a value of a multivariate discriminant, based on both (i) the concentration values of at least Lys and His contained in the amino acid concentration data of the subject and (ii) the multivariate discriminant for evaluating a lung cancer state containing at least Lys and His as explanatory variables or calculate a discriminant value that is a value of a multivariate discriminant, based on both the concentration values of at least Lys and His contained in the amino acid concentration data of the subject and the multivariate discriminant for evaluating a lung cancer state containing at least Lys and His as explanatory variables, and evaluate the lung cancer state in the subject based on at least the discriminant value; and transmit the discriminant value or an evaluation result of the lung cancer state of the subject to the terminal apparatus.

41. A lung cancer-evaluating apparatus comprising at least one CPU executing a lung cancer-evaluating program stored on a computer-readable recording medium, wherein the CPU is configured to:

evaluate a lung cancer state in a subject to be evaluated, based on a discriminant value that is a value of a multivariate discriminant, wherein the discriminant value is calculated based on both (i) concentration values of at least Lys and His contained in amino acid concentration data on the concentration values of the amino acids in blood of the subject and (ii) the multivariate discriminant for evaluating the lung cancer state containing at least Lys and His as explanatory variables.

42. A lung cancer-evaluating method carried out with an information processing apparatus comprising a at least one CPU executing a lung cancer-evaluating program stored on a computer-readable recording medium, wherein the CPU is configured to:

evaluate a lung cancer state in a subject to be evaluated, based on a discriminant value that is a value of a multivariate discriminant, wherein the discriminant value is calculated based on both (1) concentration values of at least Lys and His contained in amino acid concentration data on the concentration values of the amino acids in blood of the subject and (2) the multivariate discriminant for evaluating the lung cancer state containing at least Lys and His as explanatory variables.

43. A non-transitory computer-readable recording medium, comprising a lung cancer-evaluating program that is executed by at least one CPU, wherein the CPU is configured to:

evaluate a lung cancer state in a subject to be evaluated, based on a discriminant value that is a value of a multivariate discriminant, wherein the discriminant value is calculated based on both (1) concentration values of at least Lys and His contained in amino acid concentration data on the concentration values of the amino acids in blood of the subject and (2) the multivariate discriminant for evaluating the lung cancer state containing at least Lys and His as explanatory variables.

44. A method of evaluating lung cancer, comprising:

a discriminant value calculating step of calculating, by a CPU executing a lung cancer-evaluating program stored on a computer-readable recording medium, a discriminant value that is a value of a multivariate discriminant, based on both (i) concentration values of at least Lys and His contained in amino acid concentration data on the concentration values of the amino acids in blood in a subject to be evaluated and (ii) the multivariate discriminant for evaluating a lung cancer state containing at least Lys and His as explanatory variables.

45. The method of evaluating lung cancer according to claim 44, wherein the method further includes a discriminant value criterion evaluating step of evaluating, by the CPU, the lung cancer state in the subject, using at least the discriminant value calculated at the discriminant value calculating step.

46. A method of evaluating lung cancer, comprising:

a discriminant value criterion evaluating step of evaluating, by a CPU executing a lung cancer-evaluating program stored on a computer-readable recording medium, a lung cancer state in a subject to be evaluated based on at least a discriminant value that is a value of a multivariate discriminant, wherein the discriminant value is calculated based on both (i) concentration values of at least Lys and His contained in amino acid concentration data on the concentration values of the amino acids in blood of the subject and (ii) the multivariate discriminant for evaluating the lung cancer state containing at least Lys and His as explanatory variables.

* * * * *